(12) United States Patent
Alekshun et al.

(10) Patent No.: US 8,039,221 B2
(45) Date of Patent: Oct. 18, 2011

(54) METHODS FOR IDENTIFYING AND USING MARR FAMILY POLYPEPTIDE BINDING COMPOUNDS

(75) Inventors: Michael N. Alekshun, Wakefield, MA (US); Stuart B. Levy, Boston, MA (US); Brent L. Podlogar, Hamden, CT (US); Roger Frechette, Reading, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 12/486,972

(22) Filed: Jun. 18, 2009

(65) Prior Publication Data

US 2011/0015375 A1    Jan. 20, 2011

Related U.S. Application Data

(63) Continuation of application No. 11/296,017, filed on Dec. 7, 2005, now abandoned, which is a continuation of application No. 10/196,672, filed on Jul. 15, 2002, now Pat. No. 7,075,582.

(60) Provisional application No. 60/305,322, filed on Jul. 13, 2001, provisional application No. 60/388,618, filed on Jun. 13, 2002.

(51) Int. Cl.
  *G01N 33/53*        (2006.01)
(52) U.S. Cl. ........................................ 435/7.1
(58) Field of Classification Search .................. None
  See application file for complete search history.

(56) References Cited

U.S. PATENT DOCUMENTS

| | | | |
|---|---|---|---|
| 5,817,793 | A | 10/1998 | Levy |
| 6,346,391 | B1 | 2/2002 | Oethinger |
| 6,391,545 | B1 | 5/2002 | Levy |
| 6,448,006 | B1 | 9/2002 | Levy |
| 7,075,582 | B2 | 7/2006 | Alekshun |

FOREIGN PATENT DOCUMENTS

WO   WO 03/006626    1/2003

OTHER PUBLICATIONS

Alekshun, et al. The crystal structure of MarR, a regulator of multiple antibiotic resistance, at 2.3 A resolution.: Nat Struct Biol. Aug. 2001; 8(8):710-4.
Alekshun, M.N. et al. "Regulation of charomosomally mediated multiple antibiotic resistance: the mar regulon." Antimicrob. Agents Chemother. Oct. 1997;41(10):2067-75.
Alekshun, M.N. et al. "Characterization of MarR superrepressor mutants." J. Bacteriol. May 1999;181(10):3303-6.
Alekshun, M.N. et al. "Alteration of the repressor activity of MarR, the negative regulator of the *Escherichia coli* marRAB locus, by multiple chemicals in vitro ." J. Bacteriol. Aug. 1999; 181(15):4669-72.
Alekshun, M.N. et al. "The mar regulon: multiple resistance to antibiotics and other toxic chemicals." Trends Microbiol. Oct. 1999;7(10):410-3.
Alekshun, M.N. et al., "Mutational analysis of MarR, the negative regulator of marRAB expression in *Escherichia coli*, suggests the presence of two regions required for DNA binding." Mol. Microbiol. Mar. 2000;35(6):1394-404.
Barbosa, T.M. et al. "Differential expression of over 60 chromosomal genes in *Escherichia coli* by constitutive expression of MarA." J. Bacteriol. Jun. 2000;182(12):3467-74.
Brooun, A. et al. "Purification and ligand binding of EmrR, a regulator of a multidrug transporter." J. Bacteriol. Aug. 1999;181(16):5131-3.
Drenth, J. "Chapter 1: Crystallizing a protein." from Principles of Protein X-ray Crystallography pp. 1-18, 1994 Springer-Verlag New York, Inc.
Gajiwala, K.S. et al. "Winged helix proteins." Curr. Opin. Struct. Biol. Feb. 2000;10(1):110-6.
Gajiwala, K.S. et al. "Structure of the winged-helix protein hRFX1 reveals a new mode of DNA binding." Nature Feb. 24, 2000;403(6772):916-21.
Geneseq.sub.—101002 database, AAR4977, dated Oct. 14, 1994; Result #1.
Kem. W.V. et al. "Non-target gene mutations in the development of fluoroquinolone resistance in *Escherichia coli*." Antimicrob. Agents Chemother. Apr. 2000;44(4):814-20.
Koutsolioutsou, A. et al. "A soxRS-constitutive mutation contributing to antibotic resistance in a clinical isolate of *Salmonella enterica* (*Serovar typhimurium*)." Antimicrob. Agents Chemother. Jan. 2001;45(1):38-43.
Linde, H.J. et al. "In vivo increase in resistance to ciprofloxacin in *Escherichia coli* associated with deletion of the C-terminal part of MarR." Antimicrob. Agents Chemother. Jul. 2000;44(7):1865-8.
Maneewannakul, K. et al. "Identification for mar mutants among quinolone-resistant clinical isolates of *Escherichia coli*." Antimicrob. Agents Chemother. Jul. 1996;40(7):1695-8.
Martin, R.G. et al. "Binding of purified multiple antibiotic-resistance repressor protein (MarR) to mar operator sequences." Proc. Natl. Acad. Sci. U.S.A. Jun. 6, 1995;92(12):5456-60.
Martin, R.G. et al. "Autoactivation of the marRAB multiple antibiotic resistance operon by the MarA transcriptional activator in *Escherichia coli*." J. Bateriol. Apr. 1996;178(8):2216-23.
Nikaido, H. "Multiple antibiotic resistance and efflux." Curr. Opin. Microbiol. Oct. 1998;1(5):516-23.
Oethinger, M. et al. "Overexpression of the marA or soxS regulatory gene in clinical topoisomerase mutants of *Escherichia coli*." Antimicrob. Agents Chemother. Aug. 1998;42(8):2089-94.
Pohl, E. et al. "Motion of the DNA-binding domain with respect to the core of the diphtheria toxin repressor (DtxR) revealed in the crystal structures of apo- and holo-DtxR." J. Biol. Chem. Aug. 28, 1998;273(35):22420-7.
Providenti, M.A. et al. "Indentification and functional characterization of CbaR, a MarR-like modulator of the cbaABC-encoded chlorobenzoate catabolism pathway." Applied and Environmental Microbiology Aug. 2001: 67(8):3530-41.

(Continued)

*Primary Examiner* — Suzanne M. Noakes
(74) *Attorney, Agent, or Firm* — McCarter & English, LLP; Elizabeth A. Hanley, Esq.; Joshua K. Roth, Esq.

(57) ABSTRACT

Methods for identifying MarR family inhibiting compounds are described. The methods include the use of computer aided rational based drug design programs and three dimensional structures of MarR family polypeptides.

12 Claims, 87 Drawing Sheets

OTHER PUBLICATIONS

Randall, L.P. et al. "Multiple antibiotic resistance (mar) locus in *Salmonella enterica* serovar typhimurium DT104." Applied and Experimental Microbiology. Mar. 2001;67(3):1190-1197.

Sulavik, M.C. et al. "The MarR repressor of the multiple antibiotic resistance (mar) operon in *Escherichia coli*: prototypic member of a family of bacterial regulatory proteins involved in sensing phenolic compounds." May 1995; 1(4):436-446.

Sulavik, M.C. et al. "The *Salmonella typhimurium* mar locus: molecular and genetic analyses and assessment of its role in virulence." J. Bateriol. Mar. 1997;179(6):1857-66.

White, A. et al. "Structure of the metal-ion-activated diphtheria toxin repressor/tox operator complex." Nature Jul. 30, 1998;394(6692):502-6.

Zheng, N. et al. "Structural basis of DNA recognition by the heterodimeric cell cycle transcription factor E2F-DP." Genes Dev. Mar. 15, 1999;13(6):666-74.

Ziha-Zarifi, I. et al. "In vivo emergence of multidrug-resistant mutants of *Pseudomonas aeruginosa* overexpressing the active efflux system MexA-MexB-OprM." Antimicrob. Agents Chemother. Feb. 1999;43(2)287-91.

```
HEADER    TRANSCRIPTION                           26-JUN-01   1JGS
TITLE     MULTIPLE ANTIBIOTIC RESISTANCE REPRESSOR, MARR WITH SALICYLATE
COMPND    MOL_ID: 1;
COMPND   2 MOLECULE: MULTIPLE ANTIBIOTIC RESISTANCE PROTEIN MARR;
COMPND   3 CHAIN: A;
COMPND   4 ENGINEERED: YES
SOURCE    MOL_ID: 1;
SOURCE   2 ORGANISM_SCIENTIFIC: ESCHERICHIA COLI;
SOURCE   3 ORGANISM_COMMON: BACTERIA;
SOURCE   4 EXPRESSION_SYSTEM: ESCHERICHIA COLI;
SOURCE   5 EXPRESSION_SYSTEM_COMMON: BACTERIA;
SOURCE   6 EXPRESSION_SYSTEM_STRAIN: BL21(DE3)
KEYWDS    TRANSCRIPTION REGULATION, DNA-BINDING, REPRESSOR,
KEYWDS   2 ANTIBIOTIC RESISTANCE
EXPDTA    X-RAY DIFFRACTION
AUTHOR    M.N.ALEKSHUN,S.B.LEVY,T.R.MEALY,B.A.SEATON,J.F.HEAD
REVDAT   1   28-DEC-01 1JGS    0
JRNL        AUTH   M.N.ALEKSHUN,S.B.LEVY,T.R.MEALY,B.A.SEATON,J.F.HEAD
JRNL        TITL   THE CRYSTAL STRUCTURE OF MARR, A REGULATOR OF
JRNL        TITL 2 MULTIPLE ANTIBIOTIC RESISTANCE, AT 2.3 A
JRNL        TITL 3 RESOLUTION.
JRNL        REF    NAT.STRUCT.BIOL.              V.   8    710 2001
JRNL        REFN   ASTM NSBIEW  US ISSN 1072-8368
REMARK   1
REMARK   2
REMARK   2 RESOLUTION. 2.30 ANGSTROMS.
REMARK   3
REMARK   3 REFINEMENT.
REMARK   3   PROGRAM     : CNS 1.0
REMARK   3   AUTHORS     : BRUNGER,ADAMS,CLORE,DELANO,GROS,GROSSE-
REMARK   3               : KUNSTLEVE,JIANG,KUSZEWSKI,NILGES, PANNU,
REMARK   3               : READ,RICE,SIMONSON,WARREN
REMARK   3
REMARK   3   REFINEMENT TARGET : NULL
REMARK   3
REMARK   3   DATA USED IN REFINEMENT.
REMARK   3   RESOLUTION RANGE HIGH (ANGSTROMS) : 2.30
REMARK   3   RESOLUTION RANGE LOW  (ANGSTROMS) : 50.00
REMARK   3   DATA CUTOFF            (SIGMA(F)) : NULL
REMARK   3   OUTLIER CUTOFF HIGH (RMS(ABS(F))) : NULL
REMARK   3   COMPLETENESS (WORKING+TEST)   (%) : NULL
REMARK   3   NUMBER OF REFLECTIONS             : 5968
REMARK   3
REMARK   3   FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE          (WORKING SET)    : 0.247
REMARK   3   FREE R VALUE                      : 0.287
```

Fig. 1

```
REMARK  3   FREE R VALUE TEST SET SIZE    (%) : NULL
REMARK  3   FREE R VALUE TEST SET COUNT       : 506
REMARK  3   ESTIMATED ERROR OF FREE R VALUE   : NULL
REMARK  3
REMARK  3  FIT IN THE HIGHEST RESOLUTION BIN.
REMARK  3   TOTAL NUMBER OF BINS USED             : NULL
REMARK  3   BIN RESOLUTION RANGE HIGH       (A)   : NULL
REMARK  3   BIN RESOLUTION RANGE LOW        (A)   : NULL
REMARK  3   BIN COMPLETENESS (WORKING+TEST) (%)   : NULL
REMARK  3   REFLECTIONS IN BIN    (WORKING SET)   : NULL
REMARK  3   BIN R VALUE           (WORKING SET)   : NULL
REMARK  3   BIN FREE R VALUE                      : NULL
REMARK  3   BIN FREE R VALUE TEST SET SIZE  (%)   : NULL
REMARK  3   BIN FREE R VALUE TEST SET COUNT       : NULL
REMARK  3   ESTIMATED ERROR OF BIN FREE R VALUE   : NULL
REMARK  3
REMARK  3  NUMBER OF NON-HYDROGEN ATOMS USED IN REFINEMENT.
REMARK  3   PROTEIN ATOMS            : 1078
REMARK  3   NUCLEIC ACID ATOMS       : 0
REMARK  3   HETEROGEN ATOMS          : 20
REMARK  3   SOLVENT ATOMS            : 0
REMARK  3
REMARK  3  B VALUES.
REMARK  3   FROM WILSON PLOT            (A**2) : NULL
REMARK  3   MEAN B VALUE      (OVERALL, A**2) : NULL
REMARK  3   OVERALL ANISOTROPIC B VALUE.
REMARK  3    B11 (A**2) : NULL
REMARK  3    B22 (A**2) : NULL
REMARK  3    B33 (A**2) : NULL
REMARK  3    B12 (A**2) : NULL
REMARK  3    B13 (A**2) : NULL
REMARK  3    B23 (A**2) : NULL
REMARK  3
REMARK  3  ESTIMATED COORDINATE ERROR.
REMARK  3   ESD FROM LUZZATI PLOT        (A) : NULL
REMARK  3   ESD FROM SIGMAA              (A) : NULL
REMARK  3   LOW RESOLUTION CUTOFF        (A) : NULL
REMARK  3
REMARK  3  CROSS-VALIDATED ESTIMATED COORDINATE ERROR.
REMARK  3   ESD FROM C-V LUZZATI PLOT    (A) : NULL
REMARK  3   ESD FROM C-V SIGMAA          (A) : NULL
REMARK  3
REMARK  3  RMS DEVIATIONS FROM IDEAL VALUES.
REMARK  3   BOND LENGTHS              (A) : 0.007
REMARK  3   BOND ANGLES         (DEGREES) : NULL
REMARK  3   DIHEDRAL ANGLES     (DEGREES) : NULL
REMARK  3   IMPROPER ANGLES     (DEGREES) : NULL
REMARK  3
```

Fig. 1A

```
REMARK   3  ISOTROPIC THERMAL MODEL : NULL
REMARK   3
REMARK   3  ISOTROPIC THERMAL FACTOR RESTRAINTS.     RMS      SIGMA
REMARK   3    MAIN-CHAIN BOND              (A**2) : NULL  ; NULL
REMARK   3    MAIN-CHAIN ANGLE             (A**2) : NULL  ; NULL
REMARK   3    SIDE-CHAIN BOND              (A**2) : NULL  ; NULL
REMARK   3    SIDE-CHAIN ANGLE             (A**2) : NULL  ; NULL
REMARK   3
REMARK   3
REMARK   3  BULK SOLVENT MODELING.
REMARK   3   METHOD USED : NULL
REMARK   3   KSOL        : NULL
REMARK   3   BSOL        : NULL
REMARK   3
REMARK   3  NCS MODEL : NULL
REMARK   3
REMARK   3  NCS RESTRAINTS.                           RMS    SIGMA/WEIGHT
REMARK   3   GROUP  1  POSITIONAL            (A) : NULL  ; NULL
REMARK   3   GROUP  1  B-FACTOR           (A**2) : NULL  ; NULL
REMARK   3
REMARK   3  PARAMETER FILE  1  : NULL
REMARK   3  TOPOLOGY FILE  1   : NULL
REMARK   3
REMARK   3  OTHER REFINEMENT REMARKS: NULL
REMARK   4
REMARK   4 1JGS COMPLIES WITH FORMAT V. 2.3, 09-JULY-1998
REMARK 100
REMARK 100 THIS ENTRY HAS BEEN PROCESSED BY RCSB ON 15-JUL-2001.
REMARK 100 THE RCSB ID CODE IS RCSB013753.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : NULL
REMARK 200  TEMPERATURE           (KELVIN) : 100.0
REMARK 200  PH                             : 5.50
REMARK 200  NUMBER OF CRYSTALS USED        : 1
REMARK 200
REMARK 200  SYNCHROTRON             (Y/N) : Y
REMARK 200  RADIATION SOURCE              : NSLS X8C
REMARK 200  BEAMLINE                      : NULL
REMARK 200  X-RAY GENERATOR MODEL         : NULL
REMARK 200  MONOCHROMATIC OR LAUE   (M/L) : M
REMARK 200  WAVELENGTH OR RANGE       (A) : 1.072
REMARK 200  MONOCHROMATOR                 : NULL
REMARK 200  OPTICS                        : NULL
REMARK 200
REMARK 200  DETECTOR TYPE                 : CCD
REMARK 200  DETECTOR MANUFACTURER         : ADSC QUANTUM 4
REMARK 200  INTENSITY-INTEGRATION SOFTWARE : DENZO
```

Fig. 1B

```
REMARK 200  DATA SCALING SOFTWARE              . SCALEPACK
REMARK 200
REMARK 200  NUMBER OF UNIQUE REFLECTIONS     : 6069
REMARK 200  RESOLUTION RANGE HIGH      (A)   : 2.300
REMARK 200  RESOLUTION RANGE LOW       (A)   : 50.000
REMARK 200  REJECTION CRITERIA   (SIGMA(I))  : NULL
REMARK 200
REMARK 200 OVERALL.
REMARK 200  COMPLETENESS FOR RANGE     (%)   : 99.5
REMARK 200  DATA REDUNDANCY                  : 9.500
REMARK 200  R MERGE                    (I)   : 0.06000
REMARK 200  R SYM                      (I)   : NULL
REMARK 200  <I/SIGMA(I)> FOR THE DATA SET    : 21.1000
REMARK 200
REMARK 200 IN THE HIGHEST RESOLUTION SHELL.
REMARK 200  HIGHEST RESOLUTION SHELL, RANGE HIGH (A) : 2.30
REMARK 200  HIGHEST RESOLUTION SHELL, RANGE LOW  (A) : 2.38
REMARK 200  COMPLETENESS FOR SHELL     (%)   : 100.0
REMARK 200  DATA REDUNDANCY IN SHELL         : NULL
REMARK 200  R MERGE FOR SHELL          (I)   : 0.20000
REMARK 200  R SYM FOR SHELL            (I)   : NULL
REMARK 200  <I/SIGMA(I)> FOR SHELL           : 12.000
REMARK 200
REMARK 200 DIFFRACTION PROTOCOL: MAD
REMARK 200 METHOD USED TO DETERMINE THE STRUCTURE: MAD
REMARK 200 SOFTWARE USED: SOLVE
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: PEG MME 5000, AMMONIUM SULFATE,
REMARK 280  SODIUM SALICYLATE, HEPTANETRIOL, GLYCEROL, DTT
REMARK 290
REMARK 290 CRYSTALLOGRAPHIC SYMMETRY
REMARK 290 SYMMETRY OPERATORS FOR SPACE GROUP: I 41 2 2
REMARK 290
REMARK 290      SYMOP    SYMMETRY
REMARK 290      NNNMMM   OPERATOR
REMARK 290       1555    X,Y,Z
REMARK 290       2555    1/2-X,1/2-Y,1/2+Z
REMARK 290       3555    -Y,1/2+X,1/4+Z
REMARK 290       4555    1/2+Y,-X,3/4+Z
REMARK 290       5555    1/2-X,Y,3/4-Z
REMARK 290       6555    X,1/2-Y,1/4-Z
```

Fig. 1C

```
REMARK 290      7555    1/2+Y,1/2+X,1/2-Z
REMARK 290      8555    -Y,-X,-Z
REMARK 290      9555    1/2+X,1/2+Y,1/2+Z
REMARK 290     10555    1/1-X,1/1-Y,1/1+Z
REMARK 290     11555    1/2-Y,1/1+X,3/4+Z
REMARK 290     12555    1/1+Y,1/2-X,5/4+Z
REMARK 290     13555    1/1-X,1/2+Y,5/4-Z
REMARK 290     14555    1/2+X,1/1-Y,3/4-Z
REMARK 290     15555    1/1+Y,1/1+X,1/1-Z
REMARK 290     16555    1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290   SMTRY1   1  1.000000  0.000000  0.000000        0.00000
REMARK 290   SMTRY2   1  0.000000  1.000000  0.000000        0.00000
REMARK 290   SMTRY3   1  0.000000  0.000000  1.000000        0.00000
REMARK 290   SMTRY1   2 -1.000000  0.000000  0.000000       31.00000
REMARK 290   SMTRY2   2  0.000000 -1.000000  0.000000       31.00000
REMARK 290   SMTRY3   2  0.000000  0.000000  1.000000       66.44500
REMARK 290   SMTRY1   3  0.000000 -1.000000  0.000000        0.00000
REMARK 290   SMTRY2   3  1.000000  0.000000  0.000000       31.00000
REMARK 290   SMTRY3   3  0.000000  0.000000  1.000000       33.22250
REMARK 290   SMTRY1   4  0.000000  1.000000  0.000000       31.00000
REMARK 290   SMTRY2   4 -1.000000  0.000000  0.000000        0.00000
REMARK 290   SMTRY3   4  0.000000  0.000000  1.000000       99.66750
REMARK 290   SMTRY1   5 -1.000000  0.000000  0.000000       31.00000
REMARK 290   SMTRY2   5  0.000000  1.000000  0.000000        0.00000
REMARK 290   SMTRY3   5  0.000000  0.000000 -1.000000       99.66750
REMARK 290   SMTRY1   6  1.000000  0.000000  0.000000        0.00000
REMARK 290   SMTRY2   6  0.000000 -1.000000  0.000000       31.00000
REMARK 290   SMTRY3   6  0.000000  0.000000 -1.000000       33.22250
REMARK 290   SMTRY1   7  0.000000  1.000000  0.000000       31.00000
REMARK 290   SMTRY2   7  1.000000  0.000000  0.000000       31.00000
REMARK 290   SMTRY3   7  0.000000  0.000000 -1.000000       66.44500
REMARK 290   SMTRY1   8  0.000000 -1.000000  0.000000        0.00000
REMARK 290   SMTRY2   8 -1.000000  0.000000  0.000000        0.00000
REMARK 290   SMTRY3   8  0.000000  0.000000 -1.000000        0.00000
REMARK 290   SMTRY1   9  1.000000  0.000000  0.000000       31.00000
REMARK 290   SMTRY2   9  0.000000  1.000000  0.000000       31.00000
REMARK 290   SMTRY3   9  0.000000  0.000000  1.000000       66.44500
REMARK 290   SMTRY1  10 -1.000000  0.000000  0.000000       62.00000
REMARK 290   SMTRY2  10  0.000000 -1.000000  0.000000       62.00000
REMARK 290   SMTRY3  10  0.000000  0.000000  1.000000      132.89000
```

Fig. 1D

```
REMARK 290   SMTRY1  11   0.000000 -1.000000  0.000000       31.00000
REMARK 290   SMTRY2  11   1.000000  0.000000  0.000000       62.00000
REMARK 290   SMTRY3  11   0.000000  0.000000  1.000000       99.66750
REMARK 290   SMTRY1  12   0.000000  1.000000  0.000000       62.00000
REMARK 290   SMTRY2  12  -1.000000  0.000000  0.000000       31.00000
REMARK 290   SMTRY3  12   0.000000  0.000000  1.000000      166.11250
REMARK 290   SMTRY1  13  -1.000000  0.000000  0.000000       62.00000
REMARK 290   SMTRY2  13   0.000000  1.000000  0.000000       31.00000
REMARK 290   SMTRY3  13   0.000000  0.000000 -1.000000      166.11250
REMARK 290   SMTRY1  14   1.000000  0.000000  0.000000       31.00000
REMARK 290   SMTRY2  14   0.000000 -1.000000  0.000000       62.00000
REMARK 290   SMTRY3  14   0.000000  0.000000 -1.000000       99.66750
REMARK 290   SMTRY1  15   0.000000  1.000000  0.000000       62.00000
REMARK 290   SMTRY2  15   1.000000  0.000000  0.000000       62.00000
REMARK 290   SMTRY3  15   0.000000  0.000000 -1.000000      132.89000
REMARK 290   SMTRY1  16   0.000000 -1.000000  0.000000       31.00000
REMARK 290   SMTRY2  16  -1.000000  0.000000  0.000000       31.00000
REMARK 290   SMTRY3  16   0.000000  0.000000 -1.000000       66.44500
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350   BIOMT1   1   1.000000  0.000000  0.000000        0.00000
REMARK 350   BIOMT2   1   0.000000  1.000000  0.000000        0.00000
REMARK 350   BIOMT3   1   0.000000  0.000000  1.000000        0.00000
REMARK 350   BIOMT1   2  -1.000000  0.000000  0.000000       62.00000
REMARK 350   BIOMT2   2   0.000000 -1.000000  0.000000       62.00000
REMARK 350   BIOMT3   2   0.000000  0.000000  1.000000      132.89000
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
```

Fig. 1E

```
REMARK 500  IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
REMARK 500
REMARK 500 EXPECTED VALUES: ENGH AND HUBER, 1991
REMARK 500
REMARK 500  M RES CSSEQI ATM1    RES CSSEQI ATM2   DEVIATION
REMARK 500     MET A  74   CE    MET A  74   SD      0.043
REMARK 500     GLU A 131   CA    GLU A 131   N       0.046
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1   ATM2   ATM3
REMARK 500     LEU A  97   N  -  CA  -  C   ANGL. DEV. = -8.4 DEGREES
REMARK 500     THR A 101   N  -  CA  -  C   ANGL. DEV. = -8.9 DEGREES
REMARK 500     GLU A 131   N  -  CA  -  C   ANGL. DEV. =  9.5 DEGREES
REMARK 500     LEU A 143   N  -  CA  -  C   ANGL. DEV. =  8.6 DEGREES
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M=MODEL NUMBER; RES=RESIDUE NAME; C=CHAIN IDENTIFIER;
REMARK 500 SSEQ=SEQUENCE NUMBER; I=INSERTION CODE).
REMARK 500
REMARK 500 STANDARD TABLE:
REMARK 500 FORMAT:(10X,I3,1X,A3,1X,A1,I4,A1,4X,F7.2,3X,F7.2)
REMARK 500
REMARK 500  M RES CSSEQI         PSI       PHI
REMARK 500    ALA A  53        -60.18    70.65
DBREF  1JGS A    7   144  SWS    P27245   MARR_ECOLI       7    144
SEQRES   1 A  138  LEU PHE ASN GLU ILE ILE PRO LEU GLY ARG LEU ILE HIS
SEQRES   2 A  138  MET VAL ASN GLN LYS LYS ASP ARG LEU LEU ASN GLU TYR
SEQRES   3 A  138  LEU SER PRO LEU ASP ILE THR ALA ALA GLN PHE LYS VAL
SEQRES   4 A  138  LEU CYS SER ILE ARG CYS ALA ALA CYS ILE THR PRO VAL
SEQRES   5 A  138  GLU LEU LYS LYS VAL LEU SER VAL ASP LEU GLY ALA LEU
```

Fig. 1F

```
SEQRES   6 A  138  THR ARG MET LEU ASP ARG LEU VAL CYS LYS GLY TRP VAL
SEQRES   7 A  138  GLU ARG LEU PRO ASN PRO ASN ASP LYS ARG GLY VAL LEU
SEQRES   8 A  138  VAL LYS LEU THR THR GLY GLY ALA ALA ILE CYS GLU GLN
SEQRES   9 A  138  CYS HIS GLN LEU VAL GLY GLN ASP LEU HIS GLN GLU LEU
SEQRES  10 A  138  THR LYS ASN LEU THR ALA ASP GLU VAL ALA THR LEU GLU
SEQRES  11 A  138  TYR LEU LEU LYS LYS VAL LEU PRO
HET    SAL    256      10
HET    SAL    257      10
HETNAM     SAL 2-HYDROXYBENZOIC ACID
HETSYN     SAL SALICYLIC ACID
FORMUL   2  SAL    2(C7 H6 O3)
HELIX    1   1 PRO A   13  SER A   34  1                                  22
HELIX    2   2 THR A   39  ALA A   53  1                                  15
HELIX    3   3 THR A   56  SER A   65  1                                  10
HELIX    4   4 ASP A   67  LYS A   81  1                                  15
HELIX    5   5 THR A  101  LYS A  125  1                                  25
HELIX    6   6 GLU A  131  LYS A  141  1                                  11
SHEET    1   A 2 VAL A  84  PRO A  88  0
SHEET    2   A 2 VAL A  96  LEU A 100 -1  N  LEU A  97   O  LEU A  87
CRYST1   62.000   62.000  132.890  90.00  90.00  90.00 I 41 2 2      16
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.016129  0.000000  0.000000        0.00000
SCALE2      0.000000  0.016129  0.000000        0.00000
SCALE3      0.000000  0.000000  0.007525        0.00000
ATOM     1   N   LEU A   7      36.956  -0.266  22.798  1.00 63.50           N
ATOM     2   CA  LEU A   7      36.482   0.956  22.088  1.00 63.50           C
ATOM     3   C   LEU A   7      37.614   1.498  21.226  1.00 63.50           C
ATOM     4   O   LEU A   7      37.388   1.940  20.097  1.00 63.50           O
ATOM     5   CB  LEU A   7      36.033   2.021  23.097  1.00 65.57           C
ATOM     6   CG  LEU A   7      35.117   3.140  22.579  1.00 65.57           C
ATOM     7   CD1 LEU A   7      33.812   2.545  22.096  1.00 65.57           C
ATOM     8   CD2 LEU A   7      34.848   4.157  23.684  1.00 65.57           C
ATOM     9   N   PHE A   8      38.833   1.465  21.760  1.00 68.87           N
ATOM    10   CA  PHE A   8      40.004   1.938  21.022  1.00 68.87           C
ATOM    11   C   PHE A   8      40.644   0.777  20.278  1.00 68.87           C
ATOM    12   O   PHE A   8      41.758   0.889  19.768  1.00 68.87           O
ATOM    13   CB  PHE A   8      41.034   2.571  21.964  1.00 79.70           C
ATOM    14   CG  PHE A   8      40.611   3.901  22.524  1.00 79.70           C
ATOM    15   CD1 PHE A   8      39.571   3.988  23.450  1.00 79.70           C
ATOM    16   CD2 PHE A   8      41.249   5.072  22.122  1.00 79.70           C
ATOM    17   CE1 PHE A   8      39.174   5.220  23.967  1.00 79.70           C
ATOM    18   CE2 PHE A   8      40.858   6.311  22.634  1.00 79.70           C
ATOM    19   CZ  PHE A   8      39.820   6.383  23.557  1.00 79.70           C
ATOM    20   N   ASN A   9      39.933  -0.344  20.236  1.00 96.16           N
ATOM    21   CA  ASN A   9      40.416  -1.528  19.540  1.00 96.16           C
ATOM    22   C   ASN A   9      39.437  -1.875  18.426  1.00 96.16           C
```

Fig. 1G

| | | | | | | | | | | |
|---|---|---|---|---|---|---|---|---|---|---|
| ATOM | 23 | O | ASN | A | 9 | 39.503 | -2.953 | 17.833 | 1.00 96.16 | O |
| ATOM | 24 | CB | ASN | A | 9 | 40.551 | -2.706 | 20.510 | 1.00 93.11 | C |
| ATOM | 25 | CG | ASN | A | 9 | 41.643 | -2.489 | 21.548 | 1.00 93.11 | C |
| ATOM | 26 | OD1 | ASN | A | 9 | 41.894 | -3.351 | 22.395 | 1.00 93.11 | O |
| ATOM | 27 | ND2 | ASN | A | 9 | 42.298 | -1.333 | 21.486 | 1.00 93.11 | N |
| ATOM | 28 | N | GLU | A | 10 | 38.530 | -0.944 | 18.143 | 1.00 59.45 | N |
| ATOM | 29 | CA | GLU | A | 10 | 37.525 | -1.142 | 17.105 | 1.00 59.45 | C |
| ATOM | 30 | C | GLU | A | 10 | 37.512 | 0.040 | 16.141 | 1.00 59.45 | C |
| ATOM | 31 | O | GLU | A | 10 | 37.604 | 1.191 | 16.561 | 1.00 59.45 | O |
| ATOM | 32 | CB | GLU | A | 10 | 36.143 | -1.305 | 17.747 | 1.00 65.56 | C |
| ATOM | 33 | CG | GLU | A | 10 | 35.257 | -2.304 | 17.033 | 1.00 65.56 | C |
| ATOM | 34 | CD | GLU | A | 10 | 35.908 | -3.673 | 16.912 | 1.00 65.56 | C |
| ATOM | 35 | OE1 | GLU | A | 10 | 36.330 | -4.238 | 17.943 | 1.00 65.56 | O |
| ATOM | 36 | OE2 | GLU | A | 10 | 35.995 | -4.186 | 15.778 | 1.00 65.56 | O |
| ATOM | 37 | N | ILE | A | 11 | 37.403 | -0.247 | 14.847 | 1.00 60.35 | N |
| ATOM | 38 | CA | ILE | A | 11 | 37.383 | 0.812 | 13.846 | 1.00 60.35 | C |
| ATOM | 39 | C | ILE | A | 11 | 35.962 | 1.288 | 13.573 | 1.00 60.35 | C |
| ATOM | 40 | O | ILE | A | 11 | 35.271 | 0.780 | 12.687 | 1.00 60.35 | O |
| ATOM | 41 | CB | ILE | A | 11 | 38.020 | 0.354 | 12.519 | 1.00 49.41 | C |
| ATOM | 42 | CG1 | ILE | A | 11 | 39.485 | -0.019 | 12.752 | 1.00 49.41 | C |
| ATOM | 43 | CG2 | ILE | A | 11 | 37.925 | 1.470 | 11.475 | 1.00 49.41 | C |
| ATOM | 44 | CD1 | ILE | A | 11 | 40.133 | -0.692 | 11.564 | 1.00 49.41 | C |
| ATOM | 45 | N | ILE | A | 12 | 35.537 | 2.270 | 14.357 | 1.00 57.24 | N |
| ATOM | 46 | CA | ILE | A | 12 | 34.213 | 2.852 | 14.227 | 1.00 57.24 | C |
| ATOM | 47 | C | ILE | A | 12 | 34.362 | 4.041 | 13.286 | 1.00 57.24 | C |
| ATOM | 48 | O | ILE | A | 12 | 35.210 | 4.918 | 13.503 | 1.00 57.24 | O |
| ATOM | 49 | CB | ILE | A | 12 | 33.697 | 3.328 | 15.609 | 1.00 44.12 | C |
| ATOM | 50 | CG1 | ILE | A | 12 | 33.711 | 2.147 | 16.591 | 1.00 44.12 | C |
| ATOM | 51 | CG2 | ILE | A | 12 | 32.294 | 3.907 | 15.481 | 1.00 44.12 | C |
| ATOM | 52 | CD1 | ILE | A | 12 | 33.624 | 2.551 | 18.061 | 1.00 44.12 | C |
| ATOM | 53 | N | PRO | A | 13 | 33.559 | 4.074 | 12.208 | 1.00 56.35 | N |
| ATOM | 54 | CA | PRO | A | 13 | 33.607 | 5.166 | 11.228 | 1.00 56.35 | C |
| ATOM | 55 | C | PRO | A | 13 | 33.175 | 6.508 | 11.834 | 1.00 56.35 | C |
| ATOM | 56 | O | PRO | A | 13 | 32.278 | 6.558 | 12.678 | 1.00 56.35 | O |
| ATOM | 57 | CB | PRO | A | 13 | 32.659 | 4.679 | 10.134 | 1.00 44.76 | C |
| ATOM | 58 | CG | PRO | A | 13 | 31.628 | 3.905 | 10.919 | 1.00 44.76 | C |
| ATOM | 59 | CD | PRO | A | 13 | 32.497 | 3.110 | 11.868 | 1.00 44.76 | C |
| ATOM | 60 | N | LEU | A | 14 | 33.816 | 7.583 | 11.384 | 1.00 50.54 | N |
| ATOM | 61 | CA | LEU | A | 14 | 33.547 | 8.938 | 11.865 | 1.00 50.54 | C |
| ATOM | 62 | C | LEU | A | 14 | 32.060 | 9.240 | 12.081 | 1.00 50.54 | C |
| ATOM | 63 | O | LEU | A | 14 | 31.652 | 9.658 | 13.179 | 1.00 50.54 | O |
| ATOM | 64 | CB | LEU | A | 14 | 34.145 | 9.947 | 10.880 | 1.00 41.30 | C |
| ATOM | 65 | CG | LEU | A | 14 | 34.006 | 11.443 | 11.136 | 1.00 41.30 | C |
| ATOM | 66 | CD1 | LEU | A | 14 | 34.719 | 11.839 | 12.423 | 1.00 41.30 | C |
| ATOM | 67 | CD2 | LEU | A | 14 | 34.603 | 12.185 | 9.952 | 1.00 41.30 | C |
| ATOM | 68 | N | GLY | A | 15 | 31.260 | 9.028 | 11.034 | 1.00 49.82 | N |
| ATOM | 69 | CA | GLY | A | 15 | 29.829 | 9.276 | 11.115 | 1.00 49.82 | C |
| ATOM | 70 | C | GLY | A | 15 | 29.180 | 8.770 | 12.390 | 1.00 49.82 | C |

Fig. 1H

| ATOM | 71 | O | GLY | A | 15 | 28.489 | 9.521 | 13.080 | 1.00 | 49.82 | O |
|------|-----|-----|-----|---|----|--------|-------|--------|------|-------|---|
| ATOM | 72 | N | ARG | A | 16 | 29.389 | 7.496 | 12.708 | 1.00 | 56.39 | N |
| ATOM | 73 | CA | ARG | A | 16 | 28.807 | 6.925 | 13.917 | 1.00 | 56.39 | C |
| ATOM | 74 | C | ARG | A | 16 | 29.406 | 7.557 | 15.172 | 1.00 | 56.39 | C |
| ATOM | 75 | O | ARG | A | 16 | 28.698 | 7.776 | 16.154 | 1.00 | 56.39 | O |
| ATOM | 76 | CB | ARG | A | 16 | 29.013 | 5.409 | 13.947 | 1.00 | 100.64 | C |
| ATOM | 77 | CG | ARG | A | 16 | 28.044 | 4.622 | 13.073 | 1.00 | 100.64 | C |
| ATOM | 78 | CD | ARG | A | 16 | 28.476 | 3.163 | 12.974 | 1.00 | 100.64 | C |
| ATOM | 79 | NE | ARG | A | 16 | 28.621 | 2.532 | 14.287 | 1.00 | 100.64 | N |
| ATOM | 80 | CZ | ARG | A | 16 | 29.280 | 1.395 | 14.502 | 1.00 | 100.64 | C |
| ATOM | 81 | NH1 | ARG | A | 16 | 29.861 | 0.758 | 13.492 | 1.00 | 100.64 | N |
| ATOM | 82 | NH2 | ARG | A | 16 | 29.360 | 0.893 | 15.727 | 1.00 | 100.64 | N |
| ATOM | 83 | N | LEU | A | 17 | 30.707 | 7.853 | 15.147 | 1.00 | 42.87 | N |
| ATOM | 84 | CA | LEU | A | 17 | 31.341 | 8.466 | 16.308 | 1.00 | 42.87 | C |
| ATOM | 85 | C | LEU | A | 17 | 30.735 | 9.844 | 16.572 | 1.00 | 42.87 | C |
| ATOM | 86 | O | LEU | A | 17 | 30.456 | 10.187 | 17.716 | 1.00 | 42.87 | O |
| ATOM | 87 | CB | LEU | A | 17 | 32.859 | 8.587 | 16.115 | 1.00 | 41.77 | C |
| ATOM | 88 | CG | LEU | A | 17 | 33.683 | 7.296 | 16.205 | 1.00 | 41.77 | C |
| ATOM | 89 | CD1 | LEU | A | 17 | 35.166 | 7.592 | 15.962 | 1.00 | 41.77 | C |
| ATOM | 90 | CD2 | LEU | A | 17 | 33.487 | 6.677 | 17.571 | 1.00 | 41.77 | C |
| ATOM | 91 | N | ILE | A | 18 | 30.558 | 10.634 | 15.516 | 1.00 | 40.19 | N |
| ATOM | 92 | CA | ILE | A | 18 | 29.959 | 11.962 | 15.643 | 1.00 | 40.19 | C |
| ATOM | 93 | C | ILE | A | 18 | 28.557 | 11.779 | 16.234 | 1.00 | 40.19 | C |
| ATOM | 94 | O | ILE | A | 18 | 28.113 | 12.567 | 17.072 | 1.00 | 40.19 | O |
| ATOM | 95 | CB | ILE | A | 18 | 29.821 | 12.662 | 14.270 | 1.00 | 50.02 | C |
| ATOM | 96 | CG1 | ILE | A | 18 | 31.203 | 13.011 | 13.716 | 1.00 | 50.02 | C |
| ATOM | 97 | CG2 | ILE | A | 18 | 29.008 | 13.933 | 14.409 | 1.00 | 50.02 | C |
| ATOM | 98 | CD1 | ILE | A | 18 | 31.156 | 13.614 | 12.312 | 1.00 | 50.02 | C |
| ATOM | 99 | N | HIS | A | 19 | 27.875 | 10.726 | 15.792 | 1.00 | 61.33 | N |
| ATOM | 100 | CA | HIS | A | 19 | 26.534 | 10.419 | 16.262 | 1.00 | 61.33 | C |
| ATOM | 101 | C | HIS | A | 19 | 26.592 | 10.158 | 17.755 | 1.00 | 61.33 | C |
| ATOM | 102 | O | HIS | A | 19 | 26.050 | 10.922 | 18.557 | 1.00 | 61.33 | O |
| ATOM | 103 | CB | HIS | A | 19 | 26.007 | 9.186 | 15.532 | 1.00 | 71.93 | C |
| ATOM | 104 | CG | HIS | A | 19 | 24.670 | 8.715 | 16.009 | 1.00 | 71.93 | C |
| ATOM | 105 | ND1 | HIS | A | 19 | 23.556 | 9.526 | 16.029 | 1.00 | 71.93 | N |
| ATOM | 106 | CD2 | HIS | A | 19 | 24.257 | 7.501 | 16.445 | 1.00 | 71.93 | C |
| ATOM | 107 | CE1 | HIS | A | 19 | 22.515 | 8.833 | 16.454 | 1.00 | 71.93 | C |
| ATOM | 108 | NE2 | HIS | A | 19 | 22.913 | 7.600 | 16.712 | 1.00 | 71.93 | N |
| ATOM | 109 | N | MET | A | 20 | 27.264 | 9.072 | 18.116 | 1.00 | 42.03 | N |
| ATOM | 110 | CA | MET | A | 20 | 27.426 | 8.676 | 19.511 | 1.00 | 42.03 | C |
| ATOM | 111 | C | MET | A | 20 | 27.796 | 9.844 | 20.414 | 1.00 | 42.03 | C |
| ATOM | 112 | O | MET | A | 20 | 27.316 | 9.923 | 21.535 | 1.00 | 42.03 | O |
| ATOM | 113 | CB | MET | A | 20 | 28.515 | 7.608 | 19.634 | 1.00 | 67.14 | C |
| ATOM | 114 | CG | MET | A | 20 | 28.159 | 6.249 | 19.067 | 1.00 | 67.14 | C |
| ATOM | 115 | SD | MET | A | 20 | 29.602 | 5.147 | 19.075 | 1.00 | 67.14 | S |
| ATOM | 116 | CE | MET | A | 20 | 29.707 | 4.719 | 20.836 | 1.00 | 67.14 | C |
| ATOM | 117 | N | VAL | A | 21 | 28.664 | 10.735 | 19.938 | 1.00 | 52.70 | N |
| ATOM | 118 | CA | VAL | A | 21 | 29.092 | 11.885 | 20.733 | 1.00 | 52.70 | C |

Fig. 1I

| | | | | | | | | | | |
|---|---|---|---|---|---|---|---|---|---|---|
| ATOM | 119 | C | VAL | A | 21 | 28.002 | 12.948 | 20.875 | 1.00 52.70 | C |
| ATOM | 120 | O | VAL | A | 21 | 27.875 | 13.592 | 21.933 | 1.00 52.70 | O |
| ATOM | 121 | CB | VAL | A | 21 | 30.346 | 12.560 | 20.137 | 1.00 37.15 | C |
| ATOM | 122 | CG1 | VAL | A | 21 | 30.727 | 13.763 | 20.989 | 1.00 37.15 | C |
| ATOM | 123 | CG2 | VAL | A | 21 | 31.517 | 11.556 | 20.086 | 1.00 37.15 | C |
| ATOM | 124 | N | ASN | A | 22 | 27.231 | 13.149 | 19.810 | 1.00 51.65 | N |
| ATOM | 125 | CA | ASN | A | 22 | 26.161 | 14.131 | 19.863 | 1.00 51.65 | C |
| ATOM | 126 | C | ASN | A | 22 | 25.157 | 13.551 | 20.836 | 1.00 51.65 | C |
| ATOM | 127 | O | ASN | A | 22 | 24.591 | 14.263 | 21.671 | 1.00 51.65 | O |
| ATOM | 128 | CB | ASN | A | 22 | 25.502 | 14.323 | 18.497 | 1.00 36.79 | C |
| ATOM | 129 | CG | ASN | A | 22 | 24.601 | 15.544 | 18.465 | 1.00 36.79 | C |
| ATOM | 130 | OD1 | ASN | A | 22 | 25.067 | 16.671 | 18.633 | 1.00 36.79 | O |
| ATOM | 131 | ND2 | ASN | A | 22 | 23.304 | 15.326 | 18.257 | 1.00 36.79 | N |
| ATOM | 132 | N | GLN | A | 23 | 24.957 | 12.241 | 20.723 | 1.00 53.66 | N |
| ATOM | 133 | CA | GLN | A | 23 | 24.040 | 11.521 | 21.592 | 1.00 53.66 | C |
| ATOM | 134 | C | GLN | A | 23 | 24.419 | 11.899 | 23.018 | 1.00 53.66 | C |
| ATOM | 135 | O | GLN | A | 23 | 23.649 | 12.543 | 23.728 | 1.00 53.66 | O |
| ATOM | 136 | CB | GLN | A | 23 | 24.205 | 10.015 | 21.384 | 1.00 84.11 | C |
| ATOM | 137 | CG | GLN | A | 23 | 23.100 | 9.154 | 21.974 | 1.00 84.11 | C |
| ATOM | 138 | CD | GLN | A | 23 | 22.270 | 8.458 | 20.903 | 1.00 84.11 | C |
| ATOM | 139 | OE1 | GLN | A | 23 | 22.789 | 7.665 | 20.109 | 1.00 84.11 | O |
| ATOM | 140 | NE2 | GLN | A | 23 | 20.972 | 8.752 | 20.877 | 1.00 84.11 | N |
| ATOM | 141 | N | LYS | A | 24 | 25.631 | 11.519 | 23.412 | 1.00 47.08 | N |
| ATOM | 142 | CA | LYS | A | 24 | 26.142 | 11.801 | 24.746 | 1.00 47.08 | C |
| ATOM | 143 | C | LYS | A | 24 | 25.873 | 13.245 | 25.140 | 1.00 47.08 | C |
| ATOM | 144 | O | LYS | A | 24 | 25.342 | 13.516 | 26.213 | 1.00 47.08 | O |
| ATOM | 145 | CB | LYS | A | 24 | 27.651 | 11.540 | 24.817 | 1.00 49.11 | C |
| ATOM | 146 | CG | LYS | A | 24 | 28.214 | 11.723 | 26.218 | 1.00 49.11 | C |
| ATOM | 147 | CD | LYS | A | 24 | 29.725 | 11.840 | 26.227 | 1.00 49.11 | C |
| ATOM | 148 | CE | LYS | A | 24 | 30.273 | 12.007 | 27.651 | 1.00 49.11 | C |
| ATOM | 149 | NZ | LYS | A | 24 | 30.669 | 10.711 | 28.286 | 1.00 49.11 | N |
| ATOM | 150 | N | LYS | A | 25 | 26.253 | 14.161 | 24.260 | 1.00 49.08 | N |
| ATOM | 151 | CA | LYS | A | 25 | 26.082 | 15.592 | 24.491 | 1.00 49.08 | C |
| ATOM | 152 | C | LYS | A | 25 | 24.650 | 15.955 | 24.881 | 1.00 49.08 | C |
| ATOM | 153 | O | LYS | A | 25 | 24.428 | 16.784 | 25.767 | 1.00 49.08 | O |
| ATOM | 154 | CB | LYS | A | 25 | 26.504 | 16.365 | 23.235 | 1.00 88.21 | C |
| ATOM | 155 | CG | LYS | A | 25 | 26.525 | 17.878 | 23.381 | 1.00 88.21 | C |
| ATOM | 156 | CD | LYS | A | 25 | 25.257 | 18.516 | 22.837 | 1.00 88.21 | C |
| ATOM | 157 | CE | LYS | A | 25 | 25.373 | 20.036 | 22.832 | 1.00 88.21 | C |
| ATOM | 158 | NZ | LYS | A | 25 | 24.213 | 20.700 | 22.173 | 1.00 88.21 | N |
| ATOM | 159 | N | ASP | A | 26 | 23.677 | 15.331 | 24.227 | 1.00 49.82 | N |
| ATOM | 160 | CA | ASP | A | 26 | 22.291 | 15.635 | 24.539 | 1.00 49.82 | C |
| ATOM | 161 | C | ASP | A | 26 | 21.908 | 15.027 | 25.873 | 1.00 49.82 | C |
| ATOM | 162 | O | ASP | A | 26 | 21.190 | 15.650 | 26.661 | 1.00 49.82 | O |
| ATOM | 163 | CB | ASP | A | 26 | 21.356 | 15.137 | 23.432 | 1.00 69.22 | C |
| ATOM | 164 | CG | ASP | A | 26 | 21.429 | 15.997 | 22.174 | 1.00 69.22 | C |
| ATOM | 165 | OD1 | ASP | A | 26 | 21.641 | 17.227 | 22.294 | 1.00 69.22 | O |
| ATOM | 166 | OD2 | ASP | A | 26 | 21.259 | 15.444 | 21.065 | 1.00 69.22 | O |

Fig. 1J

```
ATOM    167  N    ARG A  27      22.403  13.819  26.129  1.00 55.02           N
ATOM    168  CA   ARG A  27      22.117  13.123  27.381  1.00 55.02           C
ATOM    169  C    ARG A  27      22.570  13.967  28.562  1.00 55.02           C
ATOM    170  O    ARG A  27      21.902  14.023  29.590  1.00 55.02           O
ATOM    171  CB   ARG A  27      22.823  11.765  27.426  1.00107.80           C
ATOM    172  CG   ARG A  27      22.687  11.072  28.770  1.00107.80           C
ATOM    173  CD   ARG A  27      23.372   9.722  28.799  1.00107.80           C
ATOM    174  NE   ARG A  27      23.381   9.171  30.151  1.00107.80           N
ATOM    175  CZ   ARG A  27      23.926   8.005  30.485  1.00107.80           C
ATOM    176  NH1  ARG A  27      24.513   7.256  29.559  1.00107.80           N
ATOM    177  NH2  ARG A  27      23.884   7.585  31.746  1.00107.80           N
ATOM    178  N    LEU A  28      23.715  14.619  28.410  1.00 41.40           N
ATOM    179  CA   LEU A  28      24.232  15.464  29.469  1.00 41.40           C
ATOM    180  C    LEU A  28      23.314  16.674  29.610  1.00 41.40           C
ATOM    181  O    LEU A  28      23.000  17.105  30.720  1.00 41.40           O
ATOM    182  CB   LEU A  28      25.662  15.913  29.142  1.00 54.85           C
ATOM    183  CG   LEU A  28      26.672  14.768  29.009  1.00 54.85           C
ATOM    184  CD1  LEU A  28      28.074  15.320  28.812  1.00 54.85           C
ATOM    185  CD2  LEU A  28      26.629  13.914  30.259  1.00 54.85           C
ATOM    186  N    LEU A  29      22.887  17.207  28.472  1.00 46.97           N
ATOM    187  CA   LEU A  29      22.001  18.359  28.432  1.00 46.97           C
ATOM    188  C    LEU A  29      20.738  18.053  29.245  1.00 46.97           C
ATOM    189  O    LEU A  29      20.399  18.793  30.172  1.00 46.97           O
ATOM    190  CB   LEU A  29      21.639  18.670  26.982  1.00 54.42           C
ATOM    191  CG   LEU A  29      20.751  19.884  26.737  1.00 54.42           C
ATOM    192  CD1  LEU A  29      21.413  21.122  27.319  1.00 54.42           C
ATOM    193  CD2  LEU A  29      20.510  20.042  25.250  1.00 54.42           C
ATOM    194  N    ASN A  30      20.043  16.965  28.903  1.00 36.87           N
ATOM    195  CA   ASN A  30      18.849  16.583  29.648  1.00 36.87           C
ATOM    196  C    ASN A  30      19.174  16.503  31.144  1.00 36.87           C
ATOM    197  O    ASN A  30      18.399  16.977  31.981  1.00 36.87           O
ATOM    198  CB   ASN A  30      18.302  15.220  29.189  1.00 52.27           C
ATOM    199  CG   ASN A  30      17.560  15.296  27.862  1.00 52.27           C
ATOM    200  OD1  ASN A  30      18.148  15.107  26.795  1.00 52.27           O
ATOM    201  ND2  ASN A  30      16.259  15.583  27.925  1.00 52.27           N
ATOM    202  N    GLU A  31      20.320  15.905  31.474  1.00 57.43           N
ATOM    203  CA   GLU A  31      20.733  15.760  32.874  1.00 57.43           C
ATOM    204  C    GLU A  31      20.946  17.092  33.588  1.00 57.43           C
ATOM    205  O    GLU A  31      20.661  17.214  34.776  1.00 57.43           O
ATOM    206  CB   GLU A  31      22.004  14.908  32.981  1.00 80.57           C
ATOM    207  CG   GLU A  31      21.742  13.406  32.919  1.00 80.57           C
ATOM    208  CD   GLU A  31      23.005  12.566  33.095  1.00 80.57           C
ATOM    209  OE1  GLU A  31      23.742  12.795  34.081  1.00 80.57           O
ATOM    210  OE2  GLU A  31      23.253  11.672  32.253  1.00 80.57           O
ATOM    211  N    TYR A  32      21.436  18.090  32.863  1.00 46.41           N
ATOM    212  CA   TYR A  32      21.676  19.408  33.446  1.00 46.41           C
ATOM    213  C    TYR A  32      20.393  20.212  33.627  1.00 46.41           C
ATOM    214  O    TYR A  32      20.319  21.063  34.511  1.00 46.41           O
```

Fig. 1K

| ATOM | 215 | CB  | TYR A | 32 | 22.622 | 20.219 | 32.565 | 1.00 | 77.48 | C |
| ATOM | 216 | CG  | TYR A | 32 | 23.960 | 19.576 | 32.316 | 1.00 | 77.48 | C |
| ATOM | 217 | CD1 | TYR A | 32 | 24.590 | 19.716 | 31.080 | 1.00 | 77.48 | C |
| ATOM | 218 | CD2 | TYR A | 32 | 24.610 | 18.853 | 33.315 | 1.00 | 77.48 | C |
| ATOM | 219 | CE1 | TYR A | 32 | 25.834 | 19.154 | 30.838 | 1.00 | 77.48 | C |
| ATOM | 220 | CE2 | TYR A | 32 | 25.859 | 18.285 | 33.089 | 1.00 | 77.48 | C |
| ATOM | 221 | CZ  | TYR A | 32 | 26.465 | 18.441 | 31.845 | 1.00 | 77.48 | C |
| ATOM | 222 | OH  | TYR A | 32 | 27.703 | 17.894 | 31.601 | 1.00 | 77.48 | O |
| ATOM | 223 | N   | LEU A | 33 | 19.393 | 19.955 | 32.784 | 1.00 | 41.53 | N |
| ATOM | 224 | CA  | LEU A | 33 | 18.120 | 20.684 | 32.858 | 1.00 | 41.53 | C |
| ATOM | 225 | C   | LEU A | 33 | 17.058 | 19.961 | 33.689 | 1.00 | 41.53 | C |
| ATOM | 226 | O   | LEU A | 33 | 15.980 | 20.502 | 33.943 | 1.00 | 41.53 | O |
| ATOM | 227 | CB  | LEU A | 33 | 17.566 | 20.931 | 31.450 | 1.00 | 35.85 | C |
| ATOM | 228 | CG  | LEU A | 33 | 18.493 | 21.636 | 30.462 | 1.00 | 35.85 | C |
| ATOM | 229 | CD1 | LEU A | 33 | 17.719 | 21.961 | 29.198 | 1.00 | 35.85 | C |
| ATOM | 230 | CD2 | LEU A | 33 | 19.038 | 22.907 | 31.080 | 1.00 | 35.85 | C |
| ATOM | 231 | N   | SER A | 34 | 17.385 | 18.740 | 34.102 | 1.00 | 49.29 | N |
| ATOM | 232 | CA  | SER A | 34 | 16.500 | 17.900 | 34.892 | 1.00 | 49.29 | C |
| ATOM | 233 | C   | SER A | 34 | 15.924 | 18.583 | 36.131 | 1.00 | 49.29 | C |
| ATOM | 234 | O   | SER A | 34 | 14.755 | 18.387 | 36.458 | 1.00 | 49.29 | O |
| ATOM | 235 | CB  | SER A | 34 | 17.240 | 16.623 | 35.304 | 1.00 | 54.11 | C |
| ATOM | 236 | OG  | SER A | 34 | 16.391 | 15.733 | 36.002 | 1.00 | 54.11 | O |
| ATOM | 237 | N   | PRO A | 35 | 16.733 | 19.374 | 36.853 | 1.00 | 36.68 | N |
| ATOM | 238 | CA  | PRO A | 35 | 16.216 | 20.049 | 38.054 | 1.00 | 36.68 | C |
| ATOM | 239 | C   | PRO A | 35 | 15.460 | 21.353 | 37.760 | 1.00 | 36.68 | C |
| ATOM | 240 | O   | PRO A | 35 | 14.772 | 21.893 | 38.638 | 1.00 | 36.68 | O |
| ATOM | 241 | CB  | PRO A | 35 | 17.481 | 20.331 | 38.883 | 1.00 | 44.90 | C |
| ATOM | 242 | CG  | PRO A | 35 | 18.530 | 19.429 | 38.291 | 1.00 | 44.90 | C |
| ATOM | 243 | CD  | PRO A | 35 | 18.204 | 19.432 | 36.823 | 1.00 | 44.90 | C |
| ATOM | 244 | N   | LEU A | 36 | 15.618 | 21.868 | 36.543 | 1.00 | 37.76 | N |
| ATOM | 245 | CA  | LEU A | 36 | 14.978 | 23.120 | 36.141 | 1.00 | 37.76 | C |
| ATOM | 246 | C   | LEU A | 36 | 13.610 | 22.879 | 35.491 | 1.00 | 37.76 | C |
| ATOM | 247 | O   | LEU A | 36 | 13.374 | 21.840 | 34.862 | 1.00 | 37.76 | O |
| ATOM | 248 | CB  | LEU A | 36 | 15.889 | 23.882 | 35.170 | 1.00 | 41.54 | C |
| ATOM | 249 | CG  | LEU A | 36 | 17.362 | 24.080 | 35.557 | 1.00 | 41.54 | C |
| ATOM | 250 | CD1 | LEU A | 36 | 18.086 | 24.902 | 34.476 | 1.00 | 41.54 | C |
| ATOM | 251 | CD2 | LEU A | 36 | 17.451 | 24.788 | 36.901 | 1.00 | 41.54 | C |
| ATOM | 252 | N   | ASP A | 37 | 12.721 | 23.857 | 35.630 | 1.00 | 31.59 | N |
| ATOM | 253 | CA  | ASP A | 37 | 11.368 | 23.757 | 35.090 | 1.00 | 31.59 | C |
| ATOM | 254 | C   | ASP A | 37 | 11.369 | 24.064 | 33.583 | 1.00 | 31.59 | C |
| ATOM | 255 | O   | ASP A | 37 | 10.747 | 25.019 | 33.109 | 1.00 | 31.59 | O |
| ATOM | 256 | CB  | ASP A | 37 | 10.469 | 24.730 | 35.856 | 1.00 | 32.69 | C |
| ATOM | 257 | CG  | ASP A | 37 | 8.990  | 24.479 | 35.628 | 1.00 | 32.69 | C |
| ATOM | 258 | OD1 | ASP A | 37 | 8.186  | 25.361 | 35.988 | 1.00 | 32.69 | O |
| ATOM | 259 | OD2 | ASP A | 37 | 8.619  | 23.420 | 35.101 | 1.00 | 32.69 | O |
| ATOM | 260 | N   | ILE A | 38 | 12.089 | 23.245 | 32.832 | 1.00 | 37.25 | N |
| ATOM | 261 | CA  | ILE A | 38 | 12.169 | 23.417 | 31.392 | 1.00 | 37.25 | C |
| ATOM | 262 | C   | ILE A | 38 | 12.734 | 22.157 | 30.781 | 1.00 | 37.25 | C |

Fig. 1L

```
ATOM    263  O    ILE A  38      13.564  21.488  31.402  1.00 37.25           O
ATOM    264  CB   ILE A  38      13.100  24.574  31.018  1.00 29.59           C
ATOM    265  CG1  ILE A  38      13.047  24.798  29.502  1.00 29.59           C
ATOM    266  CG2  ILE A  38      14.536  24.258  31.500  1.00 29.59           C
ATOM    267  CD1  ILE A  38      13.782  26.019  29.034  1.00 29.59           C
ATOM    268  N    THR A  39      12.308  21.844  29.559  1.00 37.34           N
ATOM    269  CA   THR A  39      12.798  20.656  28.875  1.00 37.34           C
ATOM    270  C    THR A  39      13.852  20.986  27.800  1.00 37.34           C
ATOM    271  O    THR A  39      13.901  22.097  27.270  1.00 37.34           O
ATOM    272  CB   THR A  39      11.648  19.897  28.216  1.00 28.45           C
ATOM    273  OG1  THR A  39      11.152  20.664  27.114  1.00 28.45           O
ATOM    274  CG2  THR A  39      10.502  19.671  29.227  1.00 28.45           C
ATOM    275  N    ALA A  40      14.693  20.001  27.489  1.00 40.45           N
ATOM    276  CA   ALA A  40      15.741  20.147  26.487  1.00 40.45           C
ATOM    277  C    ALA A  40      15.144  20.691  25.198  1.00 40.45           C
ATOM    278  O    ALA A  40      15.680  21.623  24.601  1.00 40.45           O
ATOM    279  CB   ALA A  40      16.406  18.789  26.227  1.00 37.38           C
ATOM    280  N    ALA A  41      14.024  20.112  24.774  1.00 36.96           N
ATOM    281  CA   ALA A  41      13.368  20.562  23.555  1.00 36.96           C
ATOM    282  C    ALA A  41      12.948  22.027  23.647  1.00 36.96           C
ATOM    283  O    ALA A  41      13.127  22.777  22.686  1.00 36.96           O
ATOM    284  CB   ALA A  41      12.164  19.677  23.237  1.00 24.45           C
ATOM    285  N    GLN A  42      12.386  22.434  24.790  1.00 35.44           N
ATOM    286  CA   GLN A  42      11.981  23.836  24.971  1.00 35.44           C
ATOM    287  C    GLN A  42      13.219  24.723  24.874  1.00 35.44           C
ATOM    288  O    GLN A  42      13.185  25.786  24.247  1.00 35.44           O
ATOM    289  CB   GLN A  42      11.303  24.050  26.334  1.00 33.78           C
ATOM    290  CG   GLN A  42       9.873  23.514  26.443  1.00 33.78           C
ATOM    291  CD   GLN A  42       9.324  23.554  27.870  1.00 33.78           C
ATOM    292  OE1  GLN A  42       9.838  24.264  28.735  1.00 33.78           O
ATOM    293  NE2  GLN A  42       8.270  22.801  28.111  1.00 33.78           N
ATOM    294  N    PHE A  43      14.316  24.280  25.484  1.00 35.55           N
ATOM    295  CA   PHE A  43      15.562  25.053  25.453  1.00 35.55           C
ATOM    296  C    PHE A  43      16.062  25.232  24.013  1.00 35.55           C
ATOM    297  O    PHE A  43      16.431  26.337  23.606  1.00 35.55           O
ATOM    298  CB   PHE A  43      16.633  24.365  26.299  1.00 45.48           C
ATOM    299  CG   PHE A  43      17.937  25.100  26.337  1.00 45.48           C
ATOM    300  CD1  PHE A  43      17.973  26.470  26.599  1.00 45.48           C
ATOM    301  CD2  PHE A  43      19.134  24.426  26.127  1.00 45.48           C
ATOM    302  CE1  PHE A  43      19.180  27.163  26.652  1.00 45.48           C
ATOM    303  CE2  PHE A  43      20.351  25.110  26.178  1.00 45.48           C
ATOM    304  CZ   PHE A  43      20.372  26.486  26.441  1.00 45.48           C
ATOM    305  N    LYS A  44      16.049  24.149  23.241  1.00 38.60           N
ATOM    306  CA   LYS A  44      16.479  24.191  21.844  1.00 38.60           C
ATOM    307  C    LYS A  44      15.600  25.174  21.054  1.00 38.60           C
ATOM    308  O    LYS A  44      16.107  26.007  20.297  1.00 38.60           O
ATOM    309  CB   LYS A  44      16.379  22.794  21.222  1.00 82.69           C
ATOM    310  CG   LYS A  44      17.267  21.744  21.877  1.00 82.69           C
```

Fig. 1M

| | | | | | | | | | | |
|---|---|---|---|---|---|---|---|---|---|---|
| ATOM | 311 | CD | LYS | A | 44 | 16.994 | 20.355 | 21.302 | 1.00 82.69 | C |
| ATOM | 312 | CE | LYS | A | 44 | 17.924 | 19.296 | 21.891 | 1.00 82.69 | C |
| ATOM | 313 | NZ | LYS | A | 44 | 19.348 | 19.510 | 21.502 | 1.00 82.69 | N |
| ATOM | 314 | N | VAL | A | 45 | 14.284 | 25.078 | 21.221 | 1.00 34.06 | N |
| ATOM | 315 | CA | VAL | A | 45 | 13.396 | 25.997 | 20.517 | 1.00 34.06 | C |
| ATOM | 316 | C | VAL | A | 45 | 13.710 | 27.448 | 20.877 | 1.00 34.06 | C |
| ATOM | 317 | O | VAL | A | 45 | 13.619 | 28.324 | 20.019 | 1.00 34.06 | O |
| ATOM | 318 | CB | VAL | A | 45 | 11.913 | 25.708 | 20.829 | 1.00 30.26 | C |
| ATOM | 319 | CG1 | VAL | A | 45 | 11.034 | 26.859 | 20.357 | 1.00 30.26 | C |
| ATOM | 320 | CG2 | VAL | A | 45 | 11.490 | 24.411 | 20.137 | 1.00 30.26 | C |
| ATOM | 321 | N | LEU | A | 46 | 14.085 | 27.710 | 22.129 | 1.00 42.08 | N |
| ATOM | 322 | CA | LEU | A | 46 | 14.408 | 29.086 | 22.530 | 1.00 42.08 | C |
| ATOM | 323 | C | LEU | A | 46 | 15.721 | 29.573 | 21.899 | 1.00 42.08 | C |
| ATOM | 324 | O | LEU | A | 46 | 15.816 | 30.704 | 21.423 | 1.00 42.08 | O |
| ATOM | 325 | CB | LEU | A | 46 | 14.529 | 29.228 | 24.059 | 1.00 33.35 | C |
| ATOM | 326 | CG | LEU | A | 46 | 13.316 | 29.155 | 24.989 | 1.00 33.35 | C |
| ATOM | 327 | CD1 | LEU | A | 46 | 13.772 | 29.485 | 26.416 | 1.00 33.35 | C |
| ATOM | 328 | CD2 | LEU | A | 46 | 12.243 | 30.120 | 24.554 | 1.00 33.35 | C |
| ATOM | 329 | N | CYS | A | 47 | 16.734 | 28.720 | 21.903 | 1.00 47.51 | N |
| ATOM | 330 | CA | CYS | A | 47 | 18.015 | 29.103 | 21.334 | 1.00 47.51 | C |
| ATOM | 331 | C | CYS | A | 47 | 17.874 | 29.371 | 19.841 | 1.00 47.51 | C |
| ATOM | 332 | O | CYS | A | 47 | 18.515 | 30.275 | 19.303 | 1.00 47.51 | O |
| ATOM | 333 | CB | CYS | A | 47 | 19.045 | 28.004 | 21.577 | 1.00 47.01 | C |
| ATOM | 334 | SG | CYS | A | 47 | 19.407 | 27.720 | 23.319 | 1.00 47.01 | S |
| ATOM | 335 | N | SER | A | 48 | 17.029 | 28.590 | 19.176 | 1.00 42.18 | N |
| ATOM | 336 | CA | SER | A | 48 | 16.814 | 28.747 | 17.737 | 1.00 42.18 | C |
| ATOM | 337 | C | SER | A | 48 | 16.060 | 30.018 | 17.367 | 1.00 42.18 | C |
| ATOM | 338 | O | SER | A | 48 | 16.352 | 30.638 | 16.356 | 1.00 42.18 | O |
| ATOM | 339 | CB | SER | A | 48 | 16.047 | 27.547 | 17.180 | 1.00 30.64 | C |
| ATOM | 340 | OG | SER | A | 48 | 16.769 | 26.345 | 17.382 | 1.00 30.64 | O |
| ATOM | 341 | N | ILE | A | 49 | 15.068 | 30.390 | 18.171 | 1.00 41.78 | N |
| ATOM | 342 | CA | ILE | A | 49 | 14.287 | 31.585 | 17.893 | 1.00 41.78 | C |
| ATOM | 343 | C | ILE | A | 49 | 15.181 | 32.789 | 18.171 | 1.00 41.78 | C |
| ATOM | 344 | O | ILE | A | 49 | 15.177 | 33.767 | 17.427 | 1.00 41.78 | O |
| ATOM | 345 | CB | ILE | A | 49 | 13.039 | 31.650 | 18.796 | 1.00 41.13 | C |
| ATOM | 346 | CG1 | ILE | A | 49 | 12.068 | 30.527 | 18.418 | 1.00 41.13 | C |
| ATOM | 347 | CG2 | ILE | A | 49 | 12.363 | 33.009 | 18.671 | 1.00 41.13 | C |
| ATOM | 348 | CD1 | ILE | A | 49 | 10.746 | 30.559 | 19.184 | 1.00 41.13 | C |
| ATOM | 349 | N | ARG | A | 50 | 15.948 | 32.692 | 19.253 | 1.00 49.26 | N |
| ATOM | 350 | CA | ARG | A | 50 | 16.858 | 33.747 | 19.644 | 1.00 49.26 | C |
| ATOM | 351 | C | ARG | A | 50 | 17.766 | 34.163 | 18.479 | 1.00 49.26 | C |
| ATOM | 352 | O | ARG | A | 50 | 17.680 | 35.299 | 17.978 | 1.00 49.26 | O |
| ATOM | 353 | CB | ARG | A | 50 | 17.712 | 33.279 | 20.827 | 1.00 66.71 | C |
| ATOM | 354 | CG | ARG | A | 50 | 18.819 | 34.249 | 21.219 | 1.00 66.71 | C |
| ATOM | 355 | CD | ARG | A | 50 | 19.567 | 33.783 | 22.449 | 1.00 66.71 | C |
| ATOM | 356 | NE | ARG | A | 50 | 20.818 | 34.514 | 22.581 | 1.00 66.71 | N |
| ATOM | 357 | CZ | ARG | A | 50 | 21.761 | 34.242 | 23.476 | 1.00 66.71 | C |
| ATOM | 358 | NH1 | ARG | A | 50 | 21.606 | 33.248 | 24.344 | 1.00 66.71 | N |

Fig. 1N

| | | | | | | | | | | |
|---|---|---|---|---|---|---|---|---|---|---|
| ATOM | 359 | NH2 | ARG | A | 50 | 22.879 | 34.953 | 23.485 | 1.00 66.71 | N |
| ATOM | 360 | N | CYS | A | 51 | 18.626 | 33.232 | 18.062 | 1.00 56.95 | N |
| ATOM | 361 | CA | CYS | A | 51 | 19.585 | 33.437 | 16.975 | 1.00 56.95 | C |
| ATOM | 362 | C | CYS | A | 51 | 19.000 | 34.159 | 15.790 | 1.00 56.95 | C |
| ATOM | 363 | O | CYS | A | 51 | 19.623 | 35.058 | 15.216 | 1.00 56.95 | O |
| ATOM | 364 | CB | CYS | A | 51 | 20.128 | 32.096 | 16.499 | 1.00 55.83 | C |
| ATOM | 365 | SG | CYS | A | 51 | 21.019 | 31.209 | 17.754 | 1.00 55.83 | S |
| ATOM | 366 | N | ALA | A | 52 | 17.799 | 33.746 | 15.421 | 1.00 43.02 | N |
| ATOM | 367 | CA | ALA | A | 52 | 17.107 | 34.328 | 14.295 | 1.00 43.02 | C |
| ATOM | 368 | C | ALA | A | 52 | 16.401 | 35.650 | 14.628 | 1.00 43.02 | C |
| ATOM | 369 | O | ALA | A | 52 | 15.889 | 36.319 | 13.718 | 1.00 43.02 | O |
| ATOM | 370 | CB | ALA | A | 52 | 16.112 | 33.325 | 13.764 | 1.00 30.40 | C |
| ATOM | 371 | N | ALA | A | 53 | 16.373 | 36.025 | 15.914 | 1.00 45.66 | N |
| ATOM | 372 | CA | ALA | A | 53 | 15.711 | 37.257 | 16.362 | 1.00 45.66 | C |
| ATOM | 373 | C | ALA | A | 53 | 14.196 | 37.112 | 16.249 | 1.00 45.66 | C |
| ATOM | 374 | O | ALA | A | 53 | 13.465 | 37.222 | 17.239 | 1.00 45.66 | O |
| ATOM | 375 | CB | ALA | A | 53 | 16.166 | 38.446 | 15.526 | 1.00 34.46 | C |
| ATOM | 376 | N | CYS | A | 54 | 13.749 | 36.877 | 15.021 | 1.00 42.13 | N |
| ATOM | 377 | CA | CYS | A | 54 | 12.347 | 36.690 | 14.686 | 1.00 42.13 | C |
| ATOM | 378 | C | CYS | A | 54 | 12.290 | 35.612 | 13.605 | 1.00 42.13 | C |
| ATOM | 379 | O | CYS | A | 54 | 13.032 | 35.672 | 12.626 | 1.00 42.13 | O |
| ATOM | 380 | CB | CYS | A | 54 | 11.741 | 37.976 | 14.119 | 1.00 63.33 | C |
| ATOM | 381 | SG | CYS | A | 54 | 11.425 | 39.280 | 15.311 | 1.00 63.33 | S |
| ATOM | 382 | N | ILE | A | 55 | 11.407 | 34.636 | 13.765 | 1.00 45.27 | N |
| ATOM | 383 | CA | ILE | A | 55 | 11.300 | 33.580 | 12.771 | 1.00 45.27 | C |
| ATOM | 384 | C | ILE | A | 55 | 9.881 | 33.051 | 12.687 | 1.00 45.27 | C |
| ATOM | 385 | O | ILE | A | 55 | 9.140 | 33.064 | 13.681 | 1.00 45.27 | O |
| ATOM | 386 | CB | ILE | A | 55 | 12.243 | 32.408 | 13.102 | 1.00 41.76 | C |
| ATOM | 387 | CG1 | ILE | A | 55 | 12.130 | 31.329 | 12.018 | 1.00 41.76 | C |
| ATOM | 388 | CG2 | ILE | A | 55 | 11.902 | 31.846 | 14.481 | 1.00 41.76 | C |
| ATOM | 389 | CD1 | ILE | A | 55 | 13.119 | 30.197 | 12.173 | 1.00 41.76 | C |
| ATOM | 390 | N | THR | A | 56 | 9.500 | 32.596 | 11.500 | 1.00 37.37 | N |
| ATOM | 391 | CA | THR | A | 56 | 8.161 | 32.049 | 11.302 | 1.00 37.37 | C |
| ATOM | 392 | C | THR | A | 56 | 8.092 | 30.637 | 11.890 | 1.00 37.37 | C |
| ATOM | 393 | O | THR | A | 56 | 9.103 | 29.929 | 11.974 | 1.00 37.37 | O |
| ATOM | 394 | CB | THR | A | 56 | 7.799 | 31.988 | 9.811 | 1.00 68.07 | C |
| ATOM | 395 | OG1 | THR | A | 56 | 8.687 | 31.086 | 9.137 | 1.00 68.07 | O |
| ATOM | 396 | CG2 | THR | A | 56 | 7.901 | 33.371 | 9.189 | 1.00 68.07 | C |
| ATOM | 397 | N | PRO | A | 57 | 6.904 | 30.212 | 12.327 | 1.00 37.02 | N |
| ATOM | 398 | CA | PRO | A | 57 | 6.837 | 28.864 | 12.887 | 1.00 37.02 | C |
| ATOM | 399 | C | PRO | A | 57 | 7.275 | 27.811 | 11.870 | 1.00 37.02 | C |
| ATOM | 400 | O | PRO | A | 57 | 8.020 | 26.875 | 12.208 | 1.00 37.02 | O |
| ATOM | 401 | CB | PRO | A | 57 | 5.379 | 28.741 | 13.290 | 1.00 39.03 | C |
| ATOM | 402 | CG | PRO | A | 57 | 5.043 | 30.143 | 13.708 | 1.00 39.03 | C |
| ATOM | 403 | CD | PRO | A | 57 | 5.662 | 30.958 | 12.596 | 1.00 39.03 | C |
| ATOM | 404 | N | VAL | A | 58 | 6.847 | 27.973 | 10.619 | 1.00 50.69 | N |
| ATOM | 405 | CA | VAL | A | 58 | 7.218 | 27.019 | 9.579 | 1.00 50.69 | C |
| ATOM | 406 | C | VAL | A | 58 | 8.726 | 26.999 | 9.335 | 1.00 50.69 | C |

Fig. 1O

```
ATOM    407  O   VAL A  58       9.318  25.929   9.193  1.00 50.69           O
ATOM    408  CB  VAL A  58       6.503  27.324   8.267  1.00 56.43           C
ATOM    409  CG1 VAL A  58       6.909  26.304   7.223  1.00 56.43           C
ATOM    410  CG2 VAL A  58       4.990  27.308   8.484  1.00 56.43           C
ATOM    411  N   GLU A  59       9.349  28.175   9.280  1.00 44.74           N
ATOM    412  CA  GLU A  59      10.796  28.248   9.087  1.00 44.74           C
ATOM    413  C   GLU A  59      11.443  27.568  10.299  1.00 44.74           C
ATOM    414  O   GLU A  59      12.412  26.816  10.176  1.00 44.74           O
ATOM    415  CB  GLU A  59      11.251  29.707   9.008  1.00 89.17           C
ATOM    416  CG  GLU A  59      12.746  29.900   8.766  1.00 89.17           C
ATOM    417  CD  GLU A  59      13.151  29.678   7.319  1.00 89.17           C
ATOM    418  OE1 GLU A  59      12.953  28.557   6.803  1.00 89.17           O
ATOM    419  OE2 GLU A  59      13.671  30.630   6.696  1.00 89.17           O
ATOM    420  N   LEU A  60      10.892  27.837  11.478  1.00 41.66           N
ATOM    421  CA  LEU A  60      11.405  27.241  12.702  1.00 41.66           C
ATOM    422  C   LEU A  60      11.215  25.721  12.625  1.00 41.66           C
ATOM    423  O   LEU A  60      12.053  24.940  13.088  1.00 41.66           O
ATOM    424  CB  LEU A  60      10.651  27.817  13.907  1.00 44.47           C
ATOM    425  CG  LEU A  60      11.044  27.322  15.300  1.00 44.47           C
ATOM    426  CD1 LEU A  60      12.533  27.525  15.539  1.00 44.47           C
ATOM    427  CD2 LEU A  60      10.219  28.080  16.333  1.00 44.47           C
ATOM    428  N   LYS A  61      10.101  25.314  12.028  1.00 54.28           N
ATOM    429  CA  LYS A  61       9.778  23.902  11.863  1.00 54.28           C
ATOM    430  C   LYS A  61      10.870  23.222  11.028  1.00 54.28           C
ATOM    431  O   LYS A  61      11.294  22.102  11.319  1.00 54.28           O
ATOM    432  CB  LYS A  61       8.413  23.769  11.165  1.00 53.54           C
ATOM    433  CG  LYS A  61       7.943  22.338  10.945  1.00 53.54           C
ATOM    434  CD  LYS A  61       7.356  22.167   9.548  1.00 53.54           C
ATOM    435  CE  LYS A  61       7.057  20.693   9.231  1.00 53.54           C
ATOM    436  NZ  LYS A  61       8.259  19.782   9.328  1.00 53.54           N
ATOM    437  N   LYS A  62      11.324  23.919   9.992  1.00 55.89           N
ATOM    438  CA  LYS A  62      12.359  23.401   9.103  1.00 55.89           C
ATOM    439  C   LYS A  62      13.716  23.356   9.784  1.00 55.89           C
ATOM    440  O   LYS A  62      14.466  22.396   9.624  1.00 55.89           O
ATOM    441  CB  LYS A  62      12.473  24.267   7.843  1.00 90.82           C
ATOM    442  CG  LYS A  62      11.240  24.274   6.954  1.00 90.82           C
ATOM    443  CD  LYS A  62      11.501  25.040   5.654  1.00 90.82           C
ATOM    444  CE  LYS A  62      12.551  24.348   4.783  1.00 90.82           C
ATOM    445  NZ  LYS A  62      12.107  22.996   4.325  1.00 90.82           N
ATOM    446  N   VAL A  63      14.035  24.403  10.539  1.00 51.21           N
ATOM    447  CA  VAL A  63      15.317  24.473  11.228  1.00 51.21           C
ATOM    448  C   VAL A  63      15.476  23.407  12.302  1.00 51.21           C
ATOM    449  O   VAL A  63      16.573  22.915  12.532  1.00 51.21           O
ATOM    450  CB  VAL A  63      15.508  25.834  11.897  1.00 72.29           C
ATOM    451  CG1 VAL A  63      16.841  25.867  12.624  1.00 72.29           C
ATOM    452  CG2 VAL A  63      15.427  26.933  10.854  1.00 72.29           C
ATOM    453  N   LEU A  64      14.379  23.063  12.967  1.00 55.82           N
ATOM    454  CA  LEU A  64      14.419  22.074  14.034  1.00 55.82           C
```

Fig. 1P

| ATOM | 455 | C   | LEU | A | 64 | 14.203 | 20.642 | 13.548 | 1.00 | 55.82 | C |
| ATOM | 456 | O   | LEU | A | 64 | 14.568 | 19.695 | 14.249 | 1.00 | 55.82 | O |
| ATOM | 457 | CB  | LEU | A | 64 | 13.359 | 22.413 | 15.088 | 1.00 | 42.64 | C |
| ATOM | 458 | CG  | LEU | A | 64 | 13.549 | 23.683 | 15.926 | 1.00 | 42.64 | C |
| ATOM | 459 | CD1 | LEU | A | 64 | 12.256 | 23.980 | 16.678 | 1.00 | 42.64 | C |
| ATOM | 460 | CD2 | LEU | A | 64 | 14.727 | 23.505 | 16.898 | 1.00 | 42.64 | C |
| ATOM | 461 | N   | SER | A | 65 | 13.616 | 20.490 | 12.358 | 1.00 | 57.55 | N |
| ATOM | 462 | CA  | SER | A | 65 | 13.320 | 19.167 | 11.793 | 1.00 | 57.55 | C |
| ATOM | 463 | C   | SER | A | 65 | 12.399 | 18.480 | 12.783 | 1.00 | 57.55 | C |
| ATOM | 464 | O   | SER | A | 65 | 12.774 | 17.504 | 13.423 | 1.00 | 57.55 | O |
| ATOM | 465 | CB  | SER | A | 65 | 14.596 | 18.336 | 11.626 | 1.00 | 69.01 | C |
| ATOM | 466 | OG  | SER | A | 65 | 15.462 | 18.903 | 10.657 | 1.00 | 69.01 | O |
| ATOM | 467 | N   | VAL | A | 66 | 11.185 | 18.998 | 12.900 | 1.00 | 48.95 | N |
| ATOM | 468 | CA  | VAL | A | 66 | 10.221 | 18.464 | 13.850 | 1.00 | 48.95 | C |
| ATOM | 469 | C   | VAL | A | 66 | 8.820  | 18.454 | 13.262 | 1.00 | 48.95 | C |
| ATOM | 470 | O   | VAL | A | 66 | 8.541  | 19.120 | 12.254 | 1.00 | 48.95 | O |
| ATOM | 471 | CB  | VAL | A | 66 | 10.229 | 19.329 | 15.144 | 1.00 | 70.40 | C |
| ATOM | 472 | CG1 | VAL | A | 66 | 9.074  | 18.956 | 16.050 | 1.00 | 70.40 | C |
| ATOM | 473 | CG2 | VAL | A | 66 | 11.561 | 19.155 | 15.879 | 1.00 | 70.40 | C |
| ATOM | 474 | N   | ASP | A | 67 | 7.944  | 17.676 | 13.885 | 1.00 | 54.83 | N |
| ATOM | 475 | CA  | ASP | A | 67 | 6.558  | 17.592 | 13.455 | 1.00 | 54.83 | C |
| ATOM | 476 | C   | ASP | A | 67 | 5.940  | 18.961 | 13.731 | 1.00 | 54.83 | C |
| ATOM | 477 | O   | ASP | A | 67 | 6.140  | 19.539 | 14.807 | 1.00 | 54.83 | O |
| ATOM | 478 | CB  | ASP | A | 67 | 5.821  | 16.516 | 14.259 | 1.00 | 69.23 | C |
| ATOM | 479 | CG  | ASP | A | 67 | 4.334  | 16.480 | 13.963 | 1.00 | 69.23 | C |
| ATOM | 480 | OD1 | ASP | A | 67 | 3.572  | 15.961 | 14.803 | 1.00 | 69.23 | O |
| ATOM | 481 | OD2 | ASP | A | 67 | 3.922  | 16.962 | 12.891 | 1.00 | 69.23 | O |
| ATOM | 482 | N   | LEU | A | 68 | 5.187  | 19.475 | 12.767 | 1.00 | 57.37 | N |
| ATOM | 483 | CA  | LEU | A | 68 | 4.567  | 20.776 | 12.933 | 1.00 | 57.37 | C |
| ATOM | 484 | C   | LEU | A | 68 | 3.620  | 20.750 | 14.123 | 1.00 | 57.37 | C |
| ATOM | 485 | O   | LEU | A | 68 | 3.573  | 21.694 | 14.913 | 1.00 | 57.37 | O |
| ATOM | 486 | CB  | LEU | A | 68 | 3.799  | 21.175 | 11.668 | 1.00 | 70.92 | C |
| ATOM | 487 | CG  | LEU | A | 68 | 3.297  | 22.624 | 11.655 | 1.00 | 70.92 | C |
| ATOM | 488 | CD1 | LEU | A | 68 | 4.489  | 23.553 | 11.713 | 1.00 | 70.92 | C |
| ATOM | 489 | CD2 | LEU | A | 68 | 2.473  | 22.900 | 10.410 | 1.00 | 70.92 | C |
| ATOM | 490 | N   | GLY | A | 69 | 2.871  | 19.661 | 14.249 | 1.00 | 42.69 | N |
| ATOM | 491 | CA  | GLY | A | 69 | 1.921  | 19.541 | 15.341 | 1.00 | 42.69 | C |
| ATOM | 492 | C   | GLY | A | 69 | 2.550  | 19.715 | 16.711 | 1.00 | 42.69 | C |
| ATOM | 493 | O   | GLY | A | 69 | 2.001  | 20.399 | 17.577 | 1.00 | 42.69 | O |
| ATOM | 494 | N   | ALA | A | 70 | 3.714  | 19.107 | 16.907 | 1.00 | 34.08 | N |
| ATOM | 495 | CA  | ALA | A | 70 | 4.401  | 19.180 | 18.192 | 1.00 | 34.08 | C |
| ATOM | 496 | C   | ALA | A | 70 | 5.008  | 20.556 | 18.412 | 1.00 | 34.08 | C |
| ATOM | 497 | O   | ALA | A | 70 | 5.237  | 20.961 | 19.549 | 1.00 | 34.08 | O |
| ATOM | 498 | CB  | ALA | A | 70 | 5.484  | 18.120 | 18.259 | 1.00 | 29.39 | C |
| ATOM | 499 | N   | LEU | A | 71 | 5.265  | 21.272 | 17.320 | 1.00 | 36.90 | N |
| ATOM | 500 | CA  | LEU | A | 71 | 5.846  | 22.605 | 17.401 | 1.00 | 36.90 | C |
| ATOM | 501 | C   | LEU | A | 71 | 4.790  | 23.591 | 17.883 | 1.00 | 36.90 | C |
| ATOM | 502 | O   | LEU | A | 71 | 5.045  | 24.420 | 18.768 | 1.00 | 36.90 | O |

Fig. 1Q

```
ATOM  503  CB   LEU A  71    6.368  23.040  16.030  1.00 46.47       C
ATOM  504  CG   LEU A  71    7.126  24.370  16.062  1.00 46.47       C
ATOM  505  CD1  LEU A  71    8.395  24.172  16.864  1.00 46.47       C
ATOM  506  CD2  LEU A  71    7.444  24.845  14.654  1.00 46.47       C
ATOM  507  N    THR A  72    3.603  23.477  17.296  1.00 33.18       N
ATOM  508  CA   THR A  72    2.467  24.323  17.620  1.00 33.18       C
ATOM  509  C    THR A  72    2.140  24.230  19.093  1.00 33.18       C
ATOM  510  O    THR A  72    1.956  25.249  19.761  1.00 33.18       O
ATOM  511  CB   THR A  72    1.210  23.895  16.825  1.00 64.50       C
ATOM  512  OG1  THR A  72    1.554  23.697  15.448  1.00 64.50       O
ATOM  513  CG2  THR A  72    0.129  24.965  16.921  1.00 64.50       C
ATOM  514  N    ARG A  73    2.048  23.003  19.600  1.00 32.09       N
ATOM  515  CA   ARG A  73    1.749  22.803  21.016  1.00 32.09       C
ATOM  516  C    ARG A  73    2.917  23.358  21.808  1.00 32.09       C
ATOM  517  O    ARG A  73    2.734  23.989  22.834  1.00 32.09       O
ATOM  518  CB   ARG A  73    1.558  21.309  21.343  1.00 47.77       C
ATOM  519  CG   ARG A  73    0.393  20.651  20.620  1.00 47.77       C
ATOM  520  CD   ARG A  73   -0.084  19.386  21.337  1.00 47.77       C
ATOM  521  NE   ARG A  73    0.966  18.382  21.494  1.00 47.77       N
ATOM  522  CZ   ARG A  73    1.445  17.634  20.504  1.00 47.77       C
ATOM  523  NH1  ARG A  73    0.973  17.766  19.269  1.00 47.77       N
ATOM  524  NH2  ARG A  73    2.399  16.747  20.748  1.00 47.77       N
ATOM  525  N    MET A  74    4.122  23.114  21.312  1.00 37.17       N
ATOM  526  CA   MET A  74    5.341  23.599  21.954  1.00 37.17       C
ATOM  527  C    MET A  74    5.328  25.131  22.049  1.00 37.17       C
ATOM  528  O    MET A  74    5.598  25.709  23.109  1.00 37.17       O
ATOM  529  CB   MET A  74    6.566  23.155  21.144  1.00 41.38       C
ATOM  530  CG   MET A  74    7.852  23.892  21.493  1.00 41.38       C
ATOM  531  SD   MET A  74    8.444  23.481  23.126  1.00 41.38       S
ATOM  532  CE   MET A  74    9.524  22.058  22.712  1.00 41.38       C
ATOM  533  N    LEU A  75    5.021  25.787  20.934  1.00 30.84       N
ATOM  534  CA   LEU A  75    5.001  27.240  20.930  1.00 30.84       C
ATOM  535  C    LEU A  75    3.944  27.762  21.910  1.00 30.84       C
ATOM  536  O    LEU A  75    4.182  28.744  22.628  1.00 30.84       O
ATOM  537  CB   LEU A  75    4.770  27.755  19.506  1.00 25.28       C
ATOM  538  CG   LEU A  75    5.960  27.583  18.535  1.00 25.28       C
ATOM  539  CD1  LEU A  75    5.565  28.044  17.136  1.00 25.28       C
ATOM  540  CD2  LEU A  75    7.150  28.427  19.001  1.00 25.28       C
ATOM  541  N    ASP A  76    2.795  27.084  21.971  1.00 31.28       N
ATOM  542  CA   ASP A  76    1.734  27.500  22.888  1.00 31.28       C
ATOM  543  C    ASP A  76    2.203  27.312  24.323  1.00 31.28       C
ATOM  544  O    ASP A  76    1.954  28.161  25.167  1.00 31.28       O
ATOM  545  CB   ASP A  76    0.445  26.703  22.661  1.00 35.21       C
ATOM  546  CG   ASP A  76   -0.433  27.287  21.544  1.00 35.21       C
ATOM  547  OD1  ASP A  76   -0.126  28.381  21.008  1.00 35.21       O
ATOM  548  OD2  ASP A  76   -1.451  26.643  21.211  1.00 35.21       O
ATOM  549  N    ARG A  77    2.874  26.205  24.618  1.00 31.46       N
ATOM  550  CA   ARG A  77    3.355  26.008  25.980  1.00 31.46       C
```

Fig. 1R

| | | | | | | | | | |
|---|---|---|---|---|---|---|---|---|---|
| ATOM | 551 | C | ARG | A | 77 | 4.551 | 27.119 | 26.322 | 1.00 31.46 | C |
| ATOM | 552 | O | ARG | A | 77 | 4.332 | 27.665 | 27.422 | 1.00 31.46 | O |
| ATOM | 553 | CB | ARG | A | 77 | 4.031 | 24.640 | 26.134 | 1.00 37.99 | C |
| ATOM | 554 | CG | ARG | A | 77 | 4.678 | 24.387 | 27.497 | 1.00 37.99 | C |
| ATOM | 555 | CD | ARG | A | 77 | 3.701 | 24.641 | 28.652 | 1.00 37.99 | C |
| ATOM | 556 | NE | ARG | A | 77 | 2.503 | 23.796 | 28.598 | 1.00 37.99 | N |
| ATOM | 557 | CZ | ARG | A | 77 | 2.490 | 22.492 | 28.858 | 1.00 37.99 | C |
| ATOM | 558 | NH1 | ARG | A | 77 | 3.617 | 21.869 | 29.192 | 1.00 37.99 | N |
| ATOM | 559 | NH2 | ARG | A | 77 | 1.353 | 21.809 | 28.799 | 1.00 37.99 | N |
| ATOM | 560 | N | LEU | A | 78 | 5.221 | 27.462 | 25.380 | 1.00 29.78 | N |
| ATOM | 561 | CA | LEU | A | 78 | 6.216 | 28.507 | 25.645 | 1.00 29.78 | C |
| ATOM | 562 | C | LEU | A | 78 | 5.564 | 29.868 | 25.889 | 1.00 29.78 | C |
| ATOM | 563 | O | LEU | A | 78 | 6.054 | 30.661 | 26.695 | 1.00 29.78 | O |
| ATOM | 564 | CB | LEU | A | 78 | 7.228 | 28.574 | 24.494 | 1.00 25.32 | C |
| ATOM | 565 | CG | LEU | A | 78 | 8.171 | 27.356 | 24.470 | 1.00 25.32 | C |
| ATOM | 566 | CD1 | LEU | A | 78 | 9.043 | 27.324 | 23.235 | 1.00 25.32 | C |
| ATOM | 567 | CD2 | LEU | A | 78 | 9.009 | 27.399 | 25.725 | 1.00 25.32 | C |
| ATOM | 568 | N | VAL | A | 79 | 4.460 | 30.145 | 25.199 | 1.00 31.60 | N |
| ATOM | 569 | CA | VAL | A | 79 | 3.759 | 31.412 | 25.412 | 1.00 31.60 | C |
| ATOM | 570 | C | VAL | A | 79 | 3.161 | 31.379 | 26.815 | 1.00 31.60 | C |
| ATOM | 571 | O | VAL | A | 79 | 3.244 | 32.367 | 27.536 | 1.00 31.60 | O |
| ATOM | 572 | CB | VAL | A | 79 | 2.641 | 31.623 | 24.370 | 1.00 28.89 | C |
| ATOM | 573 | CG1 | VAL | A | 79 | 1.816 | 32.851 | 24.709 | 1.00 28.89 | C |
| ATOM | 574 | CG2 | VAL | A | 79 | 3.271 | 31.765 | 22.982 | 1.00 28.89 | C |
| ATOM | 575 | N | CYS | A | 80 | 2.588 | 30.235 | 27.214 | 1.00 35.75 | N |
| ATOM | 576 | CA | CYS | A | 80 | 2.011 | 30.091 | 28.560 | 1.00 35.75 | C |
| ATOM | 577 | C | CYS | A | 80 | 3.069 | 30.345 | 29.628 | 1.00 35.75 | C |
| ATOM | 578 | O | CYS | A | 80 | 2.763 | 30.825 | 30.722 | 1.00 35.75 | O |
| ATOM | 579 | CB | CYS | A | 80 | 1.448 | 28.686 | 28.787 | 1.00 46.08 | C |
| ATOM | 580 | SG | CYS | A | 80 | -0.183 | 28.381 | 28.120 | 1.00 46.08 | S |
| ATOM | 581 | N | LYS | A | 81 | 4.311 | 29.996 | 29.331 | 1.00 40.46 | N |
| ATOM | 582 | CA | LYS | A | 81 | 5.372 | 30.215 | 30.299 | 1.00 40.46 | C |
| ATOM | 583 | C | LYS | A | 81 | 5.877 | 31.658 | 30.213 | 1.00 40.46 | C |
| ATOM | 584 | O | LYS | A | 81 | 6.719 | 32.082 | 31.014 | 1.00 40.46 | O |
| ATOM | 585 | CB | LYS | A | 81 | 6.518 | 29.233 | 30.057 | 1.00 28.93 | C |
| ATOM | 586 | CG | LYS | A | 81 | 6.207 | 27.809 | 30.479 | 1.00 28.93 | C |
| ATOM | 587 | CD | LYS | A | 81 | 7.410 | 26.901 | 30.212 | 1.00 28.93 | C |
| ATOM | 588 | CE | LYS | A | 81 | 7.281 | 25.556 | 30.910 | 1.00 28.93 | C |
| ATOM | 589 | NZ | LYS | A | 81 | 8.603 | 24.910 | 31.080 | 1.00 28.93 | N |
| ATOM | 590 | N | GLY | A | 82 | 5.350 | 32.406 | 29.244 | 1.00 34.82 | N |
| ATOM | 591 | CA | GLY | A | 82 | 5.755 | 33.794 | 29.074 | 1.00 34.82 | C |
| ATOM | 592 | C | GLY | A | 82 | 7.146 | 33.950 | 28.468 | 1.00 34.82 | C |
| ATOM | 593 | O | GLY | A | 82 | 7.778 | 34.999 | 28.604 | 1.00 34.82 | O |
| ATOM | 594 | N | TRP | A | 83 | 7.632 | 32.914 | 27.786 | 1.00 32.56 | N |
| ATOM | 595 | CA | TRP | A | 83 | 8.956 | 32.985 | 27.198 | 1.00 32.56 | C |
| ATOM | 596 | C | TRP | A | 83 | 8.961 | 33.366 | 25.730 | 1.00 32.56 | C |
| ATOM | 597 | O | TRP | A | 83 | 9.981 | 33.799 | 25.209 | 1.00 32.56 | O |
| ATOM | 598 | CB | TRP | A | 83 | 9.683 | 31.649 | 27.365 | 1.00 37.53 | C |

Fig. 1S

| | | | | | | | | | |
|---|---|---|---|---|---|---|---|---|---|
| ATOM | 599 | CG | TRP | A | 83 | 9.919 | 31.242 | 28.782 | 1.00 37.53 | C |
| ATOM | 600 | CD1 | TRP | A | 83 | 9.854 | 32.040 | 29.884 | 1.00 37.53 | C |
| ATOM | 601 | CD2 | TRP | A | 83 | 10.243 | 29.929 | 29.253 | 1.00 37.53 | C |
| ATOM | 602 | NE1 | TRP | A | 83 | 10.111 | 31.307 | 31.018 | 1.00 37.53 | N |
| ATOM | 603 | CE2 | TRP | A | 83 | 10.353 | 30.006 | 30.660 | 1.00 37.53 | C |
| ATOM | 604 | CE3 | TRP | A | 83 | 10.448 | 28.696 | 28.625 | 1.00 37.53 | C |
| ATOM | 605 | CZ2 | TRP | A | 83 | 10.658 | 28.897 | 31.454 | 1.00 37.53 | C |
| ATOM | 606 | CZ3 | TRP | A | 83 | 10.755 | 27.584 | 29.415 | 1.00 37.53 | C |
| ATOM | 607 | CH2 | TRP | A | 83 | 10.856 | 27.695 | 30.817 | 1.00 37.53 | C |
| ATOM | 608 | N | VAL | A | 84 | 7.822 | 33.218 | 25.062 | 1.00 30.33 | N |
| ATOM | 609 | CA | VAL | A | 84 | 7.727 | 33.519 | 23.640 | 1.00 30.33 | C |
| ATOM | 610 | C | VAL | A | 84 | 6.473 | 34.323 | 23.329 | 1.00 30.33 | C |
| ATOM | 611 | O | VAL | A | 84 | 5.472 | 34.212 | 24.034 | 1.00 30.33 | O |
| ATOM | 612 | CB | VAL | A | 84 | 7.703 | 32.198 | 22.825 | 1.00 28.67 | C |
| ATOM | 613 | CG1 | VAL | A | 84 | 7.370 | 32.466 | 21.374 | 1.00 28.67 | C |
| ATOM | 614 | CG2 | VAL | A | 84 | 9.051 | 31.487 | 22.946 | 1.00 28.67 | C |
| ATOM | 615 | N | GLU | A | 85 | 6.532 | 35.145 | 22.287 | 1.00 32.27 | N |
| ATOM | 616 | CA | GLU | A | 85 | 5.373 | 35.931 | 21.891 | 1.00 32.27 | C |
| ATOM | 617 | C | GLU | A | 85 | 5.314 | 35.967 | 20.373 | 1.00 32.27 | C |
| ATOM | 618 | O | GLU | A | 85 | 6.344 | 35.837 | 19.694 | 1.00 32.27 | O |
| ATOM | 619 | CB | GLU | A | 85 | 5.428 | 37.355 | 22.470 | 1.00 48.71 | C |
| ATOM | 620 | CG | GLU | A | 85 | 6.386 | 38.324 | 21.809 | 1.00 48.71 | C |
| ATOM | 621 | CD | GLU | A | 85 | 6.466 | 39.642 | 22.578 | 1.00 48.71 | C |
| ATOM | 622 | OE1 | GLU | A | 85 | 6.858 | 39.604 | 23.753 | 1.00 48.71 | O |
| ATOM | 623 | OE2 | GLU | A | 85 | 6.134 | 40.719 | 22.031 | 1.00 48.71 | O |
| ATOM | 624 | N | ARG | A | 86 | 4.101 | 36.129 | 19.862 | 1.00 41.63 | N |
| ATOM | 625 | CA | ARG | A | 86 | 3.823 | 36.156 | 18.436 | 1.00 41.63 | C |
| ATOM | 626 | C | ARG | A | 86 | 3.509 | 37.557 | 17.913 | 1.00 41.63 | C |
| ATOM | 627 | O | ARG | A | 86 | 2.742 | 38.307 | 18.525 | 1.00 41.63 | O |
| ATOM | 628 | CB | ARG | A | 86 | 2.625 | 35.255 | 18.156 | 1.00 42.32 | C |
| ATOM | 629 | CG | ARG | A | 86 | 2.826 | 34.245 | 17.066 | 1.00 42.32 | C |
| ATOM | 630 | CD | ARG | A | 86 | 1.630 | 33.345 | 17.037 | 1.00 42.32 | C |
| ATOM | 631 | NE | ARG | A | 86 | 1.424 | 32.786 | 18.363 | 1.00 42.32 | N |
| ATOM | 632 | CZ | ARG | A | 86 | 1.572 | 31.503 | 18.679 | 1.00 42.32 | C |
| ATOM | 633 | NH1 | ARG | A | 86 | 1.923 | 30.627 | 17.753 | 1.00 42.32 | N |
| ATOM | 634 | NH2 | ARG | A | 86 | 1.377 | 31.105 | 19.932 | 1.00 42.32 | N |
| ATOM | 635 | N | LEU | A | 87 | 4.095 | 37.909 | 16.775 | 1.00 39.77 | N |
| ATOM | 636 | CA | LEU | A | 87 | 3.826 | 39.209 | 16.180 | 1.00 39.77 | C |
| ATOM | 637 | C | LEU | A | 87 | 3.519 | 39.000 | 14.703 | 1.00 39.77 | C |
| ATOM | 638 | O | LEU | A | 87 | 3.853 | 37.963 | 14.131 | 1.00 39.77 | O |
| ATOM | 639 | CB | LEU | A | 87 | 5.018 | 40.151 | 16.333 | 1.00 48.09 | C |
| ATOM | 640 | CG | LEU | A | 87 | 6.305 | 39.730 | 15.630 | 1.00 48.09 | C |
| ATOM | 641 | CD1 | LEU | A | 87 | 7.061 | 40.968 | 15.171 | 1.00 48.09 | C |
| ATOM | 642 | CD2 | LEU | A | 87 | 7.156 | 38.884 | 16.578 | 1.00 48.09 | C |
| ATOM | 643 | N | PRO | A | 88 | 2.860 | 39.983 | 14.070 | 1.00 54.80 | N |
| ATOM | 644 | CA | PRO | A | 88 | 2.522 | 39.864 | 12.649 | 1.00 54.80 | C |
| ATOM | 645 | C | PRO | A | 88 | 3.785 | 39.853 | 11.804 | 1.00 54.80 | C |
| ATOM | 646 | O | PRO | A | 88 | 4.753 | 40.548 | 12.119 | 1.00 54.80 | O |

Fig. 1T

| | | | | | | | | | | |
|---|---|---|---|---|---|---|---|---|---|---|
| ATOM | 647 | CB | PRO | A | 88 | 1.661 | 41.101 | 12.392 | 1.00 66.77 | C |
| ATOM | 648 | CG | PRO | A | 88 | 1.049 | 41.386 | 13.751 | 1.00 66.77 | C |
| ATOM | 649 | CD | PRO | A | 88 | 2.235 | 41.180 | 14.661 | 1.00 66.77 | C |
| ATOM | 650 | N | ASN | A | 89 | 3.785 | 39.046 | 10.748 | 1.00 61.50 | N |
| ATOM | 651 | CA | ASN | A | 89 | 4.938 | 38.963 | 9.860 | 1.00 61.50 | C |
| ATOM | 652 | C | ASN | A | 89 | 4.808 | 40.089 | 8.839 | 1.00 61.50 | C |
| ATOM | 653 | O | ASN | A | 89 | 3.838 | 40.145 | 8.089 | 1.00 61.50 | O |
| ATOM | 654 | CB | ASN | A | 89 | 4.973 | 37.609 | 9.139 | 1.00 63.20 | C |
| ATOM | 655 | CG | ASN | A | 89 | 6.230 | 37.427 | 8.298 | 1.00 63.20 | C |
| ATOM | 656 | OD1 | ASN | A | 89 | 6.643 | 38.335 | 7.585 | 1.00 63.20 | O |
| ATOM | 657 | ND2 | ASN | A | 89 | 6.837 | 36.249 | 8.372 | 1.00 63.20 | N |
| ATOM | 658 | N | PRO | A | 90 | 5.779 | 41.015 | 8.815 | 1.00 66.40 | N |
| ATOM | 659 | CA | PRO | A | 90 | 5.762 | 42.142 | 7.878 | 1.00 66.40 | C |
| ATOM | 660 | C | PRO | A | 90 | 5.812 | 41.709 | 6.415 | 1.00 66.40 | C |
| ATOM | 661 | O | PRO | A | 90 | 4.973 | 42.114 | 5.613 | 1.00 66.40 | O |
| ATOM | 662 | CB | PRO | A | 90 | 6.993 | 42.944 | 8.288 | 1.00 66.93 | C |
| ATOM | 663 | CG | PRO | A | 90 | 7.079 | 42.679 | 9.759 | 1.00 66.93 | C |
| ATOM | 664 | CD | PRO | A | 90 | 6.854 | 41.187 | 9.805 | 1.00 66.93 | C |
| ATOM | 665 | N | ASN | A | 91 | 6.794 | 40.881 | 6.074 | 1.00 79.71 | N |
| ATOM | 666 | CA | ASN | A | 91 | 6.944 | 40.391 | 4.705 | 1.00 79.71 | C |
| ATOM | 667 | C | ASN | A | 91 | 5.781 | 39.490 | 4.271 | 1.00 79.71 | C |
| ATOM | 668 | O | ASN | A | 91 | 5.840 | 38.856 | 3.216 | 1.00 79.71 | O |
| ATOM | 669 | CB | ASN | A | 91 | 8.266 | 39.628 | 4.556 | 1.00119.06 | C |
| ATOM | 670 | CG | ASN | A | 91 | 9.477 | 40.490 | 4.867 | 1.00119.06 | C |
| ATOM | 671 | OD1 | ASN | A | 91 | 9.685 | 41.537 | 4.251 | 1.00119.06 | O |
| ATOM | 672 | ND2 | ASN | A | 91 | 10.284 | 40.051 | 5.826 | 1.00119.06 | N |
| ATOM | 673 | N | ASP | A | 92 | 4.736 | 39.430 | 5.093 | 1.00 89.89 | N |
| ATOM | 674 | CA | ASP | A | 92 | 3.551 | 38.631 | 4.792 | 1.00 89.89 | C |
| ATOM | 675 | C | ASP | A | 92 | 2.332 | 39.408 | 5.282 | 1.00 89.89 | C |
| ATOM | 676 | O | ASP | A | 92 | 2.299 | 40.635 | 5.183 | 1.00 89.89 | O |
| ATOM | 677 | CB | ASP | A | 92 | 3.627 | 37.262 | 5.483 | 1.00 66.82 | C |
| ATOM | 678 | CG | ASP | A | 92 | 2.587 | 36.275 | 4.955 | 1.00 66.82 | C |
| ATOM | 679 | OD1 | ASP | A | 92 | 2.716 | 35.061 | 5.229 | 1.00 66.82 | O |
| ATOM | 680 | OD2 | ASP | A | 92 | 1.637 | 36.709 | 4.272 | 1.00 66.82 | O |
| ATOM | 681 | N | LYS | A | 93 | 1.339 | 38.700 | 5.813 | 1.00 72.63 | N |
| ATOM | 682 | CA | LYS | A | 93 | 0.124 | 39.337 | 6.317 | 1.00 72.63 | C |
| ATOM | 683 | C | LYS | A | 93 | -0.865 | 38.247 | 6.700 | 1.00 72.63 | C |
| ATOM | 684 | O | LYS | A | 93 | -1.854 | 38.496 | 7.387 | 1.00 72.63 | O |
| ATOM | 685 | CB | LYS | A | 93 | -0.486 | 40.247 | 5.244 | 1.00 83.15 | C |
| ATOM | 686 | CG | LYS | A | 93 | -1.673 | 41.088 | 5.699 | 1.00 83.15 | C |
| ATOM | 687 | CD | LYS | A | 93 | -1.307 | 42.071 | 6.811 | 1.00 83.15 | C |
| ATOM | 688 | CE | LYS | A | 93 | -1.321 | 41.416 | 8.191 | 1.00 83.15 | C |
| ATOM | 689 | NZ | LYS | A | 93 | -1.016 | 42.381 | 9.286 | 1.00 83.15 | N |
| ATOM | 690 | N | ARG | A | 94 | -0.581 | 37.034 | 6.240 | 1.00 58.78 | N |
| ATOM | 691 | CA | ARG | A | 94 | -1.414 | 35.878 | 6.527 | 1.00 58.78 | C |
| ATOM | 692 | C | ARG | A | 94 | -0.651 | 35.036 | 7.546 | 1.00 58.78 | C |
| ATOM | 693 | O | ARG | A | 94 | -1.072 | 33.943 | 7.913 | 1.00 58.78 | O |
| ATOM | 694 | CB | ARG | A | 94 | -1.639 | 35.066 | 5.246 | 1.00 92.71 | C |

Fig. 1U

| | | | | | | | | | |
|---|---|---|---|---|---|---|---|---|---|
| ATOM | 695 | CG | ARG | A | 94 | -2.651 | 33.937 | 5.385 | 1.00 92.71 | C |
| ATOM | 696 | CD | ARG | A | 94 | -4.081 | 34.467 | 5.370 | 1.00 92.71 | C |
| ATOM | 697 | NE | ARG | A | 94 | -4.493 | 34.880 | 4.032 | 1.00 92.71 | N |
| ATOM | 698 | CZ | ARG | A | 94 | -4.746 | 34.035 | 3.039 | 1.00 92.71 | C |
| ATOM | 699 | NH1 | ARG | A | 94 | -4.634 | 32.728 | 3.236 | 1.00 92.71 | N |
| ATOM | 700 | NH2 | ARG | A | 94 | -5.091 | 34.497 | 1.844 | 1.00 92.71 | N |
| ATOM | 701 | N | GLY | A | 95 | 0.479 | 35.562 | 8.005 | 1.00 44.29 | N |
| ATOM | 702 | CA | GLY | A | 95 | 1.294 | 34.827 | 8.954 | 1.00 44.29 | C |
| ATOM | 703 | C | GLY | A | 95 | 1.842 | 35.630 | 10.111 | 1.00 44.29 | C |
| ATOM | 704 | O | GLY | A | 95 | 1.608 | 36.836 | 10.228 | 1.00 44.29 | O |
| ATOM | 705 | N | VAL | A | 96 | 2.580 | 34.949 | 10.978 | 1.00 40.14 | N |
| ATOM | 706 | CA | VAL | A | 96 | 3.159 | 35.592 | 12.143 | 1.00 40.14 | C |
| ATOM | 707 | C | VAL | A | 96 | 4.587 | 35.156 | 12.346 | 1.00 40.14 | C |
| ATOM | 708 | O | VAL | A | 96 | 5.074 | 34.230 | 11.689 | 1.00 40.14 | O |
| ATOM | 709 | CB | VAL | A | 96 | 2.387 | 35.253 | 13.441 | 1.00 35.66 | C |
| ATOM | 710 | CG1 | VAL | A | 96 | 0.964 | 35.734 | 13.329 | 1.00 35.66 | C |
| ATOM | 711 | CG2 | VAL | A | 96 | 2.439 | 33.759 | 13.718 | 1.00 35.66 | C |
| ATOM | 712 | N | LEU | A | 97 | 5.256 | 35.838 | 13.263 | 1.00 30.82 | N |
| ATOM | 713 | CA | LEU | A | 97 | 6.631 | 35.530 | 13.591 | 1.00 30.82 | C |
| ATOM | 714 | C | LEU | A | 97 | 6.568 | 35.265 | 15.078 | 1.00 30.82 | C |
| ATOM | 715 | O | LEU | A | 97 | 5.615 | 35.665 | 15.752 | 1.00 30.82 | O |
| ATOM | 716 | CB | LEU | A | 97 | 7.560 | 36.736 | 13.335 | 1.00 43.64 | C |
| ATOM | 717 | CG | LEU | A | 97 | 7.811 | 37.285 | 11.917 | 1.00 43.64 | C |
| ATOM | 718 | CD1 | LEU | A | 97 | 8.354 | 38.693 | 12.030 | 1.00 43.64 | C |
| ATOM | 719 | CD2 | LEU | A | 97 | 8.795 | 36.407 | 11.137 | 1.00 43.64 | C |
| ATOM | 720 | N | VAL | A | 98 | 7.570 | 34.577 | 15.590 | 1.00 40.02 | N |
| ATOM | 721 | CA | VAL | A | 98 | 7.614 | 34.333 | 17.007 | 1.00 40.02 | C |
| ATOM | 722 | C | VAL | A | 98 | 8.980 | 34.805 | 17.425 | 1.00 40.02 | C |
| ATOM | 723 | O | VAL | A | 98 | 9.962 | 34.607 | 16.704 | 1.00 40.02 | O |
| ATOM | 724 | CB | VAL | A | 98 | 7.442 | 32.836 | 17.356 | 1.00 33.09 | C |
| ATOM | 725 | CG1 | VAL | A | 98 | 6.027 | 32.355 | 16.945 | 1.00 33.09 | C |
| ATOM | 726 | CG2 | VAL | A | 98 | 8.519 | 32.015 | 16.669 | 1.00 33.09 | C |
| ATOM | 727 | N | LYS | A | 99 | 9.035 | 35.472 | 18.568 | 1.00 35.95 | N |
| ATOM | 728 | CA | LYS | A | 99 | 10.295 | 35.956 | 19.100 | 1.00 35.95 | C |
| ATOM | 729 | C | LYS | A | 99 | 10.212 | 35.734 | 20.593 | 1.00 35.95 | C |
| ATOM | 730 | O | LYS | A | 99 | 9.127 | 35.487 | 21.137 | 1.00 35.95 | O |
| ATOM | 731 | CB | LYS | A | 99 | 10.461 | 37.444 | 18.793 | 1.00 43.93 | C |
| ATOM | 732 | CG | LYS | A | 99 | 9.512 | 38.352 | 19.556 | 1.00 43.93 | C |
| ATOM | 733 | CD | LYS | A | 99 | 9.590 | 39.769 | 19.029 | 1.00 43.93 | C |
| ATOM | 734 | CE | LYS | A | 99 | 9.757 | 40.761 | 20.153 | 1.00 43.93 | C |
| ATOM | 735 | NZ | LYS | A | 99 | 11.015 | 40.516 | 20.922 | 1.00 43.93 | N |
| ATOM | 736 | N | LEU | A | 100 | 11.349 | 35.823 | 21.262 | 1.00 44.66 | N |
| ATOM | 737 | CA | LEU | A | 100 | 11.378 | 35.640 | 22.696 | 1.00 44.66 | C |
| ATOM | 738 | C | LEU | A | 100 | 10.928 | 36.902 | 23.401 | 1.00 44.66 | C |
| ATOM | 739 | O | LEU | A | 100 | 11.148 | 38.006 | 22.914 | 1.00 44.66 | O |
| ATOM | 740 | CB | LEU | A | 100 | 12.791 | 35.312 | 23.158 | 1.00 32.99 | C |
| ATOM | 741 | CG | LEU | A | 100 | 13.480 | 34.081 | 22.554 | 1.00 32.99 | C |
| ATOM | 742 | CD1 | LEU | A | 100 | 14.715 | 33.774 | 23.409 | 1.00 32.99 | C |

Fig. 1V

| | | | | | | | | | |
|---|---|---|---|---|---|---|---|---|---|
| ATOM | 743 | CD2 | LEU | A | 100 | 12.517 | 32.864 | 22.532 | 1.00 32.99 | C |
| ATOM | 744 | N | THR | A | 101 | 10.276 | 36.737 | 24.543 | 1.00 38.68 | N |
| ATOM | 745 | CA | THR | A | 101 | 9.871 | 37.886 | 25.332 | 1.00 38.68 | C |
| ATOM | 746 | C | THR | A | 101 | 11.131 | 38.172 | 26.167 | 1.00 38.68 | C |
| ATOM | 747 | O | THR | A | 101 | 12.059 | 37.348 | 26.179 | 1.00 38.68 | O |
| ATOM | 748 | CB | THR | A | 101 | 8.708 | 37.523 | 26.256 | 1.00 35.09 | C |
| ATOM | 749 | OG1 | THR | A | 101 | 9.092 | 36.406 | 27.073 | 1.00 35.09 | O |
| ATOM | 750 | CG2 | THR | A | 101 | 7.474 | 37.153 | 25.449 | 1.00 35.09 | C |
| ATOM | 751 | N | THR | A | 102 | 11.183 | 39.310 | 26.857 | 1.00 50.83 | N |
| ATOM | 752 | CA | THR | A | 102 | 12.364 | 39.638 | 27.673 | 1.00 50.83 | C |
| ATOM | 753 | C | THR | A | 102 | 12.678 | 38.510 | 28.647 | 1.00 50.83 | C |
| ATOM | 754 | O | THR | A | 102 | 13.816 | 38.061 | 28.745 | 1.00 50.83 | O |
| ATOM | 755 | CB | THR | A | 102 | 12.168 | 40.931 | 28.506 | 1.00 38.42 | C |
| ATOM | 756 | OG1 | THR | A | 102 | 11.800 | 42.012 | 27.645 | 1.00 38.42 | O |
| ATOM | 757 | CG2 | THR | A | 102 | 13.470 | 41.293 | 29.231 | 1.00 38.42 | C |
| ATOM | 758 | N | GLY | A | 103 | 11.665 | 38.065 | 29.381 | 1.00 42.94 | N |
| ATOM | 759 | CA | GLY | A | 103 | 11.872 | 36.976 | 30.312 | 1.00 42.94 | C |
| ATOM | 760 | C | GLY | A | 103 | 12.371 | 35.723 | 29.602 | 1.00 42.94 | C |
| ATOM | 761 | O | GLY | A | 103 | 13.289 | 35.053 | 30.082 | 1.00 42.94 | O |
| ATOM | 762 | N | GLY | A | 104 | 11.762 | 35.404 | 28.459 | 1.00 38.70 | N |
| ATOM | 763 | CA | GLY | A | 104 | 12.178 | 34.234 | 27.707 | 1.00 38.70 | C |
| ATOM | 764 | C | GLY | A | 104 | 13.656 | 34.336 | 27.384 | 1.00 38.70 | C |
| ATOM | 765 | O | GLY | A | 104 | 14.398 | 33.359 | 27.510 | 1.00 38.70 | O |
| ATOM | 766 | N | ALA | A | 105 | 14.076 | 35.534 | 26.979 | 1.00 47.24 | N |
| ATOM | 767 | CA | ALA | A | 105 | 15.471 | 35.799 | 26.634 | 1.00 47.24 | C |
| ATOM | 768 | C | ALA | A | 105 | 16.390 | 35.514 | 27.812 | 1.00 47.24 | C |
| ATOM | 769 | O | ALA | A | 105 | 17.438 | 34.893 | 27.650 | 1.00 47.24 | O |
| ATOM | 770 | CB | ALA | A | 105 | 15.634 | 37.256 | 26.183 | 1.00 42.30 | C |
| ATOM | 771 | N | ALA | A | 106 | 15.989 | 35.967 | 28.997 | 1.00 52.11 | N |
| ATOM | 772 | CA | ALA | A | 106 | 16.778 | 35.763 | 30.201 | 1.00 52.11 | C |
| ATOM | 773 | C | ALA | A | 106 | 16.876 | 34.267 | 30.503 | 1.00 52.11 | C |
| ATOM | 774 | O | ALA | A | 106 | 17.966 | 33.730 | 30.719 | 1.00 52.11 | O |
| ATOM | 775 | CB | ALA | A | 106 | 16.141 | 36.505 | 31.372 | 1.00 50.48 | C |
| ATOM | 776 | N | ILE | A | 107 | 15.735 | 33.592 | 30.519 | 1.00 47.20 | N |
| ATOM | 777 | CA | ILE | A | 107 | 15.731 | 32.160 | 30.772 | 1.00 47.20 | C |
| ATOM | 778 | C | ILE | A | 107 | 16.728 | 31.464 | 29.818 | 1.00 47.20 | C |
| ATOM | 779 | O | ILE | A | 107 | 17.558 | 30.652 | 30.241 | 1.00 47.20 | O |
| ATOM | 780 | CB | ILE | A | 107 | 14.325 | 31.563 | 30.528 | 1.00 46.42 | C |
| ATOM | 781 | CG1 | ILE | A | 107 | 13.312 | 32.166 | 31.507 | 1.00 46.42 | C |
| ATOM | 782 | CG2 | ILE | A | 107 | 14.380 | 30.052 | 30.642 | 1.00 46.42 | C |
| ATOM | 783 | CD1 | ILE | A | 107 | 13.619 | 31.905 | 32.956 | 1.00 46.42 | C |
| ATOM | 784 | N | CYS | A | 108 | 16.637 | 31.789 | 28.531 | 1.00 55.20 | N |
| ATOM | 785 | CA | CYS | A | 108 | 17.508 | 31.187 | 27.526 | 1.00 55.20 | C |
| ATOM | 786 | C | CYS | A | 108 | 18.981 | 31.472 | 27.763 | 1.00 55.20 | C |
| ATOM | 787 | O | CYS | A | 108 | 19.839 | 30.689 | 27.346 | 1.00 55.20 | O |
| ATOM | 788 | CB | CYS | A | 108 | 17.126 | 31.665 | 26.125 | 1.00 50.25 | C |
| ATOM | 789 | SG | CYS | A | 108 | 18.283 | 31.139 | 24.836 | 1.00 50.25 | S |
| ATOM | 790 | N | GLU | A | 109 | 19.275 | 32.590 | 28.425 | 1.00 53.61 | N |

Fig. 1W

```
ATOM  791  CA   GLU A 109    20.660  32.952  28.708  1.00 53.61           C
ATOM  792  C    GLU A 109    21.128  32.294  30.007  1.00 53.61           C
ATOM  793  O    GLU A 109    22.275  31.864  30.109  1.00 53.61           O
ATOM  794  CB   GLU A 109    20.813  34.472  28.795  1.00109.75           C
ATOM  795  CG   GLU A 109    22.263  34.944  28.795  1.00109.75           C
ATOM  796  CD   GLU A 109    23.044  34.423  27.598  1.00109.75           C
ATOM  797  OE1  GLU A 109    22.620  34.679  26.453  1.00109.75           O
ATOM  798  OE2  GLU A 109    24.084  33.759  27.799  1.00109.75           O
ATOM  799  N    GLN A 110    20.253  32.211  31.002  1.00 70.78           N
ATOM  800  CA   GLN A 110    20.635  31.560  32.249  1.00 70.78           C
ATOM  801  C    GLN A 110    21.020  30.123  31.918  1.00 70.78           C
ATOM  802  O    GLN A 110    22.045  29.621  32.382  1.00 70.78           O
ATOM  803  CB   GLN A 110    19.476  31.522  33.240  1.00 56.91           C
ATOM  804  CG   GLN A 110    19.214  32.789  34.020  1.00 56.91           C
ATOM  805  CD   GLN A 110    17.892  32.707  34.780  1.00 56.91           C
ATOM  806  OE1  GLN A 110    17.620  31.722  35.481  1.00 56.91           O
ATOM  807  NE2  GLN A 110    17.063  33.738  34.640  1.00 56.91           N
ATOM  808  N    CYS A 111    20.180  29.471  31.116  1.00 60.37           N
ATOM  809  CA   CYS A 111    20.397  28.087  30.714  1.00 60.37           C
ATOM  810  C    CYS A 111    21.614  27.911  29.822  1.00 60.37           C
ATOM  811  O    CYS A 111    22.456  27.047  30.077  1.00 60.37           O
ATOM  812  CB   CYS A 111    19.177  27.546  29.964  1.00 52.09           C
ATOM  813  SG   CYS A 111    17.688  27.268  30.941  1.00 52.09           S
ATOM  814  N    HIS A 112    21.693  28.716  28.767  1.00 61.76           N
ATOM  815  CA   HIS A 112    22.801  28.632  27.818  1.00 61.76           C
ATOM  816  C    HIS A 112    24.160  28.735  28.502  1.00 61.76           C
ATOM  817  O    HIS A 112    25.108  28.032  28.138  1.00 61.76           O
ATOM  818  CB   HIS A 112    22.663  29.727  26.762  1.00 68.17           C
ATOM  819  CG   HIS A 112    23.616  29.585  25.617  1.00 68.17           C
ATOM  820  ND1  HIS A 112    24.964  29.851  25.730  1.00 68.17           N
ATOM  821  CD2  HIS A 112    23.416  29.199  24.335  1.00 68.17           C
ATOM  822  CE1  HIS A 112    25.552  29.637  24.567  1.00 68.17           C
ATOM  823  NE2  HIS A 112    24.634  29.240  23.704  1.00 68.17           N
ATOM  824  N    GLN A 113    24.243  29.603  29.503  1.00 60.30           N
ATOM  825  CA   GLN A 113    25.480  29.792  30.240  1.00 60.30           C
ATOM  826  C    GLN A 113    25.812  28.603  31.125  1.00 60.30           C
ATOM  827  O    GLN A 113    26.940  28.117  31.105  1.00 60.30           O
ATOM  828  CB   GLN A 113    25.406  31.059  31.093  1.00102.85           C
ATOM  829  CG   GLN A 113    25.241  32.328  30.281  1.00102.85           C
ATOM  830  CD   GLN A 113    25.367  33.575  31.125  1.00102.85           C
ATOM  831  OE1  GLN A 113    24.708  33.707  32.155  1.00102.85           O
ATOM  832  NE2  GLN A 113    26.212  34.503  30.689  1.00102.85           N
ATOM  833  N    LEU A 114    24.836  28.132  31.896  1.00 64.71           N
ATOM  834  CA   LEU A 114    25.057  27.001  32.798  1.00 64.71           C
ATOM  835  C    LEU A 114    25.417  25.713  32.056  1.00 64.71           C
ATOM  836  O    LEU A 114    26.468  25.123  32.295  1.00 64.71           O
ATOM  837  CB   LEU A 114    23.819  26.766  33.671  1.00 66.45           C
ATOM  838  CG   LEU A 114    23.238  28.013  34.349  1.00 66.45           C
```

Fig. 1X

```
ATOM    839  CD1 LEU A 114      22.189  27.587  35.387  1.00 66.45           C
ATOM    840  CD2 LEU A 114      24.353  28.830  35.002  1.00 66.45           C
ATOM    841  N   VAL A 115      24.545  25.272  31.160  1.00115.02           N
ATOM    842  CA  VAL A 115      24.811  24.054  30.412  1.00115.02           C
ATOM    843  C   VAL A 115      26.134  24.163  29.661  1.00115.02           C
ATOM    844  O   VAL A 115      26.908  23.206  29.606  1.00115.02           O
ATOM    845  CB  VAL A 115      23.670  23.755  29.420  1.00 64.88           C
ATOM    846  CG1 VAL A 115      24.073  22.627  28.477  1.00 64.88           C
ATOM    847  CG2 VAL A 115      22.409  23.383  30.194  1.00 64.88           C
ATOM    848  N   GLY A 116      26.393  25.335  29.089  1.00119.74           N
ATOM    849  CA  GLY A 116      27.629  25.538  28.358  1.00119.74           C
ATOM    850  C   GLY A 116      28.847  25.403  29.253  1.00119.74           C
ATOM    851  O   GLY A 116      29.936  25.088  28.779  1.00119.74           O
ATOM    852  N   GLN A 117      28.661  25.636  30.549  1.00 73.12           N
ATOM    853  CA  GLN A 117      29.750  25.546  31.523  1.00 73.12           C
ATOM    854  C   GLN A 117      29.944  24.137  32.084  1.00 73.12           C
ATOM    855  O   GLN A 117      31.019  23.815  32.587  1.00 73.12           O
ATOM    856  CB  GLN A 117      29.504  26.520  32.678  1.00 96.60           C
ATOM    857  CG  GLN A 117      29.577  27.984  32.282  1.00 96.60           C
ATOM    858  CD  GLN A 117      29.080  28.919  33.374  1.00 96.60           C
ATOM    859  OE1 GLN A 117      29.094  30.141  33.215  1.00 96.60           O
ATOM    860  NE2 GLN A 117      28.632  28.347  34.488  1.00 96.60           N
ATOM    861  N   ASP A 118      28.905  23.308  32.006  1.00 69.89           N
ATOM    862  CA  ASP A 118      28.981  21.937  32.507  1.00 69.89           C
ATOM    863  C   ASP A 118      29.402  20.966  31.416  1.00 69.89           C
ATOM    864  O   ASP A 118      30.112  19.995  31.680  1.00 69.89           O
ATOM    865  CB  ASP A 118      27.632  21.487  33.070  1.00 86.01           C
ATOM    866  CG  ASP A 118      27.261  22.204  34.348  1.00 86.01           C
ATOM    867  OD1 ASP A 118      26.218  21.849  34.935  1.00 86.01           O
ATOM    868  OD2 ASP A 118      28.004  23.117  34.767  1.00 86.01           O
ATOM    869  N   LEU A 119      28.947  21.223  30.194  1.00 80.62           N
ATOM    870  CA  LEU A 119      29.285  20.368  29.065  1.00 80.62           C
ATOM    871  C   LEU A 119      30.769  20.458  28.772  1.00 80.62           C
ATOM    872  O   LEU A 119      31.467  19.448  28.731  1.00 80.62           O
ATOM    873  CB  LEU A 119      28.499  20.784  27.819  1.00 80.69           C
ATOM    874  CG  LEU A 119      27.053  20.307  27.695  1.00 80.69           C
ATOM    875  CD1 LEU A 119      26.407  20.940  26.465  1.00 80.69           C
ATOM    876  CD2 LEU A 119      27.029  18.790  27.586  1.00 80.69           C
ATOM    877  N   HIS A 120      31.244  21.680  28.569  1.00 76.91           N
ATOM    878  CA  HIS A 120      32.647  21.911  28.275  1.00 76.91           C
ATOM    879  C   HIS A 120      33.491  21.044  29.192  1.00 76.91           C
ATOM    880  O   HIS A 120      34.372  20.317  28.734  1.00 76.91           O
ATOM    881  CB  HIS A 120      32.998  23.384  28.494  1.00119.42           C
ATOM    882  CG  HIS A 120      34.363  23.758  28.006  1.00119.42           C
ATOM    883  ND1 HIS A 120      35.504  23.094  28.401  1.00119.42           N
ATOM    884  CD2 HIS A 120      34.770  24.736  27.162  1.00119.42           C
ATOM    885  CE1 HIS A 120      36.555  23.646  27.821  1.00119.42           C
ATOM    886  NE2 HIS A 120      36.137  24.644  27.065  1.00119.42           N
```

Fig. 1Y

```
ATOM   887  N    GLN A 121      33.207  21.118  30.489  1.00 79.07           N
ATOM   888  CA   GLN A 121      33.940  20.340  31.480  1.00 79.07           C
ATOM   889  C    GLN A 121      33.760  18.848  31.239  1.00 79.07           C
ATOM   890  O    GLN A 121      34.724  18.140  30.952  1.00 79.07           O
ATOM   891  CB   GLN A 121      33.458  20.685  32.889  1.00 96.87           C
ATOM   892  CG   GLN A 121      33.479  22.169  33.202  1.00 96.87           C
ATOM   893  CD   GLN A 121      34.837  22.800  32.959  1.00 96.87           C
ATOM   894  OE1  GLN A 121      35.846  22.357  33.510  1.00 96.87           O
ATOM   895  NE2  GLN A 121      34.870  23.843  32.134  1.00 96.87           N
ATOM   896  N    GLU A 122      32.523  18.375  31.349  1.00 53.54           N
ATOM   897  CA   GLU A 122      32.235  16.958  31.158  1.00 53.54           C
ATOM   898  C    GLU A 122      32.783  16.358  29.873  1.00 53.54           C
ATOM   899  O    GLU A 122      33.365  15.271  29.897  1.00 53.54           O
ATOM   900  CB   GLU A 122      30.729  16.703  31.233  1.00 88.00           C
ATOM   901  CG   GLU A 122      30.187  16.610  32.650  1.00 88.00           C
ATOM   902  CD   GLU A 122      30.991  15.657  33.510  1.00 88.00           C
ATOM   903  OE1  GLU A 122      32.017  16.091  34.076  1.00 88.00           O
ATOM   904  OE2  GLU A 122      30.604  14.472  33.606  1.00 88.00           O
ATOM   905  N    LEU A 123      32.596  17.056  28.756  1.00 72.38           N
ATOM   906  CA   LEU A 123      33.074  16.579  27.460  1.00 72.38           C
ATOM   907  C    LEU A 123      34.593  16.554  27.402  1.00 72.38           C
ATOM   908  O    LEU A 123      35.199  15.644  26.829  1.00 72.38           O
ATOM   909  CB   LEU A 123      32.564  17.484  26.331  1.00 59.40           C
ATOM   910  CG   LEU A 123      31.065  17.540  26.049  1.00 59.40           C
ATOM   911  CD1  LEU A 123      30.789  18.535  24.929  1.00 59.40           C
ATOM   912  CD2  LEU A 123      30.580  16.147  25.675  1.00 59.40           C
ATOM   913  N    THR A 124      35.195  17.573  28.000  1.00 64.43           N
ATOM   914  CA   THR A 124      36.641  17.737  28.022  1.00 64.43           C
ATOM   915  C    THR A 124      37.288  17.074  29.234  1.00 64.43           C
ATOM   916  O    THR A 124      38.507  17.043  29.341  1.00 64.43           O
ATOM   917  CB   THR A 124      36.984  19.256  28.002  1.00 67.40           C
ATOM   918  OG1  THR A 124      36.866  19.751  26.663  1.00 67.40           O
ATOM   919  CG2  THR A 124      38.376  19.527  28.528  1.00 67.40           C
ATOM   920  N    LYS A 125      36.470  16.523  30.129  1.00 52.23           N
ATOM   921  CA   LYS A 125      36.966  15.900  31.358  1.00 52.23           C
ATOM   922  C    LYS A 125      38.170  14.973  31.201  1.00 52.23           C
ATOM   923  O    LYS A 125      39.044  14.944  32.068  1.00 52.23           O
ATOM   924  CB   LYS A 125      35.846  15.127  32.065  1.00 85.46           C
ATOM   925  CG   LYS A 125      35.460  13.806  31.400  1.00 85.46           C
ATOM   926  CD   LYS A 125      34.492  13.017  32.281  1.00 85.46           C
ATOM   927  CE   LYS A 125      34.044  11.712  31.633  1.00 85.46           C
ATOM   928  NZ   LYS A 125      33.098  10.969  32.515  1.00 85.46           N
ATOM   929  N    ASN A 126      38.224  14.215  30.108  1.00 50.93           N
ATOM   930  CA   ASN A 126      39.333  13.295  29.917  1.00 50.93           C
ATOM   931  C    ASN A 126      40.208  13.447  28.682  1.00 50.93           C
ATOM   932  O    ASN A 126      41.262  12.826  28.604  1.00 50.93           O
ATOM   933  CB   ASN A 126      38.833  11.844  30.023  1.00 72.05           C
ATOM   934  CG   ASN A 126      37.528  11.609  29.285  1.00 72.05           C
```

Fig. 1Z

```
ATOM    935  OD1 ASN A 126      36.929  10.535  29.393  1.00 72.05           O
ATOM    936  ND2 ASN A 126      37.080  12.610  28.530  1.00 72.05           N
ATOM    937  N   LEU A 127      39.824  14.263  27.714  1.00113.27           N
ATOM    938  CA  LEU A 127      40.699  14.382  26.560  1.00113.27           C
ATOM    939  C   LEU A 127      41.620  15.594  26.688  1.00113.27           C
ATOM    940  O   LEU A 127      42.582  15.727  25.931  1.00113.27           O
ATOM    941  CB  LEU A 127      39.882  14.443  25.260  1.00 65.66           C
ATOM    942  CG  LEU A 127      39.297  15.758  24.754  1.00 65.66           C
ATOM    943  CD1 LEU A 127      40.410  16.733  24.365  1.00 65.66           C
ATOM    944  CD2 LEU A 127      38.436  15.466  23.538  1.00 65.66           C
ATOM    945  N   THR A 128      41.333  16.458  27.662  1.00 81.99           N
ATOM    946  CA  THR A 128      42.112  17.679  27.901  1.00 81.99           C
ATOM    947  C   THR A 128      43.609  17.562  27.596  1.00 81.99           C
ATOM    948  O   THR A 128      44.210  18.480  27.029  1.00 81.99           O
ATOM    949  CB  THR A 128      41.964  18.170  29.361  1.00 99.66           C
ATOM    950  OG1 THR A 128      40.575  18.315  29.685  1.00 99.66           O
ATOM    951  CG2 THR A 128      42.649  19.523  29.537  1.00 99.66           C
ATOM    952  N   ALA A 129      44.212  16.445  27.987  1.00102.35           N
ATOM    953  CA  ALA A 129      45.628  16.228  27.731  1.00102.35           C
ATOM    954  C   ALA A 129      45.851  16.337  26.228  1.00102.35           C
ATOM    955  O   ALA A 129      46.619  17.183  25.764  1.00102.35           O
ATOM    956  CB  ALA A 129      46.048  14.850  28.225  1.00 76.05           C
ATOM    957  N   ASP A 130      45.198  15.448  25.473  1.00 89.67           N
ATOM    958  CA  ASP A 130      45.262  15.470  24.013  1.00 89.67           C
ATOM    959  C   ASP A 130      44.908  16.860  23.521  1.00 89.67           C
ATOM    960  O   ASP A 130      45.261  17.257  22.398  1.00 89.67           O
ATOM    961  CB  ASP A 130      44.285  14.455  23.410  1.00103.50           C
ATOM    962  CG  ASP A 130      44.420  13.104  24.094  1.00103.50           C
ATOM    963  OD1 ASP A 130      44.236  13.026  25.328  1.00103.50           O
ATOM    964  OD2 ASP A 130      44.715  12.125  23.377  1.00103.50           O
ATOM    965  N   GLU A 131      44.167  17.618  24.366  1.00 61.61           N
ATOM    966  CA  GLU A 131      43.848  19.075  24.175  1.00 61.61           C
ATOM    967  C   GLU A 131      42.658  19.507  23.329  1.00 61.61           C
ATOM    968  O   GLU A 131      42.751  19.518  22.098  1.00 61.61           O
ATOM    969  CB  GLU A 131      45.075  19.734  23.589  1.00 59.54           C
ATOM    970  CG  GLU A 131      44.935  21.220  23.744  1.00 59.54           C
ATOM    971  CD  GLU A 131      44.602  21.536  25.176  1.00 59.54           C
ATOM    972  OE1 GLU A 131      43.619  22.275  25.430  1.00 59.54           O
ATOM    973  OE2 GLU A 131      45.308  21.040  26.070  1.00 59.54           O
ATOM    974  N   VAL A 132      41.502  19.874  23.920  1.00 61.80           N
ATOM    975  CA  VAL A 132      40.251  20.217  23.175  1.00 61.80           C
ATOM    976  C   VAL A 132      40.452  21.036  21.890  1.00 61.80           C
ATOM    977  O   VAL A 132      39.666  20.967  20.961  1.00 61.80           O
ATOM    978  CB  VAL A 132      39.280  20.917  24.135  1.00 77.83           C
ATOM    979  CG1 VAL A 132      37.860  20.909  23.588  1.00 77.83           C
ATOM    980  CG2 VAL A 132      39.321  20.254  25.499  1.00 77.83           C
ATOM    981  N   ALA A 133      41.519  21.812  21.920  1.00 74.99           N
ATOM    982  CA  ALA A 133      41.904  22.678  20.812  1.00 74.99
```

Fig. 1AA

```
ATOM    983   C    ALA A 133      42.214  21.873  19.546  1.00 74.99           C
ATOM    984   O    ALA A 133      41.925  22.323  18.441  1.00 74.99           O
ATOM    985   CB   ALA A 133      43.099  23.540  21.186  1.00 70.55           C
ATOM    986   N    THR A 134      42.808  20.694  19.703  1.00 59.60           N
ATOM    987   CA   THR A 134      43.129  19.845  18.557  1.00 59.60           C
ATOM    988   C    THR A 134      41.852  19.236  17.961  1.00 59.60           C
ATOM    989   O    THR A 134      41.649  19.255  16.747  1.00 59.60           O
ATOM    990   CB   THR A 134      44.076  18.714  18.978  1.00 48.57           C
ATOM    991   OG1  THR A 134      45.208  19.286  19.647  1.00 48.57           O
ATOM    992   CG2  THR A 134      44.550  17.909  17.765  1.00 48.57           C
ATOM    993   N    LEU A 135      40.997  18.687  18.818  1.00 52.11           N
ATOM    994   CA   LEU A 135      39.748  18.106  18.357  1.00 52.11           C
ATOM    995   C    LEU A 135      38.950  19.211  17.683  1.00 52.11           C
ATOM    996   O    LEU A 135      38.387  19.019  16.604  1.00 52.11           O
ATOM    997   CB   LEU A 135      38.953  17.542  19.532  1.00 28.91           C
ATOM    998   CG   LEU A 135      37.563  16.938  19.216  1.00 28.91           C
ATOM    999   CD1  LEU A 135      37.675  15.855  18.148  1.00 28.91           C
ATOM    1000  CD2  LEU A 135      36.964  16.366  20.504  1.00 28.91           C
ATOM    1001  N    GLU A 136      38.922  20.379  18.315  1.00 51.30           N
ATOM    1002  CA   GLU A 136      38.188  21.509  17.766  1.00 51.30           C
ATOM    1003  C    GLU A 136      38.750  21.874  16.396  1.00 51.30           C
ATOM    1004  O    GLU A 136      38.007  22.136  15.458  1.00 51.30           O
ATOM    1005  CB   GLU A 136      38.282  22.704  18.716  1.00 50.36           C
ATOM    1006  CG   GLU A 136      37.995  22.341  20.160  1.00 50.36           C
ATOM    1007  CD   GLU A 136      37.849  23.550  21.070  1.00 50.36           C
ATOM    1008  OE1  GLU A 136      38.667  24.495  20.971  1.00 50.36           O
ATOM    1009  OE2  GLU A 136      36.915  23.542  21.904  1.00 50.36           O
ATOM    1010  N    TYR A 137      40.070  21.871  16.286  1.00 48.14           N
ATOM    1011  CA   TYR A 137      40.728  22.197  15.038  1.00 48.14           C
ATOM    1012  C    TYR A 137      40.267  21.258  13.934  1.00 48.14           C
ATOM    1013  O    TYR A 137      39.753  21.704  12.908  1.00 48.14           O
ATOM    1014  CB   TYR A 137      42.244  22.088  15.199  1.00 62.08           C
ATOM    1015  CG   TYR A 137      42.995  22.317  13.914  1.00 62.08           C
ATOM    1016  CD1  TYR A 137      43.121  23.595  13.380  1.00 62.08           C
ATOM    1017  CD2  TYR A 137      43.543  21.247  13.209  1.00 62.08           C
ATOM    1018  CE1  TYR A 137      43.774  23.810  12.172  1.00 62.08           C
ATOM    1019  CE2  TYR A 137      44.200  21.444  11.996  1.00 62.08           C
ATOM    1020  CZ   TYR A 137      44.310  22.732  11.483  1.00 62.08           C
ATOM    1021  OH   TYR A 137      44.939  22.938  10.274  1.00 62.08           O
ATOM    1022  N    LEU A 138      40.468  19.958  14.138  1.00 37.88           N
ATOM    1023  CA   LEU A 138      40.059  18.962  13.150  1.00 37.88           C
ATOM    1024  C    LEU A 138      38.554  19.022  12.848  1.00 37.88           C
ATOM    1025  O    LEU A 138      38.146  18.864  11.700  1.00 37.88           O
ATOM    1026  CB   LEU A 138      40.439  17.555  13.624  1.00 65.29           C
ATOM    1027  CG   LEU A 138      41.937  17.223  13.657  1.00 65.29           C
ATOM    1028  CD1  LEU A 138      42.152  15.798  14.136  1.00 65.29           C
ATOM    1029  CD2  LEU A 138      42.513  17.393  12.266  1.00 65.29           C
ATOM    1030  N    LEU A 139      37.731  19.256  13.868  1.00 37.74           N
```

Fig. 1BB

```
ATOM   1031  CA   LEU A 139      36.291  19.329  13.654  1.00 37.74           C
ATOM   1032  C    LEU A 139      35.939  20.500  12.749  1.00 37.74           C
ATOM   1033  O    LEU A 139      34.915  20.479  12.068  1.00 37.74           O
ATOM   1034  CB   LEU A 139      35.547  19.468  14.987  1.00 35.40           C
ATOM   1035  CG   LEU A 139      35.320  18.190  15.805  1.00 35.40           C
ATOM   1036  CD1  LEU A 139      34.645  18.554  17.126  1.00 35.40           C
ATOM   1037  CD2  LEU A 139      34.461  17.208  15.019  1.00 35.40           C
ATOM   1038  N    LYS A 140      36.778  21.529  12.750  1.00 53.22           N
ATOM   1039  CA   LYS A 140      36.527  22.689  11.900  1.00 53.22           C
ATOM   1040  C    LYS A 140      36.822  22.323  10.459  1.00 53.22           C
ATOM   1041  O    LYS A 140      36.089  22.718   9.554  1.00 53.22           O
ATOM   1042  CB   LYS A 140      37.392  23.883  12.319  1.00 43.83           C
ATOM   1043  CG   LYS A 140      36.966  24.525  13.634  1.00 43.83           C
ATOM   1044  CD   LYS A 140      37.829  25.733  13.976  1.00 43.83           C
ATOM   1045  CE   LYS A 140      37.341  26.425  15.238  1.00 43.83           C
ATOM   1046  NZ   LYS A 140      38.091  27.695  15.494  1.00 43.83           N
ATOM   1047  N    LYS A 141      37.889  21.554  10.251  1.00 43.02           N
ATOM   1048  CA   LYS A 141      38.279  21.133   8.910  1.00 43.02           C
ATOM   1049  C    LYS A 141      37.210  20.276   8.245  1.00 43.02           C
ATOM   1050  O    LYS A 141      37.316  19.946   7.063  1.00 43.02           O
ATOM   1051  CB   LYS A 141      39.609  20.366   8.939  1.00 56.38           C
ATOM   1052  CG   LYS A 141      40.801  21.198   9.383  1.00 56.38           C
ATOM   1053  CD   LYS A 141      42.119  20.601   8.900  1.00 56.38           C
ATOM   1054  CE   LYS A 141      42.286  20.774   7.384  1.00 56.38           C
ATOM   1055  NZ   LYS A 141      43.556  20.185   6.830  1.00 56.38           N
ATOM   1056  N    VAL A 142      36.178  19.918   9.001  1.00 64.66           N
ATOM   1057  CA   VAL A 142      35.081  19.119   8.470  1.00 64.66           C
ATOM   1058  C    VAL A 142      33.940  20.008   7.952  1.00 64.66           C
ATOM   1059  O    VAL A 142      33.198  19.611   7.053  1.00 64.66           O
ATOM   1060  CB   VAL A 142      34.502  18.170   9.556  1.00 36.71           C
ATOM   1061  CG1  VAL A 142      33.236  17.503   9.044  1.00 36.71           C
ATOM   1062  CG2  VAL A 142      35.533  17.118   9.945  1.00 36.71           C
ATOM   1063  N    LEU A 143      33.815  21.212   8.504  1.00 55.78           N
ATOM   1064  CA   LEU A 143      32.736  22.126   8.125  1.00 55.78           C
ATOM   1065  C    LEU A 143      32.745  22.784   6.733  1.00 55.78           C
ATOM   1066  O    LEU A 143      31.732  22.766   6.021  1.00 55.78           O
ATOM   1067  CB   LEU A 143      32.591  23.210   9.202  1.00 39.23           C
ATOM   1068  CG   LEU A 143      32.052  22.650  10.517  1.00 39.23           C
ATOM   1069  CD1  LEU A 143      31.874  23.748  11.529  1.00 39.23           C
ATOM   1070  CD2  LEU A 143      30.736  21.952  10.247  1.00 39.23           C
ATOM   1071  N    PRO A 144      33.874  23.375   6.323  1.00 58.86           N
ATOM   1072  CA   PRO A 144      33.870  24.001   4.997  1.00 58.86           C
ATOM   1073  C    PRO A 144      33.622  23.019   3.840  1.00 58.86           C
ATOM   1074  O    PRO A 144      33.792  21.797   4.034  1.00 58.86           O
ATOM   1075  CB   PRO A 144      35.250  24.659   4.928  1.00 69.58           C
ATOM   1076  CG   PRO A 144      36.096  23.742   5.760  1.00 69.58           C
ATOM   1077  CD   PRO A 144      35.207  23.454   6.945  1.00 69.58           C
ATOM   1078  OXT  PRO A 144      33.265  23.490   2.742  1.00 69.58           O
```

Fig. 1CC

```
TER      1079          PRO A 144
HETATM 1080   C1'  SAL   256     1.600  28.984  14.971  1.00 44.77           C
HETATM 1081   O1'  SAL   256     1.140  30.228  15.037  1.00 44.77           O
HETATM 1082   O2'  SAL   256     1.829  28.336  16.002  1.00 44.77           O
HETATM 1083   C1   SAL   256     1.818  28.433  13.617  1.00 44.77           C
HETATM 1084   C2   SAL   256     2.324  27.078  13.453  1.00 44.77           C
HETATM 1085   C3   SAL   256     2.546  26.526  12.169  1.00 44.77           C
HETATM 1086   C4   SAL   256     2.286  27.268  11.019  1.00 44.77           C
HETATM 1087   C5   SAL   256     1.734  28.740  11.167  1.00 44.77           C
HETATM 1088   C6   SAL   256     1.535  29.234  12.452  1.00 44.77           C
HETATM 1089   O2   SAL   256     2.610  26.273  14.510  1.00 44.77           O
HETATM 1090   C1'  SAL   257     6.631  20.720  25.251  1.00 42.17           C
HETATM 1091   O1'  SAL   257     7.014  21.247  26.407  1.00 42.17           O
HETATM 1092   O2'  SAL   257     5.545  21.061  24.701  1.00 42.17           O
HETATM 1093   C1   SAL   257     7.558  19.723  24.673  1.00 42.17           C
HETATM 1094   C2   SAL   257     7.247  19.073  23.396  1.00 42.17           C
HETATM 1095   C3   SAL   257     8.133  18.108  22.827  1.00 42.17           C
HETATM 1096   C4   SAL   257     9.326  17.754  23.481  1.00 42.17           C
HETATM 1097   C5   SAL   257     9.668  18.454  24.869  1.00 42.17           C
HETATM 1098   C6   SAL   257     8.767  19.390  25.369  1.00 42.17           C
HETATM 1099   O2   SAL   257     6.103  19.348  22.680  1.00 42.17           O
CONECT 1080 1081 1082 1083
CONECT 1081 1080
CONECT 1082 1080
CONECT 1083 1080 1084 1088
CONECT 1084 1083 1085 1089
CONECT 1085 1084 1086
CONECT 1086 1085 1087
CONECT 1087 1086 1088
CONECT 1088 1083 1087
CONECT 1089 1084
CONECT 1090 1091 1092 1093
CONECT 1091 1090
CONECT 1092 1090
CONECT 1093 1090 1094 1098
CONECT 1094 1093 1095 1099
CONECT 1095 1094 1096
CONECT 1096 1095 1097
CONECT 1097 1096 1098
CONECT 1098 1093 1097
CONECT 1099 1094
MASTER        306    0    2    6    2    0    0    6 1098    1   20   11
END
```

Fig. 1DD

```
REMARK Apo-MarR
REMARK Written by O version 6.2.1
REMARK DATE:10-May-02  11:21:32
CRYST1 65.8   137.7  96.4    90.00  90.00 90.00 C222
ATOM      1   CB  ILE A  12      59.905  14.106  45.475  1.00 67.94           A
ATOM      2   CG2 ILE A  12      59.418  13.830  44.055  1.00 67.94           A
ATOM      3   CG1 ILE A  12      58.771  13.864  46.472  1.00 67.94           A
ATOM      4   CD1 ILE A  12      58.227  12.461  46.458  1.00 67.94           A
ATOM      5   C   ILE A  12      61.444  13.384  47.291  1.00123.94           A
ATOM      6   O   ILE A  12      61.003  12.599  48.130  1.00123.94           A
ATOM      7   N   ILE A  12      60.812  11.760  45.543  1.00123.94           A
ATOM      8   CA  ILE A  12      61.114  13.198  45.814  1.00123.94           A
ATOM      9   N   PRO A  13      62.238  14.420  47.627  1.00130.37           A
ATOM     10   CD  PRO A  13      62.932  15.390  46.760  1.00 80.29           A
ATOM     11   CA  PRO A  13      62.578  14.645  49.035  1.00130.37           A
ATOM     12   CB  PRO A  13      63.297  15.990  49.002  1.00 80.29           A
ATOM     13   CG  PRO A  13      64.011  15.937  47.685  1.00 80.29           A
ATOM     14   C   PRO A  13      61.294  14.670  49.862  1.00130.37           A
ATOM     15   O   PRO A  13      60.232  15.061  49.371  1.00130.37           A
ATOM     16   N   LEU A  14      61.396  14.254  51.115  1.00 79.03           A
ATOM     17   CA  LEU A  14      60.236  14.183  51.985  1.00 79.03           A
ATOM     18   CB  LEU A  14      60.652  13.546  53.315  1.00 46.83           A
ATOM     19   CG  LEU A  14      59.567  13.009  54.251  1.00 46.83           A
ATOM     20   CD1 LEU A  14      58.532  12.213  53.467  1.00 46.83           A
ATOM     21   CD2 LEU A  14      60.223  12.134  55.316  1.00 46.83           A
ATOM     22   C   LEU A  14      59.542  15.528  52.206  1.00 79.03           A
ATOM     23   O   LEU A  14      58.310  15.596  52.261  1.00 79.03           A
ATOM     24   N   GLY A  15      60.332  16.593  52.312  1.00 52.34           A
ATOM     25   CA  GLY A  15      59.775  17.919  52.530  1.00 52.34           A
ATOM     26   C   GLY A  15      58.591  18.254  51.642  1.00 52.34           A
ATOM     27   O   GLY A  15      57.551  18.705  52.138  1.00 52.34           A
ATOM     28   N   ARG A  16      58.741  18.039  50.335  1.00 52.47           A
ATOM     29   CA  ARG A  16      57.664  18.331  49.393  1.00 52.47           A
ATOM     30   CB  ARG A  16      58.173  18.263  47.949  1.00111.16           A
ATOM     31   CG  ARG A  16      58.538  19.623  47.367  1.00111.16           A
ATOM     32   CD  ARG A  16      58.915  19.527  45.896  1.00111.16           A
ATOM     33   NE  ARG A  16      60.105  18.707  45.692  1.00111.16           A
ATOM     34   CZ  ARG A  16      61.304  18.988  46.193  1.00111.16           A
ATOM     35   NH1 ARG A  16      61.485  20.073  46.933  1.00111.16           A
ATOM     36   NH2 ARG A  16      62.324  18.179  45.957  1.00111.16           A
ATOM     37   C   ARG A  16      56.482  17.393  49.561  1.00 52.47           A
ATOM     38   O   ARG A  16      55.330  17.786  49.361  1.00 52.47           A
ATOM     39   N   LEU A  17      56.765  16.154  49.939  1.00 37.85           A
ATOM     40   CA  LEU A  17      55.706  15.175  50.117  1.00 37.85           A
ATOM     41   CB  LEU A  17      56.315  13.788  50.319  1.00 47.48           A
ATOM     42   CG  LEU A  17      55.704  12.665  49.481  1.00 47.48           A
ATOM     43   CD1 LEU A  17      55.356  13.152  48.075  1.00 47.48           A
ATOM     44   CD2 LEU A  17      56.702  11.515  49.432  1.00 47.48           A
```

Fig. 2

| ATOM | 45 | C | LEU | A | 17 | 54.832 | 15.562 | 51.303 | 1.00 | 37.85 | A |
| ATOM | 46 | O | LEU | A | 17 | 53.600 | 15.578 | 51.199 | 1.00 | 37.85 | A |
| ATOM | 47 | N | ILE | A | 18 | 55.475 | 15.889 | 52.423 | 1.00 | 32.29 | A |
| ATOM | 48 | CA | ILE | A | 18 | 54.749 | 16.282 | 53.628 | 1.00 | 32.29 | A |
| ATOM | 49 | CB | ILE | A | 18 | 55.715 | 16.537 | 54.819 | 1.00 | 22.79 | A |
| ATOM | 50 | CG2 | ILE | A | 18 | 54.938 | 17.003 | 56.048 | 1.00 | 22.79 | A |
| ATOM | 51 | CG1 | ILE | A | 18 | 56.487 | 15.247 | 55.131 | 1.00 | 22.79 | A |
| ATOM | 52 | CD1 | ILE | A | 18 | 57.543 | 15.383 | 56.248 | 1.00 | 22.79 | A |
| ATOM | 53 | C | ILE | A | 18 | 53.983 | 17.550 | 53.307 | 1.00 | 32.29 | A |
| ATOM | 54 | O | ILE | A | 18 | 52.900 | 17.792 | 53.836 | 1.00 | 32.29 | A |
| ATOM | 55 | N | HIS | A | 19 | 54.545 | 18.353 | 52.416 | 1.00 | 38.61 | A |
| ATOM | 56 | CA | HIS | A | 19 | 53.893 | 19.587 | 52.022 | 1.00 | 38.61 | A |
| ATOM | 57 | CB | HIS | A | 19 | 54.837 | 20.437 | 51.178 | 1.00 | 36.15 | A |
| ATOM | 58 | CG | HIS | A | 19 | 54.378 | 21.850 | 51.011 | 1.00 | 36.15 | A |
| ATOM | 59 | CD2 | HIS | A | 19 | 53.819 | 22.714 | 51.890 | 1.00 | 36.15 | A |
| ATOM | 60 | ND1 | HIS | A | 19 | 54.490 | 22.534 | 49.819 | 1.00 | 36.15 | A |
| ATOM | 61 | CE1 | HIS | A | 19 | 54.019 | 23.758 | 49.971 | 1.00 | 36.15 | A |
| ATOM | 62 | NE2 | HIS | A | 19 | 53.606 | 23.892 | 51.217 | 1.00 | 36.15 | A |
| ATOM | 63 | C | HIS | A | 19 | 52.613 | 19.294 | 51.235 | 1.00 | 38.61 | A |
| ATOM | 64 | O | HIS | A | 19 | 51.550 | 19.822 | 51.567 | 1.00 | 38.61 | A |
| ATOM | 65 | N | MET | A | 20 | 52.706 | 18.447 | 50.208 | 1.00 | 40.71 | A |
| ATOM | 66 | CA | MET | A | 20 | 51.529 | 18.134 | 49.397 | 1.00 | 40.71 | A |
| ATOM | 67 | CB | MET | A | 20 | 51.932 | 17.320 | 48.167 | 1.00 | 37.11 | A |
| ATOM | 68 | CG | MET | A | 20 | 52.702 | 18.147 | 47.140 | 1.00 | 37.11 | A |
| ATOM | 69 | SD | MET | A | 20 | 53.466 | 17.123 | 45.859 | 1.00 | 37.11 | A |
| ATOM | 70 | CE | MET | A | 20 | 54.894 | 16.449 | 46.755 | 1.00 | 37.11 | A |
| ATOM | 71 | C | MET | A | 20 | 50.455 | 17.415 | 50.201 | 1.00 | 40.71 | A |
| ATOM | 72 | O | MET | A | 20 | 49.265 | 17.732 | 50.088 | 1.00 | 40.71 | A |
| ATOM | 73 | N | VAL | A | 21 | 50.873 | 16.456 | 51.020 | 1.00 | 34.62 | A |
| ATOM | 74 | CA | VAL | A | 21 | 49.920 | 15.737 | 51.845 | 1.00 | 34.62 | A |
| ATOM | 75 | CB | VAL | A | 21 | 50.623 | 14.669 | 52.700 | 1.00 | 33.69 | A |
| ATOM | 76 | CG1 | VAL | A | 21 | 49.651 | 14.074 | 53.696 | 1.00 | 33.69 | A |
| ATOM | 77 | CG2 | VAL | A | 21 | 51.181 | 13.583 | 51.798 | 1.00 | 33.69 | A |
| ATOM | 78 | C | VAL | A | 21 | 49.240 | 16.760 | 52.755 | 1.00 | 34.62 | A |
| ATOM | 79 | O | VAL | A | 21 | 48.009 | 16.759 | 52.909 | 1.00 | 34.62 | A |
| ATOM | 80 | N | ASN | A | 22 | 50.041 | 17.652 | 53.336 | 1.00 | 31.08 | A |
| ATOM | 81 | CA | ASN | A | 22 | 49.489 | 18.656 | 54.230 | 1.00 | 31.08 | A |
| ATOM | 82 | CB | ASN | A | 22 | 50.576 | 19.546 | 54.827 | 1.00 | 26.87 | A |
| ATOM | 83 | CG | ASN | A | 22 | 50.032 | 20.418 | 55.951 | 1.00 | 26.87 | A |
| ATOM | 84 | OD1 | ASN | A | 22 | 49.760 | 19.919 | 57.052 | 1.00 | 26.87 | A |
| ATOM | 85 | ND2 | ASN | A | 22 | 49.830 | 21.713 | 55.672 | 1.00 | 26.87 | A |
| ATOM | 86 | C | ASN | A | 22 | 48.457 | 19.556 | 53.555 | 1.00 | 31.08 | A |
| ATOM | 87 | O | ASN | A | 22 | 47.397 | 19.850 | 54.130 | 1.00 | 31.08 | A |
| ATOM | 88 | N | GLN | A | 23 | 48.765 | 20.015 | 52.349 | 1.00 | 22.48 | A |
| ATOM | 89 | CA | GLN | A | 23 | 47.828 | 20.871 | 51.670 | 1.00 | 22.48 | A |
| ATOM | 90 | CB | GLN | A | 23 | 48.401 | 21.383 | 50.354 | 1.00 | 42.54 | A |
| ATOM | 91 | CG | GLN | A | 23 | 49.576 | 22.309 | 50.520 | 1.00 | 42.54 | A |
| ATOM | 92 | CD | GLN | A | 23 | 49.739 | 23.255 | 49.337 | 1.00 | 42.54 | A |

Fig. 2A

| | | | | | | | | | |
|---|---|---|---|---|---|---|---|---|---|
| ATOM | 93 | OE1 | GLN | A | 23 | 49.522 | 22.876 | 48.173 | 1.00 42.54 | A |
| ATOM | 94 | NE2 | GLN | A | 23 | 50.132 | 24.498 | 49.629 | 1.00 42.54 | A |
| ATOM | 95 | C | GLN | A | 23 | 46.528 | 20.110 | 51.432 | 1.00 22.48 | A |
| ATOM | 96 | O | GLN | A | 23 | 45.447 | 20.683 | 51.600 | 1.00 22.48 | A |
| ATOM | 97 | N | LYS | A | 24 | 46.616 | 18.829 | 51.064 | 1.00 27.17 | A |
| ATOM | 98 | CA | LYS | A | 24 | 45.393 | 18.068 | 50.835 | 1.00 27.17 | A |
| ATOM | 99 | CB | LYS | A | 24 | 45.693 | 16.643 | 50.362 | 1.00 41.13 | A |
| ATOM | 100 | CG | LYS | A | 24 | 44.450 | 15.943 | 49.835 | 1.00 41.13 | A |
| ATOM | 101 | CD | LYS | A | 24 | 44.684 | 14.486 | 49.469 | 1.00 41.13 | A |
| ATOM | 102 | CE | LYS | A | 24 | 43.406 | 13.866 | 48.908 | 1.00 41.13 | A |
| ATOM | 103 | NZ | LYS | A | 24 | 43.411 | 12.372 | 49.000 | 1.00 41.13 | A |
| ATOM | 104 | C | LYS | A | 24 | 44.595 | 18.021 | 52.144 | 1.00 27.17 | A |
| ATOM | 105 | O | LYS | A | 24 | 43.381 | 18.296 | 52.151 | 1.00 27.17 | A |
| ATOM | 106 | N | LYS | A | 25 | 45.274 | 17.696 | 53.248 | 1.00 23.70 | A |
| ATOM | 107 | CA | LYS | A | 25 | 44.588 | 17.631 | 54.536 | 1.00 23.70 | A |
| ATOM | 108 | CB | LYS | A | 25 | 45.565 | 17.431 | 55.704 | 1.00 36.11 | A |
| ATOM | 109 | CG | LYS | A | 25 | 44.843 | 17.459 | 57.063 | 1.00 36.11 | A |
| ATOM | 110 | CD | LYS | A | 25 | 45.789 | 17.520 | 58.266 | 1.00 36.11 | A |
| ATOM | 111 | CE | LYS | A | 25 | 46.615 | 18.813 | 58.323 | 1.00 36.11 | A |
| ATOM | 112 | NZ | LYS | A | 25 | 45.775 | 20.034 | 58.447 | 1.00 36.11 | A |
| ATOM | 113 | C | LYS | A | 25 | 43.811 | 18.928 | 54.762 | 1.00 23.70 | A |
| ATOM | 114 | O | LYS | A | 25 | 42.604 | 18.904 | 55.046 | 1.00 23.70 | A |
| ATOM | 115 | N | ASP | A | 26 | 44.509 | 20.055 | 54.620 | 1.00 27.62 | A |
| ATOM | 116 | CA | ASP | A | 26 | 43.892 | 21.359 | 54.822 | 1.00 27.62 | A |
| ATOM | 117 | CB | ASP | A | 26 | 44.909 | 22.477 | 54.572 | 1.00 48.95 | A |
| ATOM | 118 | CG | ASP | A | 26 | 45.908 | 22.639 | 55.721 | 1.00 48.95 | A |
| ATOM | 119 | OD1 | ASP | A | 26 | 46.897 | 23.399 | 55.548 | 1.00 48.95 | A |
| ATOM | 120 | OD2 | ASP | A | 26 | 45.706 | 22.016 | 56.791 | 1.00 48.95 | A |
| ATOM | 121 | C | ASP | A | 26 | 42.656 | 21.576 | 53.959 | 1.00 27.62 | A |
| ATOM | 122 | O | ASP | A | 26 | 41.662 | 22.114 | 54.448 | 1.00 27.62 | A |
| ATOM | 123 | N | ARG | A | 27 | 42.708 | 21.168 | 52.685 | 1.00 22.30 | A |
| ATOM | 124 | CA | ARG | A | 27 | 41.563 | 21.343 | 51.798 | 1.00 22.30 | A |
| ATOM | 125 | CB | ARG | A | 27 | 41.952 | 21.014 | 50.354 | 1.00 52.90 | A |
| ATOM | 126 | CG | ARG | A | 27 | 42.798 | 22.123 | 49.697 | 1.00 52.90 | A |
| ATOM | 127 | CD | ARG | A | 27 | 43.108 | 21.870 | 48.208 | 1.00 52.90 | A |
| ATOM | 128 | NE | ARG | A | 27 | 44.493 | 21.445 | 47.986 | 1.00 52.90 | A |
| ATOM | 129 | CZ | ARG | A | 27 | 44.883 | 20.184 | 47.786 | 1.00 52.90 | A |
| ATOM | 130 | NH1 | ARG | A | 27 | 43.994 | 19.196 | 47.771 | 1.00 52.90 | A |
| ATOM | 131 | NH2 | ARG | A | 27 | 46.169 | 19.908 | 47.600 | 1.00 52.90 | A |
| ATOM | 132 | C | ARG | A | 27 | 40.388 | 20.484 | 52.284 | 1.00 22.30 | A |
| ATOM | 133 | O | ARG | A | 27 | 39.249 | 20.970 | 52.381 | 1.00 22.30 | A |
| ATOM | 134 | N | LEU | A | 28 | 40.668 | 19.226 | 52.625 | 1.00 28.23 | A |
| ATOM | 135 | CA | LEU | A | 28 | 39.628 | 18.342 | 53.124 | 1.00 28.23 | A |
| ATOM | 136 | CB | LEU | A | 28 | 40.204 | 16.951 | 53.384 | 1.00 19.62 | A |
| ATOM | 137 | CG | LEU | A | 28 | 40.644 | 16.188 | 52.133 | 1.00 19.62 | A |
| ATOM | 138 | CD1 | LEU | A | 28 | 41.264 | 14.854 | 52.538 | 1.00 19.62 | A |
| ATOM | 139 | CD2 | LEU | A | 28 | 39.431 | 15.979 | 51.225 | 1.00 19.62 | A |
| ATOM | 140 | C | LEU | A | 28 | 39.108 | 18.939 | 54.421 | 1.00 28.23 | A |

Fig. 2B

| ATOM | 141 | O | LEU | A | 28 | 37.902 | 19.103 | 54.606 | 1.00 | 28.23 | A |
| ATOM | 142 | N | LEU | A | 29 | 40.041 | 19.271 | 55.310 | 1.00 | 32.81 | A |
| ATOM | 143 | CA | LEU | A | 29 | 39.723 | 19.844 | 56.610 | 1.00 | 32.81 | A |
| ATOM | 144 | CB | LEU | A | 29 | 41.009 | 20.264 | 57.301 | 1.00 | 30.88 | A |
| ATOM | 145 | CG | LEU | A | 29 | 40.893 | 20.746 | 58.740 | 1.00 | 30.88 | A |
| ATOM | 146 | CD1 | LEU | A | 29 | 39.898 | 19.883 | 59.510 | 1.00 | 30.88 | A |
| ATOM | 147 | CD2 | LEU | A | 29 | 42.282 | 20.693 | 59.379 | 1.00 | 30.88 | A |
| ATOM | 148 | C | LEU | A | 29 | 38.794 | 21.038 | 56.471 | 1.00 | 32.81 | A |
| ATOM | 149 | O | LEU | A | 29 | 37.873 | 21.226 | 57.273 | 1.00 | 32.81 | A |
| ATOM | 150 | N | ASN | A | 30 | 39.030 | 21.839 | 55.437 | 1.00 | 33.15 | A |
| ATOM | 151 | CA | ASN | A | 30 | 38.206 | 23.010 | 55.202 | 1.00 | 33.15 | A |
| ATOM | 152 | CB | ASN | A | 30 | 38.812 | 23.879 | 54.106 | 1.00 | 37.23 | A |
| ATOM | 153 | CG | ASN | A | 30 | 38.967 | 25.325 | 54.527 | 1.00 | 37.23 | A |
| ATOM | 154 | OD1 | ASN | A | 30 | 39.241 | 26.196 | 53.706 | 1.00 | 37.23 | A |
| ATOM | 155 | ND2 | ASN | A | 30 | 38.805 | 25.587 | 55.813 | 1.00 | 37.23 | A |
| ATOM | 156 | C | ASN | A | 30 | 36.791 | 22.614 | 54.813 | 1.00 | 33.15 | A |
| ATOM | 157 | O | ASN | A | 30 | 35.847 | 23.304 | 55.156 | 1.00 | 33.15 | A |
| ATOM | 158 | N | GLU | A | 31 | 36.643 | 21.499 | 54.106 | 1.00 | 45.74 | A |
| ATOM | 159 | CA | GLU | A | 31 | 35.320 | 21.055 | 53.681 | 1.00 | 45.74 | A |
| ATOM | 160 | CB | GLU | A | 31 | 35.443 | 20.018 | 52.573 | 1.00 | 111.71 | A |
| ATOM | 161 | CG | GLU | A | 31 | 36.048 | 20.569 | 51.302 | 1.00 | 111.71 | A |
| ATOM | 162 | CD | GLU | A | 31 | 36.235 | 19.500 | 50.255 | 1.00 | 111.71 | A |
| ATOM | 163 | OE1 | GLU | A | 31 | 35.229 | 18.863 | 49.877 | 1.00 | 111.71 | A |
| ATOM | 164 | OE2 | GLU | A | 31 | 37.385 | 19.292 | 49.813 | 1.00 | 111.71 | A |
| ATOM | 165 | C | GLU | A | 31 | 34.502 | 20.493 | 54.829 | 1.00 | 45.74 | A |
| ATOM | 166 | O | GLU | A | 31 | 33.325 | 20.802 | 54.962 | 1.00 | 45.74 | A |
| ATOM | 167 | N | TYR | A | 32 | 35.119 | 19.677 | 55.668 | 1.00 | 43.75 | A |
| ATOM | 168 | CA | TYR | A | 32 | 34.393 | 19.110 | 56.790 | 1.00 | 43.75 | A |
| ATOM | 169 | CB | TYR | A | 32 | 35.171 | 17.926 | 57.355 | 1.00 | 50.30 | A |
| ATOM | 170 | CG | TYR | A | 32 | 35.296 | 16.793 | 56.364 | 1.00 | 50.30 | A |
| ATOM | 171 | CD1 | TYR | A | 32 | 36.534 | 16.445 | 55.823 | 1.00 | 50.30 | A |
| ATOM | 172 | CE1 | TYR | A | 32 | 36.646 | 15.423 | 54.881 | 1.00 | 50.30 | A |
| ATOM | 173 | CD2 | TYR | A | 32 | 34.168 | 16.089 | 55.941 | 1.00 | 50.30 | A |
| ATOM | 174 | CE2 | TYR | A | 32 | 34.264 | 15.069 | 55.001 | 1.00 | 50.30 | A |
| ATOM | 175 | CZ | TYR | A | 32 | 35.506 | 14.740 | 54.471 | 1.00 | 50.30 | A |
| ATOM | 176 | OH | TYR | A | 32 | 35.601 | 13.741 | 53.520 | 1.00 | 50.30 | A |
| ATOM | 177 | C | TYR | A | 32 | 34.117 | 20.154 | 57.876 | 1.00 | 43.75 | A |
| ATOM | 178 | O | TYR | A | 32 | 33.278 | 19.951 | 58.746 | 1.00 | 43.75 | A |
| ATOM | 179 | N | LEU | A | 33 | 34.806 | 21.286 | 57.805 | 1.00 | 31.02 | A |
| ATOM | 180 | CA | LEU | A | 33 | 34.628 | 22.343 | 58.785 | 1.00 | 31.02 | A |
| ATOM | 181 | CB | LEU | A | 33 | 35.933 | 23.120 | 58.969 | 1.00 | 26.92 | A |
| ATOM | 182 | CG | LEU | A | 33 | 36.988 | 22.548 | 59.905 | 1.00 | 26.92 | A |
| ATOM | 183 | CD1 | LEU | A | 33 | 38.137 | 23.523 | 59.973 | 1.00 | 26.92 | A |
| ATOM | 184 | CD2 | LEU | A | 33 | 36.399 | 22.324 | 61.291 | 1.00 | 26.92 | A |
| ATOM | 185 | C | LEU | A | 33 | 33.529 | 23.327 | 58.397 | 1.00 | 31.02 | A |
| ATOM | 186 | O | LEU | A | 33 | 32.846 | 23.877 | 59.266 | 1.00 | 31.02 | A |
| ATOM | 187 | N | SER | A | 34 | 33.379 | 23.561 | 57.094 | 1.00 | 47.63 | A |
| ATOM | 188 | CA | SER | A | 34 | 32.380 | 24.498 | 56.584 | 1.00 | 47.63 | A |

Fig. 2C

```
ATOM    189  CB   SER A  34     32.121  24.237  55.097  1.00 75.10      A
ATOM    190  OG   SER A  34     31.147  25.133  54.585  1.00 75.10      A
ATOM    191  C    SER A  34     31.053  24.459  57.353  1.00 47.63      A
ATOM    192  O    SER A  34     30.504  25.507  57.706  1.00 47.63      A
ATOM    193  N    PRO A  35     30.528  23.249  57.632  1.00 43.33      A
ATOM    194  CD   PRO A  35     31.030  21.949  57.157  1.00 63.21      A
ATOM    195  CA   PRO A  35     29.263  23.069  58.359  1.00 43.33      A
ATOM    196  CB   PRO A  35     29.049  21.559  58.317  1.00 63.21      A
ATOM    197  CG   PRO A  35     29.764  21.146  57.072  1.00 63.21      A
ATOM    198  C    PRO A  35     29.293  23.578  59.794  1.00 43.33      A
ATOM    199  O    PRO A  35     28.296  23.501  60.504  1.00 43.33      A
ATOM    200  N    LEU A  36     30.441  24.090  60.222  1.00 41.82      A
ATOM    201  CA   LEU A  36     30.587  24.589  61.587  1.00 41.82      A
ATOM    202  CB   LEU A  36     31.673  23.792  62.320  1.00 53.45      A
ATOM    203  CG   LEU A  36     31.335  23.115  63.659  1.00 53.45      A
ATOM    204  CD1  LEU A  36     32.514  22.238  64.077  1.00 53.45      A
ATOM    205  CD2  LEU A  36     31.026  24.153  64.741  1.00 53.45      A
ATOM    206  C    LEU A  36     30.925  26.078  61.636  1.00 41.82      A
ATOM    207  O    LEU A  36     31.226  26.612  62.700  1.00 41.82      A
ATOM    208  N    ASP A  37     30.878  26.750  60.489  1.00 34.90      A
ATOM    209  CA   ASP A  37     31.178  28.176  60.451  1.00 34.90      A
ATOM    210  CB   ASP A  37     30.202  28.950  61.337  1.00 88.32      A
ATOM    211  CG   ASP A  37     29.042  29.523  60.558  1.00 88.32      A
ATOM    212  OD1  ASP A  37     29.289  30.383  59.684  1.00 88.32      A
ATOM    213  OD2  ASP A  37     27.888  29.115  60.816  1.00 88.32      A
ATOM    214  C    ASP A  37     32.606  28.506  60.883  1.00 34.90      A
ATOM    215  O    ASP A  37     32.828  29.476  61.610  1.00 34.90      A
ATOM    216  N    ILE A  38     33.570  27.702  60.442  1.00 28.88      A
ATOM    217  CA   ILE A  38     34.964  27.952  60.779  1.00 28.88      A
ATOM    218  CB   ILE A  38     35.350  27.274  62.108  1.00 20.06      A
ATOM    219  CG2  ILE A  38     35.702  25.822  61.878  1.00 20.06      A
ATOM    220  CG1  ILE A  38     36.545  28.010  62.722  1.00 20.06      A
ATOM    221  CD1  ILE A  38     37.305  27.243  63.816  1.00 20.06      A
ATOM    222  C    ILE A  38     35.896  27.461  59.663  1.00 28.88      A
ATOM    223  O    ILE A  38     35.651  26.422  59.041  1.00 28.88      A
ATOM    224  N    THR A  39     36.959  28.215  59.399  1.00 29.25      A
ATOM    225  CA   THR A  39     37.904  27.840  58.349  1.00 29.25      A
ATOM    226  CB   THR A  39     38.426  29.068  57.605  1.00  9.47      A
ATOM    227  OG1  THR A  39     39.300  29.807  58.477  1.00  9.47      A
ATOM    228  CG2  THR A  39     37.291  29.959  57.169  1.00  9.47      A
ATOM    229  C    THR A  39     39.127  27.121  58.923  1.00 29.25      A
ATOM    230  O    THR A  39     39.458  27.278  60.101  1.00 29.25      A
ATOM    231  N    ALA A  40     39.801  26.347  58.078  1.00 29.21      A
ATOM    232  CA   ALA A  40     40.994  25.610  58.480  1.00 29.21      A
ATOM    233  CB   ALA A  40     41.616  24.918  57.280  1.00  1.00      A
ATOM    234  C    ALA A  40     42.010  26.565  59.080  1.00 29.21      A
ATOM    235  O    ALA A  40     42.684  26.245  60.064  1.00 29.21      A
ATOM    236  N    ALA A  41     42.129  27.740  58.476  1.00 28.55      A
```

Fig. 2D

```
ATOM   237  CA   ALA A  41      43.087  28.719  58.972  1.00 28.55           A
ATOM   238  CB   ALA A  41      43.012  30.003  58.145  1.00 30.67           A
ATOM   239  C    ALA A  41      42.801  29.025  60.442  1.00 28.55           A
ATOM   240  O    ALA A  41      43.675  28.890  61.309  1.00 28.55           A
ATOM   241  N    GLN A  42      41.567  29.430  60.717  1.00 23.69           A
ATOM   242  CA   GLN A  42      41.180  29.775  62.069  1.00 23.69           A
ATOM   243  CB   GLN A  42      39.712  30.183  62.088  1.00 31.90           A
ATOM   244  CG   GLN A  42      39.421  31.267  61.070  1.00 31.90           A
ATOM   245  CD   GLN A  42      37.966  31.641  61.012  1.00 31.90           A
ATOM   246  OE1  GLN A  42      37.092  30.776  60.997  1.00 31.90           A
ATOM   247  NE2  GLN A  42      37.692  32.938  60.967  1.00 31.90           A
ATOM   248  C    GLN A  42      41.417  28.596  62.988  1.00 23.69           A
ATOM   249  O    GLN A  42      42.026  28.730  64.058  1.00 23.69           A
ATOM   250  N    PHE A  43      40.949  27.429  62.561  1.00 20.02           A
ATOM   251  CA   PHE A  43      41.099  26.232  63.368  1.00 20.02           A
ATOM   252  CB   PHE A  43      40.441  25.042  62.665  1.00 21.86           A
ATOM   253  CG   PHE A  43      40.607  23.738  63.394  1.00 21.86           A
ATOM   254  CD1  PHE A  43      40.118  23.582  64.692  1.00 21.86           A
ATOM   255  CD2  PHE A  43      41.250  22.659  62.778  1.00 21.86           A
ATOM   256  CE1  PHE A  43      40.264  22.368  65.375  1.00 21.86           A
ATOM   257  CE2  PHE A  43      41.402  21.441  63.448  1.00 21.86           A
ATOM   258  CZ   PHE A  43      40.907  21.293  64.754  1.00 21.86           A
ATOM   259  C    PHE A  43      42.575  25.962  63.646  1.00 20.02           A
ATOM   260  O    PHE A  43      42.946  25.641  64.776  1.00 20.02           A
ATOM   261  N    LYS A  44      43.425  26.105  62.632  1.00 25.04           A
ATOM   262  CA   LYS A  44      44.856  25.883  62.839  1.00 25.04           A
ATOM   263  CB   LYS A  44      45.648  26.125  61.550  1.00 46.29           A
ATOM   264  CG   LYS A  44      45.596  24.991  60.552  1.00 46.29           A
ATOM   265  CD   LYS A  44      46.639  25.210  59.467  1.00 46.29           A
ATOM   266  CE   LYS A  44      46.797  23.984  58.585  1.00 46.29           A
ATOM   267  NZ   LYS A  44      48.034  24.060  57.757  1.00 46.29           A
ATOM   268  C    LYS A  44      45.402  26.802  63.940  1.00 25.04           A
ATOM   269  O    LYS A  44      46.092  26.334  64.861  1.00 25.04           A
ATOM   270  N    VAL A  45      45.103  28.102  63.836  1.00 24.20           A
ATOM   271  CA   VAL A  45      45.563  29.073  64.830  1.00 24.20           A
ATOM   272  CB   VAL A  45      45.056  30.508  64.511  1.00 17.46           A
ATOM   273  CG1  VAL A  45      45.349  31.440  65.670  1.00 17.46           A
ATOM   274  CG2  VAL A  45      45.736  31.036  63.238  1.00 17.46           A
ATOM   275  C    VAL A  45      45.053  28.665  66.213  1.00 24.20           A
ATOM   276  O    VAL A  45      45.818  28.590  67.183  1.00 24.20           A
ATOM   277  N    LEU A  46      43.755  28.398  66.294  1.00 22.98           A
ATOM   278  CA   LEU A  46      43.144  27.979  67.542  1.00 22.98           A
ATOM   279  CB   LEU A  46      41.701  27.570  67.277  1.00 18.73           A
ATOM   280  CG   LEU A  46      40.618  28.396  67.970  1.00 18.73           A
ATOM   281  CD1  LEU A  46      40.946  29.880  67.928  1.00 18.73           A
ATOM   282  CD2  LEU A  46      39.276  28.083  67.296  1.00 18.73           A
ATOM   283  C    LEU A  46      43.918  26.808  68.170  1.00 22.98           A
ATOM   284  O    LEU A  46      44.198  26.809  69.374  1.00 22.98           A
```

Fig. 2E

| ATOM | 285 | N | CYS A | 47 | 44.276 | 25.816 | 67.356 | 1.00 | 25.10 | A |
|------|-----|-----|-------|----|--------|--------|--------|------|-------|---|
| ATOM | 286 | CA | CYS A | 47 | 45.027 | 24.657 | 67.853 | 1.00 | 25.10 | A |
| ATOM | 287 | CB | CYS A | 47 | 45.147 | 23.588 | 66.764 | 1.00 | 37.95 | A |
| ATOM | 288 | SG | CYS A | 47 | 43.614 | 22.685 | 66.463 | 1.00 | 37.95 | A |
| ATOM | 289 | C | CYS A | 47 | 46.426 | 24.997 | 68.367 | 1.00 | 25.10 | A |
| ATOM | 290 | O | CYS A | 47 | 46.885 | 24.424 | 69.350 | 1.00 | 25.10 | A |
| ATOM | 291 | N | SER A | 48 | 47.113 | 25.920 | 67.703 | 1.00 | 26.62 | A |
| ATOM | 292 | CA | SER A | 48 | 48.460 | 26.286 | 68.128 | 1.00 | 26.62 | A |
| ATOM | 293 | CB | SER A | 48 | 49.082 | 27.220 | 67.100 | 1.00 | 43.10 | A |
| ATOM | 294 | OG | SER A | 48 | 49.034 | 26.614 | 65.824 | 1.00 | 43.10 | A |
| ATOM | 295 | C | SER A | 48 | 48.423 | 26.954 | 69.502 | 1.00 | 26.62 | A |
| ATOM | 296 | O | SER A | 48 | 49.246 | 26.667 | 70.385 | 1.00 | 26.62 | A |
| ATOM | 297 | N | ILE A | 49 | 47.459 | 27.850 | 69.678 | 1.00 | 23.50 | A |
| ATOM | 298 | CA | ILE A | 49 | 47.301 | 28.534 | 70.946 | 1.00 | 23.50 | A |
| ATOM | 299 | CB | ILE A | 49 | 46.226 | 29.642 | 70.852 | 1.00 | 14.67 | A |
| ATOM | 300 | CG2 | ILE A | 49 | 45.970 | 30.242 | 72.234 | 1.00 | 14.67 | A |
| ATOM | 301 | CG1 | ILE A | 49 | 46.683 | 30.720 | 69.857 | 1.00 | 14.67 | A |
| ATOM | 302 | CD1 | ILE A | 49 | 45.560 | 31.560 | 69.315 | 1.00 | 14.67 | A |
| ATOM | 303 | C | ILE A | 49 | 46.906 | 27.512 | 72.016 | 1.00 | 23.50 | A |
| ATOM | 304 | O | ILE A | 49 | 47.507 | 27.476 | 73.092 | 1.00 | 23.50 | A |
| ATOM | 305 | N | ARG A | 50 | 45.916 | 26.669 | 71.726 | 1.00 | 25.93 | A |
| ATOM | 306 | CA | ARG A | 50 | 45.505 | 25.671 | 72.713 | 1.00 | 25.93 | A |
| ATOM | 307 | CB | ARG A | 50 | 44.391 | 24.766 | 72.189 | 1.00 | 51.02 | A |
| ATOM | 308 | CG | ARG A | 50 | 44.109 | 23.617 | 73.147 | 1.00 | 51.02 | A |
| ATOM | 309 | CD | ARG A | 50 | 42.736 | 23.006 | 72.969 | 1.00 | 51.02 | A |
| ATOM | 310 | NE | ARG A | 50 | 42.773 | 21.759 | 72.211 | 1.00 | 51.02 | A |
| ATOM | 311 | CZ | ARG A | 50 | 41.765 | 20.890 | 72.165 | 1.00 | 51.02 | A |
| ATOM | 312 | NH1 | ARG A | 50 | 40.645 | 21.142 | 72.839 | 1.00 | 51.02 | A |
| ATOM | 313 | NH2 | ARG A | 50 | 41.872 | 19.772 | 71.449 | 1.00 | 51.02 | A |
| ATOM | 314 | C | ARG A | 50 | 46.678 | 24.791 | 73.124 | 1.00 | 25.93 | A |
| ATOM | 315 | O | ARG A | 50 | 46.873 | 24.491 | 74.307 | 1.00 | 25.93 | A |
| ATOM | 316 | N | CYS A | 51 | 47.459 | 24.373 | 72.138 | 1.00 | 40.32 | A |
| ATOM | 317 | CA | CYS A | 51 | 48.597 | 23.523 | 72.411 | 1.00 | 40.32 | A |
| ATOM | 318 | CB | CYS A | 51 | 49.253 | 23.092 | 71.107 | 1.00 | 66.88 | A |
| ATOM | 319 | SG | CYS A | 51 | 50.555 | 21.891 | 71.373 | 1.00 | 66.88 | A |
| ATOM | 320 | C | CYS A | 51 | 49.609 | 24.233 | 73.303 | 1.00 | 40.32 | A |
| ATOM | 321 | O | CYS A | 51 | 50.189 | 23.621 | 74.192 | 1.00 | 40.32 | A |
| ATOM | 322 | N | ALA A | 52 | 49.805 | 25.528 | 73.076 | 1.00 | 38.59 | A |
| ATOM | 323 | CA | ALA A | 52 | 50.757 | 26.304 | 73.866 | 1.00 | 38.59 | A |
| ATOM | 324 | CB | ALA A | 52 | 51.221 | 27.516 | 73.067 | 1.00 | 22.10 | A |
| ATOM | 325 | C | ALA A | 52 | 50.193 | 26.770 | 75.209 | 1.00 | 38.59 | A |
| ATOM | 326 | O | ALA A | 52 | 50.948 | 27.036 | 76.145 | 1.00 | 38.59 | A |
| ATOM | 327 | N | ALA A | 53 | 48.869 | 26.876 | 75.291 | 1.00 | 28.02 | A |
| ATOM | 328 | CA | ALA A | 53 | 48.184 | 27.343 | 76.498 | 1.00 | 28.02 | A |
| ATOM | 329 | CB | ALA A | 53 | 48.779 | 26.719 | 77.746 | 1.00 | 8.31 | A |
| ATOM | 330 | C | ALA A | 53 | 48.266 | 28.857 | 76.597 | 1.00 | 28.02 | A |
| ATOM | 331 | O | ALA A | 53 | 47.250 | 29.519 | 76.808 | 1.00 | 28.02 | A |
| ATOM | 332 | N | CYS A | 54 | 49.475 | 29.399 | 76.451 | 1.00 | 17.61 | A |

Fig. 2F

```
ATOM    333  CA   CYS A  54      49.706  30.850  76.508  1.00 17.61           A
ATOM    334  CB   CYS A  54      49.977  31.291  77.939  1.00 33.17           A
ATOM    335  SG   CYS A  54      49.981  33.078  78.102  1.00 33.17           A
ATOM    336  C    CYS A  54      50.918  31.140  75.628  1.00 17.61           A
ATOM    337  O    CYS A  54      51.918  30.424  75.698  1.00 17.61           A
ATOM    338  N    ILE A  55      50.856  32.185  74.811  1.00 19.43           A
ATOM    339  CA   ILE A  55      51.969  32.434  73.889  1.00 19.43           A
ATOM    340  CB   ILE A  55      51.881  31.396  72.727  1.00 24.10           A
ATOM    341  CG2  ILE A  55      50.660  31.703  71.856  1.00 24.10           A
ATOM    342  CG1  ILE A  55      53.142  31.411  71.865  1.00 24.10           A
ATOM    343  CD1  ILE A  55      53.142  30.324  70.750  1.00 24.10           A
ATOM    344  C    ILE A  55      51.977  33.858  73.309  1.00 19.43           A
ATOM    345  O    ILE A  55      50.928  34.492  73.181  1.00 19.43           A
ATOM    346  N    THR A  56      53.157  34.359  72.957  1.00 31.11           A
ATOM    347  CA   THR A  56      53.253  35.704  72.396  1.00 31.11           A
ATOM    348  CB   THR A  56      54.633  36.338  72.605  1.00 27.01           A
ATOM    349  OG1  THR A  56      55.611  35.560  71.903  1.00 27.01           A
ATOM    350  CG2  THR A  56      54.995  36.395  74.081  1.00 27.01           A
ATOM    351  C    THR A  56      53.041  35.598  70.898  1.00 31.11           A
ATOM    352  O    THR A  56      53.252  34.532  70.306  1.00 31.11           A
ATOM    353  N    PRO A  57      52.621  36.701  70.257  1.00 39.22           A
ATOM    354  CD   PRO A  57      52.134  37.964  70.836  1.00 28.66           A
ATOM    355  CA   PRO A  57      52.392  36.688  68.816  1.00 39.22           A
ATOM    356  CB   PRO A  57      51.892  38.098  68.541  1.00 28.66           A
ATOM    357  CG   PRO A  57      51.148  38.419  69.793  1.00 28.66           A
ATOM    358  C    PRO A  57      53.653  36.357  68.038  1.00 39.22           A
ATOM    359  O    PRO A  57      53.606  35.641  67.037  1.00 39.22           A
ATOM    360  N    VAL A  58      54.788  36.878  68.485  1.00 41.76           A
ATOM    361  CA   VAL A  58      56.020  36.585  67.778  1.00 41.76           A
ATOM    362  CB   VAL A  58      57.233  37.319  68.397  1.00 36.94           A
ATOM    363  CG1  VAL A  58      58.538  36.680  67.928  1.00 36.94           A
ATOM    364  CG2  VAL A  58      57.211  38.777  67.969  1.00 36.94           A
ATOM    365  C    VAL A  58      56.263  35.086  67.800  1.00 41.76           A
ATOM    366  O    VAL A  58      56.427  34.469  66.748  1.00 41.76           A
ATOM    367  N    GLU A  59      56.259  34.497  68.994  1.00 42.87           A
ATOM    368  CA   GLU A  59      56.506  33.068  69.117  1.00 42.87           A
ATOM    369  CB   GLU A  59      56.554  32.665  70.588  1.00 79.89           A
ATOM    370  CG   GLU A  59      57.670  31.681  70.885  1.00 79.89           A
ATOM    371  CD   GLU A  59      59.000  32.113  70.274  1.00 79.89           A
ATOM    372  OE1  GLU A  59      59.378  33.295  70.431  1.00 79.89           A
ATOM    373  OE2  GLU A  59      59.672  31.269  69.641  1.00 79.89           A
ATOM    374  C    GLU A  59      55.466  32.235  68.374  1.00 42.87           A
ATOM    375  O    GLU A  59      55.738  31.096  67.974  1.00 42.87           A
ATOM    376  N    LEU A  60      54.280  32.802  68.171  1.00 30.72           A
ATOM    377  CA   LEU A  60      53.229  32.075  67.468  1.00 30.72           A
ATOM    378  CB   LEU A  60      51.842  32.625  67.818  1.00 25.76           A
ATOM    379  CG   LEU A  60      50.703  31.829  67.164  1.00 25.76           A
ATOM    380  CD1  LEU A  60      50.673  30.422  67.744  1.00 25.76           A
```

Fig. 2G

```
ATOM   381  CD2  LEU  A   60      49.367  32.514  67.412  1.00  25.76      A
ATOM   382  C    LEU  A   60      53.399  32.115  65.953  1.00  30.72      A
ATOM   383  O    LEU  A   60      53.043  31.160  65.262  1.00  30.72      A
ATOM   384  N    LYS  A   61      53.919  33.223  65.429  1.00  59.73      A
ATOM   385  CA   LYS  A   61      54.104  33.322  63.988  1.00  59.73      A
ATOM   386  CB   LYS  A   61      54.420  34.768  63.560  1.00  50.33      A
ATOM   387  CG   LYS  A   61      55.814  35.288  63.899  1.00  50.33      A
ATOM   388  CD   LYS  A   61      56.731  35.255  62.677  1.00  50.33      A
ATOM   389  CE   LYS  A   61      58.029  36.018  62.915  1.00  50.33      A
ATOM   390  NZ   LYS  A   61      58.852  35.406  63.994  1.00  50.33      A
ATOM   391  C    LYS  A   61      55.208  32.364  63.560  1.00  59.73      A
ATOM   392  O    LYS  A   61      55.184  31.844  62.448  1.00  59.73      A
ATOM   393  N    LYS  A   62      56.168  32.113  64.445  1.00  50.25      A
ATOM   394  CA   LYS  A   62      57.237  31.190  64.112  1.00  50.25      A
ATOM   395  CB   LYS  A   62      58.297  31.165  65.212  1.00  70.74      A
ATOM   396  CG   LYS  A   62      59.040  32.475  65.350  1.00  70.74      A
ATOM   397  CD   LYS  A   62      60.177  32.384  66.357  1.00  70.74      A
ATOM   398  CE   LYS  A   62      60.894  33.727  66.474  1.00  70.74      A
ATOM   399  NZ   LYS  A   62      62.121  33.639  67.314  1.00  70.74      A
ATOM   400  C    LYS  A   62      56.609  29.812  63.953  1.00  50.25      A
ATOM   401  O    LYS  A   62      56.801  29.144  62.938  1.00  50.25      A
ATOM   402  N    VAL  A   63      55.837  29.404  64.953  1.00  44.77      A
ATOM   403  CA   VAL  A   63      55.168  28.107  64.944  1.00  44.77      A
ATOM   404  CB   VAL  A   63      54.325  27.922  66.226  1.00  51.34      A
ATOM   405  CG1  VAL  A   63      53.707  26.543  66.249  1.00  51.34      A
ATOM   406  CG2  VAL  A   63      55.200  28.130  67.455  1.00  51.34      A
ATOM   407  C    VAL  A   63      54.268  27.913  63.720  1.00  44.77      A
ATOM   408  O    VAL  A   63      54.313  26.872  63.072  1.00  44.77      A
ATOM   409  N    LEU  A   64      53.447  28.908  63.405  1.00  32.87      A
ATOM   410  CA   LEU  A   64      52.553  28.821  62.248  1.00  32.87      A
ATOM   411  CB   LEU  A   64      51.406  29.836  62.367  1.00  41.38      A
ATOM   412  CG   LEU  A   64      50.173  29.587  63.236  1.00  41.38      A
ATOM   413  CD1  LEU  A   64      49.310  28.505  62.617  1.00  41.38      A
ATOM   414  CD2  LEU  A   64      50.606  29.195  64.630  1.00  41.38      A
ATOM   415  C    LEU  A   64      53.296  29.101  60.948  1.00  32.87      A
ATOM   416  O    LEU  A   64      52.736  28.918  59.870  1.00  32.87      A
ATOM   417  N    SER  A   65      54.548  29.548  61.047  1.00  42.60      A
ATOM   418  CA   SER  A   65      55.333  29.889  59.859  1.00  42.60      A
ATOM   419  CB   SER  A   65      55.719  28.626  59.081  1.00  59.96      A
ATOM   420  OG   SER  A   65      56.738  27.908  59.759  1.00  59.96      A
ATOM   421  C    SER  A   65      54.534  30.841  58.960  1.00  42.60      A
ATOM   422  O    SER  A   65      54.162  30.501  57.833  1.00  42.60      A
ATOM   423  N    VAL  A   66      54.266  32.037  59.473  1.00  37.30      A
ATOM   424  CA   VAL  A   66      53.515  33.026  58.721  1.00  37.30      A
ATOM   425  CB   VAL  A   66      51.992  32.916  59.032  1.00  65.92      A
ATOM   426  CG1  VAL  A   66      51.434  31.630  58.447  1.00  65.92      A
ATOM   427  CG2  VAL  A   66      51.754  32.927  60.533  1.00  65.92      A
ATOM   428  C    VAL  A   66      54.004  34.436  59.024  1.00  37.30      A
```

Fig. 2H

| ATOM | 429 | O | VAL | A | 66 | 54.865 | 34.641 | 59.894 | 1.00 | 37.30 | A |
| ATOM | 430 | N | ASP | A | 67 | 53.455 | 35.396 | 58.285 | 1.00 | 42.15 | A |
| ATOM | 431 | CA | ASP | A | 67 | 53.787 | 36.812 | 58.429 | 1.00 | 42.15 | A |
| ATOM | 432 | CB | ASP | A | 67 | 53.186 | 37.587 | 57.243 | 1.00 | 69.98 | A |
| ATOM | 433 | CG | ASP | A | 67 | 53.562 | 39.059 | 57.239 | 1.00 | 69.98 | A |
| ATOM | 434 | OD1 | ASP | A | 67 | 54.770 | 39.367 | 57.146 | 1.00 | 69.98 | A |
| ATOM | 435 | OD2 | ASP | A | 67 | 52.644 | 39.908 | 57.321 | 1.00 | 69.98 | A |
| ATOM | 436 | C | ASP | A | 67 | 53.194 | 37.304 | 59.753 | 1.00 | 42.15 | A |
| ATOM | 437 | O | ASP | A | 67 | 52.018 | 37.047 | 60.046 | 1.00 | 42.15 | A |
| ATOM | 438 | N | LEU | A | 68 | 54.006 | 37.995 | 60.551 | 1.00 | 43.19 | A |
| ATOM | 439 | CA | LEU | A | 68 | 53.542 | 38.516 | 61.836 | 1.00 | 43.19 | A |
| ATOM | 440 | CB | LEU | A | 68 | 54.655 | 39.303 | 62.521 | 1.00 | 28.99 | A |
| ATOM | 441 | CG | LEU | A | 68 | 54.292 | 39.876 | 63.890 | 1.00 | 28.99 | A |
| ATOM | 442 | CD1 | LEU | A | 68 | 53.785 | 38.755 | 64.802 | 1.00 | 28.99 | A |
| ATOM | 443 | CD2 | LEU | A | 68 | 55.507 | 40.546 | 64.507 | 1.00 | 28.99 | A |
| ATOM | 444 | C | LEU | A | 68 | 52.320 | 39.416 | 61.645 | 1.00 | 43.19 | A |
| ATOM | 445 | O | LEU | A | 68 | 51.379 | 39.404 | 62.452 | 1.00 | 43.19 | A |
| ATOM | 446 | N | GLY | A | 69 | 52.338 | 40.186 | 60.563 | 1.00 | 24.15 | A |
| ATOM | 447 | CA | GLY | A | 69 | 51.236 | 41.076 | 60.276 | 1.00 | 24.15 | A |
| ATOM | 448 | C | GLY | A | 69 | 49.977 | 40.315 | 59.920 | 1.00 | 24.15 | A |
| ATOM | 449 | O | GLY | A | 69 | 48.871 | 40.711 | 60.307 | 1.00 | 24.15 | A |
| ATOM | 450 | N | ALA | A | 70 | 50.122 | 39.227 | 59.172 | 1.00 | 34.42 | A |
| ATOM | 451 | CA | ALA | A | 70 | 48.949 | 38.434 | 58.799 | 1.00 | 34.42 | A |
| ATOM | 452 | CB | ALA | A | 70 | 49.316 | 37.387 | 57.762 | 1.00 | 25.53 | A |
| ATOM | 453 | C | ALA | A | 70 | 48.412 | 37.758 | 60.053 | 1.00 | 34.42 | A |
| ATOM | 454 | O | ALA | A | 70 | 47.199 | 37.606 | 60.225 | 1.00 | 34.42 | A |
| ATOM | 455 | N | LEU | A | 71 | 49.321 | 37.356 | 60.933 | 1.00 | 33.80 | A |
| ATOM | 456 | CA | LEU | A | 71 | 48.905 | 36.718 | 62.166 | 1.00 | 33.80 | A |
| ATOM | 457 | CB | LEU | A | 71 | 50.117 | 36.208 | 62.948 | 1.00 | 27.48 | A |
| ATOM | 458 | CG | LEU | A | 71 | 49.810 | 35.500 | 64.269 | 1.00 | 27.48 | A |
| ATOM | 459 | CD1 | LEU | A | 71 | 48.665 | 34.512 | 64.089 | 1.00 | 27.48 | A |
| ATOM | 460 | CD2 | LEU | A | 71 | 51.069 | 34.784 | 64.748 | 1.00 | 27.48 | A |
| ATOM | 461 | C | LEU | A | 71 | 48.136 | 37.726 | 63.003 | 1.00 | 33.80 | A |
| ATOM | 462 | O | LEU | A | 71 | 47.015 | 37.459 | 63.446 | 1.00 | 33.80 | A |
| ATOM | 463 | N | THR | A | 72 | 48.730 | 38.895 | 63.203 | 1.00 | 29.00 | A |
| ATOM | 464 | CA | THR | A | 72 | 48.082 | 39.914 | 64.008 | 1.00 | 29.00 | A |
| ATOM | 465 | CB | THR | A | 72 | 48.895 | 41.210 | 64.002 | 1.00 | 31.46 | A |
| ATOM | 466 | OG1 | THR | A | 72 | 50.117 | 40.983 | 64.719 | 1.00 | 31.46 | A |
| ATOM | 467 | CG2 | THR | A | 72 | 48.106 | 42.349 | 64.663 | 1.00 | 31.46 | A |
| ATOM | 468 | C | THR | A | 72 | 46.657 | 40.181 | 63.555 | 1.00 | 29.00 | A |
| ATOM | 469 | O | THR | A | 72 | 45.741 | 40.242 | 64.384 | 1.00 | 29.00 | A |
| ATOM | 470 | N | ARG | A | 73 | 46.460 | 40.333 | 62.249 | 1.00 | 39.42 | A |
| ATOM | 471 | CA | ARG | A | 73 | 45.120 | 40.580 | 61.728 | 1.00 | 39.42 | A |
| ATOM | 472 | CB | ARG | A | 73 | 45.136 | 40.709 | 60.204 | 1.00 | 68.23 | A |
| ATOM | 473 | CG | ARG | A | 73 | 45.743 | 41.993 | 59.689 | 1.00 | 68.23 | A |
| ATOM | 474 | CD | ARG | A | 73 | 45.392 | 42.203 | 58.226 | 1.00 | 68.23 | A |
| ATOM | 475 | NE | ARG | A | 73 | 46.042 | 43.386 | 57.676 | 1.00 | 68.23 | A |
| ATOM | 476 | CZ | ARG | A | 73 | 47.361 | 43.536 | 57.580 | 1.00 | 68.23 | A |

Fig. 2I

| | | | | | | | | | | |
|---|---|---|---|---|---|---|---|---|---|---|
| ATOM | 477 | NH1 | ARG | A | 73 | 48.180 | 42.576 | 57.999 | 1.00 68.23 | A |
| ATOM | 478 | NH2 | ARG | A | 73 | 47.868 | 44.651 | 57.064 | 1.00 68.23 | A |
| ATOM | 479 | C | ARG | A | 73 | 44.207 | 39.423 | 62.117 | 1.00 39.42 | A |
| ATOM | 480 | O | ARG | A | 73 | 43.056 | 39.630 | 62.507 | 1.00 39.42 | A |
| ATOM | 481 | N | MET | A | 74 | 44.733 | 38.207 | 62.006 | 1.00 34.55 | A |
| ATOM | 482 | CA | MET | A | 74 | 43.972 | 37.006 | 62.342 | 1.00 34.55 | A |
| ATOM | 483 | CB | MET | A | 74 | 44.764 | 35.751 | 61.921 | 1.00 18.52 | A |
| ATOM | 484 | CG | MET | A | 74 | 44.122 | 34.405 | 62.282 | 1.00 18.52 | A |
| ATOM | 485 | SD | MET | A | 74 | 42.438 | 34.164 | 61.672 | 1.00 18.52 | A |
| ATOM | 486 | CE | MET | A | 74 | 42.765 | 32.941 | 60.397 | 1.00 18.52 | A |
| ATOM | 487 | C | MET | A | 74 | 43.651 | 36.973 | 63.840 | 1.00 34.55 | A |
| ATOM | 488 | O | MET | A | 74 | 42.504 | 36.704 | 64.235 | 1.00 34.55 | A |
| ATOM | 489 | N | LEU | A | 75 | 44.656 | 37.247 | 64.675 | 1.00 29.89 | A |
| ATOM | 490 | CA | LEU | A | 75 | 44.429 | 37.251 | 66.115 | 1.00 29.89 | A |
| ATOM | 491 | CB | LEU | A | 75 | 45.728 | 37.581 | 66.870 | 1.00 15.40 | A |
| ATOM | 492 | CG | LEU | A | 75 | 46.720 | 36.410 | 66.867 | 1.00 15.40 | A |
| ATOM | 493 | CD1 | LEU | A | 75 | 48.069 | 36.851 | 67.405 | 1.00 15.40 | A |
| ATOM | 494 | CD2 | LEU | A | 75 | 46.141 | 35.244 | 67.689 | 1.00 15.40 | A |
| ATOM | 495 | C | LEU | A | 75 | 43.349 | 38.277 | 66.422 | 1.00 29.89 | A |
| ATOM | 496 | O | LEU | A | 75 | 42.408 | 37.996 | 67.171 | 1.00 29.89 | A |
| ATOM | 497 | N | ASP | A | 76 | 43.477 | 39.456 | 65.811 | 1.00 31.44 | A |
| ATOM | 498 | CA | ASP | A | 76 | 42.508 | 40.524 | 66.013 | 1.00 31.44 | A |
| ATOM | 499 | CB | ASP | A | 76 | 42.846 | 41.722 | 65.136 | 1.00 97.34 | A |
| ATOM | 500 | CG | ASP | A | 76 | 43.324 | 42.895 | 65.948 | 1.00 97.34 | A |
| ATOM | 501 | OD1 | ASP | A | 76 | 42.531 | 43.382 | 66.781 | 1.00 97.34 | A |
| ATOM | 502 | OD2 | ASP | A | 76 | 44.484 | 43.322 | 65.770 | 1.00 97.34 | A |
| ATOM | 503 | C | ASP | A | 76 | 41.096 | 40.053 | 65.734 | 1.00 31.44 | A |
| ATOM | 504 | O | ASP | A | 76 | 40.204 | 40.244 | 66.555 | 1.00 31.44 | A |
| ATOM | 505 | N | ARG | A | 77 | 40.898 | 39.416 | 64.586 | 1.00 31.21 | A |
| ATOM | 506 | CA | ARG | A | 77 | 39.576 | 38.914 | 64.217 | 1.00 31.21 | A |
| ATOM | 507 | CB | ARG | A | 77 | 39.600 | 38.275 | 62.818 | 1.00 77.50 | A |
| ATOM | 508 | CG | ARG | A | 77 | 40.061 | 39.194 | 61.696 | 1.00 77.50 | A |
| ATOM | 509 | CD | ARG | A | 77 | 39.341 | 38.870 | 60.393 | 1.00 77.50 | A |
| ATOM | 510 | NE | ARG | A | 77 | 39.526 | 37.486 | 59.971 | 1.00 77.50 | A |
| ATOM | 511 | CZ | ARG | A | 77 | 40.620 | 37.019 | 59.375 | 1.00 77.50 | A |
| ATOM | 512 | NH1 | ARG | A | 77 | 41.645 | 37.829 | 59.120 | 1.00 77.50 | A |
| ATOM | 513 | NH2 | ARG | A | 77 | 40.687 | 35.734 | 59.032 | 1.00 77.50 | A |
| ATOM | 514 | C | ARG | A | 77 | 39.088 | 37.878 | 65.233 | 1.00 31.21 | A |
| ATOM | 515 | O | ARG | A | 77 | 37.913 | 37.885 | 65.628 | 1.00 31.21 | A |
| ATOM | 516 | N | LEU | A | 78 | 39.998 | 36.994 | 65.654 | 1.00 31.76 | A |
| ATOM | 517 | CA | LEU | A | 78 | 39.657 | 35.945 | 66.608 | 1.00 31.76 | A |
| ATOM | 518 | CB | LEU | A | 78 | 40.786 | 34.916 | 66.696 | 1.00 22.72 | A |
| ATOM | 519 | CG | LEU | A | 78 | 41.060 | 34.145 | 65.394 | 1.00 22.72 | A |
| ATOM | 520 | CD1 | LEU | A | 78 | 42.129 | 33.095 | 65.622 | 1.00 22.72 | A |
| ATOM | 521 | CD2 | LEU | A | 78 | 39.769 | 33.474 | 64.917 | 1.00 22.72 | A |
| ATOM | 522 | C | LEU | A | 78 | 39.318 | 36.488 | 67.993 | 1.00 31.76 | A |
| ATOM | 523 | O | LEU | A | 78 | 38.544 | 35.876 | 68.730 | 1.00 31.76 | A |
| ATOM | 524 | N | VAL | A | 79 | 39.889 | 37.632 | 68.355 | 1.00 25.81 | A |

Fig. 2J

| | | | | | | | | | | |
|---|---|---|---|---|---|---|---|---|---|---|
| ATOM | 525 | CA | VAL | A | 79 | 39.568 | 38.209 | 69.649 | 1.00 25.81 | A |
| ATOM | 526 | CB | VAL | A | 79 | 40.581 | 39.316 | 70.056 | 1.00 14.52 | A |
| ATOM | 527 | CG1 | VAL | A | 79 | 40.103 | 40.047 | 71.328 | 1.00 14.52 | A |
| ATOM | 528 | CG2 | VAL | A | 79 | 41.977 | 38.675 | 70.305 | 1.00 14.52 | A |
| ATOM | 529 | C | VAL | A | 79 | 38.159 | 38.766 | 69.514 | 1.00 25.81 | A |
| ATOM | 530 | O | VAL | A | 79 | 37.359 | 38.688 | 70.447 | 1.00 25.81 | A |
| ATOM | 531 | N | CYS | A | 80 | 37.834 | 39.297 | 68.338 | 1.00 30.46 | A |
| ATOM | 532 | CA | CYS | A | 80 | 36.488 | 39.825 | 68.103 | 1.00 30.46 | A |
| ATOM | 533 | CB | CYS | A | 80 | 36.381 | 40.469 | 66.724 | 1.00 75.62 | A |
| ATOM | 534 | SG | CYS | A | 80 | 37.191 | 42.062 | 66.616 | 1.00 75.62 | A |
| ATOM | 535 | C | CYS | A | 80 | 35.454 | 38.718 | 68.217 | 1.00 30.46 | A |
| ATOM | 536 | O | CYS | A | 80 | 34.404 | 38.925 | 68.802 | 1.00 30.46 | A |
| ATOM | 537 | N | LYS | A | 81 | 35.747 | 37.541 | 67.666 | 1.00 26.41 | A |
| ATOM | 538 | CA | LYS | A | 81 | 34.797 | 36.430 | 67.728 | 1.00 26.41 | A |
| ATOM | 539 | CB | LYS | A | 81 | 35.261 | 35.250 | 66.870 | 1.00 27.80 | A |
| ATOM | 540 | CG | LYS | A | 81 | 35.336 | 35.482 | 65.354 | 1.00 27.80 | A |
| ATOM | 541 | CD | LYS | A | 81 | 35.801 | 34.183 | 64.666 | 1.00 27.80 | A |
| ATOM | 542 | CE | LYS | A | 81 | 36.220 | 34.388 | 63.206 | 1.00 27.80 | A |
| ATOM | 543 | NZ | LYS | A | 81 | 35.067 | 34.552 | 62.277 | 1.00 27.80 | A |
| ATOM | 544 | C | LYS | A | 81 | 34.639 | 35.935 | 69.157 | 1.00 26.41 | A |
| ATOM | 545 | O | LYS | A | 81 | 33.690 | 35.219 | 69.473 | 1.00 26.41 | A |
| ATOM | 546 | N | GLY | A | 82 | 35.574 | 36.306 | 70.025 | 1.00 28.59 | A |
| ATOM | 547 | CA | GLY | A | 82 | 35.512 | 35.847 | 71.401 | 1.00 28.59 | A |
| ATOM | 548 | C | GLY | A | 82 | 36.158 | 34.482 | 71.602 | 1.00 28.59 | A |
| ATOM | 549 | O | GLY | A | 82 | 35.887 | 33.804 | 72.591 | 1.00 28.59 | A |
| ATOM | 550 | N | TRP | A | 83 | 37.019 | 34.067 | 70.679 | 1.00 24.24 | A |
| ATOM | 551 | CA | TRP | A | 83 | 37.678 | 32.764 | 70.797 | 1.00 24.24 | A |
| ATOM | 552 | CB | TRP | A | 83 | 37.796 | 32.088 | 69.410 | 1.00 17.27 | A |
| ATOM | 553 | CG | TRP | A | 83 | 36.457 | 31.894 | 68.722 | 1.00 17.27 | A |
| ATOM | 554 | CD2 | TRP | A | 83 | 36.236 | 31.502 | 67.365 | 1.00 17.27 | A |
| ATOM | 555 | CE2 | TRP | A | 83 | 34.838 | 31.467 | 67.158 | 1.00 17.27 | A |
| ATOM | 556 | CE3 | TRP | A | 83 | 37.083 | 31.178 | 66.297 | 1.00 17.27 | A |
| ATOM | 557 | CD1 | TRP | A | 83 | 35.215 | 32.073 | 69.273 | 1.00 17.27 | A |
| ATOM | 558 | NE1 | TRP | A | 83 | 34.237 | 31.819 | 68.338 | 1.00 17.27 | A |
| ATOM | 559 | CZ2 | TRP | A | 83 | 34.272 | 31.124 | 65.935 | 1.00 17.27 | A |
| ATOM | 560 | CZ3 | TRP | A | 83 | 36.514 | 30.839 | 65.077 | 1.00 17.27 | A |
| ATOM | 561 | CH2 | TRP | A | 83 | 35.120 | 30.816 | 64.911 | 1.00 17.27 | A |
| ATOM | 562 | C | TRP | A | 83 | 39.061 | 32.899 | 71.428 | 1.00 24.24 | A |
| ATOM | 563 | O | TRP | A | 83 | 39.547 | 31.973 | 72.083 | 1.00 24.24 | A |
| ATOM | 564 | N | VAL | A | 84 | 39.688 | 34.058 | 71.231 | 1.00 30.33 | A |
| ATOM | 565 | CA | VAL | A | 84 | 41.014 | 34.326 | 71.777 | 1.00 30.33 | A |
| ATOM | 566 | CB | VAL | A | 84 | 42.046 | 34.570 | 70.659 | 1.00 10.78 | A |
| ATOM | 567 | CG1 | VAL | A | 84 | 43.398 | 34.887 | 71.274 | 1.00 10.78 | A |
| ATOM | 568 | CG2 | VAL | A | 84 | 42.144 | 33.354 | 69.763 | 1.00 10.78 | A |
| ATOM | 569 | C | VAL | A | 84 | 40.982 | 35.570 | 72.654 | 1.00 30.33 | A |
| ATOM | 570 | O | VAL | A | 84 | 40.268 | 36.530 | 72.359 | 1.00 30.33 | A |
| ATOM | 571 | N | GLU | A | 85 | 41.785 | 35.552 | 73.712 | 1.00 30.48 | A |
| ATOM | 572 | CA | GLU | A | 85 | 41.883 | 36.651 | 74.671 | 1.00 30.48 | A |

Fig. 2K

| | | | | | | | | | |
|---|---|---|---|---|---|---|---|---|---|
| ATOM | 573 | CB | GLU | A | 85 | 41.482 | 36.121 | 76.051 | 1.00 48.81 | A |
| ATOM | 574 | CG | GLU | A | 85 | 41.723 | 37.057 | 77.224 | 1.00 48.81 | A |
| ATOM | 575 | CD | GLU | A | 85 | 41.513 | 36.359 | 78.567 | 1.00 48.81 | A |
| ATOM | 576 | OE1 | GLU | A | 85 | 41.467 | 37.055 | 79.610 | 1.00 48.81 | A |
| ATOM | 577 | OE2 | GLU | A | 85 | 41.399 | 35.110 | 78.581 | 1.00 48.81 | A |
| ATOM | 578 | C | GLU | A | 85 | 43.322 | 37.187 | 74.715 | 1.00 30.48 | A |
| ATOM | 579 | O | GLU | A | 85 | 44.273 | 36.401 | 74.689 | 1.00 30.48 | A |
| ATOM | 580 | N | ARG | A | 86 | 43.486 | 38.511 | 74.775 | 1.00 26.85 | A |
| ATOM | 581 | CA | ARG | A | 86 | 44.830 | 39.118 | 74.855 | 1.00 26.85 | A |
| ATOM | 582 | CB | ARG | A | 86 | 44.903 | 40.444 | 74.097 | 1.00 38.70 | A |
| ATOM | 583 | CG | ARG | A | 86 | 44.744 | 40.394 | 72.600 | 1.00 38.70 | A |
| ATOM | 584 | CD | ARG | A | 86 | 44.769 | 41.827 | 72.082 | 1.00 38.70 | A |
| ATOM | 585 | NE | ARG | A | 86 | 44.228 | 41.997 | 70.733 | 1.00 38.70 | A |
| ATOM | 586 | CZ | ARG | A | 86 | 44.744 | 41.439 | 69.642 | 1.00 38.70 | A |
| ATOM | 587 | NH1 | ARG | A | 86 | 45.820 | 40.656 | 69.729 | 1.00 38.70 | A |
| ATOM | 588 | NH2 | ARG | A | 86 | 44.201 | 41.687 | 68.456 | 1.00 38.70 | A |
| ATOM | 589 | C | ARG | A | 86 | 45.162 | 39.426 | 76.315 | 1.00 26.85 | A |
| ATOM | 590 | O | ARG | A | 86 | 44.304 | 39.887 | 77.059 | 1.00 26.85 | A |
| ATOM | 591 | N | LEU | A | 87 | 46.401 | 39.183 | 76.724 | 1.00 25.04 | A |
| ATOM | 592 | CA | LEU | A | 87 | 46.815 | 39.474 | 78.097 | 1.00 25.04 | A |
| ATOM | 593 | CB | LEU | A | 87 | 47.118 | 38.184 | 78.858 | 1.00 36.39 | A |
| ATOM | 594 | CG | LEU | A | 87 | 45.922 | 37.372 | 79.349 | 1.00 36.39 | A |
| ATOM | 595 | CD1 | LEU | A | 87 | 46.416 | 36.090 | 79.986 | 1.00 36.39 | A |
| ATOM | 596 | CD2 | LEU | A | 87 | 45.134 | 38.181 | 80.360 | 1.00 36.39 | A |
| ATOM | 597 | C | LEU | A | 87 | 48.053 | 40.366 | 78.090 | 1.00 25.04 | A |
| ATOM | 598 | O | LEU | A | 87 | 48.894 | 40.291 | 77.174 | 1.00 25.04 | A |
| ATOM | 599 | N | PRO | A | 88 | 48.185 | 41.237 | 79.101 | 1.00 41.37 | A |
| ATOM | 600 | CD | PRO | A | 88 | 47.257 | 41.606 | 80.178 | 1.00 36.25 | A |
| ATOM | 601 | CA | PRO | A | 88 | 49.370 | 42.099 | 79.109 | 1.00 41.37 | A |
| ATOM | 602 | CB | PRO | A | 88 | 49.106 | 43.057 | 80.271 | 1.00 36.25 | A |
| ATOM | 603 | CG | PRO | A | 88 | 47.602 | 43.063 | 80.385 | 1.00 36.25 | A |
| ATOM | 604 | C | PRO | A | 88 | 50.613 | 41.257 | 79.333 | 1.00 41.37 | A |
| ATOM | 605 | O | PRO | A | 88 | 50.626 | 40.363 | 80.192 | 1.00 41.37 | A |
| ATOM | 606 | N | ASN | A | 89 | 51.642 | 41.530 | 78.540 | 1.00 40.92 | A |
| ATOM | 607 | CA | ASN | A | 89 | 52.890 | 40.806 | 78.668 | 1.00 40.92 | A |
| ATOM | 608 | CB | ASN | A | 89 | 53.757 | 40.990 | 77.426 | 1.00 48.54 | A |
| ATOM | 609 | CG | ASN | A | 89 | 54.948 | 40.063 | 77.424 | 1.00 48.54 | A |
| ATOM | 610 | OD1 | ASN | A | 89 | 55.520 | 39.784 | 78.482 | 1.00 48.54 | A |
| ATOM | 611 | ND2 | ASN | A | 89 | 55.334 | 39.581 | 76.244 | 1.00 48.54 | A |
| ATOM | 612 | C | ASN | A | 89 | 53.612 | 41.376 | 79.881 | 1.00 40.92 | A |
| ATOM | 613 | O | ASN | A | 89 | 54.057 | 42.526 | 79.864 | 1.00 40.92 | A |
| ATOM | 614 | N | PRO | A | 90 | 53.727 | 40.578 | 80.955 | 1.00 44.27 | A |
| ATOM | 615 | CD | PRO | A | 90 | 53.271 | 39.176 | 80.997 | 1.00 40.09 | A |
| ATOM | 616 | CA | PRO | A | 90 | 54.381 | 40.941 | 82.216 | 1.00 44.27 | A |
| ATOM | 617 | CB | PRO | A | 90 | 54.617 | 39.586 | 82.875 | 1.00 40.09 | A |
| ATOM | 618 | CG | PRO | A | 90 | 53.392 | 38.836 | 82.477 | 1.00 40.09 | A |
| ATOM | 619 | C | PRO | A | 90 | 55.668 | 41.769 | 82.115 | 1.00 44.27 | A |
| ATOM | 620 | O | PRO | A | 90 | 55.866 | 42.688 | 82.911 | 1.00 44.27 | A |

Fig. 2L

| | | | | | | | | | | |
|---|---|---|---|---|---|---|---|---|---|---|
| ATOM | 621 | N | ASN | A | 91 | 56.544 | 41.462 | 81.158 | 1.00 69.68 | A |
| ATOM | 622 | CA | ASN | A | 91 | 57.785 | 42.226 | 81.060 | 1.00 69.68 | A |
| ATOM | 623 | CB | ASN | A | 91 | 59.005 | 41.288 | 81.081 | 1.00 76.88 | A |
| ATOM | 624 | CG | ASN | A | 91 | 59.169 | 40.493 | 79.797 | 1.00 76.88 | A |
| ATOM | 625 | OD1 | ASN | A | 91 | 59.444 | 41.050 | 78.732 | 1.00 76.88 | A |
| ATOM | 626 | ND2 | ASN | A | 91 | 59.008 | 39.179 | 79.896 | 1.00 76.88 | A |
| ATOM | 627 | C | ASN | A | 91 | 57.897 | 43.179 | 79.876 | 1.00 69.68 | A |
| ATOM | 628 | O | ASN | A | 91 | 58.384 | 44.303 | 80.029 | 1.00 69.68 | A |
| ATOM | 629 | N | ASP | A | 92 | 57.447 | 42.745 | 78.702 | 1.00 97.47 | A |
| ATOM | 630 | CA | ASP | A | 92 | 57.533 | 43.585 | 77.513 | 1.00 97.47 | A |
| ATOM | 631 | CB | ASP | A | 92 | 56.898 | 42.886 | 76.310 | 1.00 77.46 | A |
| ATOM | 632 | CG | ASP | A | 92 | 57.184 | 43.608 | 75.009 | 1.00 77.46 | A |
| ATOM | 633 | OD1 | ASP | A | 92 | 56.846 | 44.808 | 74.915 | 1.00 77.46 | A |
| ATOM | 634 | OD2 | ASP | A | 92 | 57.749 | 42.980 | 74.087 | 1.00 77.46 | A |
| ATOM | 635 | C | ASP | A | 92 | 56.869 | 44.941 | 77.721 | 1.00 97.47 | A |
| ATOM | 636 | O | ASP | A | 92 | 57.351 | 45.956 | 77.222 | 1.00 97.47 | A |
| ATOM | 637 | N | LYS | A | 93 | 55.758 | 44.951 | 78.451 | 1.00 79.22 | A |
| ATOM | 638 | CA | LYS | A | 93 | 55.035 | 46.187 | 78.735 | 1.00 79.22 | A |
| ATOM | 639 | CB | LYS | A | 93 | 55.964 | 47.188 | 79.439 | 1.00105.99 | A |
| ATOM | 640 | CG | LYS | A | 93 | 56.461 | 46.727 | 80.813 | 1.00105.99 | A |
| ATOM | 641 | CD | LYS | A | 93 | 57.584 | 47.619 | 81.345 | 1.00105.99 | A |
| ATOM | 642 | CE | LYS | A | 93 | 57.140 | 49.067 | 81.530 | 1.00105.99 | A |
| ATOM | 643 | NZ | LYS | A | 93 | 56.095 | 49.203 | 82.577 | 1.00105.99 | A |
| ATOM | 644 | C | LYS | A | 93 | 54.434 | 46.831 | 77.481 | 1.00 79.22 | A |
| ATOM | 645 | O | LYS | A | 93 | 53.643 | 47.770 | 77.575 | 1.00 79.22 | A |
| ATOM | 646 | N | ARG | A | 94 | 54.812 | 46.328 | 76.309 | 1.00101.34 | A |
| ATOM | 647 | CA | ARG | A | 94 | 54.298 | 46.854 | 75.047 | 1.00101.34 | A |
| ATOM | 648 | CB | ARG | A | 94 | 55.382 | 47.656 | 74.312 | 1.00133.25 | A |
| ATOM | 649 | CG | ARG | A | 94 | 55.380 | 49.164 | 74.590 | 1.00133.25 | A |
| ATOM | 650 | CD | ARG | A | 94 | 55.552 | 49.481 | 76.072 | 1.00133.25 | A |
| ATOM | 651 | NE | ARG | A | 94 | 55.707 | 50.913 | 76.325 | 1.00133.25 | A |
| ATOM | 652 | CZ | ARG | A | 94 | 55.877 | 51.447 | 77.533 | 1.00133.25 | A |
| ATOM | 653 | NH1 | ARG | A | 94 | 55.911 | 50.670 | 78.610 | 1.00133.25 | A |
| ATOM | 654 | NH2 | ARG | A | 94 | 56.026 | 52.759 | 77.663 | 1.00133.25 | A |
| ATOM | 655 | C | ARG | A | 94 | 53.808 | 45.722 | 74.152 | 1.00101.34 | A |
| ATOM | 656 | O | ARG | A | 94 | 53.294 | 45.965 | 73.060 | 1.00101.34 | A |
| ATOM | 657 | N | GLY | A | 95 | 53.974 | 44.486 | 74.618 | 1.00 68.05 | A |
| ATOM | 658 | CA | GLY | A | 95 | 53.537 | 43.336 | 73.846 | 1.00 68.05 | A |
| ATOM | 659 | C | GLY | A | 95 | 52.361 | 42.639 | 74.503 | 1.00 68.05 | A |
| ATOM | 660 | O | GLY | A | 95 | 51.963 | 42.995 | 75.611 | 1.00 68.05 | A |
| ATOM | 661 | N | VAL | A | 96 | 51.799 | 41.644 | 73.826 | 1.00 32.70 | A |
| ATOM | 662 | CA | VAL | A | 96 | 50.662 | 40.914 | 74.378 | 1.00 32.70 | A |
| ATOM | 663 | CB | VAL | A | 96 | 49.384 | 41.151 | 73.540 | 1.00 46.59 | A |
| ATOM | 664 | CG1 | VAL | A | 96 | 49.061 | 42.631 | 73.489 | 1.00 46.59 | A |
| ATOM | 665 | CG2 | VAL | A | 96 | 49.576 | 40.582 | 72.134 | 1.00 46.59 | A |
| ATOM | 666 | C | VAL | A | 96 | 50.880 | 39.401 | 74.464 | 1.00 32.70 | A |
| ATOM | 667 | O | VAL | A | 96 | 51.871 | 38.864 | 73.975 | 1.00 32.70 | A |
| ATOM | 668 | N | LEU | A | 97 | 49.938 | 38.729 | 75.112 | 1.00 23.07 | A |

Fig. 2M

| | | | | | | | | | | |
|---|---|---|---|---|---|---|---|---|---|---|
| ATOM | 669 | CA | LEU | A | 97 | 49.964 | 37.282 | 75.251 | 1.00 23.07 | A |
| ATOM | 670 | CB | LEU | A | 97 | 50.225 | 36.883 | 76.703 | 1.00 46.89 | A |
| ATOM | 671 | CG | LEU | A | 97 | 51.491 | 37.474 | 77.318 | 1.00 46.89 | A |
| ATOM | 672 | CD1 | LEU | A | 97 | 51.666 | 36.944 | 78.730 | 1.00 46.89 | A |
| ATOM | 673 | CD2 | LEU | A | 97 | 52.692 | 37.111 | 76.456 | 1.00 46.89 | A |
| ATOM | 674 | C | LEU | A | 97 | 48.570 | 36.839 | 74.831 | 1.00 23.07 | A |
| ATOM | 675 | O | LEU | A | 97 | 47.575 | 37.517 | 75.125 | 1.00 23.07 | A |
| ATOM | 676 | N | VAL | A | 98 | 48.492 | 35.724 | 74.120 | 1.00 29.54 | A |
| ATOM | 677 | CA | VAL | A | 98 | 47.199 | 35.243 | 73.682 | 1.00 29.54 | A |
| ATOM | 678 | CB | VAL | A | 98 | 47.075 | 35.216 | 72.143 | 1.00 16.38 | A |
| ATOM | 679 | CG1 | VAL | A | 98 | 47.126 | 36.631 | 71.597 | 1.00 16.38 | A |
| ATOM | 680 | CG2 | VAL | A | 98 | 48.186 | 34.384 | 71.553 | 1.00 16.38 | A |
| ATOM | 681 | C | VAL | A | 98 | 46.968 | 33.859 | 74.208 | 1.00 29.54 | A |
| ATOM | 682 | O | VAL | A | 98 | 47.908 | 33.076 | 74.396 | 1.00 29.54 | A |
| ATOM | 683 | N | LYS | A | 99 | 45.699 | 33.575 | 74.453 | 1.00 22.55 | A |
| ATOM | 684 | CA | LYS | A | 99 | 45.273 | 32.289 | 74.960 | 1.00 22.55 | A |
| ATOM | 685 | CB | LYS | A | 99 | 45.310 | 32.298 | 76.491 | 1.00 25.06 | A |
| ATOM | 686 | CG | LYS | A | 99 | 44.402 | 33.337 | 77.130 | 1.00 25.06 | A |
| ATOM | 687 | CD | LYS | A | 99 | 44.394 | 33.234 | 78.669 | 1.00 25.06 | A |
| ATOM | 688 | CE | LYS | A | 99 | 43.619 | 32.009 | 79.172 | 1.00 25.06 | A |
| ATOM | 689 | NZ | LYS | A | 99 | 42.150 | 32.101 | 78.900 | 1.00 25.06 | A |
| ATOM | 690 | C | LYS | A | 99 | 43.841 | 32.074 | 74.469 | 1.00 22.55 | A |
| ATOM | 691 | O | LYS | A | 99 | 43.173 | 33.020 | 74.042 | 1.00 22.55 | A |
| ATOM | 692 | N | LEU | A | 100 | 43.369 | 30.837 | 74.507 | 1.00 21.07 | A |
| ATOM | 693 | CA | LEU | A | 100 | 42.010 | 30.576 | 74.080 | 1.00 21.07 | A |
| ATOM | 694 | CB | LEU | A | 100 | 41.818 | 29.095 | 73.759 | 1.00 18.76 | A |
| ATOM | 695 | CG | LEU | A | 100 | 42.598 | 28.488 | 72.578 | 1.00 18.76 | A |
| ATOM | 696 | CD1 | LEU | A | 100 | 41.992 | 27.126 | 72.253 | 1.00 18.76 | A |
| ATOM | 697 | CD2 | LEU | A | 100 | 42.526 | 29.400 | 71.343 | 1.00 18.76 | A |
| ATOM | 698 | C | LEU | A | 100 | 41.053 | 30.956 | 75.195 | 1.00 21.07 | A |
| ATOM | 699 | O | LEU | A | 100 | 41.399 | 30.864 | 76.387 | 1.00 21.07 | A |
| ATOM | 700 | N | THR | A | 101 | 39.857 | 31.412 | 74.827 | 1.00 17.16 | A |
| ATOM | 701 | CA | THR | A | 101 | 38.858 | 31.711 | 75.849 | 1.00 17.16 | A |
| ATOM | 702 | CB | THR | A | 101 | 37.775 | 32.645 | 75.357 | 1.00  7.57 | A |
| ATOM | 703 | OG1 | THR | A | 101 | 37.178 | 32.067 | 74.189 | 1.00  7.57 | A |
| ATOM | 704 | CG2 | THR | A | 101 | 38.361 | 34.025 | 75.019 | 1.00  7.57 | A |
| ATOM | 705 | C | THR | A | 101 | 38.243 | 30.341 | 76.029 | 1.00 17.16 | A |
| ATOM | 706 | O | THR | A | 101 | 38.624 | 29.393 | 75.332 | 1.00 17.16 | A |
| ATOM | 707 | N | THR | A | 102 | 37.292 | 30.210 | 76.943 | 1.00 17.61 | A |
| ATOM | 708 | CA | THR | A | 102 | 36.710 | 28.892 | 77.142 | 1.00 17.61 | A |
| ATOM | 709 | CB | THR | A | 102 | 35.924 | 28.813 | 78.492 | 1.00 19.84 | A |
| ATOM | 710 | OG1 | THR | A | 102 | 34.558 | 29.190 | 78.309 | 1.00 19.84 | A |
| ATOM | 711 | CG2 | THR | A | 102 | 36.566 | 29.748 | 79.500 | 1.00 19.84 | A |
| ATOM | 712 | C | THR | A | 102 | 35.861 | 28.546 | 75.929 | 1.00 17.61 | A |
| ATOM | 713 | O | THR | A | 102 | 35.781 | 27.387 | 75.529 | 1.00 17.61 | A |
| ATOM | 714 | N | GLY | A | 103 | 35.266 | 29.560 | 75.313 | 1.00 30.04 | A |
| ATOM | 715 | CA | GLY | A | 103 | 34.470 | 29.318 | 74.121 | 1.00 30.04 | A |
| ATOM | 716 | C | GLY | A | 103 | 35.353 | 28.847 | 72.972 | 1.00 30.04 | A |

Fig. 2N

| ATOM | 717 | O | GLY | A | 103 | 34.990 | 27.928 | 72.224 | 1.00 | 30.04 | A |
|------|-----|-----|-----|---|-----|--------|--------|--------|------|-------|---|
| ATOM | 718 | N | GLY | A | 104 | 36.517 | 29.479 | 72.829 | 1.00 | 27.12 | A |
| ATOM | 719 | CA | GLY | A | 104 | 37.445 | 29.106 | 71.777 | 1.00 | 27.12 | A |
| ATOM | 720 | C | GLY | A | 104 | 37.986 | 27.703 | 71.976 | 1.00 | 27.12 | A |
| ATOM | 721 | O | GLY | A | 104 | 38.169 | 26.959 | 71.005 | 1.00 | 27.12 | A |
| ATOM | 722 | N | ALA | A | 105 | 38.244 | 27.330 | 73.228 | 1.00 | 31.63 | A |
| ATOM | 723 | CA | ALA | A | 105 | 38.762 | 25.993 | 73.512 | 1.00 | 31.63 | A |
| ATOM | 724 | CB | ALA | A | 105 | 39.180 | 25.866 | 74.977 | 1.00 | 1.17 | A |
| ATOM | 725 | C | ALA | A | 105 | 37.679 | 24.976 | 73.191 | 1.00 | 31.63 | A |
| ATOM | 726 | O | ALA | A | 105 | 37.965 | 23.900 | 72.667 | 1.00 | 31.63 | A |
| ATOM | 727 | N | ALA | A | 106 | 36.435 | 25.327 | 73.509 | 1.00 | 15.93 | A |
| ATOM | 728 | CA | ALA | A | 106 | 35.304 | 24.439 | 73.238 | 1.00 | 15.93 | A |
| ATOM | 729 | CB | ALA | A | 106 | 34.008 | 25.061 | 73.734 | 1.00 | 34.73 | A |
| ATOM | 730 | C | ALA | A | 106 | 35.218 | 24.191 | 71.739 | 1.00 | 15.93 | A |
| ATOM | 731 | O | ALA | A | 106 | 35.118 | 23.049 | 71.291 | 1.00 | 15.93 | A |
| ATOM | 732 | N | ILE | A | 107 | 35.265 | 25.264 | 70.964 | 1.00 | 24.47 | A |
| ATOM | 733 | CA | ILE | A | 107 | 35.198 | 25.144 | 69.516 | 1.00 | 24.47 | A |
| ATOM | 734 | CB | ILE | A | 107 | 35.361 | 26.531 | 68.844 | 1.00 | 27.19 | A |
| ATOM | 735 | CG2 | ILE | A | 107 | 35.734 | 26.378 | 67.377 | 1.00 | 27.19 | A |
| ATOM | 736 | CG1 | ILE | A | 107 | 34.070 | 27.324 | 69.009 | 1.00 | 27.19 | A |
| ATOM | 737 | CD1 | ILE | A | 107 | 34.170 | 28.743 | 68.513 | 1.00 | 27.19 | A |
| ATOM | 738 | C | ILE | A | 107 | 36.300 | 24.211 | 69.023 | 1.00 | 24.47 | A |
| ATOM | 739 | O | ILE | A | 107 | 36.071 | 23.338 | 68.179 | 1.00 | 24.47 | A |
| ATOM | 740 | N | CYS | A | 108 | 37.497 | 24.390 | 69.565 | 1.00 | 23.24 | A |
| ATOM | 741 | CA | CYS | A | 108 | 38.627 | 23.572 | 69.145 | 1.00 | 23.24 | A |
| ATOM | 742 | CB | CYS | A | 108 | 39.869 | 23.955 | 69.948 | 1.00 | 44.34 | A |
| ATOM | 743 | SG | CYS | A | 108 | 41.387 | 23.261 | 69.295 | 1.00 | 44.34 | A |
| ATOM | 744 | C | CYS | A | 108 | 38.307 | 22.095 | 69.336 | 1.00 | 23.24 | A |
| ATOM | 745 | O | CYS | A | 108 | 38.444 | 21.286 | 68.411 | 1.00 | 23.24 | A |
| ATOM | 746 | N | GLU | A | 109 | 37.864 | 21.755 | 70.543 | 1.00 | 34.17 | A |
| ATOM | 747 | CA | GLU | A | 109 | 37.525 | 20.379 | 70.867 | 1.00 | 34.17 | A |
| ATOM | 748 | CB | GLU | A | 109 | 37.121 | 20.269 | 72.342 | 1.00 | 54.06 | A |
| ATOM | 749 | CG | GLU | A | 109 | 36.882 | 18.841 | 72.820 | 1.00 | 54.06 | A |
| ATOM | 750 | CD | GLU | A | 109 | 38.027 | 17.892 | 72.469 | 1.00 | 54.06 | A |
| ATOM | 751 | OE1 | GLU | A | 109 | 39.195 | 18.212 | 72.790 | 1.00 | 54.06 | A |
| ATOM | 752 | OE2 | GLU | A | 109 | 37.755 | 16.822 | 71.876 | 1.00 | 54.06 | A |
| ATOM | 753 | C | GLU | A | 109 | 36.407 | 19.868 | 69.965 | 1.00 | 34.17 | A |
| ATOM | 754 | O | GLU | A | 109 | 36.491 | 18.775 | 69.423 | 1.00 | 34.17 | A |
| ATOM | 755 | N | GLN | A | 110 | 35.371 | 20.672 | 69.781 | 1.00 | 31.70 | A |
| ATOM | 756 | CA | GLN | A | 110 | 34.263 | 20.243 | 68.954 | 1.00 | 31.70 | A |
| ATOM | 757 | CB | GLN | A | 110 | 33.130 | 21.268 | 69.050 | 1.00 | 54.33 | A |
| ATOM | 758 | CG | GLN | A | 110 | 31.790 | 20.641 | 69.442 | 1.00 | 54.33 | A |
| ATOM | 759 | CD | GLN | A | 110 | 31.943 | 19.486 | 70.440 | 1.00 | 54.33 | A |
| ATOM | 760 | OE1 | GLN | A | 110 | 32.444 | 19.662 | 71.559 | 1.00 | 54.33 | A |
| ATOM | 761 | NE2 | GLN | A | 110 | 31.515 | 18.295 | 70.026 | 1.00 | 54.33 | A |
| ATOM | 762 | C | GLN | A | 110 | 34.680 | 19.988 | 67.498 | 1.00 | 31.70 | A |
| ATOM | 763 | O | GLN | A | 110 | 34.241 | 19.008 | 66.885 | 1.00 | 31.70 | A |
| ATOM | 764 | N | CYS | A | 111 | 35.535 | 20.852 | 66.947 | 1.00 | 20.80 | A |

Fig. 2O

```
ATOM    765  CA  CYS A 111      35.990  20.679  65.572  1.00 20.80           A
ATOM    766  CB  CYS A 111      36.893  21.841  65.156  1.00 32.98           A
ATOM    767  SG  CYS A 111      35.999  23.387  64.796  1.00 32.98           A
ATOM    768  C   CYS A 111      36.731  19.352  65.412  1.00 20.80           A
ATOM    769  O   CYS A 111      36.511  18.632  64.443  1.00 20.80           A
ATOM    770  N   HIS A 112      37.606  19.025  66.360  1.00 36.28           A
ATOM    771  CA  HIS A 112      38.344  17.761  66.308  1.00 36.28           A
ATOM    772  CB  HIS A 112      39.294  17.635  67.504  1.00 32.43           A
ATOM    773  CG  HIS A 112      40.594  18.365  67.339  1.00 32.43           A
ATOM    774  CD2 HIS A 112      41.170  19.340  68.085  1.00 32.43           A
ATOM    775  ND1 HIS A 112      41.493  18.072  66.334  1.00 32.43           A
ATOM    776  CE1 HIS A 112      42.566  18.830  66.470  1.00 32.43           A
ATOM    777  NE2 HIS A 112      42.397  19.608  67.525  1.00 32.43           A
ATOM    778  C   HIS A 112      37.379  16.570  66.330  1.00 36.28           A
ATOM    779  O   HIS A 112      37.537  15.610  65.575  1.00 36.28           A
ATOM    780  N   GLN A 113      36.373  16.642  67.194  1.00 32.58           A
ATOM    781  CA  GLN A 113      35.416  15.556  67.321  1.00 32.58           A
ATOM    782  CB  GLN A 113      34.575  15.737  68.585  1.00 64.21           A
ATOM    783  CG  GLN A 113      35.383  15.675  69.869  1.00 64.21           A
ATOM    784  CD  GLN A 113      34.518  15.624  71.116  1.00 64.21           A
ATOM    785  OE1 GLN A 113      35.030  15.690  72.236  1.00 64.21           A
ATOM    786  NE2 GLN A 113      33.203  15.501  70.933  1.00 64.21           A
ATOM    787  C   GLN A 113      34.493  15.334  66.133  1.00 32.58           A
ATOM    788  O   GLN A 113      34.194  14.193  65.793  1.00 32.58           A
ATOM    789  N   LEU A 114      34.050  16.406  65.487  1.00 43.53           A
ATOM    790  CA  LEU A 114      33.124  16.267  64.370  1.00 43.53           A
ATOM    791  CB  LEU A 114      32.095  17.399  64.416  1.00 83.39           A
ATOM    792  CG  LEU A 114      31.191  17.440  65.658  1.00 83.39           A
ATOM    793  CD1 LEU A 114      30.424  18.760  65.725  1.00 83.39           A
ATOM    794  CD2 LEU A 114      30.231  16.258  65.615  1.00 83.39           A
ATOM    795  C   LEU A 114      33.801  16.262  63.022  1.00 43.53           A
ATOM    796  O   LEU A 114      33.144  16.383  61.995  1.00 43.53           A
ATOM    797  N   VAL A 115      35.113  16.094  63.016  1.00 22.15           A
ATOM    798  CA  VAL A 115      35.867  16.129  61.768  1.00 22.15           A
ATOM    799  CB  VAL A 115      36.511  17.528  61.597  1.00 22.88           A
ATOM    800  CG1 VAL A 115      37.978  17.412  61.200  1.00 22.88           A
ATOM    801  CG2 VAL A 115      35.728  18.329  60.572  1.00 22.88           A
ATOM    802  C   VAL A 115      36.948  15.064  61.712  1.00 22.15           A
ATOM    803  O   VAL A 115      37.257  14.522  60.642  1.00 22.15           A
ATOM    804  N   GLY A 116      37.522  14.779  62.873  1.00 30.44           A
ATOM    805  CA  GLY A 116      38.581  13.797  62.966  1.00 30.44           A
ATOM    806  C   GLY A 116      38.384  12.527  62.163  1.00 30.44           A
ATOM    807  O   GLY A 116      39.139  12.257  61.224  1.00 30.44           A
ATOM    808  N   GLN A 117      37.363  11.749  62.511  1.00 39.45           A
ATOM    809  CA  GLN A 117      37.117  10.483  61.823  1.00 39.45           A
ATOM    810  CB  GLN A 117      35.899   9.783  62.424  1.00 99.18           A
ATOM    811  CG  GLN A 117      36.100   8.289  62.577  1.00 99.18           A
ATOM    812  CD  GLN A 117      37.439   7.956  63.222  1.00 99.18           A
```

Fig. 2P

```
ATOM    813  OE1 GLN A 117      37.735   8.397  64.336  1.00 99.18           A
ATOM    814  NE2 GLN A 117      38.259   7.179  62.520  1.00 99.18           A
ATOM    815  C   GLN A 117      36.947  10.619  60.317  1.00 39.45           A
ATOM    816  O   GLN A 117      37.662   9.982  59.543  1.00 39.45           A
ATOM    817  N   ASP A 118      36.004  11.453  59.901  1.00 47.18           A
ATOM    818  CA  ASP A 118      35.759  11.662  58.480  1.00 47.18           A
ATOM    819  CB  ASP A 118      34.688  12.740  58.281  1.00 77.40           A
ATOM    820  CG  ASP A 118      33.306  12.275  58.704  1.00 77.40           A
ATOM    821  OD1 ASP A 118      32.401  13.127  58.810  1.00 77.40           A
ATOM    822  OD2 ASP A 118      33.121  11.057  58.923  1.00 77.40           A
ATOM    823  C   ASP A 118      37.032  12.053  57.733  1.00 47.18           A
ATOM    824  O   ASP A 118      37.314  11.517  56.663  1.00 47.18           A
ATOM    825  N   LEU A 119      37.796  12.985  58.300  1.00 42.24           A
ATOM    826  CA  LEU A 119      39.032  13.447  57.675  1.00 42.24           A
ATOM    827  CB  LEU A 119      39.676  14.561  58.515  1.00 15.97           A
ATOM    828  CG  LEU A 119      41.092  14.941  58.055  1.00 15.97           A
ATOM    829  CD1 LEU A 119      41.020  15.406  56.612  1.00 15.97           A
ATOM    830  CD2 LEU A 119      41.684  16.010  58.936  1.00 15.97           A
ATOM    831  C   LEU A 119      40.015  12.295  57.531  1.00 42.24           A
ATOM    832  O   LEU A 119      40.662  12.137  56.496  1.00 42.24           A
ATOM    833  N   HIS A 120      40.129  11.507  58.594  1.00 39.36           A
ATOM    834  CA  HIS A 120      41.026  10.365  58.619  1.00 39.36           A
ATOM    835  CB  HIS A 120      40.947   9.655  59.959  1.00 36.14           A
ATOM    836  CG  HIS A 120      41.656   8.342  59.971  1.00 36.14           A
ATOM    837  CD2 HIS A 120      41.204   7.084  59.763  1.00 36.14           A
ATOM    838  ND1 HIS A 120      43.015   8.233  60.172  1.00 36.14           A
ATOM    839  CE1 HIS A 120      43.369   6.963  60.089  1.00 36.14           A
ATOM    840  NE2 HIS A 120      42.289   6.245  59.842  1.00 36.14           A
ATOM    841  C   HIS A 120      40.619   9.377  57.549  1.00 39.36           A
ATOM    842  O   HIS A 120      41.449   8.780  56.865  1.00 39.36           A
ATOM    843  N   GLN A 121      39.317   9.191  57.436  1.00 35.35           A
ATOM    844  CA  GLN A 121      38.738   8.281  56.467  1.00 35.35           A
ATOM    845  CB  GLN A 121      37.223   8.336  56.618  1.00 61.52           A
ATOM    846  CG  GLN A 121      36.466   7.174  56.059  1.00 61.52           A
ATOM    847  CD  GLN A 121      35.049   7.152  56.584  1.00 61.52           A
ATOM    848  OE1 GLN A 121      34.827   7.055  57.798  1.00 61.52           A
ATOM    849  NE2 GLN A 121      34.077   7.253  55.679  1.00 61.52           A
ATOM    850  C   GLN A 121      39.149   8.675  55.047  1.00 35.35           A
ATOM    851  O   GLN A 121      39.795   7.907  54.335  1.00 35.35           A
ATOM    852  N   GLU A 122      38.779   9.885  54.643  1.00 27.29           A
ATOM    853  CA  GLU A 122      39.096  10.380  53.309  1.00 27.29           A
ATOM    854  CB  GLU A 122      38.586  11.815  53.155  1.00 50.77           A
ATOM    855  CG  GLU A 122      38.783  12.414  51.772  1.00 50.77           A
ATOM    856  CD  GLU A 122      38.039  11.659  50.681  1.00 50.77           A
ATOM    857  OE1 GLU A 122      38.145  12.066  49.499  1.00 50.77           A
ATOM    858  OE2 GLU A 122      37.349  10.663  51.004  1.00 50.77           A
ATOM    859  C   GLU A 122      40.597  10.318  52.996  1.00 27.29           A
ATOM    860  O   GLU A 122      40.991   9.922  51.895  1.00 27.29           A
```

Fig. 2Q

| ATOM | 861 | N   | LEU | A | 123 | 41.436 | 10.693 | 53.956 | 1.00 | 37.09 | A |
| ATOM | 862 | CA  | LEU | A | 123 | 42.871 | 10.675 | 53.718 | 1.00 | 37.09 | A |
| ATOM | 863 | CB  | LEU | A | 123 | 43.628 | 11.267 | 54.915 | 1.00 | 42.11 | A |
| ATOM | 864 | CG  | LEU | A | 123 | 43.574 | 12.766 | 55.229 | 1.00 | 42.11 | A |
| ATOM | 865 | CD1 | LEU | A | 123 | 44.474 | 13.051 | 56.431 | 1.00 | 42.11 | A |
| ATOM | 866 | CD2 | LEU | A | 123 | 44.036 | 13.575 | 54.027 | 1.00 | 42.11 | A |
| ATOM | 867 | C   | LEU | A | 123 | 43.406 | 9.269  | 53.443 | 1.00 | 37.09 | A |
| ATOM | 868 | O   | LEU | A | 123 | 44.435 | 9.106  | 52.775 | 1.00 | 37.09 | A |
| ATOM | 869 | N   | THR | A | 124 | 42.710 | 8.256  | 53.948 | 1.00 | 47.34 | A |
| ATOM | 870 | CA  | THR | A | 124 | 43.165 | 6.881  | 53.779 | 1.00 | 47.34 | A |
| ATOM | 871 | CB  | THR | A | 124 | 43.280 | 6.189  | 55.147 | 1.00 | 51.95 | A |
| ATOM | 872 | OG1 | THR | A | 124 | 41.992 | 6.173  | 55.778 | 1.00 | 51.95 | A |
| ATOM | 873 | CG2 | THR | A | 124 | 44.263 | 6.935  | 56.040 | 1.00 | 51.95 | A |
| ATOM | 874 | C   | THR | A | 124 | 42.293 | 6.006  | 52.885 | 1.00 | 47.34 | A |
| ATOM | 875 | O   | THR | A | 124 | 42.402 | 4.785  | 52.926 | 1.00 | 47.34 | A |
| ATOM | 876 | N   | LYS | A | 125 | 41.441 | 6.612  | 52.070 | 1.00 | 44.88 | A |
| ATOM | 877 | CA  | LYS | A | 125 | 40.572 | 5.821  | 51.209 | 1.00 | 44.88 | A |
| ATOM | 878 | CB  | LYS | A | 125 | 39.633 | 6.732  | 50.411 | 1.00 | 45.55 | A |
| ATOM | 879 | CG  | LYS | A | 125 | 40.317 | 7.559  | 49.354 | 1.00 | 45.55 | A |
| ATOM | 880 | CD  | LYS | A | 125 | 39.353 | 8.555  | 48.745 | 1.00 | 45.55 | A |
| ATOM | 881 | CE  | LYS | A | 125 | 40.063 | 9.392  | 47.694 | 1.00 | 45.55 | A |
| ATOM | 882 | NZ  | LYS | A | 125 | 39.217 | 10.513 | 47.202 | 1.00 | 45.55 | A |
| ATOM | 883 | C   | LYS | A | 125 | 41.338 | 4.899  | 50.257 | 1.00 | 44.88 | A |
| ATOM | 884 | O   | LYS | A | 125 | 40.821 | 3.854  | 49.864 | 1.00 | 44.88 | A |
| ATOM | 885 | N   | ASN | A | 126 | 42.561 | 5.276  | 49.886 | 1.00 | 32.03 | A |
| ATOM | 886 | CA  | ASN | A | 126 | 43.366 | 4.455  | 48.979 | 1.00 | 32.03 | A |
| ATOM | 887 | CB  | ASN | A | 126 | 44.005 | 5.313  | 47.885 | 1.00 | 55.44 | A |
| ATOM | 888 | CG  | ASN | A | 126 | 42.987 | 6.043  | 47.047 | 1.00 | 55.44 | A |
| ATOM | 889 | OD1 | ASN | A | 126 | 42.162 | 5.422  | 46.370 | 1.00 | 55.44 | A |
| ATOM | 890 | ND2 | ASN | A | 126 | 43.034 | 7.377  | 47.082 | 1.00 | 55.44 | A |
| ATOM | 891 | C   | ASN | A | 126 | 44.480 | 3.711  | 49.709 | 1.00 | 32.03 | A |
| ATOM | 892 | O   | ASN | A | 126 | 45.527 | 3.426  | 49.124 | 1.00 | 32.03 | A |
| ATOM | 893 | N   | LEU | A | 127 | 44.280 | 3.411  | 50.986 | 1.00 | 29.87 | A |
| ATOM | 894 | CA  | LEU | A | 127 | 45.289 | 2.680  | 51.736 | 1.00 | 29.87 | A |
| ATOM | 895 | CB  | LEU | A | 127 | 45.969 | 3.586  | 52.759 | 1.00 | 41.10 | A |
| ATOM | 896 | CG  | LEU | A | 127 | 46.688 | 4.836  | 52.259 | 1.00 | 41.10 | A |
| ATOM | 897 | CD1 | LEU | A | 127 | 47.585 | 5.351  | 53.383 | 1.00 | 41.10 | A |
| ATOM | 898 | CD2 | LEU | A | 127 | 47.524 | 4.516  | 51.029 | 1.00 | 41.10 | A |
| ATOM | 899 | C   | LEU | A | 127 | 44.689 | 1.482  | 52.465 | 1.00 | 29.87 | A |
| ATOM | 900 | O   | LEU | A | 127 | 43.617 | 1.576  | 53.065 | 1.00 | 29.87 | A |
| ATOM | 901 | N   | THR | A | 128 | 45.381 | 0.350  | 52.410 | 1.00 | 63.04 | A |
| ATOM | 902 | CA  | THR | A | 128 | 44.919 | -0.845 | 53.102 | 1.00 | 63.04 | A |
| ATOM | 903 | CB  | THR | A | 128 | 45.728 | -2.087 | 52.685 | 1.00 | 36.80 | A |
| ATOM | 904 | OG1 | THR | A | 128 | 47.102 | -1.913 | 53.074 | 1.00 | 36.80 | A |
| ATOM | 905 | CG2 | THR | A | 128 | 45.638 | -2.304 | 51.164 | 1.00 | 36.80 | A |
| ATOM | 906 | C   | THR | A | 128 | 45.161 | -0.595 | 54.585 | 1.00 | 63.04 | A |
| ATOM | 907 | O   | THR | A | 128 | 45.999 | 0.232  | 54.951 | 1.00 | 63.04 | A |
| ATOM | 908 | N   | ALA | A | 129 | 44.435 | -1.301 | 55.440 | 1.00 | 39.48 | A |

Fig. 2R

| | | | | | | | | | | |
|---|---|---|---|---|---|---|---|---|---|---|
| ATOM | 909 | CA | ALA | A | 129 | 44.606 | -1.125 | 56.875 | 1.00 | 39.48 | A |
| ATOM | 910 | CB | ALA | A | 129 | 43.749 | -2.128 | 57.639 | 1.00 | 39.02 | A |
| ATOM | 911 | C | ALA | A | 129 | 46.072 | -1.277 | 57.271 | 1.00 | 39.48 | A |
| ATOM | 912 | O | ALA | A | 129 | 46.544 | -0.596 | 58.179 | 1.00 | 39.48 | A |
| ATOM | 913 | N | ASP | A | 130 | 46.797 | -2.160 | 56.589 | 1.00 | 50.74 | A |
| ATOM | 914 | CA | ASP | A | 130 | 48.206 | -2.371 | 56.912 | 1.00 | 50.74 | A |
| ATOM | 915 | CB | ASP | A | 130 | 48.738 | -3.631 | 56.229 | 1.00 | 98.04 | A |
| ATOM | 916 | CG | ASP | A | 130 | 48.257 | -4.899 | 56.900 | 1.00 | 98.04 | A |
| ATOM | 917 | OD1 | ASP | A | 130 | 47.035 | -5.156 | 56.873 | 1.00 | 98.04 | A |
| ATOM | 918 | OD2 | ASP | A | 130 | 49.100 | -5.633 | 57.461 | 1.00 | 98.04 | A |
| ATOM | 919 | C | ASP | A | 130 | 49.060 | -1.179 | 56.519 | 1.00 | 50.74 | A |
| ATOM | 920 | O | ASP | A | 130 | 49.963 | -0.781 | 57.265 | 1.00 | 50.74 | A |
| ATOM | 921 | N | GLU | A | 131 | 48.771 | -0.618 | 55.347 | 1.00 | 61.99 | A |
| ATOM | 922 | CA | GLU | A | 131 | 49.500 | 0.543 | 54.848 | 1.00 | 61.99 | A |
| ATOM | 923 | CB | GLU | A | 131 | 49.018 | 0.905 | 53.432 | 1.00 | 35.87 | A |
| ATOM | 924 | CG | GLU | A | 131 | 49.255 | -0.199 | 52.383 | 1.00 | 35.87 | A |
| ATOM | 925 | CD | GLU | A | 131 | 48.725 | 0.156 | 50.991 | 1.00 | 35.87 | A |
| ATOM | 926 | OE1 | GLU | A | 131 | 47.518 | 0.469 | 50.867 | 1.00 | 35.87 | A |
| ATOM | 927 | OE2 | GLU | A | 131 | 49.514 | 0.116 | 50.019 | 1.00 | 35.87 | A |
| ATOM | 928 | C | GLU | A | 131 | 49.285 | 1.720 | 55.805 | 1.00 | 61.99 | A |
| ATOM | 929 | O | GLU | A | 131 | 50.210 | 2.494 | 56.061 | 1.00 | 61.99 | A |
| ATOM | 930 | N | VAL | A | 132 | 48.066 | 1.835 | 56.338 | 1.00 | 41.47 | A |
| ATOM | 931 | CA | VAL | A | 132 | 47.716 | 2.899 | 57.282 | 1.00 | 41.47 | A |
| ATOM | 932 | CB | VAL | A | 132 | 46.227 | 2.827 | 57.703 | 1.00 | 27.86 | A |
| ATOM | 933 | CG1 | VAL | A | 132 | 45.971 | 3.746 | 58.890 | 1.00 | 27.86 | A |
| ATOM | 934 | CG2 | VAL | A | 132 | 45.345 | 3.243 | 56.550 | 1.00 | 27.86 | A |
| ATOM | 935 | C | VAL | A | 132 | 48.566 | 2.789 | 58.541 | 1.00 | 41.47 | A |
| ATOM | 936 | O | VAL | A | 132 | 49.214 | 3.755 | 58.958 | 1.00 | 41.47 | A |
| ATOM | 937 | N | ALA | A | 133 | 48.551 | 1.607 | 59.146 | 1.00 | 41.81 | A |
| ATOM | 938 | CA | ALA | A | 133 | 49.327 | 1.358 | 60.351 | 1.00 | 41.81 | A |
| ATOM | 939 | CB | ALA | A | 133 | 49.198 | -0.103 | 60.759 | 1.00 | 40.85 | A |
| ATOM | 940 | C | ALA | A | 133 | 50.790 | 1.700 | 60.096 | 1.00 | 41.81 | A |
| ATOM | 941 | O | ALA | A | 133 | 51.426 | 2.374 | 60.904 | 1.00 | 41.81 | A |
| ATOM | 942 | N | THR | A | 134 | 51.320 | 1.232 | 58.970 | 1.00 | 46.90 | A |
| ATOM | 943 | CA | THR | A | 134 | 52.712 | 1.497 | 58.633 | 1.00 | 46.90 | A |
| ATOM | 944 | CB | THR | A | 134 | 53.106 | 0.851 | 57.293 | 1.00 | 46.04 | A |
| ATOM | 945 | OG1 | THR | A | 134 | 53.111 | -0.574 | 57.439 | 1.00 | 46.04 | A |
| ATOM | 946 | CG2 | THR | A | 134 | 54.494 | 1.324 | 56.857 | 1.00 | 46.04 | A |
| ATOM | 947 | C | THR | A | 134 | 52.957 | 2.992 | 58.538 | 1.00 | 46.90 | A |
| ATOM | 948 | O | THR | A | 134 | 53.908 | 3.518 | 59.130 | 1.00 | 46.90 | A |
| ATOM | 949 | N | LEU | A | 135 | 52.097 | 3.668 | 57.784 | 1.00 | 53.07 | A |
| ATOM | 950 | CA | LEU | A | 135 | 52.206 | 5.109 | 57.611 | 1.00 | 53.07 | A |
| ATOM | 951 | CB | LEU | A | 135 | 50.997 | 5.629 | 56.838 | 1.00 | 28.73 | A |
| ATOM | 952 | CG | LEU | A | 135 | 50.926 | 7.133 | 56.591 | 1.00 | 28.73 | A |
| ATOM | 953 | CD1 | LEU | A | 135 | 52.240 | 7.647 | 56.003 | 1.00 | 28.73 | A |
| ATOM | 954 | CD2 | LEU | A | 135 | 49.763 | 7.405 | 55.650 | 1.00 | 28.73 | A |
| ATOM | 955 | C | LEU | A | 135 | 52.295 | 5.803 | 58.972 | 1.00 | 53.07 | A |
| ATOM | 956 | O | LEU | A | 135 | 53.204 | 6.601 | 59.214 | 1.00 | 53.07 | A |

Fig. 2S

```
ATOM    957  N    GLU A 136      51.361   5.484  59.863  1.00 44.05           A
ATOM    958  CA   GLU A 136      51.360   6.088  61.186  1.00 44.05           A
ATOM    959  CB   GLU A 136      50.082   5.723  61.938  1.00 46.25           A
ATOM    960  CG   GLU A 136      48.848   6.270  61.250  1.00 46.25           A
ATOM    961  CD   GLU A 136      47.720   6.554  62.208  1.00 46.25           A
ATOM    962  OE1  GLU A 136      46.624   6.927  61.737  1.00 46.25           A
ATOM    963  OE2  GLU A 136      47.932   6.413  63.433  1.00 46.25           A
ATOM    964  C    GLU A 136      52.583   5.692  62.000  1.00 44.05           A
ATOM    965  O    GLU A 136      53.122   6.497  62.768  1.00 44.05           A
ATOM    966  N    TYR A 137      53.034   4.457  61.836  1.00 42.24           A
ATOM    967  CA   TYR A 137      54.205   4.012  62.572  1.00 42.24           A
ATOM    968  CB   TYR A 137      54.504   2.545  62.263  1.00 52.94           A
ATOM    969  CG   TYR A 137      55.858   2.111  62.761  1.00 52.94           A
ATOM    970  CD1  TYR A 137      56.111   1.973  64.123  1.00 52.94           A
ATOM    971  CE1  TYR A 137      57.379   1.636  64.586  1.00 52.94           A
ATOM    972  CD2  TYR A 137      56.904   1.897  61.870  1.00 52.94           A
ATOM    973  CE2  TYR A 137      58.174   1.560  62.316  1.00 52.94           A
ATOM    974  CZ   TYR A 137      58.410   1.431  63.674  1.00 52.94           A
ATOM    975  OH   TYR A 137      59.679   1.099  64.109  1.00 52.94           A
ATOM    976  C    TYR A 137      55.402   4.876  62.180  1.00 42.24           A
ATOM    977  O    TYR A 137      56.093   5.425  63.039  1.00 42.24           A
ATOM    978  N    LEU A 138      55.631   4.995  60.874  1.00 37.69           A
ATOM    979  CA   LEU A 138      56.745   5.780  60.351  1.00 37.69           A
ATOM    980  CB   LEU A 138      56.878   5.554  58.836  1.00 52.05           A
ATOM    981  CG   LEU A 138      57.143   4.104  58.390  1.00 52.05           A
ATOM    982  CD1  LEU A 138      57.126   4.020  56.870  1.00 52.05           A
ATOM    983  CD2  LEU A 138      58.482   3.626  58.933  1.00 52.05           A
ATOM    984  C    LEU A 138      56.611   7.275  60.657  1.00 37.69           A
ATOM    985  O    LEU A 138      57.566   7.900  61.111  1.00 37.69           A
ATOM    986  N    LEU A 139      55.437   7.849  60.411  1.00 53.38           A
ATOM    987  CA   LEU A 139      55.238   9.264  60.696  1.00 53.38           A
ATOM    988  CB   LEU A 139      53.782   9.674  60.428  1.00 22.81           A
ATOM    989  CG   LEU A 139      53.510  10.039  58.957  1.00 22.81           A
ATOM    990  CD1  LEU A 139      52.025  10.086  58.665  1.00 22.81           A
ATOM    991  CD2  LEU A 139      54.167  11.368  58.656  1.00 22.81           A
ATOM    992  C    LEU A 139      55.615   9.570  62.144  1.00 53.38           A
ATOM    993  O    LEU A 139      56.289  10.569  62.424  1.00 53.38           A
ATOM    994  N    LYS A 140      55.196   8.708  63.065  1.00 46.77           A
ATOM    995  CA   LYS A 140      55.517   8.912  64.473  1.00 46.77           A
ATOM    996  CB   LYS A 140      54.854   7.830  65.324  1.00 58.30           A
ATOM    997  CG   LYS A 140      53.336   7.886  65.328  1.00 58.30           A
ATOM    998  CD   LYS A 140      52.751   6.751  66.144  1.00 58.30           A
ATOM    999  CE   LYS A 140      51.240   6.713  66.029  1.00 58.30           A
ATOM   1000  NZ   LYS A 140      50.658   5.553  66.765  1.00 58.30           A
ATOM   1001  C    LYS A 140      57.035   8.900  64.696  1.00 46.77           A
ATOM   1002  O    LYS A 140      57.559   9.669  65.503  1.00 46.77           A
ATOM   1003  N    LYS A 141      57.736   8.025  63.980  1.00 52.29           A
ATOM   1004  CA   LYS A 141      59.183   7.927  64.102  1.00 52.29           A
```

Fig. 2T

```
ATOM  1005  CB   LYS A 141    59.733   6.906  63.103  1.00 78.01      A
ATOM  1006  CG   LYS A 141    59.234   5.485  63.304  1.00 78.01      A
ATOM  1007  CD   LYS A 141    59.917   4.803  64.483  1.00 78.01      A
ATOM  1008  CE   LYS A 141    61.401   4.570  64.211  1.00 78.01      A
ATOM  1009  NZ   LYS A 141    61.626   3.676  63.039  1.00 78.01      A
ATOM  1010  C    LYS A 141    59.822   9.283  63.831  1.00 52.29      A
ATOM  1011  O    LYS A 141    60.721   9.710  64.561  1.00 52.29      A
ATOM  1012  N    VAL A 142    59.351   9.962  62.785  1.00 48.93      A
ATOM  1013  CA   VAL A 142    59.889  11.268  62.410  1.00 48.93      A
ATOM  1014  CB   VAL A 142    59.205  11.796  61.126  1.00 31.55      A
ATOM  1015  CG1  VAL A 142    59.666  13.211  60.816  1.00 31.55      A
ATOM  1016  CG2  VAL A 142    59.540  10.881  59.962  1.00 31.55      A
ATOM  1017  C    VAL A 142    59.792  12.321  63.522  1.00 48.93      A
ATOM  1018  O    VAL A 142    60.540  13.297  63.520  1.00 48.93      A
ATOM  1019  N    LEU A 143    58.877  12.129  64.466  1.00 67.04      A
ATOM  1020  CA   LEU A 143    58.737  13.062  65.583  1.00 67.04      A
ATOM  1021  CB   LEU A 143    57.302  13.053  66.120  1.00 42.71      A
ATOM  1022  CG   LEU A 143    56.178  13.434  65.151  1.00 42.71      A
ATOM  1023  CD1  LEU A 143    54.823  13.233  65.821  1.00 42.71      A
ATOM  1024  CD2  LEU A 143    56.355  14.874  64.714  1.00 42.71      A
ATOM  1025  C    LEU A 143    59.695  12.601  66.682  1.00 67.04      A
ATOM  1026  O    LEU A 143    60.170  11.461  66.660  1.00 67.04      A
ATOM  1027  N    PRO A 144    59.987  13.467  67.667  1.00135.51      A
ATOM  1028  CD   PRO A 144    60.809  13.066  68.823  1.00 96.05      A
ATOM  1029  CA   PRO A 144    59.495  14.840  67.835  1.00135.51      A
ATOM  1030  CB   PRO A 144    60.165  15.287  69.135  1.00 96.05      A
ATOM  1031  CG   PRO A 144    60.316  14.001  69.895  1.00 96.05      A
ATOM  1032  C    PRO A 144    59.851  15.747  66.656  1.00135.51      A
ATOM  1033  O    PRO A 144    58.923  16.371  66.093  1.00135.51      A
ATOM  1034  OXT  PRO A 144    61.053  15.826  66.317  1.00 96.05      A
ATOM  1035  CB   ASN B   9    51.205   2.213  67.233  1.00135.37      B
ATOM  1036  CG   ASN B   9    50.539   1.403  66.123  1.00135.37      B
ATOM  1037  OD1  ASN B   9    50.453   0.173  66.194  1.00135.37      B
ATOM  1038  ND2  ASN B   9    50.060   2.096  65.091  1.00135.37      B
ATOM  1039  C    ASN B   9    48.981   2.335  68.349  1.00 66.09      B
ATOM  1040  O    ASN B   9    48.315   1.572  67.640  1.00 66.09      B
ATOM  1041  N    ASN B   9    50.712   0.757  69.190  1.00 66.09      B
ATOM  1042  CA   ASN B   9    50.471   2.096  68.577  1.00 66.09      B
ATOM  1043  N    GLU B  10    48.458   3.398  68.949  1.00129.71      B
ATOM  1044  CA   GLU B  10    47.050   3.722  68.781  1.00129.71      B
ATOM  1045  CB   GLU B  10    46.538   4.558  69.965  1.00111.04      B
ATOM  1046  CG   GLU B  10    47.613   5.022  70.946  1.00111.04      B
ATOM  1047  CD   GLU B  10    48.429   6.195  70.432  1.00111.04      B
ATOM  1048  OE1  GLU B  10    49.073   6.062  69.369  1.00111.04      B
ATOM  1049  OE2  GLU B  10    48.425   7.253  71.099  1.00111.04      B
ATOM  1050  C    GLU B  10    46.817   4.471  67.472  1.00129.71      B
ATOM  1051  O    GLU B  10    47.241   5.619  67.314  1.00129.71      B
ATOM  1052  N    ILE B  11    46.165   3.803  66.523  1.00 72.20      B
```

Fig. 2U

| ATOM | 1053 | CA | ILE | B | 11 | 45.859 | 4.430 | 65.249 | 1.00 | 72.20 | B |
|------|------|-----|-----|---|----|--------|-------|--------|------|-------|---|
| ATOM | 1054 | CB | ILE | B | 11 | 45.047 | 3.482 | 64.321 | 1.00 | 44.08 | B |
| ATOM | 1055 | CG2 | ILE | B | 11 | 44.363 | 4.273 | 63.215 | 1.00 | 44.08 | B |
| ATOM | 1056 | CG1 | ILE | B | 11 | 45.981 | 2.447 | 63.685 | 1.00 | 44.08 | B |
| ATOM | 1057 | CD1 | ILE | B | 11 | 47.045 | 3.052 | 62.771 | 1.00 | 44.08 | B |
| ATOM | 1058 | C | ILE | B | 11 | 45.030 | 5.664 | 65.570 | 1.00 | 72.20 | B |
| ATOM | 1059 | O | ILE | B | 11 | 43.859 | 5.559 | 65.931 | 1.00 | 72.20 | B |
| ATOM | 1060 | N | ILE | B | 12 | 45.659 | 6.830 | 65.468 | 1.00 | 83.43 | B |
| ATOM | 1061 | CA | ILE | B | 12 | 44.990 | 8.093 | 65.740 | 1.00 | 83.43 | B |
| ATOM | 1062 | CB | ILE | B | 12 | 45.914 | 9.042 | 66.517 | 1.00 | 57.67 | B |
| ATOM | 1063 | CG2 | ILE | B | 12 | 46.291 | 8.415 | 67.849 | 1.00 | 57.67 | B |
| ATOM | 1064 | CG1 | ILE | B | 12 | 47.169 | 9.336 | 65.696 | 1.00 | 57.67 | B |
| ATOM | 1065 | CD1 | ILE | B | 12 | 48.155 | 10.247 | 66.400 | 1.00 | 57.67 | B |
| ATOM | 1066 | C | ILE | B | 12 | 44.614 | 8.733 | 64.410 | 1.00 | 83.43 | B |
| ATOM | 1067 | O | ILE | B | 12 | 45.108 | 8.318 | 63.361 | 1.00 | 83.43 | B |
| ATOM | 1068 | N | PRO | B | 13 | 43.734 | 9.751 | 64.430 | 1.00 | 40.24 | B |
| ATOM | 1069 | CD | PRO | B | 13 | 43.092 | 10.404 | 65.582 | 1.00 | 21.06 | B |
| ATOM | 1070 | CA | PRO | B | 13 | 43.332 | 10.404 | 63.178 | 1.00 | 40.24 | B |
| ATOM | 1071 | CB | PRO | B | 13 | 42.435 | 11.547 | 63.657 | 1.00 | 21.06 | B |
| ATOM | 1072 | CG | PRO | B | 13 | 41.867 | 11.005 | 64.948 | 1.00 | 21.06 | B |
| ATOM | 1073 | C | PRO | B | 13 | 44.567 | 10.892 | 62.428 | 1.00 | 40.24 | B |
| ATOM | 1074 | O | PRO | B | 13 | 45.298 | 11.766 | 62.903 | 1.00 | 40.24 | B |
| ATOM | 1075 | N | LEU | B | 14 | 44.806 | 10.306 | 61.262 | 1.00 | 44.39 | B |
| ATOM | 1076 | CA | LEU | B | 14 | 45.969 | 10.670 | 60.479 | 1.00 | 44.39 | B |
| ATOM | 1077 | CB | LEU | B | 14 | 45.908 | 9.983 | 59.117 | 1.00 | 19.34 | B |
| ATOM | 1078 | CG | LEU | B | 14 | 47.107 | 10.215 | 58.191 | 1.00 | 19.34 | B |
| ATOM | 1079 | CD1 | LEU | B | 14 | 48.395 | 9.890 | 58.927 | 1.00 | 19.34 | B |
| ATOM | 1080 | CD2 | LEU | B | 14 | 46.967 | 9.347 | 56.941 | 1.00 | 19.34 | B |
| ATOM | 1081 | C | LEU | B | 14 | 46.076 | 12.185 | 60.314 | 1.00 | 44.39 | B |
| ATOM | 1082 | O | LEU | B | 14 | 47.176 | 12.743 | 60.347 | 1.00 | 44.39 | B |
| ATOM | 1083 | N | GLY | B | 15 | 44.932 | 12.848 | 60.153 | 1.00 | 31.14 | B |
| ATOM | 1084 | CA | GLY | B | 15 | 44.931 | 14.292 | 59.983 | 1.00 | 31.14 | B |
| ATOM | 1085 | C | GLY | B | 15 | 45.771 | 14.999 | 61.030 | 1.00 | 31.14 | B |
| ATOM | 1086 | O | GLY | B | 15 | 46.495 | 15.959 | 60.725 | 1.00 | 31.14 | B |
| ATOM | 1087 | N | ARG | B | 16 | 45.673 | 14.531 | 62.272 | 1.00 | 41.91 | B |
| ATOM | 1088 | CA | ARG | B | 16 | 46.440 | 15.101 | 63.382 | 1.00 | 41.91 | B |
| ATOM | 1089 | CB | ARG | B | 16 | 45.947 | 14.523 | 64.716 | 1.00 | 51.45 | B |
| ATOM | 1090 | CG | ARG | B | 16 | 44.787 | 15.262 | 65.386 | 1.00 | 51.45 | B |
| ATOM | 1091 | CD | ARG | B | 16 | 43.456 | 15.229 | 64.609 | 1.00 | 51.45 | B |
| ATOM | 1092 | NE | ARG | B | 16 | 43.346 | 16.273 | 63.581 | 1.00 | 51.45 | B |
| ATOM | 1093 | CZ | ARG | B | 16 | 42.194 | 16.797 | 63.167 | 1.00 | 51.45 | B |
| ATOM | 1094 | NH1 | ARG | B | 16 | 41.052 | 16.376 | 63.696 | 1.00 | 51.45 | B |
| ATOM | 1095 | NH2 | ARG | B | 16 | 42.186 | 17.736 | 62.228 | 1.00 | 51.45 | B |
| ATOM | 1096 | C | ARG | B | 16 | 47.945 | 14.811 | 63.223 | 1.00 | 41.91 | B |
| ATOM | 1097 | O | ARG | B | 16 | 48.793 | 15.676 | 63.462 | 1.00 | 41.91 | B |
| ATOM | 1098 | N | LEU | B | 17 | 48.272 | 13.588 | 62.820 | 1.00 | 38.48 | B |
| ATOM | 1099 | CA | LEU | B | 17 | 49.667 | 13.186 | 62.634 | 1.00 | 38.48 | B |
| ATOM | 1100 | CB | LEU | B | 17 | 49.747 | 11.706 | 62.251 | 1.00 | 42.44 | B |

Fig. 2V

| | | | | | | | | | | |
|---|---|---|---|---|---|---|---|---|---|---|
| ATOM | 1101 | CG | LEU | B | 17 | 50.527 | 10.781 | 63.183 | 1.00 42.44 | B |
| ATOM | 1102 | CD1 | LEU | B | 17 | 50.582 | 9.383 | 62.577 | 1.00 42.44 | B |
| ATOM | 1103 | CD2 | LEU | B | 17 | 51.933 | 11.312 | 63.380 | 1.00 42.44 | B |
| ATOM | 1104 | C | LEU | B | 17 | 50.318 | 14.027 | 61.541 | 1.00 38.48 | B |
| ATOM | 1105 | O | LEU | B | 17 | 51.416 | 14.560 | 61.722 | 1.00 38.48 | B |
| ATOM | 1106 | N | ILE | B | 18 | 49.639 | 14.127 | 60.398 | 1.00 33.51 | B |
| ATOM | 1107 | CA | ILE | B | 18 | 50.131 | 14.919 | 59.273 | 1.00 33.51 | B |
| ATOM | 1108 | CB | ILE | B | 18 | 49.089 | 14.986 | 58.154 | 1.00 35.12 | B |
| ATOM | 1109 | CG2 | ILE | B | 18 | 49.478 | 16.025 | 57.131 | 1.00 35.12 | B |
| ATOM | 1110 | CG1 | ILE | B | 18 | 48.953 | 13.616 | 57.505 | 1.00 35.12 | B |
| ATOM | 1111 | CD1 | ILE | B | 18 | 47.936 | 13.574 | 56.392 | 1.00 35.12 | B |
| ATOM | 1112 | C | ILE | B | 18 | 50.407 | 16.335 | 59.768 | 1.00 33.51 | B |
| ATOM | 1113 | O | ILE | B | 18 | 51.434 | 16.926 | 59.430 | 1.00 33.51 | B |
| ATOM | 1114 | N | HIS | B | 19 | 49.488 | 16.865 | 60.579 | 1.00 26.80 | B |
| ATOM | 1115 | CA | HIS | B | 19 | 49.634 | 18.207 | 61.131 | 1.00 26.80 | B |
| ATOM | 1116 | CB | HIS | B | 19 | 48.402 | 18.596 | 61.953 | 1.00 38.93 | B |
| ATOM | 1117 | CG | HIS | B | 19 | 48.514 | 19.943 | 62.609 | 1.00 38.93 | B |
| ATOM | 1118 | CD2 | HIS | B | 19 | 47.842 | 21.101 | 62.391 | 1.00 38.93 | B |
| ATOM | 1119 | ND1 | HIS | B | 19 | 49.422 | 20.212 | 63.613 | 1.00 38.93 | B |
| ATOM | 1120 | CE1 | HIS | B | 19 | 49.305 | 21.474 | 63.985 | 1.00 38.93 | B |
| ATOM | 1121 | NE2 | HIS | B | 19 | 48.354 | 22.035 | 63.259 | 1.00 38.93 | B |
| ATOM | 1122 | C | HIS | B | 19 | 50.883 | 18.324 | 62.010 | 1.00 26.80 | B |
| ATOM | 1123 | O | HIS | B | 19 | 51.666 | 19.259 | 61.852 | 1.00 26.80 | B |
| ATOM | 1124 | N | MET | B | 20 | 51.063 | 17.394 | 62.943 | 1.00 28.60 | B |
| ATOM | 1125 | CA | MET | B | 20 | 52.232 | 17.433 | 63.821 | 1.00 28.60 | B |
| ATOM | 1126 | CB | MET | B | 20 | 52.227 | 16.259 | 64.820 | 1.00 39.32 | B |
| ATOM | 1127 | CG | MET | B | 20 | 51.096 | 16.297 | 65.880 | 1.00 39.32 | B |
| ATOM | 1128 | SD | MET | B | 20 | 50.911 | 14.776 | 66.939 | 1.00 39.32 | B |
| ATOM | 1129 | CE | MET | B | 20 | 49.664 | 13.868 | 66.026 | 1.00 39.32 | B |
| ATOM | 1130 | C | MET | B | 20 | 53.509 | 17.374 | 62.981 | 1.00 28.60 | B |
| ATOM | 1131 | O | MET | B | 20 | 54.360 | 18.257 | 63.067 | 1.00 28.60 | B |
| ATOM | 1132 | N | VAL | B | 21 | 53.645 | 16.337 | 62.165 | 1.00 44.11 | B |
| ATOM | 1133 | CA | VAL | B | 21 | 54.831 | 16.202 | 61.328 | 1.00 44.11 | B |
| ATOM | 1134 | CB | VAL | B | 21 | 54.750 | 14.920 | 60.419 | 1.00 25.48 | B |
| ATOM | 1135 | CG1 | VAL | B | 21 | 55.871 | 14.909 | 59.369 | 1.00 25.48 | B |
| ATOM | 1136 | CG2 | VAL | B | 21 | 54.851 | 13.667 | 61.296 | 1.00 25.48 | B |
| ATOM | 1137 | C | VAL | B | 21 | 55.024 | 17.453 | 60.472 | 1.00 44.11 | B |
| ATOM | 1138 | O | VAL | B | 21 | 56.147 | 17.951 | 60.365 | 1.00 44.11 | B |
| ATOM | 1139 | N | ASN | B | 22 | 53.941 | 17.967 | 59.880 | 1.00 30.47 | B |
| ATOM | 1140 | CA | ASN | B | 22 | 54.033 | 19.161 | 59.038 | 1.00 30.47 | B |
| ATOM | 1141 | CB | ASN | B | 22 | 52.663 | 19.551 | 58.476 | 1.00 26.19 | B |
| ATOM | 1142 | CG | ASN | B | 22 | 52.696 | 20.880 | 57.708 | 1.00 26.19 | B |
| ATOM | 1143 | OD1 | ASN | B | 22 | 53.363 | 21.014 | 56.676 | 1.00 26.19 | B |
| ATOM | 1144 | ND2 | ASN | B | 22 | 51.965 | 21.867 | 58.218 | 1.00 26.19 | B |
| ATOM | 1145 | C | ASN | B | 22 | 54.592 | 20.317 | 59.851 | 1.00 30.47 | B |
| ATOM | 1146 | O | ASN | B | 22 | 55.460 | 21.061 | 59.377 | 1.00 30.47 | B |
| ATOM | 1147 | N | GLN | B | 23 | 54.082 | 20.460 | 61.073 | 1.00 46.49 | B |
| ATOM | 1148 | CA | GLN | B | 23 | 54.518 | 21.507 | 61.988 | 1.00 46.49 | B |

Fig. 2W

```
ATOM   1149  CB   GLN B  23      53.941  21.261  63.380  1.00 78.77           B
ATOM   1150  CG   GLN B  23      52.673  22.015  63.661  1.00 78.77           B
ATOM   1151  CD   GLN B  23      52.923  23.495  63.762  1.00 78.77           B
ATOM   1152  OE1  GLN B  23      53.721  23.937  64.588  1.00 78.77           B
ATOM   1153  NE2  GLN B  23      52.247  24.277  62.921  1.00 78.77           B
ATOM   1154  C    GLN B  23      56.030  21.474  62.075  1.00 46.49           B
ATOM   1155  O    GLN B  23      56.717  22.470  61.805  1.00 46.49           B
ATOM   1156  N    LYS B  24      56.541  20.310  62.463  1.00 34.97           B
ATOM   1157  CA   LYS B  24      57.976  20.100  62.603  1.00 34.97           B
ATOM   1158  CB   LYS B  24      58.270  18.647  62.982  1.00 37.02           B
ATOM   1159  CG   LYS B  24      59.722  18.264  62.762  1.00 37.02           B
ATOM   1160  CD   LYS B  24      60.128  16.985  63.486  1.00 37.02           B
ATOM   1161  CE   LYS B  24      61.567  16.611  63.127  1.00 37.02           B
ATOM   1162  NZ   LYS B  24      62.174  15.628  64.082  1.00 37.02           B
ATOM   1163  C    LYS B  24      58.729  20.448  61.322  1.00 34.97           B
ATOM   1164  O    LYS B  24      59.758  21.123  61.355  1.00 34.97           B
ATOM   1165  N    LYS B  25      58.220  19.976  60.193  1.00 37.64           B
ATOM   1166  CA   LYS B  25      58.855  20.255  58.919  1.00 37.64           B
ATOM   1167  CB   LYS B  25      57.990  19.746  57.762  1.00 42.01           B
ATOM   1168  CG   LYS B  25      58.655  19.922  56.407  1.00 42.01           B
ATOM   1169  CD   LYS B  25      57.650  20.235  55.311  1.00 42.01           B
ATOM   1170  CE   LYS B  25      57.095  21.642  55.459  1.00 42.01           B
ATOM   1171  NZ   LYS B  25      56.097  21.963  54.394  1.00 42.01           B
ATOM   1172  C    LYS B  25      59.075  21.761  58.752  1.00 37.64           B
ATOM   1173  O    LYS B  25      60.199  22.200  58.489  1.00 37.64           B
ATOM   1174  N    ASP B  26      58.001  22.542  58.907  1.00 35.53           B
ATOM   1175  CA   ASP B  26      58.088  23.994  58.748  1.00 35.53           B
ATOM   1176  CB   ASP B  26      56.699  24.640  58.880  1.00 56.04           B
ATOM   1177  CG   ASP B  26      55.787  24.341  57.681  1.00 56.04           B
ATOM   1178  OD1  ASP B  26      56.233  24.520  56.522  1.00 56.04           B
ATOM   1179  OD2  ASP B  26      54.618  23.937  57.897  1.00 56.04           B
ATOM   1180  C    ASP B  26      59.072  24.629  59.739  1.00 35.53           B
ATOM   1181  O    ASP B  26      59.735  25.614  59.417  1.00 35.53           B
ATOM   1182  N    ARG B  27      59.171  24.070  60.940  1.00 25.58           B
ATOM   1183  CA   ARG B  27      60.101  24.602  61.926  1.00 25.58           B
ATOM   1184  CB   ARG B  27      60.023  23.818  63.245  1.00 59.09           B
ATOM   1185  CG   ARG B  27      61.276  23.954  64.121  1.00 59.09           B
ATOM   1186  CD   ARG B  27      61.081  23.472  65.571  1.00 59.09           B
ATOM   1187  NE   ARG B  27      60.843  22.034  65.700  1.00 59.09           B
ATOM   1188  CZ   ARG B  27      59.642  21.475  65.865  1.00 59.09           B
ATOM   1189  NH1  ARG B  27      58.546  22.230  65.922  1.00 59.09           B
ATOM   1190  NH2  ARG B  27      59.537  20.154  65.991  1.00 59.09           B
ATOM   1191  C    ARG B  27      61.492  24.460  61.333  1.00 25.58           B
ATOM   1192  O    ARG B  27      62.217  25.445  61.145  1.00 25.58           B
ATOM   1193  N    LEU B  28      61.866  23.221  61.031  1.00 30.74           B
ATOM   1194  CA   LEU B  28      63.173  22.958  60.454  1.00 30.74           B
ATOM   1195  CB   LEU B  28      63.303  21.490  60.060  1.00 25.37           B
ATOM   1196  CG   LEU B  28      63.317  20.479  61.204  1.00 25.37           B
```

Fig. 2X

| ATOM | 1197 | CD1 | LEU | B | 28 | 63.329 | 19.085 | 60.628 | 1.00 | 25.37 | B |
| ATOM | 1198 | CD2 | LEU | B | 28 | 64.532 | 20.705 | 62.088 | 1.00 | 25.37 | B |
| ATOM | 1199 | C | LEU | B | 28 | 63.402 | 23.826 | 59.227 | 1.00 | 30.74 | B |
| ATOM | 1200 | O | LEU | B | 28 | 64.450 | 24.468 | 59.100 | 1.00 | 30.74 | B |
| ATOM | 1201 | N | LEU | B | 29 | 62.422 | 23.843 | 58.323 | 1.00 | 35.92 | B |
| ATOM | 1202 | CA | LEU | B | 29 | 62.519 | 24.635 | 57.097 | 1.00 | 35.92 | B |
| ATOM | 1203 | CB | LEU | B | 29 | 61.193 | 24.617 | 56.335 | 1.00 | 29.83 | B |
| ATOM | 1204 | CG | LEU | B | 29 | 61.253 | 25.212 | 54.924 | 1.00 | 29.83 | B |
| ATOM | 1205 | CD1 | LEU | B | 29 | 62.079 | 24.314 | 54.024 | 1.00 | 29.83 | B |
| ATOM | 1206 | CD2 | LEU | B | 29 | 59.859 | 25.341 | 54.356 | 1.00 | 29.83 | B |
| ATOM | 1207 | C | LEU | B | 29 | 62.892 | 26.083 | 57.422 | 1.00 | 35.92 | B |
| ATOM | 1208 | O | LEU | B | 29 | 63.767 | 26.675 | 56.783 | 1.00 | 35.92 | B |
| ATOM | 1209 | N | ASN | B | 30 | 62.232 | 26.652 | 58.423 | 1.00 | 32.28 | B |
| ATOM | 1210 | CA | ASN | B | 30 | 62.519 | 28.018 | 58.811 | 1.00 | 32.28 | B |
| ATOM | 1211 | CB | ASN | B | 30 | 61.609 | 28.440 | 59.960 | 1.00 | 55.71 | B |
| ATOM | 1212 | CG | ASN | B | 30 | 60.475 | 29.325 | 59.501 | 1.00 | 55.71 | B |
| ATOM | 1213 | OD1 | ASN | B | 30 | 59.407 | 29.356 | 60.118 | 1.00 | 55.71 | B |
| ATOM | 1214 | ND2 | ASN | B | 30 | 60.699 | 30.064 | 58.418 | 1.00 | 55.71 | B |
| ATOM | 1215 | C | ASN | B | 30 | 63.977 | 28.170 | 59.215 | 1.00 | 32.28 | B |
| ATOM | 1216 | O | ASN | B | 30 | 64.655 | 29.106 | 58.790 | 1.00 | 32.28 | B |
| ATOM | 1217 | N | GLU | B | 31 | 64.464 | 27.248 | 60.034 | 1.00 | 28.98 | B |
| ATOM | 1218 | CA | GLU | B | 31 | 65.840 | 27.315 | 60.492 | 1.00 | 28.98 | B |
| ATOM | 1219 | CB | GLU | B | 31 | 66.158 | 26.172 | 61.453 | 1.00 | 46.83 | B |
| ATOM | 1220 | CG | GLU | B | 31 | 65.361 | 26.133 | 62.739 | 1.00 | 46.83 | B |
| ATOM | 1221 | CD | GLU | B | 31 | 65.784 | 24.959 | 63.607 | 1.00 | 46.83 | B |
| ATOM | 1222 | OE1 | GLU | B | 31 | 66.487 | 24.059 | 63.085 | 1.00 | 46.83 | B |
| ATOM | 1223 | OE2 | GLU | B | 31 | 65.410 | 24.926 | 64.799 | 1.00 | 46.83 | B |
| ATOM | 1224 | C | GLU | B | 31 | 66.794 | 27.222 | 59.319 | 1.00 | 28.98 | B |
| ATOM | 1225 | O | GLU | B | 31 | 67.678 | 28.054 | 59.159 | 1.00 | 28.98 | B |
| ATOM | 1226 | N | TYR | B | 32 | 66.628 | 26.193 | 58.503 | 1.00 | 35.77 | B |
| ATOM | 1227 | CA | TYR | B | 32 | 67.506 | 26.014 | 57.362 | 1.00 | 35.77 | B |
| ATOM | 1228 | CB | TYR | B | 32 | 67.223 | 24.672 | 56.668 | 1.00 | 40.71 | B |
| ATOM | 1229 | CG | TYR | B | 32 | 67.928 | 23.494 | 57.302 | 1.00 | 40.71 | B |
| ATOM | 1230 | CD1 | TYR | B | 32 | 67.209 | 22.441 | 57.873 | 1.00 | 40.71 | B |
| ATOM | 1231 | CE1 | TYR | B | 32 | 67.861 | 21.338 | 58.449 | 1.00 | 40.71 | B |
| ATOM | 1232 | CD2 | TYR | B | 32 | 69.319 | 23.426 | 57.323 | 1.00 | 40.71 | B |
| ATOM | 1233 | CE2 | TYR | B | 32 | 69.984 | 22.339 | 57.896 | 1.00 | 40.71 | B |
| ATOM | 1234 | CZ | TYR | B | 32 | 69.251 | 21.296 | 58.455 | 1.00 | 40.71 | B |
| ATOM | 1235 | OH | TYR | B | 32 | 69.918 | 20.213 | 58.998 | 1.00 | 40.71 | B |
| ATOM | 1236 | C | TYR | B | 32 | 67.432 | 27.148 | 56.346 | 1.00 | 35.77 | B |
| ATOM | 1237 | O | TYR | B | 32 | 68.383 | 27.342 | 55.581 | 1.00 | 35.77 | B |
| ATOM | 1238 | N | LEU | B | 33 | 66.326 | 27.896 | 56.335 | 1.00 | 52.15 | B |
| ATOM | 1239 | CA | LEU | B | 33 | 66.170 | 28.996 | 55.380 | 1.00 | 52.15 | B |
| ATOM | 1240 | CB | LEU | B | 33 | 64.707 | 29.153 | 54.940 | 1.00 | 25.90 | B |
| ATOM | 1241 | CG | LEU | B | 33 | 64.061 | 28.198 | 53.921 | 1.00 | 25.90 | B |
| ATOM | 1242 | CD1 | LEU | B | 33 | 62.616 | 28.613 | 53.731 | 1.00 | 25.90 | B |
| ATOM | 1243 | CD2 | LEU | B | 33 | 64.793 | 28.219 | 52.587 | 1.00 | 25.90 | B |
| ATOM | 1244 | C | LEU | B | 33 | 66.662 | 30.348 | 55.878 | 1.00 | 52.15 | B |

Fig. 2Y

| | | | | | | | | | | |
|---|---|---|---|---|---|---|---|---|---|---|
| ATOM | 1245 | O | LEU | B | 33 | 67.086 | 31.182 | 55.077 | 1.00 52.15 | B |
| ATOM | 1246 | N | SER | B | 34 | 66.601 | 30.563 | 57.191 | 1.00 35.65 | B |
| ATOM | 1247 | CA | SER | B | 34 | 67.018 | 31.829 | 57.809 | 1.00 35.65 | B |
| ATOM | 1248 | CB | SER | B | 34 | 67.164 | 31.619 | 59.319 | 1.00 47.51 | B |
| ATOM | 1249 | OG | SER | B | 34 | 66.819 | 32.791 | 60.039 | 1.00 47.51 | B |
| ATOM | 1250 | C | SER | B | 34 | 68.309 | 32.458 | 57.222 | 1.00 35.65 | B |
| ATOM | 1251 | O | SER | B | 34 | 68.354 | 33.664 | 56.930 | 1.00 35.65 | B |
| ATOM | 1252 | N | PRO | B | 35 | 69.377 | 31.657 | 57.061 | 1.00 45.02 | B |
| ATOM | 1253 | CD | PRO | B | 35 | 69.647 | 30.355 | 57.695 | 1.00 42.17 | B |
| ATOM | 1254 | CA | PRO | B | 35 | 70.609 | 32.218 | 56.502 | 1.00 45.02 | B |
| ATOM | 1255 | CB | PRO | B | 35 | 71.662 | 31.150 | 56.828 | 1.00 42.17 | B |
| ATOM | 1256 | CG | PRO | B | 35 | 70.878 | 29.894 | 56.944 | 1.00 42.17 | B |
| ATOM | 1257 | C | PRO | B | 35 | 70.562 | 32.579 | 55.012 | 1.00 45.02 | B |
| ATOM | 1258 | O | PRO | B | 35 | 71.604 | 32.831 | 54.400 | 1.00 45.02 | B |
| ATOM | 1259 | N | LEU | B | 36 | 69.365 | 32.614 | 54.428 | 1.00 41.85 | B |
| ATOM | 1260 | CA | LEU | B | 36 | 69.230 | 32.985 | 53.021 | 1.00 41.85 | B |
| ATOM | 1261 | CB | LEU | B | 36 | 68.741 | 31.794 | 52.198 | 1.00 42.76 | B |
| ATOM | 1262 | CG | LEU | B | 36 | 69.454 | 30.458 | 52.439 | 1.00 42.76 | B |
| ATOM | 1263 | CD1 | LEU | B | 36 | 69.045 | 29.466 | 51.351 | 1.00 42.76 | B |
| ATOM | 1264 | CD2 | LEU | B | 36 | 70.964 | 30.649 | 52.427 | 1.00 42.76 | B |
| ATOM | 1265 | C | LEU | B | 36 | 68.256 | 34.160 | 52.893 | 1.00 41.85 | B |
| ATOM | 1266 | O | LEU | B | 36 | 67.936 | 34.610 | 51.785 | 1.00 41.85 | B |
| ATOM | 1267 | N | ASP | B | 37 | 67.811 | 34.663 | 54.043 | 1.00 46.79 | B |
| ATOM | 1268 | CA | ASP | B | 37 | 66.872 | 35.782 | 54.107 | 1.00 46.79 | B |
| ATOM | 1269 | CB | ASP | B | 37 | 67.464 | 37.026 | 53.442 | 1.00 96.46 | B |
| ATOM | 1270 | CG | ASP | B | 37 | 68.133 | 37.952 | 54.441 | 1.00 96.46 | B |
| ATOM | 1271 | OD1 | ASP | B | 37 | 67.437 | 38.425 | 55.365 | 1.00 96.46 | B |
| ATOM | 1272 | OD2 | ASP | B | 37 | 69.348 | 38.206 | 54.308 | 1.00 96.46 | B |
| ATOM | 1273 | C | ASP | B | 37 | 65.527 | 35.446 | 53.483 | 1.00 46.79 | B |
| ATOM | 1274 | O | ASP | B | 37 | 64.991 | 36.195 | 52.653 | 1.00 46.79 | B |
| ATOM | 1275 | N | ILE | B | 38 | 64.986 | 34.303 | 53.889 | 1.00 41.11 | B |
| ATOM | 1276 | CA | ILE | B | 38 | 63.697 | 33.859 | 53.396 | 1.00 41.11 | B |
| ATOM | 1277 | CB | ILE | B | 38 | 63.835 | 32.886 | 52.230 | 1.00 28.68 | B |
| ATOM | 1278 | CG2 | ILE | B | 38 | 62.540 | 32.872 | 51.436 | 1.00 28.68 | B |
| ATOM | 1279 | CG1 | ILE | B | 38 | 64.997 | 33.300 | 51.337 | 1.00 28.68 | B |
| ATOM | 1280 | CD1 | ILE | B | 38 | 65.143 | 32.438 | 50.104 | 1.00 28.68 | B |
| ATOM | 1281 | C | ILE | B | 38 | 62.980 | 33.113 | 54.499 | 1.00 41.11 | B |
| ATOM | 1282 | O | ILE | B | 38 | 63.599 | 32.360 | 55.253 | 1.00 41.11 | B |
| ATOM | 1283 | N | THR | B | 39 | 61.674 | 33.319 | 54.592 | 1.00 26.87 | B |
| ATOM | 1284 | CA | THR | B | 39 | 60.885 | 32.625 | 55.594 | 1.00 26.87 | B |
| ATOM | 1285 | CB | THR | B | 39 | 59.815 | 33.541 | 56.153 | 1.00 31.96 | B |
| ATOM | 1286 | OG1 | THR | B | 39 | 58.964 | 33.981 | 55.084 | 1.00 31.96 | B |
| ATOM | 1287 | CG2 | THR | B | 39 | 60.466 | 34.752 | 56.837 | 1.00 31.96 | B |
| ATOM | 1288 | C | THR | B | 39 | 60.231 | 31.447 | 54.893 | 1.00 26.87 | B |
| ATOM | 1289 | O | THR | B | 39 | 60.110 | 31.455 | 53.659 | 1.00 26.87 | B |
| ATOM | 1290 | N | ALA | B | 40 | 59.819 | 30.431 | 55.651 | 1.00 35.79 | B |
| ATOM | 1291 | CA | ALA | B | 40 | 59.178 | 29.267 | 55.030 | 1.00 35.79 | B |
| ATOM | 1292 | CB | ALA | B | 40 | 58.996 | 28.135 | 56.047 | 1.00  6.71 | B |

Fig. 2Z

| | | | | | | | | | | |
|---|---|---|---|---|---|---|---|---|---|---|
| ATOM | 1293 | C   | ALA | B | 40 | 57.836 | 29.700 | 54.459 | 1.00 35.79 | B |
| ATOM | 1294 | O   | ALA | B | 40 | 57.346 | 29.121 | 53.490 | 1.00 35.79 | B |
| ATOM | 1295 | N   | ALA | B | 41 | 57.266 | 30.742 | 55.056 | 1.00 35.78 | B |
| ATOM | 1296 | CA  | ALA | B | 41 | 55.986 | 31.284 | 54.616 | 1.00 35.78 | B |
| ATOM | 1297 | CB  | ALA | B | 41 | 55.616 | 32.512 | 55.465 | 1.00 11.87 | B |
| ATOM | 1298 | C   | ALA | B | 41 | 56.106 | 31.679 | 53.151 | 1.00 35.78 | B |
| ATOM | 1299 | O   | ALA | B | 41 | 55.376 | 31.179 | 52.281 | 1.00 35.78 | B |
| ATOM | 1300 | N   | GLN | B | 42 | 57.050 | 32.575 | 52.890 | 1.00 33.53 | B |
| ATOM | 1301 | CA  | GLN | B | 42 | 57.291 | 33.061 | 51.538 | 1.00 33.53 | B |
| ATOM | 1302 | CB  | GLN | B | 42 | 58.394 | 34.107 | 51.569 | 1.00 34.68 | B |
| ATOM | 1303 | CG  | GLN | B | 42 | 58.068 | 35.300 | 52.437 | 1.00 34.68 | B |
| ATOM | 1304 | CD  | GLN | B | 42 | 59.279 | 36.195 | 52.665 | 1.00 34.68 | B |
| ATOM | 1305 | OE1 | GLN | B | 42 | 59.133 | 37.359 | 53.034 | 1.00 34.68 | B |
| ATOM | 1306 | NE2 | GLN | B | 42 | 60.485 | 35.647 | 52.460 | 1.00 34.68 | B |
| ATOM | 1307 | C   | GLN | B | 42 | 57.679 | 31.915 | 50.613 | 1.00 33.53 | B |
| ATOM | 1308 | O   | GLN | B | 42 | 57.219 | 31.847 | 49.470 | 1.00 33.53 | B |
| ATOM | 1309 | N   | PHE | B | 43 | 58.514 | 31.013 | 51.123 | 1.00 29.03 | B |
| ATOM | 1310 | CA  | PHE | B | 43 | 58.974 | 29.872 | 50.343 | 1.00 29.03 | B |
| ATOM | 1311 | CB  | PHE | B | 43 | 59.971 | 29.047 | 51.145 | 1.00 37.88 | B |
| ATOM | 1312 | CG  | PHE | B | 43 | 60.544 | 27.894 | 50.377 | 1.00 37.88 | B |
| ATOM | 1313 | CD1 | PHE | B | 43 | 61.275 | 28.114 | 49.210 | 1.00 37.88 | B |
| ATOM | 1314 | CD2 | PHE | B | 43 | 60.350 | 26.583 | 50.808 | 1.00 37.88 | B |
| ATOM | 1315 | CE1 | PHE | B | 43 | 61.804 | 27.041 | 48.479 | 1.00 37.88 | B |
| ATOM | 1316 | CE2 | PHE | B | 43 | 60.876 | 25.501 | 50.082 | 1.00 37.88 | B |
| ATOM | 1317 | CZ  | PHE | B | 43 | 61.603 | 25.732 | 48.918 | 1.00 37.88 | B |
| ATOM | 1318 | C   | PHE | B | 43 | 57.814 | 28.983 | 49.908 | 1.00 29.03 | B |
| ATOM | 1319 | O   | PHE | B | 43 | 57.734 | 28.566 | 48.746 | 1.00 29.03 | B |
| ATOM | 1320 | N   | LYS | B | 44 | 56.912 | 28.698 | 50.841 | 1.00 36.68 | B |
| ATOM | 1321 | CA  | LYS | B | 44 | 55.768 | 27.851 | 50.532 | 1.00 36.68 | B |
| ATOM | 1322 | CB  | LYS | B | 44 | 54.913 | 27.635 | 51.792 | 1.00 86.09 | B |
| ATOM | 1323 | CG  | LYS | B | 44 | 55.545 | 26.659 | 52.801 | 1.00 86.09 | B |
| ATOM | 1324 | CD  | LYS | B | 44 | 54.913 | 26.748 | 54.194 | 1.00 86.09 | B |
| ATOM | 1325 | CE  | LYS | B | 44 | 53.467 | 26.253 | 54.234 | 1.00 86.09 | B |
| ATOM | 1326 | NZ  | LYS | B | 44 | 53.345 | 24.763 | 54.191 | 1.00 86.09 | B |
| ATOM | 1327 | C   | LYS | B | 44 | 54.947 | 28.466 | 49.399 | 1.00 36.68 | B |
| ATOM | 1328 | O   | LYS | B | 44 | 54.622 | 27.786 | 48.431 | 1.00 36.68 | B |
| ATOM | 1329 | N   | VAL | B | 45 | 54.629 | 29.750 | 49.508 | 1.00 34.37 | B |
| ATOM | 1330 | CA  | VAL | B | 45 | 53.860 | 30.406 | 48.471 | 1.00 34.37 | B |
| ATOM | 1331 | CB  | VAL | B | 45 | 53.622 | 31.876 | 48.816 | 1.00 27.32 | B |
| ATOM | 1332 | CG1 | VAL | B | 45 | 52.980 | 32.594 | 47.631 | 1.00 27.32 | B |
| ATOM | 1333 | CG2 | VAL | B | 45 | 52.717 | 31.968 | 50.026 | 1.00 27.32 | B |
| ATOM | 1334 | C   | VAL | B | 45 | 54.569 | 30.301 | 47.119 | 1.00 34.37 | B |
| ATOM | 1335 | O   | VAL | B | 45 | 53.952 | 29.895 | 46.119 | 1.00 34.37 | B |
| ATOM | 1336 | N   | LEU | B | 46 | 55.856 | 30.660 | 47.079 | 1.00 34.02 | B |
| ATOM | 1337 | CA  | LEU | B | 46 | 56.630 | 30.574 | 45.837 | 1.00 34.02 | B |
| ATOM | 1338 | CB  | LEU | B | 46 | 58.097 | 30.928 | 46.089 | 1.00 41.81 | B |
| ATOM | 1339 | CG  | LEU | B | 46 | 58.407 | 32.358 | 46.526 | 1.00 41.81 | B |
| ATOM | 1340 | CD1 | LEU | B | 46 | 59.911 | 32.538 | 46.588 | 1.00 41.81 | B |

Fig. 2AA

| | | | | | | | | | | |
|---|---|---|---|---|---|---|---|---|---|---|
| ATOM | 1341 | CD2 | LEU | B | 46 | 57.793 | 33.356 | 45.548 | 1.00 41.81 | B |
| ATOM | 1342 | C | LEU | B | 46 | 56.552 | 29.178 | 45.203 | 1.00 34.02 | B |
| ATOM | 1343 | O | LEU | B | 46 | 56.477 | 29.056 | 43.982 | 1.00 34.02 | B |
| ATOM | 1344 | N | CYS | B | 47 | 56.575 | 28.130 | 46.025 | 1.00 34.11 | B |
| ATOM | 1345 | CA | CYS | B | 47 | 56.495 | 26.762 | 45.509 | 1.00 34.11 | B |
| ATOM | 1346 | CB | CYS | B | 47 | 56.771 | 25.748 | 46.620 | 1.00 73.82 | B |
| ATOM | 1347 | SG | CYS | B | 47 | 58.491 | 25.691 | 47.144 | 1.00 73.82 | B |
| ATOM | 1348 | C | CYS | B | 47 | 55.132 | 26.467 | 44.897 | 1.00 34.11 | B |
| ATOM | 1349 | O | CYS | B | 47 | 55.030 | 25.800 | 43.861 | 1.00 34.11 | B |
| ATOM | 1350 | N | SER | B | 48 | 54.086 | 26.972 | 45.540 | 1.00 30.53 | B |
| ATOM | 1351 | CA | SER | B | 48 | 52.727 | 26.757 | 45.068 | 1.00 30.53 | B |
| ATOM | 1352 | CB | SER | B | 48 | 51.734 | 27.371 | 46.055 | 1.00 28.82 | B |
| ATOM | 1353 | OG | SER | B | 48 | 51.984 | 26.926 | 47.380 | 1.00 28.82 | B |
| ATOM | 1354 | C | SER | B | 48 | 52.546 | 27.394 | 43.693 | 1.00 30.53 | B |
| ATOM | 1355 | O | SER | B | 48 | 51.934 | 26.811 | 42.791 | 1.00 30.53 | B |
| ATOM | 1356 | N | ILE | B | 49 | 53.083 | 28.596 | 43.537 | 1.00 27.84 | B |
| ATOM | 1357 | CA | ILE | B | 49 | 52.971 | 29.298 | 42.275 | 1.00 27.84 | B |
| ATOM | 1358 | CB | ILE | B | 49 | 53.401 | 30.771 | 42.439 | 1.00 22.70 | B |
| ATOM | 1359 | CG2 | ILE | B | 49 | 53.243 | 31.526 | 41.113 | 1.00 22.70 | B |
| ATOM | 1360 | CG1 | ILE | B | 49 | 52.528 | 31.421 | 43.526 | 1.00 22.70 | B |
| ATOM | 1361 | CD1 | ILE | B | 49 | 53.047 | 32.738 | 44.026 | 1.00 22.70 | B |
| ATOM | 1362 | C | ILE | B | 49 | 53.820 | 28.599 | 41.224 | 1.00 27.84 | B |
| ATOM | 1363 | O | ILE | B | 49 | 53.382 | 28.402 | 40.092 | 1.00 27.84 | B |
| ATOM | 1364 | N | ARG | B | 50 | 55.027 | 28.203 | 41.607 | 1.00 18.56 | B |
| ATOM | 1365 | CA | ARG | B | 50 | 55.925 | 27.512 | 40.687 | 1.00 18.56 | B |
| ATOM | 1366 | CB | ARG | B | 50 | 57.239 | 27.200 | 41.396 | 1.00 82.28 | B |
| ATOM | 1367 | CG | ARG | B | 50 | 58.304 | 26.600 | 40.514 | 1.00 82.28 | B |
| ATOM | 1368 | CD | ARG | B | 50 | 59.495 | 26.222 | 41.356 | 1.00 82.28 | B |
| ATOM | 1369 | NE | ARG | B | 50 | 60.697 | 25.996 | 40.562 | 1.00 82.28 | B |
| ATOM | 1370 | CZ | ARG | B | 50 | 61.877 | 25.682 | 41.088 | 1.00 82.28 | B |
| ATOM | 1371 | NH1 | ARG | B | 50 | 62.002 | 25.555 | 42.405 | 1.00 82.28 | B |
| ATOM | 1372 | NH2 | ARG | B | 50 | 62.933 | 25.507 | 40.303 | 1.00 82.28 | B |
| ATOM | 1373 | C | ARG | B | 50 | 55.271 | 26.206 | 40.213 | 1.00 18.56 | B |
| ATOM | 1374 | O | ARG | B | 50 | 55.241 | 25.893 | 39.014 | 1.00 18.56 | B |
| ATOM | 1375 | N | CYS | B | 51 | 54.740 | 25.444 | 41.160 | 1.00 43.60 | B |
| ATOM | 1376 | CA | CYS | B | 51 | 54.107 | 24.186 | 40.819 | 1.00 43.60 | B |
| ATOM | 1377 | CB | CYS | B | 51 | 53.584 | 23.504 | 42.081 | 1.00 84.70 | B |
| ATOM | 1378 | SG | CYS | B | 51 | 52.553 | 22.064 | 41.740 | 1.00 84.70 | B |
| ATOM | 1379 | C | CYS | B | 51 | 52.961 | 24.398 | 39.826 | 1.00 43.60 | B |
| ATOM | 1380 | O | CYS | B | 51 | 52.780 | 23.612 | 38.889 | 1.00 43.60 | B |
| ATOM | 1381 | N | ALA | B | 52 | 52.198 | 25.470 | 40.029 | 1.00 31.36 | B |
| ATOM | 1382 | CA | ALA | B | 52 | 51.059 | 25.776 | 39.172 | 1.00 31.36 | B |
| ATOM | 1383 | CB | ALA | B | 52 | 50.083 | 26.633 | 39.920 | 1.00 17.44 | B |
| ATOM | 1384 | C | ALA | B | 52 | 51.455 | 26.474 | 37.881 | 1.00 31.36 | B |
| ATOM | 1385 | O | ALA | B | 52 | 50.676 | 26.510 | 36.931 | 1.00 31.36 | B |
| ATOM | 1386 | N | ALA | B | 53 | 52.660 | 27.037 | 37.857 | 1.00 34.68 | B |
| ATOM | 1387 | CA | ALA | B | 53 | 53.156 | 27.743 | 36.688 | 1.00 34.68 | B |
| ATOM | 1388 | CB | ALA | B | 53 | 52.944 | 26.903 | 35.440 | 1.00 31.90 | B |

Fig. 2BB

| | | | | | | | | | | |
|---|---|---|---|---|---|---|---|---|---|---|
| ATOM | 1389 | C | ALA | B | 53 | 52.467 | 29.083 | 36.518 | 1.00 34.68 | B |
| ATOM | 1390 | O | ALA | B | 53 | 53.118 | 30.111 | 36.368 | 1.00 34.68 | B |
| ATOM | 1391 | N | CYS | B | 54 | 51.142 | 29.058 | 36.567 | 1.00 32.06 | B |
| ATOM | 1392 | CA | CYS | B | 54 | 50.316 | 30.245 | 36.368 | 1.00 32.06 | B |
| ATOM | 1393 | CB | CYS | B | 54 | 50.058 | 30.370 | 34.872 | 1.00 58.96 | B |
| ATOM | 1394 | SG | CYS | B | 54 | 49.247 | 31.838 | 34.359 | 1.00 58.96 | B |
| ATOM | 1395 | C | CYS | B | 54 | 49.008 | 30.003 | 37.137 | 1.00 32.06 | B |
| ATOM | 1396 | O | CYS | B | 54 | 48.354 | 28.979 | 36.949 | 1.00 32.06 | B |
| ATOM | 1397 | N | ILE | B | 55 | 48.605 | 30.936 | 37.990 | 1.00 18.46 | B |
| ATOM | 1398 | CA | ILE | B | 55 | 47.404 | 30.692 | 38.777 | 1.00 18.46 | B |
| ATOM | 1399 | CB | ILE | B | 55 | 47.762 | 29.766 | 39.974 | 1.00 12.62 | B |
| ATOM | 1400 | CG2 | ILE | B | 55 | 48.683 | 30.502 | 40.950 | 1.00 12.62 | B |
| ATOM | 1401 | CG1 | ILE | B | 55 | 46.510 | 29.340 | 40.734 | 1.00 12.62 | B |
| ATOM | 1402 | CD1 | ILE | B | 55 | 46.796 | 28.230 | 41.760 | 1.00 12.62 | B |
| ATOM | 1403 | C | ILE | B | 55 | 46.739 | 31.963 | 39.302 | 1.00 18.46 | B |
| ATOM | 1404 | O | ILE | B | 55 | 47.411 | 32.961 | 39.598 | 1.00 18.46 | B |
| ATOM | 1405 | N | THR | B | 56 | 45.416 | 31.925 | 39.415 | 1.00 29.52 | B |
| ATOM | 1406 | CA | THR | B | 56 | 44.670 | 33.066 | 39.924 | 1.00 29.52 | B |
| ATOM | 1407 | CB | THR | B | 56 | 43.196 | 32.976 | 39.544 | 1.00 27.79 | B |
| ATOM | 1408 | OG1 | THR | B | 56 | 42.613 | 31.853 | 40.213 | 1.00 27.79 | B |
| ATOM | 1409 | CG2 | THR | B | 56 | 43.041 | 32.806 | 38.039 | 1.00 27.79 | B |
| ATOM | 1410 | C | THR | B | 56 | 44.765 | 33.030 | 41.443 | 1.00 29.52 | B |
| ATOM | 1411 | O | THR | B | 56 | 44.974 | 31.964 | 42.033 | 1.00 29.52 | B |
| ATOM | 1412 | N | PRO | B | 57 | 44.620 | 34.194 | 42.094 | 1.00 30.29 | B |
| ATOM | 1413 | CD | PRO | B | 57 | 44.561 | 35.518 | 41.456 | 1.00 29.70 | B |
| ATOM | 1414 | CA | PRO | B | 57 | 44.687 | 34.318 | 43.555 | 1.00 30.29 | B |
| ATOM | 1415 | CB | PRO | B | 57 | 44.508 | 35.812 | 43.782 | 1.00 29.70 | B |
| ATOM | 1416 | CG | PRO | B | 57 | 45.119 | 36.410 | 42.535 | 1.00 29.70 | B |
| ATOM | 1417 | C | PRO | B | 57 | 43.600 | 33.502 | 44.250 | 1.00 30.29 | B |
| ATOM | 1418 | O | PRO | B | 57 | 43.823 | 32.925 | 45.321 | 1.00 30.29 | B |
| ATOM | 1419 | N | VAL | B | 58 | 42.420 | 33.461 | 43.641 | 1.00 38.22 | B |
| ATOM | 1420 | CA | VAL | B | 58 | 41.319 | 32.713 | 44.221 | 1.00 38.22 | B |
| ATOM | 1421 | CB | VAL | B | 58 | 39.996 | 32.966 | 43.435 | 1.00 66.42 | B |
| ATOM | 1422 | CG1 | VAL | B | 58 | 40.088 | 32.407 | 42.020 | 1.00 66.42 | B |
| ATOM | 1423 | CG2 | VAL | B | 58 | 38.828 | 32.372 | 44.192 | 1.00 66.42 | B |
| ATOM | 1424 | C | VAL | B | 58 | 41.668 | 31.219 | 44.260 | 1.00 38.22 | B |
| ATOM | 1425 | O | VAL | B | 58 | 41.516 | 30.572 | 45.295 | 1.00 38.22 | B |
| ATOM | 1426 | N | GLU | B | 59 | 42.153 | 30.673 | 43.149 | 1.00 36.09 | B |
| ATOM | 1427 | CA | GLU | B | 59 | 42.534 | 29.262 | 43.114 | 1.00 36.09 | B |
| ATOM | 1428 | CB | GLU | B | 59 | 42.827 | 28.833 | 41.678 | 1.00 40.02 | B |
| ATOM | 1429 | CG | GLU | B | 59 | 41.640 | 28.926 | 40.734 | 1.00 40.02 | B |
| ATOM | 1430 | CD | GLU | B | 59 | 40.609 | 27.810 | 40.936 | 1.00 40.02 | B |
| ATOM | 1431 | OE1 | GLU | B | 59 | 39.800 | 27.876 | 41.895 | 1.00 40.02 | B |
| ATOM | 1432 | OE2 | GLU | B | 59 | 40.614 | 26.858 | 40.122 | 1.00 40.02 | B |
| ATOM | 1433 | C | GLU | B | 59 | 43.776 | 29.002 | 43.991 | 1.00 36.09 | B |
| ATOM | 1434 | O | GLU | B | 59 | 43.998 | 27.881 | 44.455 | 1.00 36.09 | B |
| ATOM | 1435 | N | LEU | B | 60 | 44.583 | 30.038 | 44.207 | 1.00 32.50 | B |
| ATOM | 1436 | CA | LEU | B | 60 | 45.781 | 29.912 | 45.022 | 1.00 32.50 | B |

Fig. 2CC

```
ATOM  1437  CB   LEU B  60      46.677  31.135  44.833  1.00 29.62      B
ATOM  1438  CG   LEU B  60      47.978  31.130  45.642  1.00 29.62      B
ATOM  1439  CD1  LEU B  60      48.835  29.920  45.253  1.00 29.62      B
ATOM  1440  CD2  LEU B  60      48.732  32.435  45.385  1.00 29.62      B
ATOM  1441  C    LEU B  60      45.375  29.789  46.486  1.00 32.50      B
ATOM  1442  O    LEU B  60      45.877  28.939  47.220  1.00 32.50      B
ATOM  1443  N    LYS B  61      44.460  30.654  46.895  1.00 35.36      B
ATOM  1444  CA   LYS B  61      43.933  30.674  48.248  1.00 35.36      B
ATOM  1445  CB   LYS B  61      42.790  31.688  48.315  1.00 67.16      B
ATOM  1446  CG   LYS B  61      41.883  31.550  49.515  1.00 67.16      B
ATOM  1447  CD   LYS B  61      40.659  32.433  49.367  1.00 67.16      B
ATOM  1448  CE   LYS B  61      39.915  32.122  48.078  1.00 67.16      B
ATOM  1449  NZ   LYS B  61      39.618  30.668  47.968  1.00 67.16      B
ATOM  1450  C    LYS B  61      43.424  29.285  48.645  1.00 35.36      B
ATOM  1451  O    LYS B  61      43.628  28.835  49.778  1.00 35.36      B
ATOM  1452  N    LYS B  62      42.746  28.613  47.719  1.00 56.38      B
ATOM  1453  CA   LYS B  62      42.237  27.275  47.991  1.00 56.38      B
ATOM  1454  CB   LYS B  62      41.448  26.744  46.794  1.00 56.12      B
ATOM  1455  CG   LYS B  62      40.146  27.469  46.524  1.00 56.12      B
ATOM  1456  CD   LYS B  62      39.429  26.878  45.313  1.00 56.12      B
ATOM  1457  CE   LYS B  62      38.081  27.546  45.070  1.00 56.12      B
ATOM  1458  NZ   LYS B  62      38.199  29.033  44.949  1.00 56.12      B
ATOM  1459  C    LYS B  62      43.414  26.342  48.275  1.00 56.38      B
ATOM  1460  O    LYS B  62      43.404  25.595  49.257  1.00 56.38      B
ATOM  1461  N    VAL B  63      44.424  26.396  47.407  1.00 37.26      B
ATOM  1462  CA   VAL B  63      45.607  25.567  47.549  1.00 37.26      B
ATOM  1463  CB   VAL B  63      46.641  25.874  46.440  1.00 20.35      B
ATOM  1464  CG1  VAL B  63      48.013  25.281  46.813  1.00 20.35      B
ATOM  1465  CG2  VAL B  63      46.160  25.301  45.125  1.00 20.35      B
ATOM  1466  C    VAL B  63      46.268  25.784  48.899  1.00 37.26      B
ATOM  1467  O    VAL B  63      46.497  24.837  49.652  1.00 37.26      B
ATOM  1468  N    LEU B  64      46.568  27.037  49.203  1.00 37.82      B
ATOM  1469  CA   LEU B  64      47.230  27.377  50.454  1.00 37.82      B
ATOM  1470  CB   LEU B  64      47.786  28.800  50.381  1.00 50.74      B
ATOM  1471  CG   LEU B  64      49.053  29.018  49.560  1.00 50.74      B
ATOM  1472  CD1  LEU B  64      48.961  28.277  48.243  1.00 50.74      B
ATOM  1473  CD2  LEU B  64      49.241  30.520  49.342  1.00 50.74      B
ATOM  1474  C    LEU B  64      46.334  27.258  51.680  1.00 37.82      B
ATOM  1475  O    LEU B  64      46.819  27.268  52.814  1.00 37.82      B
ATOM  1476  N    SER B  65      45.031  27.149  51.454  1.00 47.27      B
ATOM  1477  CA   SER B  65      44.083  27.052  52.552  1.00 47.27      B
ATOM  1478  CB   SER B  65      44.261  25.729  53.302  1.00 79.02      B
ATOM  1479  OG   SER B  65      44.033  24.624  52.444  1.00 79.02      B
ATOM  1480  C    SER B  65      44.288  28.227  53.504  1.00 47.27      B
ATOM  1481  O    SER B  65      44.569  28.037  54.697  1.00 47.27      B
ATOM  1482  N    VAL B  66      44.168  29.444  52.970  1.00 24.67      B
ATOM  1483  CA   VAL B  66      44.321  30.652  53.790  1.00 24.67      B
ATOM  1484  CB   VAL B  66      45.750  31.269  53.701  1.00 43.56      B
```

Fig. 2DD

| | | | | | | | | | | |
|---|---|---|---|---|---|---|---|---|---|---|
| ATOM | 1485 | CG1 | VAL | B | 66 | 46.801 | 30.190 | 53.939 | 1.00 43.56 | B |
| ATOM | 1486 | CG2 | VAL | B | 66 | 45.948 | 31.969 | 52.346 | 1.00 43.56 | B |
| ATOM | 1487 | C | VAL | B | 66 | 43.329 | 31.753 | 53.407 | 1.00 24.67 | B |
| ATOM | 1488 | O | VAL | B | 66 | 42.554 | 31.620 | 52.453 | 1.00 24.67 | B |
| ATOM | 1489 | N | ASP | B | 67 | 43.361 | 32.840 | 54.169 | 1.00 57.77 | B |
| ATOM | 1490 | CA | ASP | B | 67 | 42.490 | 33.980 | 53.924 | 1.00 57.77 | B |
| ATOM | 1491 | CB | ASP | B | 67 | 42.546 | 34.932 | 55.127 | 1.00 65.50 | B |
| ATOM | 1492 | CG | ASP | B | 67 | 41.804 | 36.236 | 54.883 | 1.00 65.50 | B |
| ATOM | 1493 | OD1 | ASP | B | 67 | 40.948 | 36.273 | 53.973 | 1.00 65.50 | B |
| ATOM | 1494 | OD2 | ASP | B | 67 | 42.067 | 37.222 | 55.607 | 1.00 65.50 | B |
| ATOM | 1495 | C | ASP | B | 67 | 42.931 | 34.702 | 52.645 | 1.00 57.77 | B |
| ATOM | 1496 | O | ASP | B | 67 | 44.105 | 35.057 | 52.504 | 1.00 57.77 | B |
| ATOM | 1497 | N | LEU | B | 68 | 41.990 | 34.912 | 51.722 | 1.00 50.58 | B |
| ATOM | 1498 | CA | LEU | B | 68 | 42.274 | 35.584 | 50.450 | 1.00 50.58 | B |
| ATOM | 1499 | CB | LEU | B | 68 | 40.999 | 35.779 | 49.625 | 1.00 44.31 | B |
| ATOM | 1500 | CG | LEU | B | 68 | 41.160 | 36.605 | 48.337 | 1.00 44.31 | B |
| ATOM | 1501 | CD1 | LEU | B | 68 | 42.422 | 36.198 | 47.587 | 1.00 44.31 | B |
| ATOM | 1502 | CD2 | LEU | B | 68 | 39.943 | 36.407 | 47.453 | 1.00 44.31 | B |
| ATOM | 1503 | C | LEU | B | 68 | 42.934 | 36.933 | 50.637 | 1.00 50.58 | B |
| ATOM | 1504 | O | LEU | B | 68 | 43.783 | 37.332 | 49.832 | 1.00 50.58 | B |
| ATOM | 1505 | N | GLY | B | 69 | 42.528 | 37.647 | 51.682 | 1.00 44.91 | B |
| ATOM | 1506 | CA | GLY | B | 69 | 43.132 | 38.936 | 51.957 | 1.00 44.91 | B |
| ATOM | 1507 | C | GLY | B | 69 | 44.561 | 38.698 | 52.404 | 1.00 44.91 | B |
| ATOM | 1508 | O | GLY | B | 69 | 45.481 | 39.391 | 51.975 | 1.00 44.91 | B |
| ATOM | 1509 | N | ALA | B | 70 | 44.753 | 37.705 | 53.264 | 1.00 46.62 | B |
| ATOM | 1510 | CA | ALA | B | 70 | 46.083 | 37.374 | 53.750 | 1.00 46.62 | B |
| ATOM | 1511 | CB | ALA | B | 70 | 46.016 | 36.136 | 54.632 | 1.00 21.93 | B |
| ATOM | 1512 | C | ALA | B | 70 | 46.988 | 37.106 | 52.552 | 1.00 46.62 | B |
| ATOM | 1513 | O | ALA | B | 70 | 48.123 | 37.609 | 52.482 | 1.00 46.62 | B |
| ATOM | 1514 | N | LEU | B | 71 | 46.472 | 36.304 | 51.619 | 1.00 61.44 | B |
| ATOM | 1515 | CA | LEU | B | 71 | 47.207 | 35.931 | 50.411 | 1.00 61.44 | B |
| ATOM | 1516 | CB | LEU | B | 71 | 46.366 | 35.019 | 49.505 | 1.00 24.15 | B |
| ATOM | 1517 | CG | LEU | B | 71 | 47.104 | 34.526 | 48.251 | 1.00 24.15 | B |
| ATOM | 1518 | CD1 | LEU | B | 71 | 48.421 | 33.875 | 48.657 | 1.00 24.15 | B |
| ATOM | 1519 | CD2 | LEU | B | 71 | 46.241 | 33.525 | 47.488 | 1.00 24.15 | B |
| ATOM | 1520 | C | LEU | B | 71 | 47.581 | 37.168 | 49.631 | 1.00 61.44 | B |
| ATOM | 1521 | O | LEU | B | 71 | 48.746 | 37.375 | 49.281 | 1.00 61.44 | B |
| ATOM | 1522 | N | THR | B | 72 | 46.570 | 37.984 | 49.357 | 1.00 48.36 | B |
| ATOM | 1523 | CA | THR | B | 72 | 46.765 | 39.213 | 48.612 | 1.00 48.36 | B |
| ATOM | 1524 | CB | THR | B | 72 | 45.493 | 40.033 | 48.585 | 1.00 28.65 | B |
| ATOM | 1525 | OG1 | THR | B | 72 | 44.508 | 39.340 | 47.811 | 1.00 28.65 | B |
| ATOM | 1526 | CG2 | THR | B | 72 | 45.754 | 41.376 | 47.959 | 1.00 28.65 | B |
| ATOM | 1527 | C | THR | B | 72 | 47.891 | 40.078 | 49.160 | 1.00 48.36 | B |
| ATOM | 1528 | O | THR | B | 72 | 48.725 | 40.552 | 48.394 | 1.00 48.36 | B |
| ATOM | 1529 | N | ARG | B | 73 | 47.922 | 40.289 | 50.473 | 1.00 34.07 | B |
| ATOM | 1530 | CA | ARG | B | 73 | 48.982 | 41.104 | 51.045 | 1.00 34.07 | B |
| ATOM | 1531 | CB | ARG | B | 73 | 48.726 | 41.380 | 52.527 | 1.00 63.70 | B |
| ATOM | 1532 | CG | ARG | B | 73 | 47.497 | 42.242 | 52.771 | 1.00 63.70 | B |

Fig. 2EE

| ATOM | 1533 | CD | ARG | B | 73 | 47.368 | 42.666 | 54.223 | 1.00 | 63.70 | B |
| --- | --- | --- | --- | --- | --- | --- | --- | --- | --- | --- | --- |
| ATOM | 1534 | NE | ARG | B | 73 | 46.082 | 43.311 | 54.459 | 1.00 | 63.70 | B |
| ATOM | 1535 | CZ | ARG | B | 73 | 44.910 | 42.685 | 54.372 | 1.00 | 63.70 | B |
| ATOM | 1536 | NH1 | ARG | B | 73 | 44.867 | 41.394 | 54.063 | 1.00 | 63.70 | B |
| ATOM | 1537 | NH2 | ARG | B | 73 | 43.777 | 43.350 | 54.578 | 1.00 | 63.70 | B |
| ATOM | 1538 | C | ARG | B | 73 | 50.321 | 40.417 | 50.853 | 1.00 | 34.07 | B |
| ATOM | 1539 | O | ARG | B | 73 | 51.337 | 41.084 | 50.649 | 1.00 | 34.07 | B |
| ATOM | 1540 | N | MET | B | 74 | 50.332 | 39.087 | 50.902 | 1.00 | 33.57 | B |
| ATOM | 1541 | CA | MET | B | 74 | 51.578 | 38.358 | 50.699 | 1.00 | 33.57 | B |
| ATOM | 1542 | CB | MET | B | 74 | 51.405 | 36.866 | 51.030 | 1.00 | 28.43 | B |
| ATOM | 1543 | CG | MET | B | 74 | 52.644 | 36.005 | 50.727 | 1.00 | 28.43 | B |
| ATOM | 1544 | SD | MET | B | 74 | 54.177 | 36.471 | 51.632 | 1.00 | 28.43 | B |
| ATOM | 1545 | CE | MET | B | 74 | 54.311 | 35.010 | 52.755 | 1.00 | 28.43 | B |
| ATOM | 1546 | C | MET | B | 74 | 52.020 | 38.524 | 49.240 | 1.00 | 33.57 | B |
| ATOM | 1547 | O | MET | B | 74 | 53.196 | 38.799 | 48.958 | 1.00 | 33.57 | B |
| ATOM | 1548 | N | LEU | B | 75 | 51.075 | 38.370 | 48.313 | 1.00 | 27.16 | B |
| ATOM | 1549 | CA | LEU | B | 75 | 51.396 | 38.502 | 46.892 | 1.00 | 27.16 | B |
| ATOM | 1550 | CB | LEU | B | 75 | 50.148 | 38.291 | 46.017 | 1.00 | 20.11 | B |
| ATOM | 1551 | CG | LEU | B | 75 | 49.595 | 36.867 | 46.001 | 1.00 | 20.11 | B |
| ATOM | 1552 | CD1 | LEU | B | 75 | 48.347 | 36.813 | 45.155 | 1.00 | 20.11 | B |
| ATOM | 1553 | CD2 | LEU | B | 75 | 50.657 | 35.910 | 45.471 | 1.00 | 20.11 | B |
| ATOM | 1554 | C | LEU | B | 75 | 51.986 | 39.873 | 46.617 | 1.00 | 27.16 | B |
| ATOM | 1555 | O | LEU | B | 75 | 52.999 | 39.991 | 45.930 | 1.00 | 27.16 | B |
| ATOM | 1556 | N | ASP | B | 76 | 51.353 | 40.911 | 47.155 | 1.00 | 33.17 | B |
| ATOM | 1557 | CA | ASP | B | 76 | 51.846 | 42.262 | 46.954 | 1.00 | 33.17 | B |
| ATOM | 1558 | CB | ASP | B | 76 | 50.982 | 43.275 | 47.703 | 1.00 | 123.73 | B |
| ATOM | 1559 | CG | ASP | B | 76 | 49.670 | 43.555 | 46.993 | 1.00 | 123.73 | B |
| ATOM | 1560 | OD1 | ASP | B | 76 | 48.815 | 42.646 | 46.923 | 1.00 | 123.73 | B |
| ATOM | 1561 | OD2 | ASP | B | 76 | 49.496 | 44.687 | 46.494 | 1.00 | 123.73 | B |
| ATOM | 1562 | C | ASP | B | 76 | 53.291 | 42.350 | 47.428 | 1.00 | 33.17 | B |
| ATOM | 1563 | O | ASP | B | 76 | 54.157 | 42.870 | 46.715 | 1.00 | 33.17 | B |
| ATOM | 1564 | N | ARG | B | 77 | 53.559 | 41.819 | 48.620 | 1.00 | 43.84 | B |
| ATOM | 1565 | CA | ARG | B | 77 | 54.909 | 41.858 | 49.165 | 1.00 | 43.84 | B |
| ATOM | 1566 | CB | ARG | B | 77 | 54.921 | 41.315 | 50.599 | 1.00 | 55.30 | B |
| ATOM | 1567 | CG | ARG | B | 77 | 54.155 | 42.179 | 51.599 | 1.00 | 55.30 | B |
| ATOM | 1568 | CD | ARG | B | 77 | 54.376 | 41.708 | 53.035 | 1.00 | 55.30 | B |
| ATOM | 1569 | NE | ARG | B | 77 | 53.743 | 40.420 | 53.322 | 1.00 | 55.30 | B |
| ATOM | 1570 | CZ | ARG | B | 77 | 52.461 | 40.262 | 53.657 | 1.00 | 55.30 | B |
| ATOM | 1571 | NH1 | ARG | B | 77 | 51.651 | 41.314 | 53.758 | 1.00 | 55.30 | B |
| ATOM | 1572 | NH2 | ARG | B | 77 | 51.979 | 39.042 | 53.885 | 1.00 | 55.30 | B |
| ATOM | 1573 | C | ARG | B | 77 | 55.873 | 41.072 | 48.282 | 1.00 | 43.84 | B |
| ATOM | 1574 | O | ARG | B | 77 | 57.025 | 41.475 | 48.103 | 1.00 | 43.84 | B |
| ATOM | 1575 | N | LEU | B | 78 | 55.399 | 39.961 | 47.717 | 1.00 | 32.40 | B |
| ATOM | 1576 | CA | LEU | B | 78 | 56.241 | 39.139 | 46.849 | 1.00 | 32.40 | B |
| ATOM | 1577 | CB | LEU | B | 78 | 55.617 | 37.750 | 46.628 | 1.00 | 31.07 | B |
| ATOM | 1578 | CG | LEU | B | 78 | 55.564 | 36.814 | 47.857 | 1.00 | 31.07 | B |
| ATOM | 1579 | CD1 | LEU | B | 78 | 54.824 | 35.526 | 47.494 | 1.00 | 31.07 | B |
| ATOM | 1580 | CD2 | LEU | B | 78 | 56.975 | 36.482 | 48.350 | 1.00 | 31.07 | B |

Fig. 2FF

| ATOM | 1581 | C | LEU | B | 78 | 56.474 | 39.827 | 45.513 | 1.00 | 32.40 | B |
| --- | --- | --- | --- | --- | --- | --- | --- | --- | --- | --- | --- |
| ATOM | 1582 | O | LEU | B | 78 | 57.538 | 39.671 | 44.903 | 1.00 | 32.40 | B |
| ATOM | 1583 | N | VAL | B | 79 | 55.486 | 40.585 | 45.046 | 1.00 | 62.46 | B |
| ATOM | 1584 | CA | VAL | B | 79 | 55.641 | 41.298 | 43.781 | 1.00 | 62.46 | B |
| ATOM | 1585 | CB | VAL | B | 79 | 54.293 | 41.884 | 43.283 | 1.00 | 32.18 | B |
| ATOM | 1586 | CG1 | VAL | B | 79 | 54.531 | 42.947 | 42.220 | 1.00 | 32.18 | B |
| ATOM | 1587 | CG2 | VAL | B | 79 | 53.434 | 40.766 | 42.690 | 1.00 | 32.18 | B |
| ATOM | 1588 | C | VAL | B | 79 | 56.663 | 42.418 | 43.981 | 1.00 | 62.46 | B |
| ATOM | 1589 | O | VAL | B | 79 | 57.467 | 42.702 | 43.089 | 1.00 | 62.46 | B |
| ATOM | 1590 | N | CYS | B | 80 | 56.637 | 43.037 | 45.160 | 1.00 | 54.33 | B |
| ATOM | 1591 | CA | CYS | B | 80 | 57.575 | 44.102 | 45.483 | 1.00 | 54.33 | B |
| ATOM | 1592 | CB | CYS | B | 80 | 57.187 | 44.772 | 46.795 | 1.00 | 78.30 | B |
| ATOM | 1593 | SG | CYS | B | 80 | 55.867 | 45.974 | 46.623 | 1.00 | 78.30 | B |
| ATOM | 1594 | C | CYS | B | 80 | 59.008 | 43.589 | 45.585 | 1.00 | 54.33 | B |
| ATOM | 1595 | O | CYS | B | 80 | 59.944 | 44.286 | 45.207 | 1.00 | 54.33 | B |
| ATOM | 1596 | N | LYS | B | 81 | 59.189 | 42.376 | 46.096 | 1.00 | 65.17 | B |
| ATOM | 1597 | CA | LYS | B | 81 | 60.530 | 41.825 | 46.217 | 1.00 | 65.17 | B |
| ATOM | 1598 | CB | LYS | B | 81 | 60.546 | 40.660 | 47.213 | 1.00 | 59.31 | B |
| ATOM | 1599 | CG | LYS | B | 81 | 59.864 | 40.991 | 48.543 | 1.00 | 59.31 | B |
| ATOM | 1600 | CD | LYS | B | 81 | 60.115 | 39.938 | 49.612 | 1.00 | 59.31 | B |
| ATOM | 1601 | CE | LYS | B | 81 | 61.515 | 40.062 | 50.192 | 1.00 | 59.31 | B |
| ATOM | 1602 | NZ | LYS | B | 81 | 61.815 | 39.005 | 51.206 | 1.00 | 59.31 | B |
| ATOM | 1603 | C | LYS | B | 81 | 61.015 | 41.367 | 44.847 | 1.00 | 65.17 | B |
| ATOM | 1604 | O | LYS | B | 81 | 62.185 | 41.025 | 44.674 | 1.00 | 65.17 | B |
| ATOM | 1605 | N | GLY | B | 82 | 60.111 | 41.364 | 43.871 | 1.00 | 29.81 | B |
| ATOM | 1606 | CA | GLY | B | 82 | 60.480 | 40.967 | 42.522 | 1.00 | 29.81 | B |
| ATOM | 1607 | C | GLY | B | 82 | 60.550 | 39.472 | 42.261 | 1.00 | 29.81 | B |
| ATOM | 1608 | O | GLY | B | 82 | 61.260 | 39.037 | 41.346 | 1.00 | 29.81 | B |
| ATOM | 1609 | N | TRP | B | 83 | 59.821 | 38.681 | 43.045 | 1.00 | 33.85 | B |
| ATOM | 1610 | CA | TRP | B | 83 | 59.829 | 37.232 | 42.860 | 1.00 | 33.85 | B |
| ATOM | 1611 | CB | TRP | B | 83 | 59.997 | 36.524 | 44.208 | 1.00 | 51.71 | B |
| ATOM | 1612 | CG | TRP | B | 83 | 61.213 | 36.946 | 44.993 | 1.00 | 51.71 | B |
| ATOM | 1613 | CD2 | TRP | B | 83 | 61.436 | 36.753 | 46.399 | 1.00 | 51.71 | B |
| ATOM | 1614 | CE2 | TRP | B | 83 | 62.729 | 37.244 | 46.689 | 1.00 | 51.71 | B |
| ATOM | 1615 | CE3 | TRP | B | 83 | 60.670 | 36.212 | 47.440 | 1.00 | 51.71 | B |
| ATOM | 1616 | CD1 | TRP | B | 83 | 62.347 | 37.532 | 44.504 | 1.00 | 51.71 | B |
| ATOM | 1617 | NE1 | TRP | B | 83 | 63.262 | 37.713 | 45.517 | 1.00 | 51.71 | B |
| ATOM | 1618 | CZ2 | TRP | B | 83 | 63.274 | 37.209 | 47.979 | 1.00 | 51.71 | B |
| ATOM | 1619 | CZ3 | TRP | B | 83 | 61.215 | 36.178 | 48.727 | 1.00 | 51.71 | B |
| ATOM | 1620 | CH2 | TRP | B | 83 | 62.504 | 36.674 | 48.980 | 1.00 | 51.71 | B |
| ATOM | 1621 | C | TRP | B | 83 | 58.539 | 36.744 | 42.180 | 1.00 | 33.85 | B |
| ATOM | 1622 | O | TRP | B | 83 | 58.519 | 35.684 | 41.540 | 1.00 | 33.85 | B |
| ATOM | 1623 | N | VAL | B | 84 | 57.471 | 37.527 | 42.324 | 1.00 | 31.00 | B |
| ATOM | 1624 | CA | VAL | B | 84 | 56.173 | 37.203 | 41.741 | 1.00 | 31.00 | B |
| ATOM | 1625 | CB | VAL | B | 84 | 55.127 | 36.956 | 42.847 | 1.00 | 24.28 | B |
| ATOM | 1626 | CG1 | VAL | B | 84 | 53.739 | 36.784 | 42.239 | 1.00 | 24.28 | B |
| ATOM | 1627 | CG2 | VAL | B | 84 | 55.508 | 35.728 | 43.645 | 1.00 | 24.28 | B |
| ATOM | 1628 | C | VAL | B | 84 | 55.692 | 38.346 | 40.832 | 1.00 | 31.00 | B |

Fig. 2GG

| | | | | | | | | | | |
|---|---|---|---|---|---|---|---|---|---|---|
| ATOM | 1629 | O | VAL | B | 84 | 55.840 | 39.529 | 41.162 | 1.00 31.00 | B |
| ATOM | 1630 | N | GLU | B | 85 | 55.104 | 37.971 | 39.697 | 1.00 29.82 | B |
| ATOM | 1631 | CA | GLU | B | 85 | 54.621 | 38.920 | 38.706 | 1.00 29.82 | B |
| ATOM | 1632 | CB | GLU | B | 85 | 55.355 | 38.673 | 37.394 | 1.00 50.76 | B |
| ATOM | 1633 | CG | GLU | B | 85 | 55.113 | 39.708 | 36.331 | 1.00 50.76 | B |
| ATOM | 1634 | CD | GLU | B | 85 | 55.596 | 39.248 | 34.968 | 1.00 50.76 | B |
| ATOM | 1635 | OE1 | GLU | B | 85 | 55.594 | 40.076 | 34.030 | 1.00 50.76 | B |
| ATOM | 1636 | OE2 | GLU | B | 85 | 55.968 | 38.057 | 34.838 | 1.00 50.76 | B |
| ATOM | 1637 | C | GLU | B | 85 | 53.123 | 38.759 | 38.489 | 1.00 29.82 | B |
| ATOM | 1638 | O | GLU | B | 85 | 52.605 | 37.638 | 38.516 | 1.00 29.82 | B |
| ATOM | 1639 | N | ARG | B | 86 | 52.425 | 39.875 | 38.280 | 1.00 29.70 | B |
| ATOM | 1640 | CA | ARG | B | 86 | 50.976 | 39.854 | 38.034 | 1.00 29.70 | B |
| ATOM | 1641 | CB | ARG | B | 86 | 50.269 | 40.980 | 38.782 | 1.00 41.84 | B |
| ATOM | 1642 | CG | ARG | B | 86 | 50.075 | 40.752 | 40.245 | 1.00 41.84 | B |
| ATOM | 1643 | CD | ARG | B | 86 | 49.029 | 41.718 | 40.769 | 1.00 41.84 | B |
| ATOM | 1644 | NE | ARG | B | 86 | 48.848 | 41.623 | 42.215 | 1.00 41.84 | B |
| ATOM | 1645 | CZ | ARG | B | 86 | 49.639 | 42.211 | 43.108 | 1.00 41.84 | B |
| ATOM | 1646 | NH1 | ARG | B | 86 | 50.674 | 42.947 | 42.705 | 1.00 41.84 | B |
| ATOM | 1647 | NH2 | ARG | B | 86 | 49.388 | 42.069 | 44.404 | 1.00 41.84 | B |
| ATOM | 1648 | C | ARG | B | 86 | 50.657 | 40.015 | 36.548 | 1.00 29.70 | B |
| ATOM | 1649 | O | ARG | B | 86 | 51.264 | 40.826 | 35.857 | 1.00 29.70 | B |
| ATOM | 1650 | N | LEU | B | 87 | 49.688 | 39.242 | 36.071 | 1.00 43.02 | B |
| ATOM | 1651 | CA | LEU | B | 87 | 49.270 | 39.303 | 34.673 | 1.00 43.02 | B |
| ATOM | 1652 | CB | LEU | B | 87 | 49.695 | 38.047 | 33.922 | 1.00 34.18 | B |
| ATOM | 1653 | CG | LEU | B | 87 | 51.161 | 37.829 | 33.616 | 1.00 34.18 | B |
| ATOM | 1654 | CD1 | LEU | B | 87 | 51.319 | 36.505 | 32.877 | 1.00 34.18 | B |
| ATOM | 1655 | CD2 | LEU | B | 87 | 51.673 | 38.999 | 32.779 | 1.00 34.18 | B |
| ATOM | 1656 | C | LEU | B | 87 | 47.760 | 39.421 | 34.522 | 1.00 43.02 | B |
| ATOM | 1657 | O | LEU | B | 87 | 46.993 | 38.931 | 35.356 | 1.00 43.02 | B |
| ATOM | 1658 | N | PRO | B | 88 | 47.313 | 40.072 | 33.440 | 1.00 39.72 | B |
| ATOM | 1659 | CD | PRO | B | 88 | 48.111 | 40.752 | 32.405 | 1.00 25.30 | B |
| ATOM | 1660 | CA | PRO | B | 88 | 45.875 | 40.230 | 33.190 | 1.00 39.72 | B |
| ATOM | 1661 | CB | PRO | B | 88 | 45.827 | 41.092 | 31.934 | 1.00 25.30 | B |
| ATOM | 1662 | CG | PRO | B | 88 | 47.171 | 41.810 | 31.941 | 1.00 25.30 | B |
| ATOM | 1663 | C | PRO | B | 88 | 45.366 | 38.830 | 32.885 | 1.00 39.72 | B |
| ATOM | 1664 | O | PRO | B | 88 | 45.949 | 38.145 | 32.047 | 1.00 39.72 | B |
| ATOM | 1665 | N | ASN | B | 89 | 44.308 | 38.378 | 33.546 | 1.00 30.26 | B |
| ATOM | 1666 | CA | ASN | B | 89 | 43.803 | 37.044 | 33.242 | 1.00 30.26 | B |
| ATOM | 1667 | CB | ASN | B | 89 | 42.859 | 36.566 | 34.338 | 1.00 30.59 | B |
| ATOM | 1668 | CG | ASN | B | 89 | 42.274 | 35.195 | 34.046 | 1.00 30.59 | B |
| ATOM | 1669 | OD1 | ASN | B | 89 | 41.576 | 34.630 | 34.885 | 1.00 30.59 | B |
| ATOM | 1670 | ND2 | ASN | B | 89 | 42.551 | 34.653 | 32.860 | 1.00 30.59 | B |
| ATOM | 1671 | C | ASN | B | 89 | 43.057 | 37.126 | 31.921 | 1.00 30.26 | B |
| ATOM | 1672 | O | ASN | B | 89 | 42.085 | 37.870 | 31.796 | 1.00 30.26 | B |
| ATOM | 1673 | N | PRO | B | 90 | 43.514 | 36.382 | 30.903 | 1.00 32.35 | B |
| ATOM | 1674 | CD | PRO | B | 90 | 44.768 | 35.613 | 30.819 | 1.00 35.64 | B |
| ATOM | 1675 | CA | PRO | B | 90 | 42.838 | 36.419 | 29.600 | 1.00 32.35 | B |
| ATOM | 1676 | CB | PRO | B | 90 | 43.831 | 35.716 | 28.674 | 1.00 35.64 | B |

Fig. 2HH

| | | | | | | | | | |
|---|---|---|---|---|---|---|---|---|---|
| ATOM | 1677 | CG | PRO | B | 90 | 44.529 | 34.757 | 29.595 | 1.00 35.64 | B |
| ATOM | 1678 | C | PRO | B | 90 | 41.447 | 35.783 | 29.559 | 1.00 32.35 | B |
| ATOM | 1679 | O | PRO | B | 90 | 40.638 | 36.132 | 28.699 | 1.00 32.35 | B |
| ATOM | 1680 | N | ASN | B | 91 | 41.159 | 34.868 | 30.482 | 1.00 36.98 | B |
| ATOM | 1681 | CA | ASN | B | 91 | 39.855 | 34.199 | 30.506 | 1.00 36.98 | B |
| ATOM | 1682 | CB | ASN | B | 91 | 39.987 | 32.760 | 31.023 | 1.00 38.48 | B |
| ATOM | 1683 | CG | ASN | B | 91 | 41.044 | 31.963 | 30.280 | 1.00 38.48 | B |
| ATOM | 1684 | OD1 | ASN | B | 91 | 41.044 | 31.897 | 29.043 | 1.00 38.48 | B |
| ATOM | 1685 | ND2 | ASN | B | 91 | 41.957 | 31.346 | 31.035 | 1.00 38.48 | B |
| ATOM | 1686 | C | ASN | B | 91 | 38.844 | 34.932 | 31.381 | 1.00 36.98 | B |
| ATOM | 1687 | O | ASN | B | 91 | 37.744 | 34.426 | 31.623 | 1.00 36.98 | B |
| ATOM | 1688 | N | ASP | B | 92 | 39.215 | 36.112 | 31.872 | 1.00 42.26 | B |
| ATOM | 1689 | CA | ASP | B | 92 | 38.317 | 36.880 | 32.720 | 1.00 42.26 | B |
| ATOM | 1690 | CB | ASP | B | 92 | 38.276 | 36.281 | 34.124 | 1.00 70.87 | B |
| ATOM | 1691 | CG | ASP | B | 92 | 37.060 | 36.723 | 34.903 | 1.00 70.87 | B |
| ATOM | 1692 | OD1 | ASP | B | 92 | 35.939 | 36.530 | 34.389 | 1.00 70.87 | B |
| ATOM | 1693 | OD2 | ASP | B | 92 | 37.219 | 37.259 | 36.021 | 1.00 70.87 | B |
| ATOM | 1694 | C | ASP | B | 92 | 38.739 | 38.342 | 32.787 | 1.00 42.26 | B |
| ATOM | 1695 | O | ASP | B | 92 | 39.629 | 38.724 | 33.555 | 1.00 42.26 | B |
| ATOM | 1696 | N | LYS | B | 93 | 38.070 | 39.141 | 31.966 | 1.00 54.34 | B |
| ATOM | 1697 | CA | LYS | B | 93 | 38.290 | 40.575 | 31.834 | 1.00 54.34 | B |
| ATOM | 1698 | CB | LYS | B | 93 | 36.934 | 41.265 | 31.649 | 1.00 66.28 | B |
| ATOM | 1699 | CG | LYS | B | 93 | 37.001 | 42.673 | 31.085 | 1.00 66.28 | B |
| ATOM | 1700 | CD | LYS | B | 93 | 35.604 | 43.180 | 30.748 | 1.00 66.28 | B |
| ATOM | 1701 | CE | LYS | B | 93 | 35.651 | 44.550 | 30.100 | 1.00 66.28 | B |
| ATOM | 1702 | NZ | LYS | B | 93 | 36.332 | 45.540 | 30.977 | 1.00 66.28 | B |
| ATOM | 1703 | C | LYS | B | 93 | 39.071 | 41.265 | 32.951 | 1.00 54.34 | B |
| ATOM | 1704 | O | LYS | B | 93 | 40.190 | 41.728 | 32.736 | 1.00 54.34 | B |
| ATOM | 1705 | N | ARG | B | 94 | 38.496 | 41.326 | 34.145 | 1.00 36.91 | B |
| ATOM | 1706 | CA | ARG | B | 94 | 39.159 | 42.004 | 35.251 | 1.00 36.91 | B |
| ATOM | 1707 | CB | ARG | B | 94 | 38.131 | 42.845 | 36.008 | 1.00 45.25 | B |
| ATOM | 1708 | CG | ARG | B | 94 | 37.482 | 43.880 | 35.114 | 1.00 45.25 | B |
| ATOM | 1709 | CD | ARG | B | 94 | 36.332 | 44.580 | 35.794 | 1.00 45.25 | B |
| ATOM | 1710 | NE | ARG | B | 94 | 35.640 | 45.503 | 34.893 | 1.00 45.25 | B |
| ATOM | 1711 | CZ | ARG | B | 94 | 36.204 | 46.569 | 34.325 | 1.00 45.25 | B |
| ATOM | 1712 | NH1 | ARG | B | 94 | 37.482 | 46.864 | 34.554 | 1.00 45.25 | B |
| ATOM | 1713 | NH2 | ARG | B | 94 | 35.481 | 47.351 | 33.531 | 1.00 45.25 | B |
| ATOM | 1714 | C | ARG | B | 94 | 39.944 | 41.126 | 36.221 | 1.00 36.91 | B |
| ATOM | 1715 | O | ARG | B | 94 | 40.325 | 41.576 | 37.303 | 1.00 36.91 | B |
| ATOM | 1716 | N | GLY | B | 95 | 40.207 | 39.882 | 35.838 | 1.00 47.16 | B |
| ATOM | 1717 | CA | GLY | B | 95 | 40.967 | 39.010 | 36.717 | 1.00 47.16 | B |
| ATOM | 1718 | C | GLY | B | 95 | 42.467 | 39.094 | 36.477 | 1.00 47.16 | B |
| ATOM | 1719 | O | GLY | B | 95 | 42.920 | 39.707 | 35.516 | 1.00 47.16 | B |
| ATOM | 1720 | N | VAL | B | 96 | 43.250 | 38.491 | 37.360 | 1.00 27.95 | B |
| ATOM | 1721 | CA | VAL | B | 96 | 44.698 | 38.490 | 37.197 | 1.00 27.95 | B |
| ATOM | 1722 | CB | VAL | B | 96 | 45.409 | 39.413 | 38.197 | 1.00 23.13 | B |
| ATOM | 1723 | CG1 | VAL | B | 96 | 44.808 | 40.802 | 38.149 | 1.00 23.13 | B |
| ATOM | 1724 | CG2 | VAL | B | 96 | 45.330 | 38.820 | 39.583 | 1.00 23.13 | B |

Fig. 2II

| ATOM | 1725 | C | VAL | B | 96 | 45.252 | 37.101 | 37.433 | 1.00 | 27.95 | B |
|------|------|-----|-----|---|-----|--------|--------|--------|------|-------|---|
| ATOM | 1726 | O | VAL | B | 96 | 44.616 | 36.253 | 38.054 | 1.00 | 27.95 | B |
| ATOM | 1727 | N | LEU | B | 97 | 46.445 | 36.872 | 36.915 | 1.00 | 27.10 | B |
| ATOM | 1728 | CA | LEU | B | 97 | 47.118 | 35.605 | 37.107 | 1.00 | 27.10 | B |
| ATOM | 1729 | CB | LEU | B | 97 | 47.356 | 34.880 | 35.778 | 1.00 | 15.99 | B |
| ATOM | 1730 | CG | LEU | B | 97 | 46.199 | 34.238 | 35.001 | 1.00 | 15.99 | B |
| ATOM | 1731 | CD1 | LEU | B | 97 | 46.712 | 33.848 | 33.610 | 1.00 | 15.99 | B |
| ATOM | 1732 | CD2 | LEU | B | 97 | 45.656 | 33.011 | 35.748 | 1.00 | 15.99 | B |
| ATOM | 1733 | C | LEU | B | 97 | 48.455 | 35.975 | 37.718 | 1.00 | 27.10 | B |
| ATOM | 1734 | O | LEU | B | 97 | 48.999 | 37.058 | 37.447 | 1.00 | 27.10 | B |
| ATOM | 1735 | N | VAL | B | 98 | 48.972 | 35.098 | 38.567 | 1.00 | 24.64 | B |
| ATOM | 1736 | CA | VAL | B | 98 | 50.268 | 35.346 | 39.165 | 1.00 | 24.64 | B |
| ATOM | 1737 | CB | VAL | B | 98 | 50.197 | 35.434 | 40.709 | 1.00 | 17.53 | B |
| ATOM | 1738 | CG1 | VAL | B | 98 | 49.701 | 36.806 | 41.128 | 1.00 | 17.53 | B |
| ATOM | 1739 | CG2 | VAL | B | 98 | 49.287 | 34.345 | 41.244 | 1.00 | 17.53 | B |
| ATOM | 1740 | C | VAL | B | 98 | 51.187 | 34.211 | 38.772 | 1.00 | 24.64 | B |
| ATOM | 1741 | O | VAL | B | 98 | 50.752 | 33.060 | 38.629 | 1.00 | 24.64 | B |
| ATOM | 1742 | N | LYS | B | 99 | 52.452 | 34.550 | 38.569 | 1.00 | 25.92 | B |
| ATOM | 1743 | CA | LYS | B | 99 | 53.450 | 33.565 | 38.216 | 1.00 | 25.92 | B |
| ATOM | 1744 | CB | LYS | B | 99 | 53.527 | 33.410 | 36.707 | 1.00 | 28.24 | B |
| ATOM | 1745 | CG | LYS | B | 99 | 54.279 | 34.520 | 36.008 | 1.00 | 28.24 | B |
| ATOM | 1746 | CD | LYS | B | 99 | 54.341 | 34.259 | 34.515 | 1.00 | 28.24 | B |
| ATOM | 1747 | CE | LYS | B | 99 | 55.558 | 34.910 | 33.911 | 1.00 | 28.24 | B |
| ATOM | 1748 | NZ | LYS | B | 99 | 56.805 | 34.299 | 34.459 | 1.00 | 28.24 | B |
| ATOM | 1749 | C | LYS | B | 99 | 54.768 | 34.084 | 38.783 | 1.00 | 25.92 | B |
| ATOM | 1750 | O | LYS | B | 99 | 54.852 | 35.237 | 39.226 | 1.00 | 25.92 | B |
| ATOM | 1751 | N | LEU | B | 100 | 55.791 | 33.242 | 38.801 | 1.00 | 23.47 | B |
| ATOM | 1752 | CA | LEU | B | 100 | 57.064 | 33.678 | 39.342 | 1.00 | 23.47 | B |
| ATOM | 1753 | CB | LEU | B | 100 | 57.900 | 32.476 | 39.796 | 1.00 | 16.95 | B |
| ATOM | 1754 | CG | LEU | B | 100 | 57.355 | 31.635 | 40.952 | 1.00 | 16.95 | B |
| ATOM | 1755 | CD1 | LEU | B | 100 | 58.353 | 30.573 | 41.322 | 1.00 | 16.95 | B |
| ATOM | 1756 | CD2 | LEU | B | 100 | 57.101 | 32.522 | 42.152 | 1.00 | 16.95 | B |
| ATOM | 1757 | C | LEU | B | 100 | 57.823 | 34.449 | 38.279 | 1.00 | 23.47 | B |
| ATOM | 1758 | O | LEU | B | 100 | 57.671 | 34.181 | 37.082 | 1.00 | 23.47 | B |
| ATOM | 1759 | N | THR | B | 101 | 58.616 | 35.421 | 38.724 | 1.00 | 21.01 | B |
| ATOM | 1760 | CA | THR | B | 101 | 59.438 | 36.222 | 37.833 | 1.00 | 21.01 | B |
| ATOM | 1761 | CB | THR | B | 101 | 59.763 | 37.573 | 38.446 | 1.00 | 28.80 | B |
| ATOM | 1762 | OG1 | THR | B | 101 | 60.482 | 37.365 | 39.667 | 1.00 | 28.80 | B |
| ATOM | 1763 | CG2 | THR | B | 101 | 58.494 | 38.341 | 38.742 | 1.00 | 28.80 | B |
| ATOM | 1764 | C | THR | B | 101 | 60.723 | 35.427 | 37.750 | 1.00 | 21.01 | B |
| ATOM | 1765 | O | THR | B | 101 | 60.891 | 34.459 | 38.488 | 1.00 | 21.01 | B |
| ATOM | 1766 | N | THR | B | 102 | 61.629 | 35.826 | 36.865 | 1.00 | 29.71 | B |
| ATOM | 1767 | CA | THR | B | 102 | 62.906 | 35.124 | 36.717 | 1.00 | 29.71 | B |
| ATOM | 1768 | CB | THR | B | 102 | 63.881 | 35.908 | 35.818 | 1.00 | 48.84 | B |
| ATOM | 1769 | OG1 | THR | B | 102 | 63.233 | 36.248 | 34.585 | 1.00 | 48.84 | B |
| ATOM | 1770 | CG2 | THR | B | 102 | 65.122 | 35.070 | 35.528 | 1.00 | 48.84 | B |
| ATOM | 1771 | C | THR | B | 102 | 63.566 | 34.983 | 38.081 | 1.00 | 29.71 | B |
| ATOM | 1772 | O | THR | B | 102 | 63.982 | 33.898 | 38.477 | 1.00 | 29.71 | B |

Fig. 2JJ

```
ATOM   1773  N    GLY B 103      63.654  36.107  38.783  1.00 40.41           B
ATOM   1774  CA   GLY B 103      64.266  36.131  40.096  1.00 40.41           B
ATOM   1775  C    GLY B 103      63.611  35.177  41.061  1.00 40.41           B
ATOM   1776  O    GLY B 103      64.295  34.412  41.743  1.00 40.41           B
ATOM   1777  N    GLY B 104      62.284  35.225  41.122  1.00 39.22           B
ATOM   1778  CA   GLY B 104      61.557  34.341  42.015  1.00 39.22           B
ATOM   1779  C    GLY B 104      61.868  32.872  41.781  1.00 39.22           B
ATOM   1780  O    GLY B 104      62.178  32.140  42.717  1.00 39.22           B
ATOM   1781  N    ALA B 105      61.798  32.437  40.528  1.00 35.18           B
ATOM   1782  CA   ALA B 105      62.072  31.041  40.198  1.00 35.18           B
ATOM   1783  CB   ALA B 105      61.925  30.811  38.696  1.00  1.00           B
ATOM   1784  C    ALA B 105      63.470  30.649  40.644  1.00 35.18           B
ATOM   1785  O    ALA B 105      63.693  29.529  41.104  1.00 35.18           B
ATOM   1786  N    ALA B 106      64.403  31.585  40.497  1.00 35.53           B
ATOM   1787  CA   ALA B 106      65.797  31.382  40.868  1.00 35.53           B
ATOM   1788  CB   ALA B 106      66.624  32.565  40.420  1.00  9.21           B
ATOM   1789  C    ALA B 106      65.901  31.217  42.368  1.00 35.53           B
ATOM   1790  O    ALA B 106      66.643  30.370  42.855  1.00 35.53           B
ATOM   1791  N    ILE B 107      65.162  32.039  43.102  1.00 27.57           B
ATOM   1792  CA   ILE B 107      65.173  31.948  44.559  1.00 27.57           B
ATOM   1793  CB   ILE B 107      64.166  32.933  45.212  1.00 42.27           B
ATOM   1794  CG2  ILE B 107      64.085  32.674  46.715  1.00 42.27           B
ATOM   1795  CG1  ILE B 107      64.598  34.377  44.951  1.00 42.27           B
ATOM   1796  CD1  ILE B 107      65.995  34.708  45.459  1.00 42.27           B
ATOM   1797  C    ILE B 107      64.758  30.531  44.926  1.00 27.57           B
ATOM   1798  O    ILE B 107      65.406  29.868  45.739  1.00 27.57           B
ATOM   1799  N    CYS B 108      63.676  30.069  44.307  1.00 33.42           B
ATOM   1800  CA   CYS B 108      63.186  28.726  44.581  1.00 33.42           B
ATOM   1801  CB   CYS B 108      61.964  28.402  43.725  1.00 38.41           B
ATOM   1802  SG   CYS B 108      60.451  28.849  44.535  1.00 38.41           B
ATOM   1803  C    CYS B 108      64.243  27.673  44.343  1.00 33.42           B
ATOM   1804  O    CYS B 108      64.538  26.873  45.231  1.00 33.42           B
ATOM   1805  N    GLU B 109      64.810  27.668  43.142  1.00 37.97           B
ATOM   1806  CA   GLU B 109      65.818  26.678  42.835  1.00 37.97           B
ATOM   1807  CB   GLU B 109      66.343  26.854  41.412  1.00 73.89           B
ATOM   1808  CG   GLU B 109      67.143  25.648  40.926  1.00 73.89           B
ATOM   1809  CD   GLU B 109      66.377  24.325  41.060  1.00 73.89           B
ATOM   1810  OE1  GLU B 109      66.989  23.259  40.830  1.00 73.89           B
ATOM   1811  OE2  GLU B 109      65.167  24.344  41.391  1.00 73.89           B
ATOM   1812  C    GLU B 109      66.959  26.763  43.843  1.00 37.97           B
ATOM   1813  O    GLU B 109      67.442  25.740  44.323  1.00 37.97           B
ATOM   1814  N    GLN B 110      67.365  27.985  44.182  1.00 42.51           B
ATOM   1815  CA   GLN B 110      68.450  28.208  45.135  1.00 42.51           B
ATOM   1816  CB   GLN B 110      68.719  29.709  45.300  1.00 63.33           B
ATOM   1817  CG   GLN B 110      69.443  30.355  44.133  1.00 63.33           B
ATOM   1818  CD   GLN B 110      70.799  30.905  44.534  1.00 63.33           B
ATOM   1819  OE1  GLN B 110      70.893  31.775  45.403  1.00 63.33           B
ATOM   1820  NE2  GLN B 110      71.861  30.397  43.904  1.00 63.33           B
```

Fig. 2KK

| | | | | | | | | | | |
|---|---|---|---|---|---|---|---|---|---|---|
| ATOM | 1821 | C | GLN | B | 110 | 68.151 | 27.597 | 46.501 | 1.00 42.51 | B |
| ATOM | 1822 | O | GLN | B | 110 | 69.008 | 26.952 | 47.100 | 1.00 42.51 | B |
| ATOM | 1823 | N | CYS | B | 111 | 66.941 | 27.806 | 47.004 | 1.00 43.30 | B |
| ATOM | 1824 | CA | CYS | B | 111 | 66.581 | 27.247 | 48.294 | 1.00 43.30 | B |
| ATOM | 1825 | CB | CYS | B | 111 | 65.213 | 27.750 | 48.721 | 1.00 38.30 | B |
| ATOM | 1826 | SG | CYS | B | 111 | 65.269 | 29.469 | 49.201 | 1.00 38.30 | B |
| ATOM | 1827 | C | CYS | B | 111 | 66.598 | 25.724 | 48.277 | 1.00 43.30 | B |
| ATOM | 1828 | O | CYS | B | 111 | 67.238 | 25.104 | 49.124 | 1.00 43.30 | B |
| ATOM | 1829 | N | HIS | B | 112 | 65.903 | 25.120 | 47.316 | 1.00 88.21 | B |
| ATOM | 1830 | CA | HIS | B | 112 | 65.861 | 23.664 | 47.220 | 1.00 88.21 | B |
| ATOM | 1831 | CB | HIS | B | 112 | 65.104 | 23.229 | 45.964 | 1.00 61.47 | B |
| ATOM | 1832 | CG | HIS | B | 112 | 63.620 | 23.414 | 46.053 | 1.00 61.47 | B |
| ATOM | 1833 | CD2 | HIS | B | 112 | 62.772 | 24.180 | 45.327 | 1.00 61.47 | B |
| ATOM | 1834 | ND1 | HIS | B | 112 | 62.842 | 22.754 | 46.980 | 1.00 61.47 | B |
| ATOM | 1835 | CE1 | HIS | B | 112 | 61.578 | 23.106 | 46.822 | 1.00 61.47 | B |
| ATOM | 1836 | NE2 | HIS | B | 112 | 61.509 | 23.970 | 45.825 | 1.00 61.47 | B |
| ATOM | 1837 | C | HIS | B | 112 | 67.269 | 23.098 | 47.172 | 1.00 88.21 | B |
| ATOM | 1838 | O | HIS | B | 112 | 67.545 | 22.030 | 47.718 | 1.00 88.21 | B |
| ATOM | 1839 | N | GLN | B | 113 | 68.156 | 23.843 | 46.522 | 1.00 61.47 | B |
| ATOM | 1840 | CA | GLN | B | 113 | 69.546 | 23.451 | 46.343 | 1.00 61.47 | B |
| ATOM | 1841 | CB | GLN | B | 113 | 70.184 | 24.349 | 45.280 | 1.00104.41 | B |
| ATOM | 1842 | CG | GLN | B | 113 | 71.604 | 23.972 | 44.906 | 1.00104.41 | B |
| ATOM | 1843 | CD | GLN | B | 113 | 71.674 | 22.689 | 44.100 | 1.00104.41 | B |
| ATOM | 1844 | OE1 | GLN | B | 113 | 71.223 | 21.631 | 44.548 | 1.00104.41 | B |
| ATOM | 1845 | NE2 | GLN | B | 113 | 72.245 | 22.775 | 42.902 | 1.00104.41 | B |
| ATOM | 1846 | C | GLN | B | 113 | 70.410 | 23.483 | 47.607 | 1.00 61.47 | B |
| ATOM | 1847 | O | GLN | B | 113 | 71.276 | 22.624 | 47.792 | 1.00 61.47 | B |
| ATOM | 1848 | N | LEU | B | 114 | 70.184 | 24.468 | 48.472 | 1.00 73.58 | B |
| ATOM | 1849 | CA | LEU | B | 114 | 70.991 | 24.592 | 49.680 | 1.00 73.58 | B |
| ATOM | 1850 | CB | LEU | B | 114 | 71.600 | 25.997 | 49.761 | 1.00 50.36 | B |
| ATOM | 1851 | CG | LEU | B | 114 | 71.926 | 26.724 | 48.445 | 1.00 50.36 | B |
| ATOM | 1852 | CD1 | LEU | B | 114 | 72.690 | 28.017 | 48.745 | 1.00 50.36 | B |
| ATOM | 1853 | CD2 | LEU | B | 114 | 72.742 | 25.817 | 47.529 | 1.00 50.36 | B |
| ATOM | 1854 | C | LEU | B | 114 | 70.215 | 24.309 | 50.955 | 1.00 73.58 | B |
| ATOM | 1855 | O | LEU | B | 114 | 70.520 | 24.869 | 52.006 | 1.00 73.58 | B |
| ATOM | 1856 | N | VAL | B | 115 | 69.218 | 23.436 | 50.871 | 1.00 50.97 | B |
| ATOM | 1857 | CA | VAL | B | 115 | 68.413 | 23.100 | 52.040 | 1.00 50.97 | B |
| ATOM | 1858 | CB | VAL | B | 115 | 67.269 | 24.127 | 52.255 | 1.00 93.44 | B |
| ATOM | 1859 | CG1 | VAL | B | 115 | 66.397 | 23.698 | 53.419 | 1.00 93.44 | B |
| ATOM | 1860 | CG2 | VAL | B | 115 | 67.841 | 25.512 | 52.523 | 1.00 93.44 | B |
| ATOM | 1861 | C | VAL | B | 115 | 67.797 | 21.717 | 51.894 | 1.00 50.97 | B |
| ATOM | 1862 | O | VAL | B | 115 | 67.458 | 21.072 | 52.885 | 1.00 50.97 | B |
| ATOM | 1863 | N | GLY | B | 116 | 67.657 | 21.265 | 50.653 | 1.00 40.00 | B |
| ATOM | 1864 | CA | GLY | B | 116 | 67.062 | 19.964 | 50.401 | 1.00 40.00 | B |
| ATOM | 1865 | C | GLY | B | 116 | 67.715 | 18.821 | 51.152 | 1.00 40.00 | B |
| ATOM | 1866 | O | GLY | B | 116 | 67.045 | 18.088 | 51.892 | 1.00 40.00 | B |
| ATOM | 1867 | N | GLN | B | 117 | 69.024 | 18.663 | 50.963 | 1.00 36.16 | B |
| ATOM | 1868 | CA | GLN | B | 117 | 69.751 | 17.593 | 51.630 | 1.00 36.16 | B |

Fig. 2LL

```
ATOM   1869  CB   GLN B 117      71.205  17.564  51.150  1.00 97.53      B
ATOM   1870  CG   GLN B 117      71.382  16.732  49.894  1.00 97.53      B
ATOM   1871  CD   GLN B 117      70.848  15.326  50.086  1.00 97.53      B
ATOM   1872  OE1  GLN B 117      71.406  14.542  50.853  1.00 97.53      B
ATOM   1873  NE2  GLN B 117      69.750  15.008  49.407  1.00 97.53      B
ATOM   1874  C    GLN B 117      69.685  17.695  53.149  1.00 36.16      B
ATOM   1875  O    GLN B 117      69.240  16.762  53.818  1.00 36.16      B
ATOM   1876  N    ASP B 118      70.115  18.831  53.689  1.00 45.11      B
ATOM   1877  CA   ASP B 118      70.094  19.051  55.128  1.00 45.11      B
ATOM   1878  CB   ASP B 118      70.466  20.497  55.422  1.00 63.00      B
ATOM   1879  CG   ASP B 118      71.856  20.847  54.934  1.00 63.00      B
ATOM   1880  OD1  ASP B 118      72.217  22.046  54.974  1.00 63.00      B
ATOM   1881  OD2  ASP B 118      72.587  19.919  54.514  1.00 63.00      B
ATOM   1882  C    ASP B 118      68.722  18.741  55.725  1.00 45.11      B
ATOM   1883  O    ASP B 118      68.607  18.024  56.720  1.00 45.11      B
ATOM   1884  N    LEU B 119      67.676  19.270  55.104  1.00 38.08      B
ATOM   1885  CA   LEU B 119      66.332  19.055  55.602  1.00 38.08      B
ATOM   1886  CB   LEU B 119      65.329  19.879  54.790  1.00 55.08      B
ATOM   1887  CG   LEU B 119      63.895  19.822  55.327  1.00 55.08      B
ATOM   1888  CD1  LEU B 119      63.893  20.275  56.778  1.00 55.08      B
ATOM   1889  CD2  LEU B 119      62.978  20.693  54.486  1.00 55.08      B
ATOM   1890  C    LEU B 119      65.954  17.586  55.549  1.00 38.08      B
ATOM   1891  O    LEU B 119      65.353  17.046  56.484  1.00 38.08      B
ATOM   1892  N    HIS B 120      66.312  16.934  54.452  1.00 37.90      B
ATOM   1893  CA   HIS B 120      65.982  15.534  54.284  1.00 37.90      B
ATOM   1894  CB   HIS B 120      66.324  15.107  52.866  1.00 44.03      B
ATOM   1895  CG   HIS B 120      65.762  13.777  52.491  1.00 44.03      B
ATOM   1896  CD2  HIS B 120      64.508  13.407  52.138  1.00 44.03      B
ATOM   1897  ND1  HIS B 120      66.519  12.626  52.477  1.00 44.03      B
ATOM   1898  CE1  HIS B 120      65.757  11.604  52.132  1.00 44.03      B
ATOM   1899  NE2  HIS B 120      64.531  12.050  51.921  1.00 44.03      B
ATOM   1900  C    HIS B 120      66.723  14.680  55.308  1.00 37.90      B
ATOM   1901  O    HIS B 120      66.182  13.704  55.831  1.00 37.90      B
ATOM   1902  N    GLN B 121      67.956  15.074  55.606  1.00 42.58      B
ATOM   1903  CA   GLN B 121      68.785  14.362  56.563  1.00 42.58      B
ATOM   1904  CB   GLN B 121      70.195  14.959  56.555  1.00 84.48      B
ATOM   1905  CG   GLN B 121      71.264  14.100  57.206  1.00 84.48      B
ATOM   1906  CD   GLN B 121      72.658  14.658  56.985  1.00 84.48      B
ATOM   1907  OE1  GLN B 121      73.047  14.951  55.852  1.00 84.48      B
ATOM   1908  NE2  GLN B 121      73.419  14.804  58.064  1.00 84.48      B
ATOM   1909  C    GLN B 121      68.168  14.467  57.957  1.00 42.58      B
ATOM   1910  O    GLN B 121      67.945  13.449  58.618  1.00 42.58      B
ATOM   1911  N    GLU B 122      67.885  15.696  58.392  1.00 47.08      B
ATOM   1912  CA   GLU B 122      67.299  15.949  59.709  1.00 47.08      B
ATOM   1913  CB   GLU B 122      67.150  17.456  59.935  1.00 73.03      B
ATOM   1914  CG   GLU B 122      68.154  18.027  60.913  1.00 73.03      B
ATOM   1915  CD   GLU B 122      67.966  17.476  62.312  1.00 73.03      B
ATOM   1916  OE1  GLU B 122      66.934  17.789  62.944  1.00 73.03      B
```

Fig. 2MM

| ATOM | 1917 | OE2 | GLU | B | 122 | 68.847 | 16.722 | 62.777 | 1.00 | 73.03 | B |
| ---- | ---- | --- | --- | - | --- | ------ | ------ | ------ | ---- | ----- | - |
| ATOM | 1918 | C | GLU | B | 122 | 65.944 | 15.271 | 59.913 | 1.00 | 47.08 | B |
| ATOM | 1919 | O | GLU | B | 122 | 65.693 | 14.664 | 60.959 | 1.00 | 47.08 | B |
| ATOM | 1920 | N | LEU | B | 123 | 65.068 | 15.385 | 58.917 | 1.00 | 59.13 | B |
| ATOM | 1921 | CA | LEU | B | 123 | 63.745 | 14.783 | 59.000 | 1.00 | 59.13 | B |
| ATOM | 1922 | CB | LEU | B | 123 | 62.905 | 15.155 | 57.776 | 1.00 | 52.32 | B |
| ATOM | 1923 | CG | LEU | B | 123 | 62.127 | 16.471 | 57.797 | 1.00 | 52.32 | B |
| ATOM | 1924 | CD1 | LEU | B | 123 | 61.355 | 16.622 | 56.488 | 1.00 | 52.32 | B |
| ATOM | 1925 | CD2 | LEU | B | 123 | 61.173 | 16.482 | 58.979 | 1.00 | 52.32 | B |
| ATOM | 1926 | C | LEU | B | 123 | 63.787 | 13.266 | 59.117 | 1.00 | 59.13 | B |
| ATOM | 1927 | O | LEU | B | 123 | 63.037 | 12.682 | 59.901 | 1.00 | 59.13 | B |
| ATOM | 1928 | N | THR | B | 124 | 64.664 | 12.631 | 58.341 | 1.00 | 49.05 | B |
| ATOM | 1929 | CA | THR | B | 124 | 64.768 | 11.174 | 58.341 | 1.00 | 49.05 | B |
| ATOM | 1930 | CB | THR | B | 124 | 64.987 | 10.639 | 56.911 | 1.00 | 64.49 | B |
| ATOM | 1931 | OG1 | THR | B | 124 | 66.173 | 11.221 | 56.363 | 1.00 | 64.49 | B |
| ATOM | 1932 | CG2 | THR | B | 124 | 63.813 | 10.993 | 56.019 | 1.00 | 64.49 | B |
| ATOM | 1933 | C | THR | B | 124 | 65.862 | 10.589 | 59.233 | 1.00 | 49.05 | B |
| ATOM | 1934 | O | THR | B | 124 | 66.059 | 9.370 | 59.255 | 1.00 | 49.05 | B |
| ATOM | 1935 | N | LYS | B | 125 | 66.560 | 11.444 | 59.978 | 1.00 | 66.45 | B |
| ATOM | 1936 | CA | LYS | B | 125 | 67.642 | 10.982 | 60.843 | 1.00 | 66.45 | B |
| ATOM | 1937 | CB | LYS | B | 125 | 68.193 | 12.143 | 61.671 | 1.00 | 68.58 | B |
| ATOM | 1938 | CG | LYS | B | 125 | 67.284 | 12.598 | 62.794 | 1.00 | 68.58 | B |
| ATOM | 1939 | CD | LYS | B | 125 | 67.964 | 13.659 | 63.645 | 1.00 | 68.58 | B |
| ATOM | 1940 | CE | LYS | B | 125 | 67.083 | 14.099 | 64.803 | 1.00 | 68.58 | B |
| ATOM | 1941 | NZ | LYS | B | 125 | 67.767 | 15.137 | 65.628 | 1.00 | 68.58 | B |
| ATOM | 1942 | C | LYS | B | 125 | 67.248 | 9.835 | 61.778 | 1.00 | 66.45 | B |
| ATOM | 1943 | O | LYS | B | 125 | 68.114 | 9.148 | 62.316 | 1.00 | 66.45 | B |
| ATOM | 1944 | N | ASN | B | 126 | 65.950 | 9.628 | 61.973 | 1.00 | 53.40 | B |
| ATOM | 1945 | CA | ASN | B | 126 | 65.480 | 8.560 | 62.853 | 1.00 | 53.40 | B |
| ATOM | 1946 | CB | ASN | B | 126 | 64.369 | 9.077 | 63.777 | 1.00 | 70.54 | B |
| ATOM | 1947 | CG | ASN | B | 126 | 64.877 | 10.066 | 64.818 | 1.00 | 70.54 | B |
| ATOM | 1948 | OD1 | ASN | B | 126 | 64.086 | 10.728 | 65.494 | 1.00 | 70.54 | B |
| ATOM | 1949 | ND2 | ASN | B | 126 | 66.196 | 10.162 | 64.958 | 1.00 | 70.54 | B |
| ATOM | 1950 | C | ASN | B | 126 | 64.952 | 7.373 | 62.058 | 1.00 | 53.40 | B |
| ATOM | 1951 | O | ASN | B | 126 | 64.430 | 6.418 | 62.632 | 1.00 | 53.40 | B |
| ATOM | 1952 | N | LEU | B | 127 | 65.090 | 7.433 | 60.738 | 1.00 | 70.93 | B |
| ATOM | 1953 | CA | LEU | B | 127 | 64.601 | 6.361 | 59.884 | 1.00 | 70.93 | B |
| ATOM | 1954 | CB | LEU | B | 127 | 63.448 | 6.860 | 59.008 | 1.00 | 58.67 | B |
| ATOM | 1955 | CG | LEU | B | 127 | 62.158 | 7.291 | 59.707 | 1.00 | 58.67 | B |
| ATOM | 1956 | CD1 | LEU | B | 127 | 61.174 | 7.793 | 58.668 | 1.00 | 58.67 | B |
| ATOM | 1957 | CD2 | LEU | B | 127 | 61.565 | 6.126 | 60.480 | 1.00 | 58.67 | B |
| ATOM | 1958 | C | LEU | B | 127 | 65.671 | 5.771 | 58.985 | 1.00 | 70.93 | B |
| ATOM | 1959 | O | LEU | B | 127 | 66.562 | 6.473 | 58.512 | 1.00 | 70.93 | B |
| ATOM | 1960 | N | THR | B | 128 | 65.567 | 4.469 | 58.749 | 1.00 | 75.76 | B |
| ATOM | 1961 | CA | THR | B | 128 | 66.500 | 3.769 | 57.884 | 1.00 | 75.76 | B |
| ATOM | 1962 | CB | THR | B | 128 | 66.343 | 2.258 | 58.021 | 1.00 | 67.91 | B |
| ATOM | 1963 | OG1 | THR | B | 128 | 65.106 | 1.854 | 57.417 | 1.00 | 67.91 | B |
| ATOM | 1964 | CG2 | THR | B | 128 | 66.330 | 1.863 | 59.495 | 1.00 | 67.91 | B |

Fig. 2NN

```
ATOM   1965  C    THR B 128      66.138   4.157  56.457  1.00 75.76      B
ATOM   1966  O    THR B 128      65.112   4.795  56.224  1.00 75.76      B
ATOM   1967  N    ALA B 129      66.970   3.767  55.502  1.00 76.39      B
ATOM   1968  CA   ALA B 129      66.711   4.090  54.107  1.00 76.39      B
ATOM   1969  CB   ALA B 129      67.891   3.657  53.249  1.00 63.22      B
ATOM   1970  C    ALA B 129      65.431   3.411  53.623  1.00 76.39      B
ATOM   1971  O    ALA B 129      64.695   3.960  52.801  1.00 76.39      B
ATOM   1972  N    ASP B 130      65.167   2.217  54.141  1.00 80.92      B
ATOM   1973  CA   ASP B 130      63.983   1.464  53.743  1.00 80.92      B
ATOM   1974  CB   ASP B 130      64.112   0.000  54.179  1.00118.02      B
ATOM   1975  CG   ASP B 130      65.261  -0.716  53.487  1.00118.02      B
ATOM   1976  OD1  ASP B 130      66.425  -0.317  53.701  1.00118.02      B
ATOM   1977  OD2  ASP B 130      65.002  -1.673  52.726  1.00118.02      B
ATOM   1978  C    ASP B 130      62.700   2.059  54.301  1.00 80.92      B
ATOM   1979  O    ASP B 130      61.682   2.108  53.609  1.00 80.92      B
ATOM   1980  N    GLU B 131      62.748   2.505  55.552  1.00 71.60      B
ATOM   1981  CA   GLU B 131      61.575   3.102  56.180  1.00 71.60      B
ATOM   1982  CB   GLU B 131      61.865   3.406  57.657  1.00 50.30      B
ATOM   1983  CG   GLU B 131      62.214   2.161  58.462  1.00 50.30      B
ATOM   1984  CD   GLU B 131      62.588   2.448  59.915  1.00 50.30      B
ATOM   1985  OE1  GLU B 131      63.536   3.232  60.154  1.00 50.30      B
ATOM   1986  OE2  GLU B 131      61.938   1.872  60.822  1.00 50.30      B
ATOM   1987  C    GLU B 131      61.216   4.376  55.416  1.00 71.60      B
ATOM   1988  O    GLU B 131      60.043   4.651  55.156  1.00 71.60      B
ATOM   1989  N    VAL B 132      62.242   5.133  55.038  1.00 47.01      B
ATOM   1990  CA   VAL B 132      62.070   6.375  54.292  1.00 47.01      B
ATOM   1991  CB   VAL B 132      63.434   7.031  53.979  1.00 59.53      B
ATOM   1992  CG1  VAL B 132      63.236   8.246  53.086  1.00 59.53      B
ATOM   1993  CG2  VAL B 132      64.131   7.427  55.273  1.00 59.53      B
ATOM   1994  C    VAL B 132      61.342   6.146  52.974  1.00 47.01      B
ATOM   1995  O    VAL B 132      60.407   6.873  52.640  1.00 47.01      B
ATOM   1996  N    ALA B 133      61.776   5.139  52.224  1.00 62.22      B
ATOM   1997  CA   ALA B 133      61.156   4.832  50.939  1.00 62.22      B
ATOM   1998  CB   ALA B 133      61.968   3.768  50.211  1.00 45.41      B
ATOM   1999  C    ALA B 133      59.713   4.364  51.122  1.00 62.22      B
ATOM   2000  O    ALA B 133      58.849   4.636  50.288  1.00 62.22      B
ATOM   2001  N    THR B 134      59.456   3.656  52.216  1.00 43.56      B
ATOM   2002  CA   THR B 134      58.112   3.162  52.507  1.00 43.56      B
ATOM   2003  CB   THR B 134      58.128   2.233  53.728  1.00 52.11      B
ATOM   2004  OG1  THR B 134      59.117   1.212  53.538  1.00 52.11      B
ATOM   2005  CG2  THR B 134      56.761   1.599  53.927  1.00 52.11      B
ATOM   2006  C    THR B 134      57.187   4.346  52.817  1.00 43.56      B
ATOM   2007  O    THR B 134      56.058   4.436  52.321  1.00 43.56      B
ATOM   2008  N    LEU B 135      57.696   5.246  53.652  1.00 41.37      B
ATOM   2009  CA   LEU B 135      56.980   6.439  54.067  1.00 41.37      B
ATOM   2010  CB   LEU B 135      57.849   7.243  55.030  1.00 38.54      B
ATOM   2011  CG   LEU B 135      57.203   8.484  55.640  1.00 38.54      B
ATOM   2012  CD1  LEU B 135      56.004   8.075  56.502  1.00 38.54      B
```

Fig. 2OO

| | | | | | | | | | |
|---|---|---|---|---|---|---|---|---|---|
| ATOM | 2013 | CD2 | LEU | B | 135 | 58.238 | 9.217 | 56.471 | 1.00 38.54 | B |
| ATOM | 2014 | C | LEU | B | 135 | 56.606 | 7.308 | 52.870 | 1.00 41.37 | B |
| ATOM | 2015 | O | LEU | B | 135 | 55.540 | 7.938 | 52.855 | 1.00 41.37 | B |
| ATOM | 2016 | N | GLU | B | 136 | 57.485 | 7.337 | 51.871 | 1.00 39.88 | B |
| ATOM | 2017 | CA | GLU | B | 136 | 57.249 | 8.137 | 50.675 | 1.00 39.88 | B |
| ATOM | 2018 | CB | GLU | B | 136 | 58.555 | 8.358 | 49.913 | 1.00 58.39 | B |
| ATOM | 2019 | CG | GLU | B | 136 | 59.605 | 9.113 | 50.707 | 1.00 58.39 | B |
| ATOM | 2020 | CD | GLU | B | 136 | 60.620 | 9.807 | 49.820 | 1.00 58.39 | B |
| ATOM | 2021 | OE1 | GLU | B | 136 | 61.445 | 10.575 | 50.363 | 1.00 58.39 | B |
| ATOM | 2022 | OE2 | GLU | B | 136 | 60.593 | 9.594 | 48.585 | 1.00 58.39 | B |
| ATOM | 2023 | C | GLU | B | 136 | 56.216 | 7.504 | 49.749 | 1.00 39.88 | B |
| ATOM | 2024 | O | GLU | B | 136 | 55.408 | 8.209 | 49.136 | 1.00 39.88 | B |
| ATOM | 2025 | N | TYR | B | 137 | 56.234 | 6.178 | 49.643 | 1.00 45.26 | B |
| ATOM | 2026 | CA | TYR | B | 137 | 55.280 | 5.506 | 48.778 | 1.00 45.26 | B |
| ATOM | 2027 | CB | TYR | B | 137 | 55.630 | 4.021 | 48.626 | 1.00 69.50 | B |
| ATOM | 2028 | CG | TYR | B | 137 | 54.622 | 3.258 | 47.795 | 1.00 69.50 | B |
| ATOM | 2029 | CD1 | TYR | B | 137 | 54.160 | 3.773 | 46.584 | 1.00 69.50 | B |
| ATOM | 2030 | CE1 | TYR | B | 137 | 53.193 | 3.106 | 45.841 | 1.00 69.50 | B |
| ATOM | 2031 | CD2 | TYR | B | 137 | 54.097 | 2.045 | 48.240 | 1.00 69.50 | B |
| ATOM | 2032 | CE2 | TYR | B | 137 | 53.130 | 1.366 | 47.502 | 1.00 69.50 | B |
| ATOM | 2033 | CZ | TYR | B | 137 | 52.680 | 1.904 | 46.307 | 1.00 69.50 | B |
| ATOM | 2034 | OH | TYR | B | 137 | 51.701 | 1.258 | 45.588 | 1.00 69.50 | B |
| ATOM | 2035 | C | TYR | B | 137 | 53.876 | 5.668 | 49.349 | 1.00 45.26 | B |
| ATOM | 2036 | O | TYR | B | 137 | 52.938 | 6.023 | 48.626 | 1.00 45.26 | B |
| ATOM | 2037 | N | LEU | B | 138 | 53.736 | 5.414 | 50.648 | 1.00 35.44 | B |
| ATOM | 2038 | CA | LEU | B | 138 | 52.442 | 5.545 | 51.307 | 1.00 35.44 | B |
| ATOM | 2039 | CB | LEU | B | 138 | 52.543 | 5.088 | 52.765 | 1.00 36.43 | B |
| ATOM | 2040 | CG | LEU | B | 138 | 52.936 | 3.625 | 52.990 | 1.00 36.43 | B |
| ATOM | 2041 | CD1 | LEU | B | 138 | 52.990 | 3.326 | 54.486 | 1.00 36.43 | B |
| ATOM | 2042 | CD2 | LEU | B | 138 | 51.929 | 2.716 | 52.305 | 1.00 36.43 | B |
| ATOM | 2043 | C | LEU | B | 138 | 51.940 | 6.996 | 51.242 | 1.00 35.44 | B |
| ATOM | 2044 | O | LEU | B | 138 | 50.769 | 7.244 | 50.932 | 1.00 35.44 | B |
| ATOM | 2045 | N | LEU | B | 139 | 52.823 | 7.952 | 51.534 | 1.00 33.21 | B |
| ATOM | 2046 | CA | LEU | B | 139 | 52.439 | 9.355 | 51.482 | 1.00 33.21 | B |
| ATOM | 2047 | CB | LEU | B | 139 | 53.616 | 10.259 | 51.872 | 1.00 38.76 | B |
| ATOM | 2048 | CG | LEU | B | 139 | 53.835 | 10.434 | 53.383 | 1.00 38.76 | B |
| ATOM | 2049 | CD1 | LEU | B | 139 | 55.119 | 11.198 | 53.656 | 1.00 38.76 | B |
| ATOM | 2050 | CD2 | LEU | B | 139 | 52.635 | 11.170 | 53.983 | 1.00 38.76 | B |
| ATOM | 2051 | C | LEU | B | 139 | 51.966 | 9.685 | 50.078 | 1.00 33.21 | B |
| ATOM | 2052 | O | LEU | B | 139 | 50.958 | 10.368 | 49.905 | 1.00 33.21 | B |
| ATOM | 2053 | N | LYS | B | 140 | 52.687 | 9.190 | 49.073 | 1.00 32.26 | B |
| ATOM | 2054 | CA | LYS | B | 140 | 52.315 | 9.437 | 47.679 | 1.00 32.26 | B |
| ATOM | 2055 | CB | LYS | B | 140 | 53.355 | 8.824 | 46.735 | 1.00 53.55 | B |
| ATOM | 2056 | CG | LYS | B | 140 | 54.738 | 9.452 | 46.831 | 1.00 53.55 | B |
| ATOM | 2057 | CD | LYS | B | 140 | 55.753 | 8.716 | 45.969 | 1.00 53.55 | B |
| ATOM | 2058 | CE | LYS | B | 140 | 57.152 | 9.289 | 46.159 | 1.00 53.55 | B |
| ATOM | 2059 | NZ | LYS | B | 140 | 58.197 | 8.604 | 45.334 | 1.00 53.55 | B |
| ATOM | 2060 | C | LYS | B | 140 | 50.926 | 8.875 | 47.350 | 1.00 32.26 | B |

Fig. 2PP

| | | | | | | | | | | |
|---|---|---|---|---|---|---|---|---|---|---|
| ATOM | 2061 | O | LYS | B | 140 | 50.256 | 9.370 | 46.446 | 1.00 32.26 | B |
| ATOM | 2062 | N | LYS | B | 141 | 50.496 | 7.846 | 48.085 | 1.00 46.02 | B |
| ATOM | 2063 | CA | LYS | B | 141 | 49.185 | 7.237 | 47.852 | 1.00 46.02 | B |
| ATOM | 2064 | CB | LYS | B | 141 | 49.103 | 5.840 | 48.479 | 1.00 51.68 | B |
| ATOM | 2065 | CG | LYS | B | 141 | 49.941 | 4.782 | 47.767 | 1.00 51.68 | B |
| ATOM | 2066 | CD | LYS | B | 141 | 49.637 | 3.365 | 48.258 | 1.00 51.68 | B |
| ATOM | 2067 | CE | LYS | B | 141 | 48.242 | 2.904 | 47.838 | 1.00 51.68 | B |
| ATOM | 2068 | NZ | LYS | B | 141 | 47.928 | 1.518 | 48.308 | 1.00 51.68 | B |
| ATOM | 2069 | C | LYS | B | 141 | 48.043 | 8.085 | 48.383 | 1.00 46.02 | B |
| ATOM | 2070 | O | LYS | B | 141 | 46.895 | 7.910 | 47.981 | 1.00 46.02 | B |
| ATOM | 2071 | N | VAL | B | 142 | 48.355 | 9.005 | 49.285 | 1.00 38.10 | B |
| ATOM | 2072 | CA | VAL | B | 142 | 47.328 | 9.864 | 49.855 | 1.00 38.10 | B |
| ATOM | 2073 | CB | VAL | B | 142 | 47.785 | 10.504 | 51.186 | 1.00 34.97 | B |
| ATOM | 2074 | CG1 | VAL | B | 142 | 46.649 | 11.321 | 51.776 | 1.00 34.97 | B |
| ATOM | 2075 | CG2 | VAL | B | 142 | 48.245 | 9.423 | 52.166 | 1.00 34.97 | B |
| ATOM | 2076 | C | VAL | B | 142 | 46.990 | 10.985 | 48.886 | 1.00 38.10 | B |
| ATOM | 2077 | O | VAL | B | 142 | 45.833 | 11.402 | 48.784 | 1.00 38.10 | B |
| ATOM | 2078 | N | LEU | B | 143 | 47.999 | 11.466 | 48.166 | 1.00 45.02 | B |
| ATOM | 2079 | CA | LEU | B | 143 | 47.790 | 12.565 | 47.231 | 1.00 45.02 | B |
| ATOM | 2080 | CB | LEU | B | 143 | 49.105 | 12.915 | 46.525 | 1.00 26.86 | B |
| ATOM | 2081 | CG | LEU | B | 143 | 50.062 | 13.627 | 47.486 | 1.00 26.86 | B |
| ATOM | 2082 | CD1 | LEU | B | 143 | 51.383 | 13.934 | 46.802 | 1.00 26.86 | B |
| ATOM | 2083 | CD2 | LEU | B | 143 | 49.394 | 14.906 | 47.974 | 1.00 26.86 | B |
| ATOM | 2084 | C | LEU | B | 143 | 46.668 | 12.370 | 46.211 | 1.00 45.02 | B |
| ATOM | 2085 | O | LEU | B | 143 | 45.824 | 13.256 | 46.035 | 1.00 45.02 | B |
| ATOM | 2086 | N | PRO | B | 144 | 46.643 | 11.220 | 45.521 | 1.00 136.81 | B |
| ATOM | 2087 | CD | PRO | B | 144 | 47.703 | 10.213 | 45.346 | 1.00 119.29 | B |
| ATOM | 2088 | CA | PRO | B | 144 | 45.570 | 11.019 | 44.543 | 1.00 136.81 | B |
| ATOM | 2089 | CB | PRO | B | 144 | 46.035 | 9.785 | 43.768 | 1.00 119.29 | B |
| ATOM | 2090 | CG | PRO | B | 144 | 47.535 | 9.845 | 43.895 | 1.00 119.29 | B |
| ATOM | 2091 | C | PRO | B | 144 | 44.224 | 10.792 | 45.237 | 1.00 136.81 | B |
| ATOM | 2092 | O | PRO | B | 144 | 43.451 | 9.933 | 44.760 | 1.00 136.81 | B |
| ATOM | 2093 | OXT | PRO | B | 144 | 43.955 | 11.484 | 46.244 | 1.00 119.29 | B |
| ATOM | 2094 | O | HOH | S | 1 | 48.178 | 40.496 | 68.629 | 1.00 35.76 | S |
| ATOM | 2095 | O | HOH | S | 2 | 46.684 | 40.021 | 43.558 | 1.00 29.93 | S |
| ATOM | 2096 | O | HOH | S | 3 | 34.364 | 30.965 | 80.945 | 1.00 25.52 | S |
| ATOM | 2097 | O | HOH | S | 4 | 40.671 | 32.039 | 57.247 | 1.00 33.95 | S |
| ATOM | 2098 | O | HOH | S | 5 | 54.783 | 40.457 | 73.829 | 1.00 29.99 | S |
| ATOM | 2099 | O | HOH | S | 6 | 44.763 | 28.859 | 75.845 | 1.00 18.35 | S |
| ATOM | 2100 | O | HOH | S | 7 | 68.120 | 36.357 | 49.261 | 1.00 38.62 | S |
| ATOM | 2101 | O | HOH | S | 8 | 41.008 | 40.210 | 74.710 | 1.00 29.13 | S |
| ATOM | 2102 | O | HOH | S | 9 | 58.797 | 33.370 | 61.148 | 1.00 34.94 | S |
| ATOM | 2103 | O | HOH | S | 10 | 51.657 | 20.370 | 74.794 | 1.00 34.89 | S |
| ATOM | 2104 | O | HOH | S | 11 | 34.356 | 12.998 | 61.568 | 1.00 19.59 | S |
| ATOM | 2105 | O | HOH | S | 12 | 31.589 | 17.449 | 58.590 | 1.00 33.06 | S |
| ATOM | 2106 | O | HOH | S | 13 | 51.809 | 23.559 | 46.413 | 1.00 42.58 | S |
| ATOM | 2107 | O | HOH | S | 14 | 41.787 | 36.216 | 41.713 | 1.00 34.36 | S |
| END | | | | | | | | | | |

Fig. 2QQ

```
Sequence 1: SlyA (Top) = SEQ ID NO:6
Sequence 2: MarR (Bottom) = SEQ ID NO:2
Identity score: 21.2 %

10        20        30        40        50        60        70        80
MKLESPLGSDLARLVRIWRALIDHRLKPLELTQTHWVTLHNIHQLPPDQSQIQLAKAIGIEQPSLVRTLDQLEDKGLIS   - SEQ ID NO:6
LFNEIIPLGRLIHMVNQKKDRLLNEYLSPLDITAAQFKVLCSIRC AACITPVELKKVLSVDLGALTRMLDRLVCKGWVE   - SEQ ID NO:2

90       100       110       120       130       140       150       160
RQTCASDRRAKRIKLTEKAEPLIAEMEEVI HKTRGEILAGISSEEIELLIKLIAKLEHNIMELHSHD              - SEQ ID NO:6
RLPNPNDKRGVLVKLTTGGAAICEQCHQLVGQDLHQELTKNLTADEVATLEYLLKKV         LP              - SEQ ID NO:2
```

Fig. 11

Sequence 1: SlyA (Top) = SEQ ID NO:6
Sequence 2: MarR (Bottom) = SEQ ID NO:2

MKLESPLGSDLARLVRIWRALIDHRLKPLELTQTHWVTLHNIHQLPPDQSQIQLAKAIGIEQPSLVRTLDQLEDKGLISR - SEQ ID NO:6
         LGRLIHMVNQKDRL         AAQFKVLCSIRCA         LGALTRMLDRLVG         VER - SEQ ID NO:2

QTCASDRRAKRIKLTEKAEPLIAEMEEVIHKTRGEILAGISSEELLIKLIAKLEHNIMELHSHD - SEQ ID NO:6
LP    VLVKL IGGAAICEQCHQLVGQDLHQELIKNL VATLEYLLK                  - SEQ ID NO:2

Fig. 12

SEQUENCE LISTING

```
<160> NUMBER OF SEQ ID NOS: 8

<210> SEQ ID NO 1
<211> LENGTH: 1
<212> TYPE: PRT
<213> ORGANISM: Escherichia coli

<400> SEQUENCE: 1

Met
 1

<210> SEQ ID NO 2
<211> LENGTH: 143
<212> TYPE: PRT
<213> ORGANISM: Escherichia coli

<400> SEQUENCE: 2

Met Lys Ser Thr Ser Asp Leu Phe Asn Glu Ile Ile Pro Leu Gly Arg
 1               5                  10                  15

Leu Ile His Met Val Asn Gln Lys Lys Asp Arg Leu Leu Asn Glu Tyr
            20                  25                  30

Leu Ser Pro Leu Asp Ile Thr Ala Ala Gln Phe Lys Val Leu Ser Cys
        35                  40                  45
```

```
Ile Arg Cys Ala Ala Cys Ile Thr Pro Val Glu Leu Lys Lys Val Leu
 50                  55                  60

Ser Val Asp Leu Gly Ala Leu Thr Arg Met Leu Asp Arg Leu Val Cys
 65                  70                  75                  80

Lys Gly Trp Val Glu Arg Leu Pro Asn Pro Asn Asp Lys Arg Gly Val
                 85                  90                  95

Leu Val Lys Leu Thr Gly Gly Ala Ala Ile Cys Glu Gln Cys His Gln
            100                 105                 110

Leu Val Gly Gln Asp Leu His Gln Glu Leu Thr Lys Asn Leu Thr Ala
            115                 120                 125

Asp Glu Val Ala Thr Leu Glu Tyr Leu Leu Lys Lys Val Leu Pro
            130                 135                 140

<210> SEQ ID NO 3
<211> LENGTH: 173
<212> TYPE: PRT
<213> ORGANISM: Escherichia coli

<400> SEQUENCE: 3

Met Asp Ser Ser Phe Thr Pro Ile Glu Gln Met Leu Lys Phe Arg Ala
 1                   5                  10                  15

Ser Arg His Glu Asp Phe Pro Tyr Gln Glu Ile Leu Leu Thr Arg Leu
                 20                  25                  30

Cys Met His Met Gln Ser Lys Leu Leu Glu Asn Arg Asn Lys Met Leu
             35                  40                  45

Lys Ala Gln Gly Ile Asn Glu Thr Leu Phe Met Ala Leu Ile Thr Leu
 50                  55                  60

Glu Ser Gln Glu Asn His Ser Ile Gln Pro Ser Glu Leu Ser Cys Ala
 65                  70                  75                  80

Leu Gly Ser Ser Arg Thr Asn Ala Thr Arg Ile Asp Ala Asp Glu Leu
                 85                  90                  95

Glu Leu Arg Gly Trp Ile Glu Arg Glu Ser Asp Asn Asp Arg Arg Cys
            100                 105                 110

Leu His Leu Gln Leu Thr Glu Lys Gly His Glu Phe Leu Arg Glu Val
            115                 120                 125

Leu Pro Pro Gln His Asn Cys Leu His Gln Leu Trp Ser Ala Leu Ser
            130                 135                 140

Thr Thr Glu Lys Asp Gln Leu Glu Gln Ile Thr Arg Lys Leu Ser Arg
145                 150                 155                 160

Leu Asp Met Glu Asp Gly Val Val Leu Glu Ala Met Ser
            165                 170

<210> SEQ ID NO 4
<211> LENGTH: 146
<212> TYPE: PRT
<213> ORGANISM: Escherichia coli

<400> SEQUENCE: 4

Met Asn Tyr Pro Val Asn Pro Asp Leu Met Pro Ala Leu Met Ala Val
 1                   5                  10                  15

Phe Gln His Val Arg Thr Arg Ile Gln Ser Glu Leu Asp Cys Gln Arg
                 20                  25                  30

Leu Asp Leu Thr Pro Pro Asp Val His Val Leu Lys Leu Ile Asp Glu
             35                  40                  45

Gln Arg Gly Leu Asn Leu Gln Asp Leu Gly Arg Gln Met Cys Arg Asp
 50                  55                  60
```

```
Lys Ala Leu Ile Thr Arg Lys Ile Arg Glu Leu Glu Gly Arg Asn Leu
 65                  70                  75                  80

Val Arg Arg Glu Arg Asn Pro Ser Asp Gln Arg Ser Phe Gln Leu Phe
                 85                  90                  95

Thr Asp Glu Phe Leu Ala Ile His Gln His Ala Glu Ala Ile Met Ser
            100                 105                 110

Arg Val His Asp Glu Leu Phe Ala Pro Leu Thr Pro Val Glu Gln Ala
        115                 120                 125

Thr Leu Val His Leu Leu Asp Gln Cys Leu Ala Ala Gln Pro Leu Glu
130                 135                 140

Asp Ile
145

<210> SEQ ID NO 5
<211> LENGTH: 139
<212> TYPE: PRT
<213> ORGANISM: Escherichia coli

<400> SEQUENCE: 5

Met Gly Leu Ala Asp Asp Ala Pro Leu Gly Tyr Leu Leu Tyr Arg Val
  1               5                  10                  15

Gly Ala Val Leu Arg Pro Glu Val Ser Ala Ala Leu Ser Pro Leu Gly
                 20                  25                  30

Leu Thr Leu Pro Glu Phe Val Cys Leu Arg Met Leu Ser Gln Ser Pro
             35                  40                  45

Gly Leu Ser Ser Ala Glu Leu Ala Arg His Ala Ser Val Thr Pro Gln
         50                  55                  60

Ala Met Asn Thr Val Leu Arg Lys Leu Glu Asp Ala Gly Ala Val Ala
 65                  70                  75                  80

Arg Pro Ala Ser Val Ser Ser Gly Arg Ser Leu Pro Ala Thr Leu Thr
                 85                  90                  95

Ala Arg Gly Arg Ala Leu Ala Lys Arg Ala Glu Ala Val Val Arg Ala
            100                 105                 110

Ala Asp Ala Arg Val Leu Ala Arg Leu Thr Ala Pro Gln Gln Arg Glu
        115                 120                 125

Phe Lys Arg Met Leu Glu Lys Leu Gly Ser Asp
130                 135

<210> SEQ ID NO 6
<211> LENGTH: 146
<212> TYPE: PRT
<213> ORGANISM: Escherichia coli

<400> SEQUENCE: 6

Met Lys Leu Glu Ser Pro Leu Gly Ser Asp Leu Ala Arg Leu Val Arg
  1               5                  10                  15

Ile Trp Arg Ala Leu Ile Asp His Arg Leu Lys Pro Leu Glu Leu Thr
                 20                  25                  30

Gln Thr His Trp Val Thr Leu His Asn Ile His Gln Leu Pro Pro Asp
             35                  40                  45

Gln Ser Gln Ile Gln Leu Ala Lys Ala Ile Gly Ile Glu Gln Pro Ser
         50                  55                  60

Leu Val Arg Thr Leu Asp Gln Leu Glu Asp Lys Gly Leu Ile Ser Arg
 65                  70                  75                  80

Gln Thr Cys Ala Asp Ser Asp Arg Arg Ala Lys Arg Ile Lys Leu Thr
                 85                  90                  95
```

Glu Lys Ala Glu Pro Leu Ile Ala Glu Met Glu Val Ile His Lys
                100                 105                 110

Thr Arg Gly Glu Ile Leu Ala Gly Ile Ser Ser Glu Ile Glu Leu
            115                 120                 125

Leu Ile Lys Leu Ile Ala Lys Leu Glu His Asn Ile Met Glu Leu His
130                 135                 140

Ser Asp
145

<210> SEQ ID NO 7
<211> LENGTH: 165
<212> TYPE: PRT
<213> ORGANISM: Escherichia coli

<400> SEQUENCE: 7

Met Ala Arg Tyr Leu Glu Val Ser Asp Ile Val Gln Gln Trp Arg Asn
1               5                   10                  15

Glu Arg Pro Asp Leu Asp Val Glu Pro Met Leu Val Ile Gly Thr Leu
            20                  25                  30

Ser Arg Val Ser Leu Leu Ile Asp Arg Ala Leu Asp Lys Val Phe Ser
        35                  40                  45

Lys Tyr Lys Leu Ser Ala Arg Glu Phe Asp Ile Leu Ala Thr Leu Arg
    50                  55                  60

Arg Arg Gly Ala Pro Tyr Ala Tyr Ser Pro Ser Gln Ile Val Asn Ala
65                  70                  75                  80

Leu Met Ile Asn Asn Ser Thr Leu Thr Ser Arg Leu Asp Arg Leu Glu
                85                  90                  95

Gln Ala Gly Trp Leu Arg Arg Met Pro Ile Glu Gly Asp Arg Arg Ser
            100                 105                 110

Val Asn Ile Gln Leu Thr Asp Glu Gly Phe Ala Leu Ile Asn Arg Val
        115                 120                 125

Val Glu Glu His Val Glu Asn Val Arg Asp Ile Leu Ser Pro Phe Ser
    130                 135                 140

Glu Glu Lys Thr His Leu Arg Ala Leu Leu Gly Arg Val Glu Lys His
145                 150                 155                 160

Leu Val Asn Asn Arg
                165

<210> SEQ ID NO 8
<211> LENGTH: 143
<212> TYPE: PRT
<213> ORGANISM: Escherichia coli

<400> SEQUENCE: 8

Met Lys Tyr Asp Lys Phe Phe Met Ala Leu Leu Gly Ala Tyr Ala Ala
1               5                   10                  15

His Gly Asp Ala Ser Arg Gln Ile Phe Asn Asp Tyr Gly Leu Thr Glu
            20                  25                  30

Ala Gln Pro Lys Ile Leu Tyr Ile Leu Gly Phe Asn Glu Gly Ile Val
        35                  40                  45

Gln Lys Asp Phe Ala Lys Leu Cys Ala Ile Lys Pro Ser Thr Met Thr
    50                  55                  60

Val Gln Leu Ala Arg Leu Glu Lys Asp Ala Gly Leu Ile Arg Arg Glu
65                  70                  75                  80

Ser Cys Tyr Ile Ser Gly Gly Lys Lys Ala Tyr Arg Val Tyr Leu Thr
                85                  90                  95

```
Lys Arg Gly Lys Glu Ile Ala Asp Ser Leu Ile Glu Arg Ile Asp Asn
            100                 105                 110

Leu Glu Asp Ile Ser Phe Lys Gly Phe Thr Ala Lys Glu Gln Ala Thr
            115                 120                 125

Leu Leu Ser Leu Leu Glu Arg Val Glu Asp Asn Leu Arg Gly Arg
            130                 135                 140
```

METHODS FOR IDENTIFYING AND USING MARR FAMILY POLYPEPTIDE BINDING COMPOUNDS

RELATED APPLICATIONS

This application is a continuation application of U.S. Ser. No. 11/296,017, filed Dec. 7, 2005; which is a continuation of U.S. Ser. No. 10/196,672, filed Jul. 15, 2002, now U.S. Pat. No. 7,202,339, issued Apr. 10, 2007; which claims priority to U.S. Application Ser. No. 60/388,618, filed on Jun. 13, 2002; and U.S. Application Ser. No. 60/305,322, filed on Jul. 13, 2001. This application is related to U.S. Ser. No. 10/196,655, filed Jul. 15, 2002; U.S. Ser. No. 60/388,622, filed Jun. 13, 2002; and U.S. Ser. No. 60/305,404, filed on Jul. 13, 2001. The entire contents each of the aforementioned applications are hereby incorporated herein by reference.

BACKGROUND OF THE INVENTION

The Mar phenotype in *E. coli* is attributed largely to the action of MarA, the expression of which is regulated by MarR (Alekshun, M. N. supra (1997)). MarA is a transcription factor that autoactivates expression of the marRAB operon and regulates the expression of a global network of more than 60 chromosomal genes (Martin, R. G. et al. *J. Bact.* 178, 2216-2223 (1996); Barbosa, T. M. & Levy, S. B. *J. Bact.* 182, 3467-3474 (2000)). Mar mutants in isolates of clinical origin have now been identified (Maneewannakul, K. & Levy, S. B. *Antimicrob. Agents Chemother.* 40, 1695-1698 (1996); Oethinger, M. et al. *Antimicrob. Agents Chemother.* 42, 2089-2094 (1998); Linde, H. J. et al. *Antimicrob. Agents Chemother.* 44, 1865-1868 (2000); Ziha-Zarifi, I., et al. *Antimicrob. Agents Chemother.* 43, 287-291 (1999); Koutsolioutsou, A et al. *Antimicrob. Agents Chemother.* 45, 38-43 (2001)). Constitutive overexpression of MarA or a MarA homolog in many of these strains is a key contributor to the maintenance of the resistance phenotype, particularly with respect to the fluoroquinolones, and recent studies have documented the selection of Mar mutants, bearing mutations in MarR, MexR, or other homologous loci, in *E. coli, Pseudomonas aeruginosa*, and other organisms during antimicrobial chemotherapy (Oethinger, M supra; Linde, H. J. et al.; supra; Ziha-Zarifi, I. et al. supra; Kern, W. V., et al. *Antimicrob. Agents Chemother.* 44, 814-820 (2000)).

MarR is a regulator of multiple antibiotic resistance in *Escherichia coli*. It is the prototypic member of a family of regulatory proteins found in the Bacteria and the Archae that play important roles in the development of antibiotic resistance, a global health problem. In the absence of an appropriate stimulus, MarR negatively regulates expression of the marRAB operon (Cohen, S. P., et al. 1993. *J. Bacteriol.* 175: 1484-1492.; Martin, R. G. and Rosner, J. L. 1995. *Proc. Natl. Acad. Sci.* 92: 5456-5460; Seoane, A. S. and Levy, S. B. 1995. *J. Bacteriol.* 177: 3414-3419, 1995). DNA footprinting experiments suggest that MarR dimerizes at two locations, sites I and II, within the mar operator (marO) (Martin and Rosner, 1995, supra). Site I is positioned among the −35 and −10 hexamers and site II spans the putative MarR ribosome binding site (reviewed in Alekshun, M. N. and Levy, S. B. 1997. *Antimicrob. Agents Chemother.* 10: 2067-2075).

MarR is a member of a newly recognized family of regulatory proteins (Alekshun, M. N. and Levy, S. B. 1997. *Antimicrob. Agents Chemother.* 10: 2067-2075. Sulavik, M. C., et al. 1995. *Mol. Med.* 1: 436-446) and many functional homologues have been identified in a variety of important human pathogens and have been found to regulate a variety of different processes. For example, some MarR homologues have been found to control expression of multiple antibiotic resistance operons, some regulate tissue-specific adhesive properties, some control expression of a cryptic hemolysin, some regulate protease production, and some regulate sporulation. Proteins of the MarR family control an assortment of biological functions including resistance to multiple antibiotics, organic solvents, household disinfectants, and oxidative stress agents, collectively termed the multiple antibiotic resistance (Mar) phenotype (Alekshun, M. N. & Levy, S. B. *Trends Microbiol.* 7, 410-413 (1999)). These proteins also regulate the synthesis of pathogenic factors in microbes that infect humans and plants (Miller, P. F. & Sulavik, M. C. *Mol. Microbiol.* 21, 441-448 (1996)). Insight into the three dimensional structure of MarR family proteins would be of great value in designing drugs that interact with this family of proteins and modulate MarR function, for example, antibiotic resistance and virulence.

SUMMARY OF THE INVENTION

The instant invention advances the prior art by providing the crystal structure of a MarR family polypeptide, MarR. The crystal structure of MarR provides the three-dimensional structure, as well as the shape and electronic properties of its active sites. It can be used in a comprehensive rational drug design program to develop novel chemotherapeutics targeted toward the MarR/MarA transcription system. The atomic coordinates of a MarR crystal structure cocrystallized with and without salicylate are given in FIG. 1 and FIG. 2, respectively.

In one embodiment, the invention pertains, at least in part, to methods for identifying a MarR family modulating compound. The method includes selecting a candidate MarR family modulating compound by performing rational drug design with the set of atomic coordinates in FIG. 1 or 2. The method may further include contacting the candidate MarR family modulating compound with the MarR family polypeptide, and determining the ability of the candidate MarR family modulating compound to modulate the MarR family polypeptide. The invention also pertains to compounds identified by these methods and methods of using the compounds to modulate MarR family polypeptides.

In another embodiment, the invention pertains, at least in part, to methods for identifying a MarR family modulating compound. The methods include determining the structure of a MarR family polypeptide using the structure of MarR and identifying a candidate MarR family modulating compound by performing rational drug design based on the structure. The method may further include the steps of contacting the candidate MarR family modulating compound with a MarR family peptide, and a nucleic acid molecule, and measuring the binding affinity of the MarR family polypeptide peptide with the nucleic acid molecule. The invention also pertains to compounds identified by these methods and methods of using the compounds to modulate polypeptides.

In yet another embodiment, the invention pertains, at least in part, to a method for identifying a MarR modulating compound. The method includes obtaining a set of atomic coordinates defining the three-dimensional structure of MarR and selecting a candidate MarR modulating compound by performing rational drug design with the three dimensional structure of MarR. The method may further include the steps of contacting the candidate MarR modulating compound with MarR, measuring the ability of the candidate MarR modulating compound to modulate the activity of MarR. The invention also pertains to compounds identified by these methods and methods for modulating MarR using the compounds of the invention.

In another embodiment, the invention pertains, at least in part, to a MarR modulating compound of the formula (I):

X—Y—Z    (I)

wherein X is an interacting moiety; Y is a hydrophobic moiety; and Z is a polar moiety.

The invention also pertains, at least in part, to methods for inhibiting expression of MarA, by contacting MarR with a MarR modulating compound of formula (I).

In yet another embodiment, the invention also pertains to methods for decreasing multidrug resistance in a microbe. The method includes contacting the microbe with a MarR modulating compound of formula (I).

BRIEF DESCRIPTION OF THE DRAWINGS

FIG. 1 shows the atomic coordinates of the MarR-salicylate co-crystal.

FIG. 2 shows the atomic coordinates of the MarR crystal without salicylate.

FIG. 11 shows a sequence comparison and alignment of MarR and SlyA.

FIG. 12 shows structurally conserved regions of SlyA and MarR as determined by COMPOSER.

DETAILED DESCRIPTION OF THE INVENTION

Figure 3:
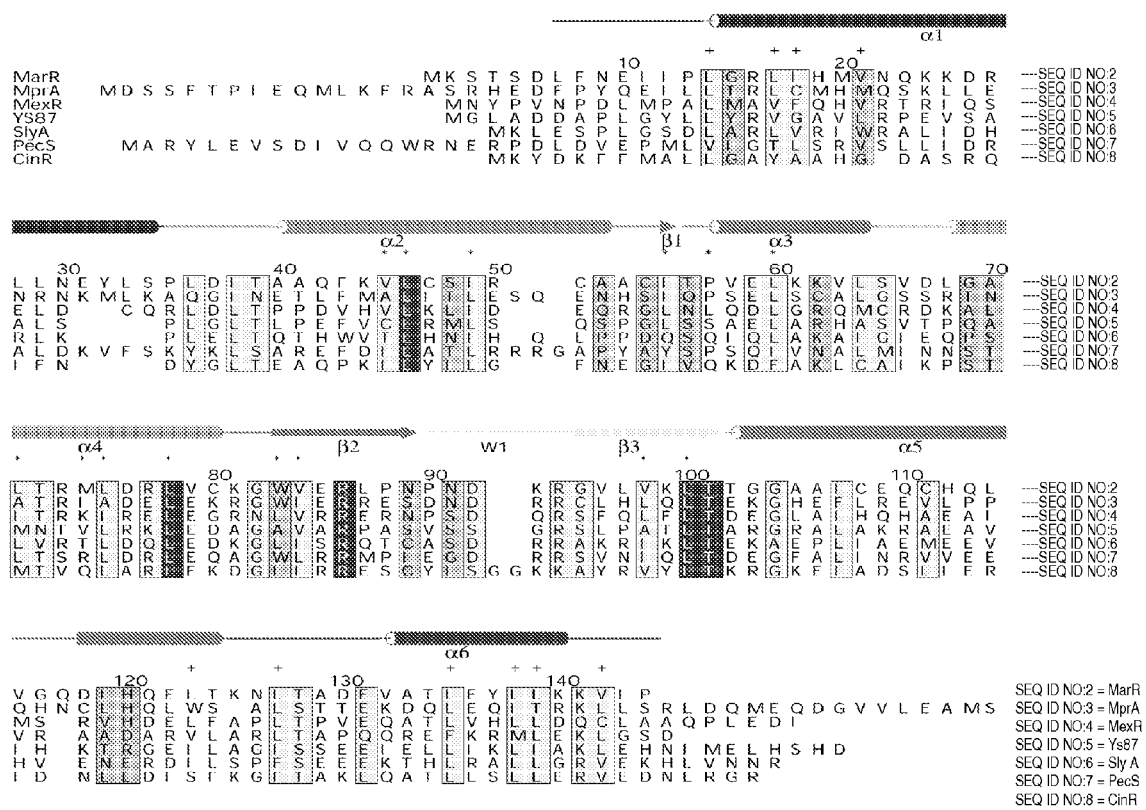
FIG. 3 shows the sequence alignment of MarR with representative members of the MarR family.

Chemotherapeutic intervention for the treatment and prevention of disease is predicated upon the ability of small molecules (drugs) to infiltrate a biological system and to interact with the components of the biological system (e.g. proteins, RNA, DNA, membranes, etc.) in a manner that modulates their normal function. Rational drug design attempts to formulate drug design hypotheses that specify and optimize the physical contacts between the drug and target. Koshland has used a lock and key analogy to characterize drug-target interactions; a specific "key" (drug) interacts only with its respective molecular "lock" (target) (Koshland, D. E., Jr. Angew. Chem. 1994, 106, 2468-2472). This model asserts that an appropriate degree of shape and electronic complimentarily between the drug and target must occur to produce productive drug-target interactions—those that cause a desired pharmacological response. The specific location on the "lock" or target is referred to as the active or catalytic site. The three dimensional shape and electronic properties of the active site form the basis for rational drug design and provides information toward the systematic chemical modifications of potential drugs.

In one embodiment, the invention pertains to methods for identifying MarR family modulating compounds using the three-dimensional structure of a MarR family polypeptide. The method includes selecting a candidate MarR family modulating compound by performing rational drug design with the atomic coordinates of a MarR family polypeptide. The method may also include contacting the candidate MarR family modulating compound with MarR family polypeptide; and determining the ability of said candidate MarR family modulating compound to a modulate MarR family polypeptide. In one embodiment, the MarR family polypeptide is MarR. The atomic coordinates of MarR in the presence and absence of salicylate are given in FIGS. 1 and 2, respectively.

MarR Family Polypeptides and Nucleic Acid Molecules

The term "MarR family polypeptide" includes molecules related to MarR, e.g., having certain shared structural and functional features. MarR family polypeptides also include those which are structural homologs of MarR. The structural homologs include those having a crystallized form which are structurally similar to that of crystallized MarR. Generally, it is believed that there is a strong relationship between the tertiary structure of a protein and its function within the biological system. Furthermore, it is known that a protein's overall tertiary structure is related to its primary amino acid sequence. Therefore, it has been demonstrated that proteins with similar amino acid make up and sequence will possess similar overall structure and will likely share similar function. MarR family members, in addition to having similarity to MarR, may bind to DNA and regulate transcription. While some MarR family members negatively control transcription (e.g., MarR), others have positive/activator functions (e.g., SlyA, BadR, NhhD, and MexR). MarR family polypeptides comprise DNA and protein binding domains. In addition, MarR family polypeptides can interact with a variety of structurally unrelated compounds that regulate their activity.

Exemplary MarR family members are taught in the art and can be found, e.g., in Sulavik et al. (1995. *Molecular Medicine*. 1:436), Miller and Sulavik (1996. *Molecular Microbiology*. 21:441) in which alignments of MarR and related proteins are shown, or through the use of BLAST searches and other techniques known in the art. Exemplary MarR family polypeptides are also illustrated in the following chart:

| MarR Family Polypeptides | | |
|---|---|---|
| Gram-negative | Gram-positive | Acid-fast |
| *Escherichia coli* | *Bacillus subtilus* | *Mycobacterium tuberculosis* |
| MarR | YdcH | 14.7 kD |
| SlyA | YhbI | Rv1404 |

-continued

| MarR Family Polypeptides | | |
|---|---|---|
| EmrR (MprA) | YkmA | Rv0737 |
| PapX | YkoM | Rv0042c |
| PrsX | Orf7 | Yz08 (15.6 kD) |
| HpcR | YfiV | *Mycobacterium leprae* |
| Ec17kD | YetL | Yz08 (15.6 kD) |
| *Slamonella typhimurium* | YdgJ | Archaea |
| MarR | YwoH | *Methanobacterium* |
| SlyA | YwaE | *thermoautotrophicum* |
| EmrR | YwhA | MTH313 |
| *Pseudomonas aeruginosa* | Hpr | *Sulfolobus solfataricus* |
| MexR | YybA | Lrs14 |
| *Erwinia chrysanthemi* | YxaD | *Archaeoglobus fulgidus* |
| PecS | YsmB | CinR |
| *Rhodopseudomonas palustris* | YusO | Purple non-sulfur |
| BadR | YpoP | *Rhodobacter capsulatus* |
| *Burkholderia pseudomallei* | YkvE | PetP |
| OrfE | *Bacillus firmus* | *Sinorhizobium meliloti* |
| | Orf7 | SlyA (E293909) |
| | *Staphylococcus sciuri* | |
| | Orf145 | |
| | Orf141 | |
| | *Butyrivibrio fibrisolvens* | |
| | CinR | |
| | *Sphingomonas aromaticivorans* | |
| | Orf158 | |
| | *Rhodococcus rhodochrous* | |
| | NhhD | |
| | *Streptomyces peucetius* | |
| | Orf1 | |

Preferably, a MarR family polypeptide is MarR. Other preferred MarR family polypeptides include: EmrR, Ec17kD, and MexR.

In a further embodiment, the MarR family polypeptide has a winged-helix structure, such as the three dimensional structure of MarR.

FIG. 3 shows a sequence alignment of MarR with representative MarR family polypeptides. The MarR secondary structure elements were identified in its crystal structure and are illustrated in FIG. 3 (e.g., as tubes for α-helices (α) and arrows for β-sheets (β) and the single wing region (W1)). The numbering in FIG. 3 is according to the MarR primary sequence. Furthermore, residues that are identical in all homologs are colored in red, highly conserved amino acids are colored in yellow, and moderately conserved residues are colored in blue. The MarR family polypeptides used for the alignment were from the following organisms: MarR, *E. coli*; MprA (EmrR), *E. coli*; MexR, *Pseudomonas aeruginosa*; YS87, *Mycobacterium tuberculosis*; SlyA, *Salmonella typhimurium*; PecS, *Erwinia chrysanthemi*; CinR, *Butyrivibrio fibrisolvens*. In a further embodiment, the MarR family polypeptide comprises, consists essentially of, or consists of the polypeptide sequence shown in Sequence Listing SEQ ID NO:1. Other MarR family polypeptides of interest include EmrR, YS87, PecS, CinR, SlyA, Ec17kD, MexR.

In another embodiment, the MarR family polypeptide is found, for example, in one of the following organisms *Escherichia coli, Salmonella typhimurium, Salmonella enterica, Enterobacter cloacae, Enterobacter aerogenes, Erwinia chrysanthemi, Yersinia pestis, Yersinia enterocolitica, Kluyvera cryocrescens, Edwardsiella tarda, Pseudomonas aeruginosa, Vibrio cholera, Xanthomonas axonopodis, Xanthomonas campestris, Ralstonia solanacearum, Burkholderia pseudomallei, Burkholderia cepacia, Vogesella indigofera, Mesorhizobium loti, Agrobacterium tumefaciens, Sinorhizobium meliloti, Brucella melitensis, Caulobacter crescentus, Bacillus anthracis, Bacillus subtilis, Bacillus halodurans, Listeria monocytogenes, Listeria innocua, Listeria welshimeri, Staphylococcus sciuri, Streptococcus criceti, Streptococcus pneumoniae, Clostridium perfringens, Clostridium difficile, Streptomyces coelicolor, Streptomyces avermitilis, Mycobacterium tuberculosis, Mycobacterium leprae, Corynebacterium glutamicum, Thermotoga maritima, Methanosarcina acetivorans, Methanosarcina mazei,* and *Sulfolobus solfataricus*.

In another embodiment, the MarR family polypeptide is from an organism belonging to one of the following biological classifications: Enterobacteriaceae, *Enterobacter, Yersinia, Kluyvera, Edwardsiella, Xanthomonas* group, Xanthomonadales, Pseudomonaceae/Moraxellaceae group, Pseudomonadaceae, Vibrionaceae group, Burkholderia/Oxalobacter/Ralstonia group, Ralstonia group, Burkholderia group, Neisseriaceae, Vogesella, Rhizobiaceae group, Phyllobacteriaceae, Mesorhizobium, Rhizobiaceae, Sinorhizobium, Brucellaceae, Brucella, Caulobacter group, Firmicutes, *Bacillus/Clostridium* group, Bacilli, Bacillales, *Bacillus*, Bacillaceae, *Bacillus cereus* group, *Listeria*, Listeriaceae, Staphylococcaceae, *Staphylococcus, Streptococcus*, Lactobacillales, Streptococcaceae, *Clostridium*, Clostridiaceae, Clostridiales, *Clostridia*, Actinomycetales, Actinobacteria, Actinobacteridae, *Streptomyces*, Streptomycineae, Streptomycetaceae, Corynebacterineae, *Mycobacterium*, Mycobacteriaceae, Corynebacteriaceae, *Corynebacterium, Nostocales*, Nostocaceae, Nostoc, Thermotogae, Thermotogales, Thermotogaceae; Thermotoga, Methanosarcina, Euryarchaeota, Methanococci; Methanosarcinales, Methanosarcinaceae, Crenarchaeota, Thermoprotei; Sulfolobales, Sulfolobaceae, *Sulfolobus*, Proteobacteria, Pectobacterium, Cyanobacteria, or Archaea.

In one embodiment, the MarR family polypeptides of the invention are naturally occurring. In another embodiment, the subject crystal structures can be generated using non-naturally occurring forms of MarR family polypeptides, e.g. mutants or synthetic forms of MarR family polypeptides not found in nature.

In one embodiment, the MarR family polypeptide comprises one or more conservative mutations as compared to the wild type protein for the particular MarR family polypeptide. The term "MarR family polypeptide" also includes fragments of MarR family polypeptides which minimally retain at least a portion of the tertiary structure of the MarR family protein.

MarR family member polypeptide sequences are "structurally related" to one or more known MarR family members, preferably to MarR. This structural relatedness is shown by sequence similarity between two MarR family polypeptide sequences or between two MarR family nucleotide sequences. Sequence similarity can be shown, e.g., by optimally aligning MarR family member sequences using an alignment program for purposes of comparison and comparing corresponding positions. To determine the degree of similarity between sequences, they will be aligned for optimal comparison purposes (e.g., gaps may be introduced in the sequence of one protein or nucleic acid molecule for optimal alignment with the other protein or nucleic acid molecules). The amino acid residues or bases and corresponding amino acid positions or bases are then compared. When a position in one sequence is occupied by the same amino acid residue or by the same base as the corresponding position in the other sequence, then the molecules are identical at that position. If amino acid residues are not identical, they may be similar. An amino acid residue is "similar" to another amino acid residue if the two amino acid residues are members of the same family of residues having similar side chains. Families of amino acid residues having similar side chains have been defined in the art (see, for example, Altschul et al. 1990. *J. Mol. Biol.* 215:403) including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). The degree (percentage) of identity or similarity between sequences, therefore, can be calculated as a function of the number of identical or similar positions shared by two sequences (i.e., % homology=# of identical or similar positions/total # of positions×100). Alignment strategies are well known in the art; see, for example, Altschul et al. supra for optimal sequence alignment.

MarR family polypeptides share some amino acid sequence similarity with MarR. The nucleic acid and amino acid sequences of MarR as well as other MarR family polypeptides are available in the art. For example, the nucleic acid and amino acid sequence of MarR can be found, e.g., on GeneBank (accession number M96235 or in Cohen et al. 1993. J. Bacteriol. 175:1484, or in SEQ ID NO:1).

The nucleic acid and protein sequences of MarR can be used as "query sequences" to perform a search against databases (e.g., either public or private) to, for example, identify other MarR family members having related sequences. Such searches can be performed, e.g., using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to MarR family nucleic acid molecules. BLAST protein searches can be performed with the XBLAST program, score=50, wordlength=3 to obtain amino acid sequences homologous to MarR protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

MarR family members can also be identified as being structurally similar based on their ability to specifically hybridize to the complement of nucleic acid sequences specifying MarR. Such stringent conditions are known to those skilled in the art and can be found e.g., in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Conditions for hybridizations are largely dependent on the melting temperature that is observed for half of the molecules of a substantially pure population of a double-stranded nucleic acid. The melting temperature is the temperature in ° C. at which half the molecules of a given sequence are melted or single-stranded. For nucleic acids of sequence 11 to 23 bases, the melting temperature can be estimated in degrees C. as 2(number of A+T residues)+4(number of C+G residues). Hybridization or annealing of nucleic acid molecules should be conducted at a temperature lower than the melting temperature, e.g., 15° C., 20° C., 25° C. or 30° C. lower than the melting temperature. The effect of salt concentration (in M of NaCl) can also be calculated, see for example, Brown, A., "Hybridization" pp. 503-506, in *The Encyclopedia of Molec. Biol.*, J. Kendrew, Ed., Blackwell, Oxford (1994).

Preferably, the nucleic acid sequence of a MarR family member identified in this way is at least about 10%, 20%, more preferably at least about 30%, more preferably at least about 40% identical and most preferably at least about 50%, or 60% identical or more with a MarR nucleotide sequence. Preferably, MarR family members have an amino acid sequence at least about 20%, more preferably at least about 30%, more preferably at least about 40% identical and most preferably at least about 50%, or 60% or more identical with a MarR amino acid sequence. However, it will be understood that the level of sequence similarity among microbial regulators of gene transcription, even though members of the same family, is not necessarily high. This is particularly true in the case of divergent genomes where the level of sequence identity may be low, e.g., less than 20% (e.g., *B. burgdorferi* as compared e.g., to *B. subtilis*). For example, the level of amino acid sequence homology between MarR and Pecs is about 31% and the level of amino acid sequence homology between MarR and PapX is about 28% when determined as described above. Accordingly, structural similarity among MarR family members can also be determined based on "three-dimensional correspondence" of amino acid residues.

The language "three-dimensional correspondence" includes residues which spatially correspond, e.g., are in the same functional position of a MarR family protein member as determined, e.g., by x-ray crystallography, but which may not correspond when aligned using a linear alignment program. The language "three-dimensional correspondence" also includes residues which perform the same function, e.g., bind to DNA or bind the same cofactor, as determined, e.g., by mutational analysis. Thus, MarR family members can be identified based on functional homology and sequence homology, e.g., as described in the art (Li et al. 2001. EMBO Journal 20:4854).

Preferred MarR family polypeptides include: MarR, EmrR, Ec17kD, MexR, PapX, SlyA, Hpr, PecS, Hpr, MprA, or (EmrR). In a more preferred embodiment, a MarR family polypeptide is selected from the group consisting of: MarR, EmrR, Ec17kD, and MexR. In a particularly preferred embodiment, a MarR family polypeptide is MarR.

In addition to sharing structural similarity, MarR family members have a MarR family polypeptide activity, i.e., they bind to DNA and regulate transcription. Some MarR family members positively regulate transcription (e.g., SlyA, BadR, NhhD, or MexR), while others negatively regulate transcription (e.g., MarR). While all MarR family members bind to DNA and regulate transcription, the different loci controlled by each family member regulate different processes in microbes. For example, MarR family polypeptides can control the expression of microbial loci involved in: regulation of antibiotic resistance [e.g., MarR (Cohen et al. 1993. J. Bacteriol. 175:1484), EmrR (Lomovskaya and Lewis. 1992. Proc. Natl. Acad. Sci. 89:8938), and Ec17kD (Sulavik et al. 1995. Mol. Med. 1:436), and MexR (Poole et al. 1996. Antimicrob. Agents. Chemother. 40:2021)], regulation of tissue-specific adhesive properties [e.g., PapX (Marklund et al., 1992. Mol. Microbiol. 6:2225)], regulation of expression of a cryptic hemolysin [e.g., SlyA (Ludwig et al. 1995 249:4740)], regulation of protease production [e.g., Hpr from *B. subtilis* (Perago and Hoch. 1988. J. Bacteriol. 170:2560) and PecS from *Erwinia chrysanthemi* (Reverchon et al., 1994. Mol. Microbiol. 11:1127)] and regulation of sporulation [e.g., Hpr (Perego and Hoch. 1988. J. Bacteriol. 170:2560)], regulation of the breakdown of plant materials [e.g., CinR (Dalymple and Swadling 1997 Microbiology)] sensing of phenolic compounds [(e.g., Sulvik et al. 1995. Mol. Med. 1:436], and repress marRAB expression when introduced into *E. coli* [e.g., Ec17kd (Marklund et al. 1992. Mol. Microbiol. 6:2225) and MprA (EmrR) (del Castillo et al., 1991. J. Bacteriol. 173:3924)]. The activity of MarR family polypeptides is antagonized by salicylate (Lomovskaya et al., 1995. J. Bacteriol. 177:2328; Sulavik et al. 1995. Mol. Med. 1:436).

Preferred MarR family polypeptide activities include regulation of multiple drug resistance and/or regulation of virulence.

In addition to full length MarR family polypeptide fragments MarR family polypeptide which are useful in making crystals are also within the scope of the invention. Accordingly, MarR family polypeptides for use in the instant screening assays can be full length MarR family member proteins or fragments thereof. Thus, a MarR family polypeptide can comprise, consist essentially of, or consist of an amino acid sequence derived from the full length amino acid sequence of a MarR family member. For example, in one embodiment, a polypeptide comprising a MarR family polypeptide DNA interacting domain or a polypeptide comprising a MarR family member protein interacting domain can be used.

In addition, naturally or non-naturally occurring variants of these polypeptides and nucleic acid molecules which retain the same functional activity, e.g., the ability to bind to DNA and regulate transcription. Such variants can be made, e.g., by mutation using techniques which are known in the art. Alternatively, variants can be chemically synthesized.

For example, it will be understood that the MarR family polypeptides described herein, are also meant to include equivalents thereof. For instance, mutant forms of MarR family polypeptides which are functionally equivalent, (e.g., have the ability to bind to DNA and to regulate transcription from an operon) can be made using techniques which are well known in the art. Mutations can include, e.g., at least one of a discrete point mutation which can give rise to a substitution, or by at least one deletion or insertion. For example, random mutagenesis can be used. Mutations can be made, e.g., by random mutagenesis or using cassette mutagenesis. For the former, the entire coding region of a molecule is mutagenized by one of several methods (chemical, PCR, doped oligonucleotide synthesis) and that collection of randomly mutated molecules is subjected to selection or screening procedures. In the latter, discrete regions of a protein, corresponding either to defined structural or functional determinants (e.g., the first or second helix of a helix-turn-helix domain) are subjected to saturating or semi-random mutagenesis and these mutagenized cassettes are re-introduced into the context of the otherwise wild type allele. In one embodiment, PCR mutagenesis can be used. For example, Megaprimer PCR can be used (O. H. Landt, Gene 96:125-128).

In addition, other portions of the above described polypeptides suitable for use in the claimed assays, such as those which retain their function (e.g., the ability to bind to DNA, to regulate transcription from an operon) or those which are critical for binding to regulatory molecules (such as compounds) can be easily determined by one of ordinary skill in the art (e.g, using standard truncation or mutagenesis techniques) and used in the instant assays. Exemplary techniques are described by Gallegos et al. (1996. J. Bacteriol. 178: 6427).

It shall be understood that the instant invention also pertains to isolated MarR family member polypeptides, portions thereof, and the nucleic acid molecules encoding them, including naturally occurring and mutant forms.

Preparation of MarR Family Polypeptides

Preferred MarR family polypeptides for use in screening assays are synthesized, isolated or recombinant polypeptides. In one embodiment, MarR family polypeptides can be made from nucleic acid molecules. Nucleic acid molecules encoding MarR family polypeptides can be used to produce MarR family polypeptides. For example, nucleic acid molecules encoding a MarR family polypeptide can be isolated (e.g., isolated from the sequences which naturally flank it in the genome and from cellular components) and can be used to produce a MarR family polypeptide. In one embodiment, a nucleic acid molecule which has been (1) amplified in vitro by, for example, polymerase chain reaction (PCR); (2) recombinantly produced by cloning, or (3) purified, as by cleavage and gel separation; or (4) synthesized by, for example, chemical synthesis can be used to produce MarR family polypeptides. The term "nucleic acid" refers to polynucleotides such as deoxyribonucleic acid (DNA) and ribonucleic acid (RNA).

Nucleic acid molecules specifying MarR family polypeptides can be placed in a vector. The term "vector" refers to a nucleic acid molecule capable of transporting another nucleic acid molecule to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

Exemplary expression vectors for expression of a gene encoding a MarR family polypeptide and capable of replication in a bacterium, such a bacterium from a genus selected from the group consisting of: *Escherichia, Bacillus, Streptomyces, Streptococcus*, or in a cell of a simple eukaryotic fungus such as a *Saccharomyces or, Pichia*, or in a cell of a eukaryotic organism such as an insect, a bird, a mammal, or a plant, are known in the art. Such vectors may carry functional replication-specifying sequences (replicons) both for a host for expression, for example a *Streptomyces*, and for a host, for example, *E. coli*, for genetic manipulations and vector construction. See e.g. U.S. Pat. No. 4,745,056. Suitable vectors for a variety of organisms are described in Ausubel, F. et al.,

*Short Protocols in Molecular Biology*, Wiley, New York (1995), and for example, for *Pichia*, can be obtained from Invitrogen (Carlsbad, Calif.).

Useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. A useful translational enhancer sequence is described in U.S. Pat. No. 4,820,639.

It should be understood that the design of the expression vector may depend on such factors as the choice of the host cell to be transformed and/or the type of protein desired to be expressed.

"Transcriptional regulatory sequence" is a generic term to refer to DNA sequences, such as initiation signals, enhancers, operators, and promoters, which induce or control transcription of nucleic acid sequences with which they are operably linked. It will also be understood that a recombinant gene encoding a MarR family polypeptide can be under the control of transcriptional regulatory sequences which are the same or which are different from those sequences which control transcription of the naturally-occurring MarR family gene. Exemplary regulatory sequences are described in Goeddel; *Gene Expression Technology Methods in Enzymology* 185, Academic Press, San Diego, Calif. (1990). For instance, any of a wide variety of expression control sequences, that control the expression of a DNA sequence when operatively linked to it, may be used in these vectors to express DNA sequences encoding the MarR family proteins of this invention.

Appropriate vectors are widely available commercially and it is within the knowledge and discretion of one of ordinary skill in the art to choose a vector which is appropriate for use with a given microbial cell. The sequences encoding MarR family polypeptides can be introduced into a cell on a self-replicating vector or may be introduced into the chromosome of a microbe using homologous recombination or by an insertion element such as a transposon.

Such vectors can be introduced into cells using standard techniques, e.g., transformation or transfection. The terms "transformation" and "transfection" mean the introduction of a nucleic acid, e.g., an expression vector, into a recipient or "host" cell. The term "transduction" means transfer of a nucleic acid sequence, preferably DNA, from a donor to a recipient cell, by means of infection with a virus previously grown in the donor, preferably a bacteriophage. Nucleic acids can also be introduced into microbial cells by transformation using calcium chloride or electroporation.

"Cells," "host cells," "recipient cells, are terms used interchangeably herein. It is understood that such terms refer not only to the particular subject cell but to the progeny or potential progeny of such a cell. In preferred embodiments, cells used to express MarR family polypeptides for purification, e.g., host cells, comprise a mutation which renders any endogenous MarR family polypeptide nonfunctional or causes the endogenous polypeptide to not be expressed. In other embodiments, mutations may also be made in other related genes of the host cell, such that there will be no interference from the endogenous host loci.

Purification of a MarR family polypeptides, e.g., recombinantly expressed polypeptides, can be accomplished using techniques known in the art. For example, if the MarR family polypeptide is expressed in a form that is secreted from cells, the medium can be collected. Alternatively, if the MarR family polypeptide is expressed in a form that is retained by cells, the host cells can be lysed to release the MarR family polypeptide. Such spent medium or cell lysate can be used to concentrate and purify the MarR family polypeptide. For example, the medium or lysate can be passed over a column, e.g., a column to which antibodies specific for the MarR family member polypeptide have been bound. Alternatively, such antibodies can be specific for a non-MarR family member polypeptide which has been fused to the MarR family polypeptide (e.g., as a tag) to facilitate purification of the MarR family member polypeptide. Other means of purifying MarR family member polypeptides are known in the art.

Architecture of the MarR-Salicylate Co-Crystal Structure

The term "three dimensional structure" includes both pictorial representations of MarR family polypeptides (e.g., such as those shown for MarR in the Figures) as well as atomic coordinates (e.g., such as those given in FIG. 1 for MarR-salicylate cocrystal, or in FIG. 2 for MarR) and other renditions of the shape, size, or symmetry of a MarR family polypeptide of interest. In a further embodiment, the three dimensional structure of the crystallized MarR family polypeptide is determined to a resolution of 5 Å or better, 3 Å or better, 2.5 Å or better, or, advantageously, 2.3 Å or better. The three dimensional structure of MarR, a MarR family polypeptide, is described in greater detail below.

Figure 4:
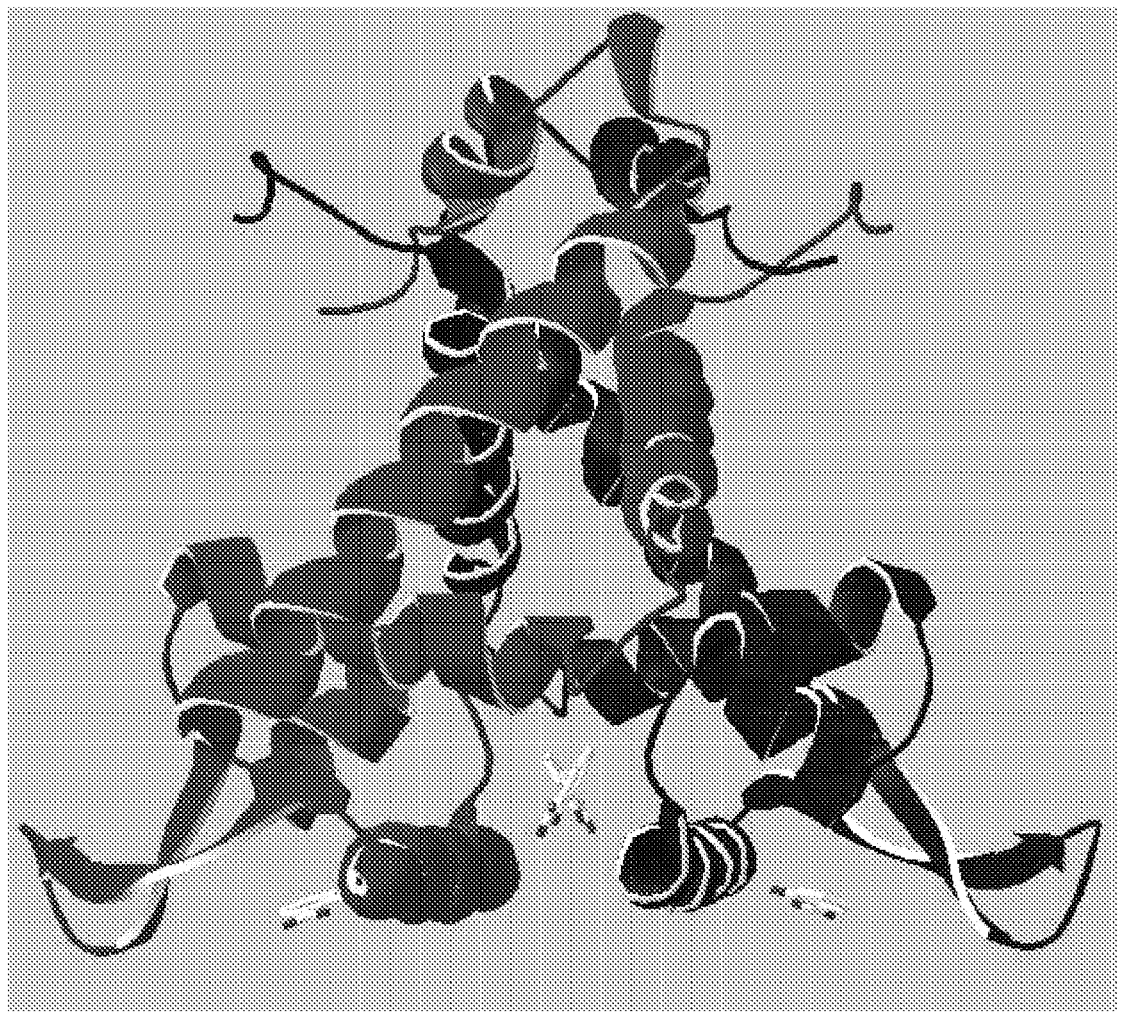
FIG. 4 is a ribbon representation of the salicylate containing MarR dimer with the two-fold axis near vertical. There are two salicylate molecules per monomer and each is represented by a stick model.

The salicylate containing MarR consists of a dimer with approximate overall dimensions of 50×55×45 Å, as shown in FIG. 4. There is one monomer in the asymmetric unit of the crystal with the dimer composed of subunits related by a crystallographic two-fold rotation. The dimeric structure is consistent with the results of earlier in vitro experiments suggesting that MarR binds the mar operator (marO) as a dimer (Martin, R. G. et al. supra (1996); Martin, R. G. & Rosner, J. L. *Proc. Natl. Acad. Sci. U.S.A.* 92, 5456-5460 (1995)). Another family member, MprA (EmrR) (FIG. 3) is also believed to function as a dimer (Brooun, A., et al. *J. Bact.* 181, 5131-5133 (1999)).

Figure 5:
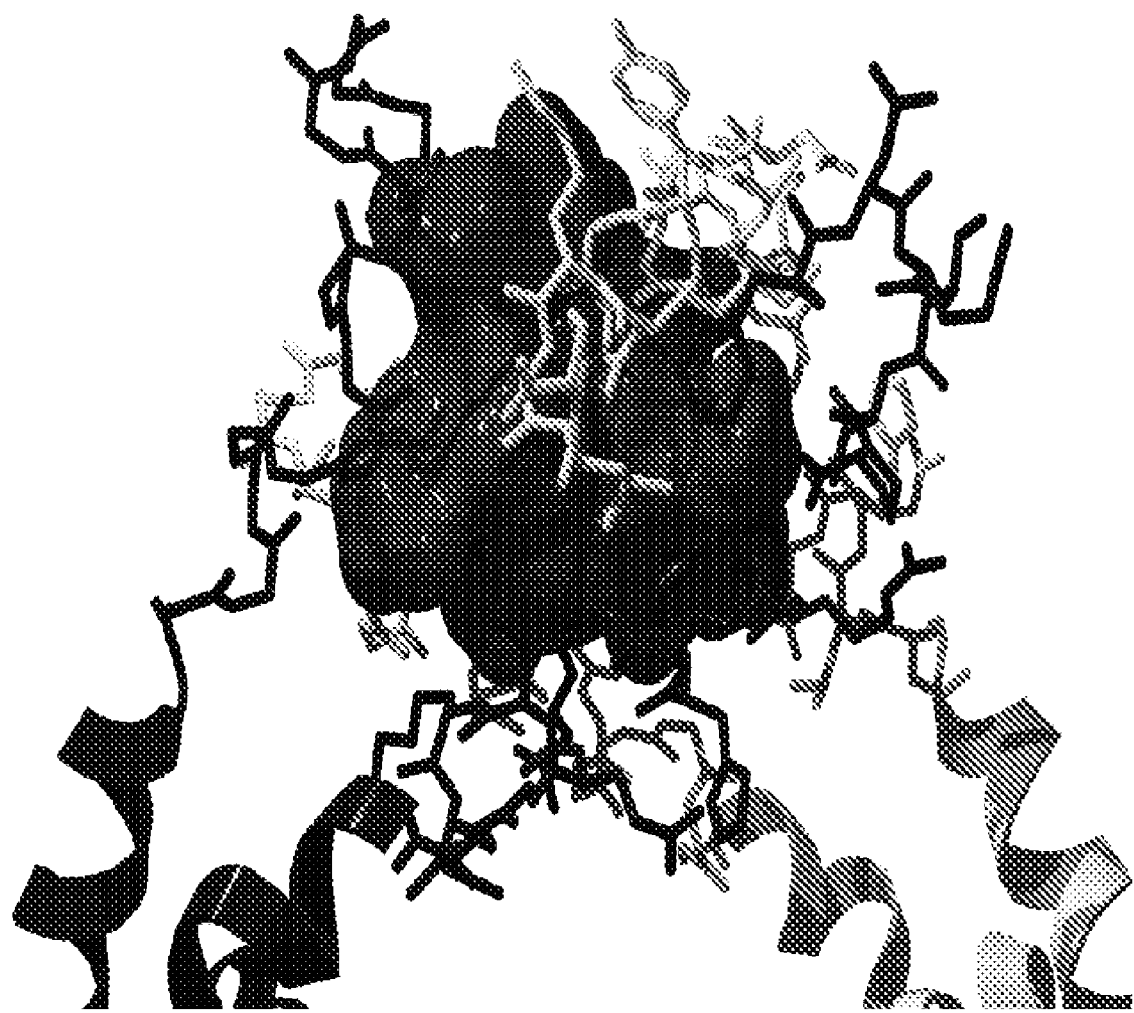
FIG. 5 is a representation of the N-/C-terminal domain represented by a surface (red) around the van der Waals radii of the side chain atoms only of the hydrophobic core residues. The main chain and other residues of the domain are shown in yellow for one subunit and blue for the other. Helices leading to and from the domain are shown in ribbon representation.
Figure 6:
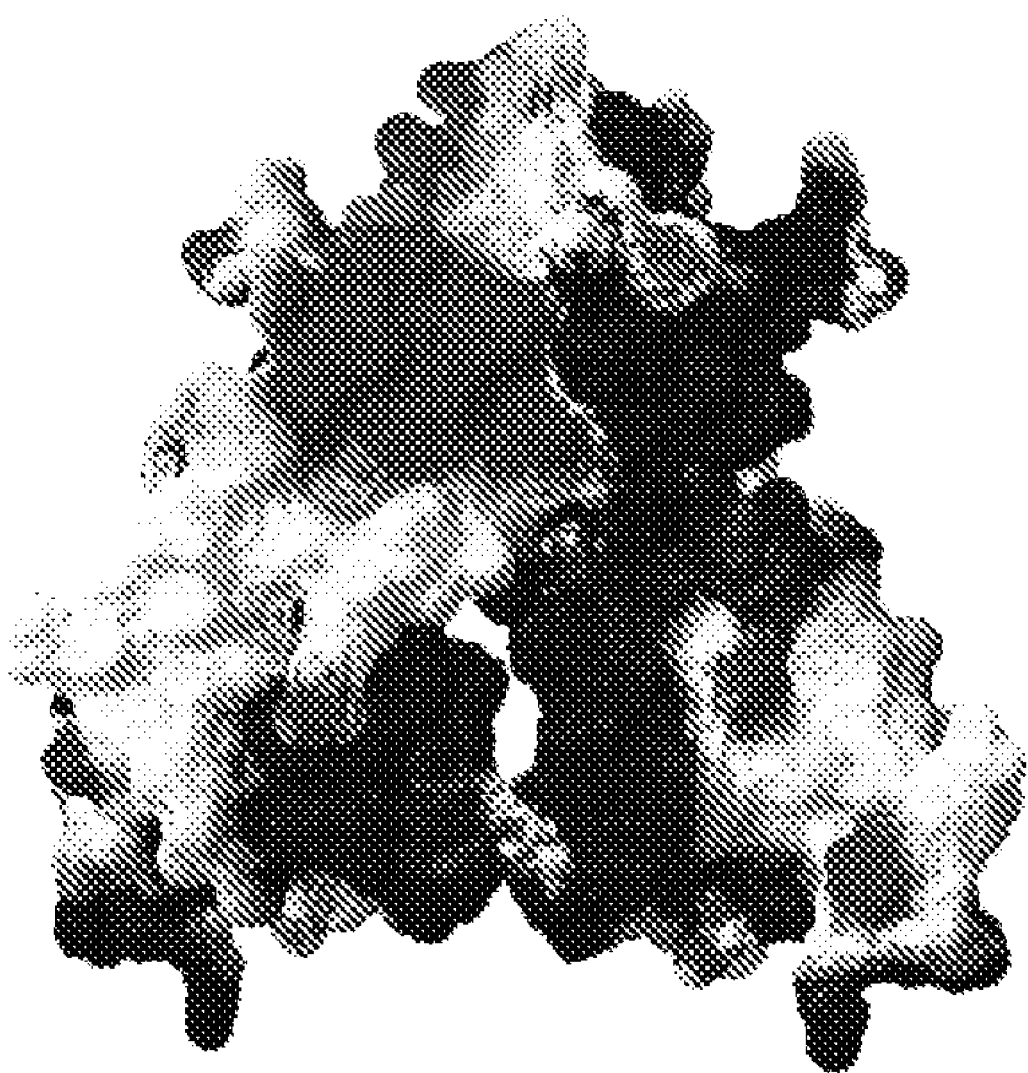
FIG. 6 is an electrostatic surface representation of the MarR dimer.
Figure 7:
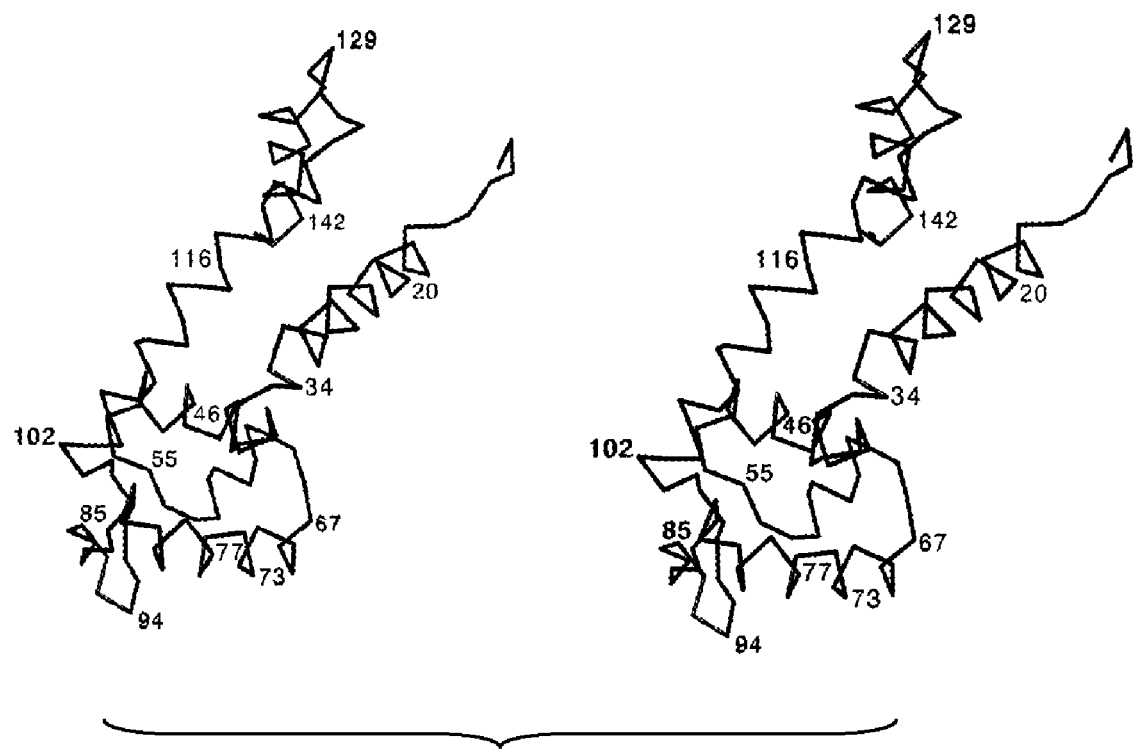
FIG. 7 is a Cα trace of a MarR subunit in stereo representation.

Each MarR salicylate subunit is an α/β protein with approximate dimensions of 35×25×60 Å and can be divided into two domains as shown in FIG. 4. FIG. 4 is a ribbon representation of the co-crystal structure of the MarR dimer viewed with the subunit 2-fold axis near vertical. The N- and C-terminal regions are closely juxtaposed and intertwine with the equivalent regions of the second subunit to form a domain that holds the subunits together (FIG. 5). This N-/C-terminal domain is linked to the remainder of the protein by two long antiparallel helices in each subunit. These helices lead to a globular domain that is likely to be responsible for DNA binding (see below). Although the globular DNA-binding domains of the dimer are adjacent to one another, they make minimal contact with each other and are situated to function independently. The overall organization of the N-/C-terminal domain and the two DNA-binding domains results in the formation of an approximately 6 Å wide channel through the center of the dimer (FIGS. 6 and 7). The electrostatic surface potential is consistent with the putative DNA-binding regions being strongly electropositive, as observed in other such winged-helix DNA-binding proteins (Gajiwala, K. S. & Burley, S. K. *Curr. Opin. Str. Biol.* 10, 110-116 (2000)).

Genetic and biochemical data have previously identified the N-terminus of MarR to be important for mediating protein-protein contacts between repressor subunits and have demonstrated that the C-terminus is important for protein function (Alekshun, M. N., et al. *Mol. Microbiol.* 35, 1394-404 (2000); Linde, H. J. et al. supra). The present structure shows that α-helices in the N- and C-terminal regions of each monomer fold around and interdigitate with those of the other subunit to form a well-packed hydrophobic core (FIG. 5) burying a surface area of 3,570 Å$^2$ (the total buried surface area for the whole dimer is 3,700 Å$^2$). The dimer is further stabilized in this region by several intermolecular hydrogen bonds, notably that between the ϵ-amino group of Lys 24 and the main chain carbonyl oxygen of Pro 144' in the C-terminus of the second subunit and that between the main chain carbonyl oxygen of Glu 10 and the side chain amino group of Lys 140'.

Figure 8:
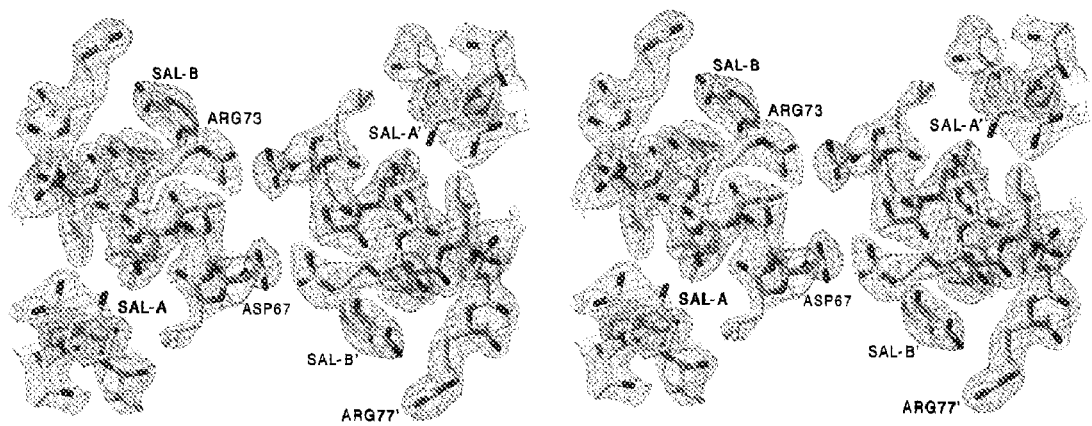
FIG. 8 is a diagram which shows interactions between the DNA-binding domains of the dimer in the region of the Arg 73-Asp 67' salt bridges. The stereo view is coincident with the 2-fold rotation axis of the dimer. Electron density shown is a $2F_O$—$F_C$ map contoured at 1σ.

While the DNA-binding lobe of each subunit also forms a well-packed hydrophobic core, the only interactions between these lobes of the two subunits are salt bridges formed between Asp 67 and Arg 73' and the reciprocal pair (FIG. 8). These salt bridges stabilize the relationship between the two lobes of the dimer in the crystal form of the protein but if disrupted by other interactions, such as might occur during the binding of MarR to marO, the two lobes would be able to act independently. Relative movement of the lobes would require distortion of the helices that link them to the N-/C-terminal domain. The long linker helix region encompassing residues 103-126 (α5/α5') appears poorly ordered in the region of Gly 116, as is the loop (residues 128-131) that connects this helix to the C-terminal helix (α6/α6'). It is possible that flexibility at these sites in MarR helps to accommodate relative shifts of the two lobes of the dimer that might occur on binding to DNA.

Architecture of the MarR Crystal Structure

The MarR without salicylate structure is a dimer and both subunits of the dimer are in the asymmetric unit. These individual subunits are joined by protein-protein interactions mediated by amino acids within both the N- and C-termini of the monomers. Like the MarR-salicylate structure, MarR without salicylate is an α/β protein. The MarR without salicylate structure is, however, conformationally different from the salicylate bound protein in that the caliper created by the dimer is more closed in the form of the protein without salicylate. Thus, the channel through the center of the dimer has been lost.

Figure 9:
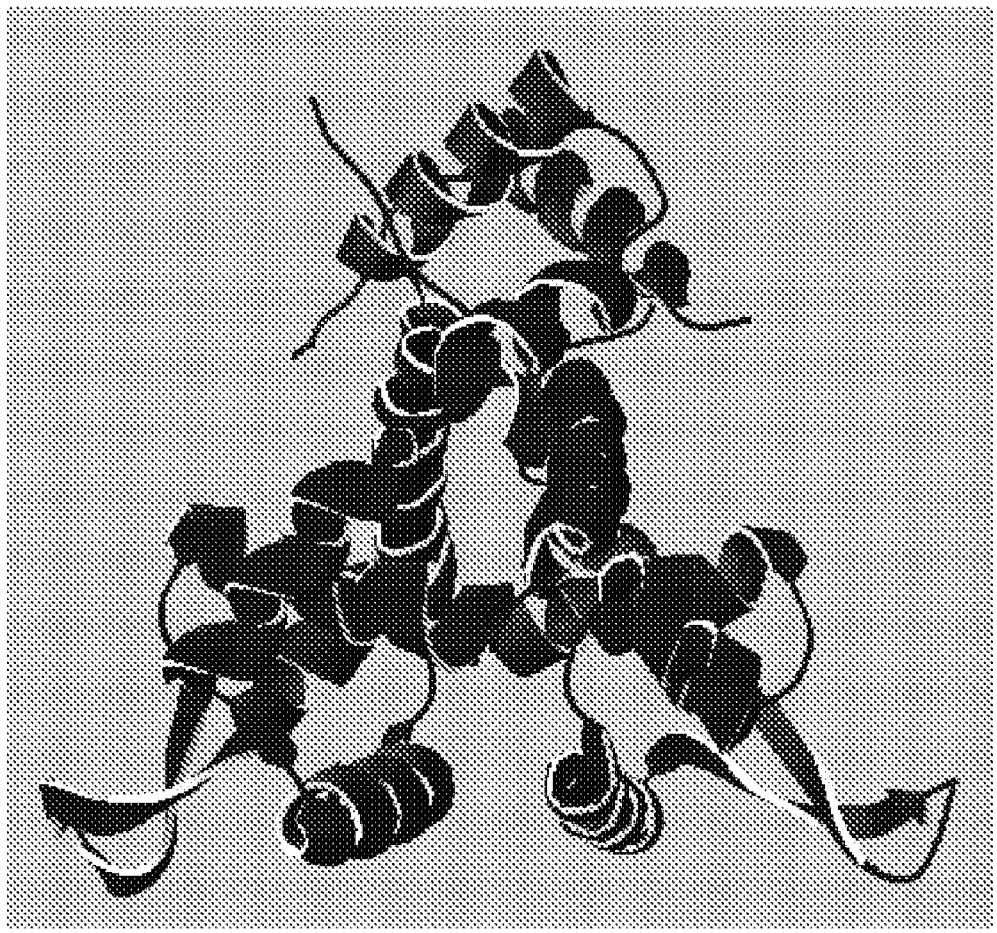
FIG. 9 shows a ribbon representation of the MarR dimer with the two-fold axis near vertical.

The overall architecture of the MarR without salicylate structure is comparable to that of the salicylate bound protein. The presumed DNA binding lobes or domains are linked to the remainder of the protein by two long α-helices. The positioning of the two DNA binding lobes in the MarR without salicylate structure is fixed by hydrogen bonds between the two lobes. This arrangement is believed to be mediated by interactions between Asp 67 and Arg 77'. In addition, Asp 26 is involved in hydrogen bonds with the side chains of Lys 44 and Lys 25. Together, the presumed recognition helices within the DNA binds lobes overlap by approximately one helical turn. FIG. 9 shows a ribbon representation of the MarR dimer with the two-fold axis near vertical.

The DNA Binding Domain

Previous studies have shown the region spanning amino acids 61-121 in MarR to be required for its DNA binding activity (Alekshun, M. N et al., supra, (2000)). In the crystal structure, amino acids 55-100 [β1-α3-α4-β2-W1 (wing)-β3] adopt the winged-helix fold (Clark, K. L. et al. *Nature* 364, 412-420 (1993)). The overall topology [H1 (α2)-S1 (β1)-H2 (α3)-H3 (α4, recognition helix)-S2 (β2)-W1-S3 (β3)] of this region is similar to other winged-helix DNA binding proteins (the terminology applied for these and subsequent structural elements is according to Gajiwala and Burley, supra (2000)) except that a third strand of sheet present in most members of the group appears to be represented in this MarR structure only by an interaction with Ile 55 (β1). The presence of this residue as the third component in the sheet interaction is similar to that observed in OmpR (Martinez-Hackert, E. & Stock, A. M. *Structure* 5, 109-124 (1997)), a winged helix protein, where Leu 180 interacts with the two strands of the antiparallel sheet that forms part of the "wing" in this transcription factor.

Within the winged-helix family of DNA-binding proteins, there are multiple modes of DNA binding. Members such as HNF-3γ use the recognition helix (H3) of the motif as the primary determinant for DNA-protein interactions in the major groove, and a wing region(s) (W1) to form minor groove or phosphodiester backbone nucleoprotein contacts (Clark, K. L. et al. supra (1993)). Others, such as hRFX1, use W1 to interact with the major groove and the H3 helix makes only a single minor groove contact (Gajiwala, K. S. et al. *Nature* 403, 916-921 (2000)). The juxtaposition of the DNA-binding lobes in the present structure does not allow for modeling of the whole dimer onto a B-DNA representation of the operator. However, since mutations in both α4 (H3) and W1 affect the DNA binding activity of MarR it is expected that amino acids from each of these regions would contribute to the DNA binding activity of the protein. For example, mutations in α4, including an R73c change, abolish MarR DNA binding activity in whole cells and in vitro (Alekshun, M. N et al., supra, (2000)). In the present crystal structure, it is the side chain of Arg 73 that is hydrogen bonded to Asp 67' of the other subunit, an interaction that stabilizes the relative orientation of the two DNA-binding lobes. Also, an R94C mutation at the tip of W1 is inactive in a whole cell assay while a G95S "superrepressor" mutation increases the DNA binding activity of MarR 30-fold in vitro (Alekshun, M. N et al., supra, (2000); Alekshun, M. N. & Levy, S. B. *J. Bact.* 181, 3303-3306 (1999)). In the absence of protein-DNA co-crystal structures, the precise mechanism by which these mutations affect the DNA binding activity of the protein is uncertain.

Footprinting experiments have suggested that MarR binds as a dimer at two separate but very similar sites in marO, the protein protects ~21-bp of DNA on both strands at a single site, and does not bend its target (Martin, R. G. et al., supra (1996); Martin, R. G. et al. *Proc. Natl. Acad. Sci. U.S.A.* 92, 5456-5460 (1995)). Each MarR binding site is composed of two half-sites whose organization is such that they are on different faces of the DNA double helix (Alekshun, M. N. et al. *Mol. Microbiol.* 35, 1394-404 (2000)), an arrangement that is very similar to the hRFX1 binding site (Gajiwala, K. S. et al. *Nature* 403, 916-921 (2000)). For MarR to bind as a dimer, with each winged-helix DNA binding domain contacting one half-site on B-DNA, geometric constraints suggest only a few possible modes of binding. One scenario, involving the binding of a single dimer to one MarR binding site, would require reorientation of the DNA binding lobes so that each could reach one half-site. This would be analogous to the binding of an E2F-DP heterodimer (a eukaryotic transcription factor in which each subunit also has a winged-helix DNA binding domain) to its cognate binding site (Zheng, N. et al. *Genes Dev.* 13, 666-74. (1999)). A second scenario would involve the binding of two dimers, on opposite faces of the double helix, to a single MarR binding site. This model would be analogous to the binding of DtxR (a bacterial protein with a winged-helix DNA binding domain) to its target, although in DtxR the half-sites are on the same face of the DNA helix (Pohl, E. et al. *J. Biol. Chem.* 273, 22420-22427 (1998); White, A. et al. *Nature* 394, 502-506 (1998)).

The term "appropriate conditions" include those conditions which result in the formation of a crystal which can by analyzed to a resolution of 5.0 Å or less. The crystals may be formed using suitable art recognized techniques, such as hanging droplet vapor diffusion. In one embodiment, the temperature of crystallization of the MarR family polypeptide is from about 1° C. to about 30° C., from about 10° C. to about 25° C., from about 15° C. to about 20° C., or abut 17° C. In a further embodiment, the conditions are selected such that crystals of said MarR family polypeptide grow within an acceptable time and reach dimensions which are suitable for structural determination, e.g., by using X-ray diffraction. In one embodiment, the acceptable time is 8 weeks or less, 6 weeks or less, 4 weeks or less, or 3 weeks or less. In an embodiment, the dimensions of the crystal are approximately 0.1 mm or greater per side, 0.2 mm or greater per said, or approximately 0.3 mm per side or greater.

In a further embodiment, the appropriate conditions include a cocrystallization agent which interacts with the protein such that the three dimensional structure of the protein can be determined.

The term "cocrystallization agent" includes substances which can be crystallized with the MarR family polypeptide such that the three dimensional structure can be determined. In an embodiment, the cocrystallization agent is a MarR family polypeptide modulator. The term "MarR family polypeptide modulator" includes compounds which interact with MarR family polypeptides, either to inhibit or enhance the activity of the MarR family polypeptides, such that they alter its activity in its non-crystallized form. In one embodiment, the MarR family polypeptide modulator is a MarR inhibitor (e.g., salicylate, plombagin, or DNP). In an embodiment, the concentration of the salicylate is about 100 mM or less, 150 mM or less, 200 mM or less, or 250 mM or less.

The crystal structure or MarR has been solved using crystals grown in the presence and in the absence of high concentrations (250 mM) of sodium salicylate. This agent, at millimolar concentrations, is known to inhibit MarR activity both in vitro and in whole cells (Alekshun, M. N. supra (1999)). It is routinely used as a model inhibitor of MarR to induce MarA expression in *E. coli* and *S. typhimurium* (Cohen, S. P. et al. *J. Bact.* 175, 7856-7862 (1993); Sulavik, M. C. et al. *J. Bact.* 179, 1857-1866 (1997)) and thus, to confer a Mar phenotype (Alekshun, M. N. supra (1999)). In one example, salicylate was included in the current crystal growth conditions to provide stable crystals. In another example, the crystal structure of MarR was determined using MarR without salicylate.

Electron density that is consistent with bound salicylate is apparent at two sites on each subunit in the present structure. These sites are on the surface of the molecule on either side of the proposed DNA-binding helix α4 (H3). In one site (SAL-A), the salicylate hydroxyl is hydrogen bonded to the hydroxyl side chain of Thr 72 in the α4 (H3) helix and the salicylate carboxylate hydrogen bonds to the guanidinium group of Arg 86. In the other site (SAL-B), the salicylate hydroxyl hydrogen bonds to the backbone carbonyl of Ala 70 and its carboxyl hydrogen bonds to Arg 77. In each of these sites, the salicylate ring sits over a hydrophobic side chain in the pocket; Pro 57 in SAL-A and Met 74 in SAL-B and other surface hydrophobes are also located laterally within 3.5 Å of the unsubstituted side of the ring. Although SAL-B is solvent exposed, SAL-A packs in the crystal with Val 96 of a symmetry mate situated 3.6 Å above the salicylate ring and adjacent to the SAL-A site of this symmetry mate. Since both SAL-A and SAL-B are close to the DNA binding helix, they may be positioned to influence DNA binding.

The crystal structure of MarR was solved by multiwavelength anomalous dispersion methods using protein containing selenomethionine. Diffraction data were collected to 2.3 Å from crystals of both seleno and native protein.

Use of the MarR Crystal Structure to Model the Structures of Other MarR Family Polypeptides In one embodiment, the invention pertains to a method for determining the structure of a MarR family polypeptide comprising analyzing the sequence of the related polypeptide and then modeling its structure based on the structure of MarR. The invention also pertains to the use of the MarR family polypeptide structures in the methods described below, e.g., for the identification of MarR family polypeptide modulating compounds.

Given the sequence-structure relationship described, the MarR crystal structure (described below) in the presence or absence of a MarR family polypeptide modulating compound can be used as a template to generate a computational three-dimensional model of any of the other members of the MarR protein family. In another embodiment, both crystals can be compared and the resulting information (including information regarding the binding site of the MarR family modulator) can be used. The resulting structure(s) can be subjected to the entire complement of computational approaches discussed and demonstrated above. Computer software packages such as COMPOSER (SYBYL. Tripos, Inc. 1699 Hanley Rd. St. Louis, Mo. 63144; Sutcliffe, M. J. et al. *Protein Eng.* 1987, 1, 385-392), MODELLER (Accelrys, Inc. 9685 Scranton Road San Diego, Calif. 92121-3752 U.S.A.; Sali, A. B. *J. Mol. Biol.* 1993, 234, 779-815) are widely utilized. The process of generating a structure as described is known as homology modeling or comparative molecular modeling. Generically, the process includes overall protein sequence alignment, determination of structurally conserved regions (SCR's), transposition of the template structure onto the undetermined sequence, loop building and refinement. As an example of how the MarR structure can be used for this purpose, a three-dimensional model of SlyA was generated as described in the appended examples.

Design of MarR Family Modulating Compounds Using Rational Drug Design Techniques The term "MarR family modulating compound" includes small molecules and other chemical entities which are capable of modulating, e.g., increasing or decreasing or otherwise altering the activity of a MarR family polypeptide or its down stream products, e.g., a MarR modulating compound may modulate the binding of MarR to DNA (e.g., the marO operon) or otherwise alter the expression of MarA. In one embodiment, the MarR family modulating compound is a MarR activator that enhances the binding of MarR to DNA (e.g., the marO operon), such that MarA expression is reduced.

The term "MarR family modulating compound candidate" includes compounds which are being screened or otherwise tested (e.g., computationally or in the laboratory) to determine whether or not they modulate MarR or a MarR family polypeptide.

The term "rational drug design" includes both computer aided and non-computer techniques where a protein is analyzed for active sites, and then modulating compound candidates are designed to interact with the particular spatial and electrochemical requirements of the particular site.

The term "active site" includes regions of a protein where a MarR family modulating compound physically interacts with a MarR family polypeptide. Any portion of the surface of a MarR family polypeptide can be considered an active site region or locus. In one embodiment, the portion of the MarR family protein immediately adjacent to the binding site of a MarR family modulating compound (e.g., a salicylate moiety) is referred to as the active site for the MarR family polypeptide. Other active sites include the DNA binding regions and regions necessary for interactions with other biological components, e.g., DNA or protein.

The term "interacts" includes interactions between the MarR family polypeptide and the MarR family modulating compound which result in modulation of a MarR family associated activity, e.g., expression of MarA when the MarR family polypeptide is MarR. The term also includes interactions which are determined by the shape and electronic complementarity between the MarR family polypeptide and the MarR family modulating compound. The term "interact" includes detectable interactions between molecules. The term interact is also meant to include "binding" interactions between molecules. Exemplary interactions include protein-protein and protein-nucleic acid interactions.

Specific knowledge of the three-dimensional shape and electronic properties of the MarR family polypeptide's active site provides information on how a MarR family modulating compound candidate may be modified to optimize interactions with a MarR family polypeptide. Several computer programs may be used to graphically depict the shape and electronic properties of the active site. These include, but are not restricted to CoMFA, (See Podlogar, B. L.; et al. *Drug Des. Discov.* 2000, 17, 4-12. and references therein), GRID (See GRID: Molecular Discovery Ltd., 4 Chandos St., London, W1A 3AQ, Goodford, P. J. et al. *J. Med. Chem.* 1985, 28, 849-857), and LIG BUILDER (See LIGBUILDER: Wang, R. et al. *J. Mol. Model.* 2000, 6, 498-516).

In these approaches, the active site is postulated and then placed within a three-dimensional lattice of evenly distributed grid points. A small molecular fragment or atom is placed on each lattice point, and a mathematical evaluation is made to determine the electronic and spatial properties at that point. After each lattice point within the active site is thus defined, the spatial and electronic "values" are contoured to generate maps or graphical representations that indicate the locations within the active site that are capable of accommodating additional "atomic bulk" and whether the atomic bulk should be charge positive, negative or neutral. It is the general theory that "filling" the active site with appropriate "atomic bulk" will optimize the drug-target interaction, thereby producing the maximal pharmacological response.

For example, the program LigBuilder was used to characterize one of the MarR active sites (SAL-A) in terms of its spatial and electronic properties. The results from this program represent a collection of colored crosses that depict an "inverse cast" of the MarR active site. Each cross represents a point where a mathematical determination was made. The shape of the inverse cast is dependent upon the van der Waals radii of the target's atoms constituting the active site as defined by the crystal structure of MarR. The colors indicate where the active site prefers positive or negative charge complemetarity. For example, arginine #86 of MarR is positively charged at physiologic pH. Consequently, atoms or atom fragments that are negatively charged would produce the optimal complimentarily about that point, which is correctly depicted by the LigBuilder program.

Once the active site has been graphically defined, the spatial and electronic representations of a MarR family modulating compound candidate can be fit or docked within the target active site. Specific modifications of an initial candidate can be made electronically, and then tested to determine whether the complementarity between the active site and the modulating compound candidate has been increased.

To demonstrate the use of the crystal structure for docking, the coordinates of the salicylate (a MarR modulator, which, in one embodiment, can be cocrystallized with MarR) were artificially removed from the MarR active site. Using this newly created empty active site as input, the program FLEXX is able to predict the proper binding orientation of salicylate with MarR (FLEXX Module, in SYBYL. Tripos, Inc. 1699 Hanley Rd. St. Louis, Mo. 63144. Rarey, M. et al. *J. Mol. Bio.* 1996, 261, 470-489). The result of this docking experiment is shown in green, which can be compared to the original salicylate orientation as determined crystallographically. As shown, the dominant molecular interactions between the cocrystallized salicylate molecule and the active site residues are predicted by the docking algorithm, e.g. the carboxylate and hydroxyl groups. The greatest variation between the computationally predicted docking and that determined by experiment occurs at the 4- and 5-positions of the aromatic ring. These correspond to the regions of the cocrystallized salicylate molecule with the largest crystallographic b-factors, and indicate that the carboxylate and hydroxyl groups of the salicylate moiety create the primary interactions within the active site. These two major interactions create a hinge point where the aromatic ring pivots within the active site.

As used in a drug discovery program, small modifications of the salicylate molecule can be made computationally, and then subjected to the identical FLEXX docking as demonstrated above for salicylate. The score of the modified salicylate can be compared to the original to ascertain the modification's benefit to overall target site complimentarily. This is a time consuming process, and is typically utilized only as part of the lead optimization process in an active drug discovery program. A variant of this approach is the automated application to large virtual libraries of potential drug candidates, known as automated ligand docking (Muegge, I.; Rarey, M. Small Molecule Docking and Scoring. *Reviews in Computational Chemistry*; Wiley: New York, 2000). This approach is typically employed as a part of the lead identification or screening process of a drug discovery program, since a large number of modulating compound candidates can quickly be assessed for active site complimentarily. Programs available include, but are not restricted to DOCK (DOCK Suite of Programs: Reagents of the University of California: DesJarlais et al. *J. Med. Chem.* 1988, 31, 722-729), AUTO_DOCK (AUTO_DOCK: Olson, A. J., SCRIPPS, La Jolla, Calif. Goodsell, D. S., et al. *J. Mol. Recognit.* 1996, 9), GLIDE, and FLEXX (FLEXX Module, SYBYL. Tripos, Inc.; Rarey, M. et al. *J. Mol. Bio.* 1996, 261, 470-489). Each requires an electronic representation of a library of potential drug candidates. Early versions of these approaches treated the drug candidate as a rigid body, wherein conformational flexibility was neglected. Algorithmic improvements and increases in computational speed now allow the flexibility of a potential candidate to be included. Based on the relative values of these scores, a virtual library of structures can be quickly screened for members that would produce the best interaction within the active site. As such, large libraries, originating from commercial vendors, from proprietary template enumeration or other sources, can be culled to eliminate compounds that are not promising (data reduction) and/or prioritized to highlight compounds warranting further consideration. Compounds with better overall docking scores will be placed higher on the list.

Each of the techniques described above are included as rational drug design methods. Other rational drug design techniques include de novo drug design which utilizes the structure of the protein to generate molecules to dock within the active site. In this approach, a "seed" atom, or seed-molecule with pre-defined attachment points is placed within the active site. Programs are available to systematically "grow" chemical modifications at the attachment points resulting in novel molecules. Through an iterative process of growing and assessing the complimentarily of the new structures, productive attachments can be saved, while unproductive attachments are discarded. Subsequent redefinition of the seed based on productive attachments can produce large number of drug candidates for the specified target. This is an unbiased approach since the resulting compound is not taken from a pre-existing virtual library, and is often used to generate compounds that would otherwise not be considered based on current proprietary knowledge or chemist's intuition. For example, this approach was applied to one of the MarR active sites using the program LigBuilder to produce a list of novel potential drug candidates. The compounds generated by LigBuilder are merely representative of one class of compounds which may be useful as MarR family protein modulating compounds. The invention also pertains to other compounds which may interact with other portions and thus have little or no structural similarity to these compounds.

Rational drug design also may involve the identification of pharmacophoric elements. In drug design, important functional groups are referred to as pharmacophoric elements and are useful for productive drug-target interaction. For example, for MarR salicylate site A (SAL-A), certain interactions between the salicylate moiety and the MarR active site may be attributable to the two main functional groups of the salicylate moiety, namely the carboxylate and the hydroxyl groups. At this site, the carboxylate creates a charge-charge interaction with arginine #86, and the hydroxyl group interacts strongly with threonine #72 by virtue of hydrogen bonding. Furthermore, the absence of either of these elements may diminish the degree of complementarity. The collection of pharmacophoric elements and their mutual spatial disposition within the active site defines the pharmacophore of the active site (See, e.g., WO 97/27219). In one embodiment, a MarR family modulating compound of the invention interacts with an amino acid corresponding (e.g., linearly or three dimensionally) to arginine at position #86 of SEQ ID NO:1 and/or threonine at position #72 SEQ ID NO:1.

For MarR, the carboxylate and hydroxyl groups of an inhibitor are separated by a distance of about 1.5 Å. As such, any compound with a similar functional groups thus positioned will possess the pharmacophore for MarR. Such information can be deduced from a known collection of compounds that demonstrate interaction with MarR. However, the crystal structure of MarR and its active site can be used to define a series of testable pharmacophore hypothesis. Programs, such as CoMFA, GRID and LigBuilder are instrumental in defining these hypotheses in a manner similar to that detailed by Clackson. In one embodiment, a MarR family modulating compound of the invention comprises a carboxylate and a hydroxyl group separated by a distance of 1.5 Angstroms.

In one embodiment, a known drug candidate is co-crystallized in the active site (e.g., salicylate, plumbagin, or DNP for MarR), since the exact coordinates of the pharmacophore can be determined. In another embodiment, the MarR family member is crystallized without a cocrystallizing agent. In another embodiment, the crystal structures of the MarR family member in the presence and absence of the co-crystallizing agent are compared to determine the effect of binding of the cocrystallizing agent. Thus, with or without a co-crystallizing compound, the pharmacophore can be used as a search query to identify structures from virtual libraries of commercial (known) or hypothetical structures. Programs including, but not restricted to UNITY (UNITY Module, in SYBYL. Tripos, Inc. 1699 Hanley Rd. St. Louis, Mo. 63144), CATALYST (CATALYST, Accelrys, Inc. 9685 Scranton Road San Diego, Calif. 92121-3752 U.S.A. Sprague, P. W. *Comput.-Assisted Lead Find. Optim., [Eur. Symp. Quant. Struct.-Act. Relat.]* 1997, 225-240) may be used for this purpose (Greer, J. et al. *J. Med. Chem.* 1994, 37, 1035-1054; WO 99/45389). The pharmacophore elements can also be used as the seeds for de novo design. LigBuilder was applied to the active site of MarR using the carboxylate and hydroxyl groups as "seed" groups to approximate the pharmacophore hypothesis. Common among these structures are the actual elements of the pharmacophore as expected, but in nearly all of the structures examined, another hydrogen bond acceptor was present, indicating the possibility of yet another pharmacophoric element in the pharmacophore.

In another embodiment, the invention pertains to a method for identifying a MarR family modulating compound using the three-dimensional structure of a MarR family polypeptide. The method includes selecting a candidate MarR family modulating compound by performing rational drug design with the set of atomic coordinates in FIG. 1 and/or FIG. 2 using computer aided techniques, as described herein. In one embodiment, the method also includes contacting the candidate MarR family modulating compound with a MarR family peptide, and a nucleic acid molecule, and then measuring the binding affinity of the MarR family polypeptide peptide with the nucleic acid molecule, such that MarR family modulating compounds are identified. In one embodiment, the nucleic acid molecule is a nucleic acid molecule to which a particular MarR family member is known to bind. For example, for MarR, the nucleic acid used for the binding acid may be, for example, marO.

In a further embodiment, the MarR family modulating compound is a MarR activator that acts, e.g., to inhibit the expression of MarA.

The invention also pertains to a method of identifying a MarR family member modulating compound. The method includes obtaining a set of atomic coordinates defining the three-dimensional structure of MarR or a MarR family polypeptide; selecting a candidate MarR family modulating compound by performing rational drug design with said three dimensional structure of the MarR family polypeptide; contacting said candidate MarR family modulating compound with MarR family polypeptide; and measuring the ability of the candidate MarR family modulating compound to modulate the activity of the MarR family polypeptide, thus identifying a MarR modulating compound.

In one embodiment, the rational drug design is aided by a computer program described supra. In one embodiment, the MarR family polypeptide is MarR and has the polypeptide sequence given in SEQ ID NO. 1 and has the atomic coordinates given in FIG. 1, when cocrystallized with salicylate or FIG. 2, when crystallized without.

In another embodiment, the invention pertains to compounds generated by the methods of the invention, described above. For example, the invention pertains to the MarR family modulating compounds and MarR modulating compounds generated by the rational drug design techniques described above. Examples of MarR modulating compounds include those of the formula (I):

X—Y—Z                                      (I)

wherein
X is an interacting moiety;
Y is a hydrophobic moiety; and
Z is a polar moiety.

The term "interacting moiety" includes moieties which are capable of interacting with a MarR family member. Preferably, such interacting moieties interact with Thr 72 of SEQ ID. 1 or an amino acid molecule that corresponds to Thr 72 in a MarR family polypeptide. In a further embodiment, the interacting moiety is capable of interacting by hydrogen bonding. Examples of interacting moieties include, but are not limited to, hydroxyl, thiol, sulfanyl, sulfonyl, amino, carbonyl, alkyl, and acyl moieties. The term "interacting moiety" includes moieties which allow the MarR modulating compound to perform its intended function, e.g., modulate MarR family member activity. In a further embodiment, the interacting moiety is hydroxy, thiol, or amino.

The term "hydrophobic moiety" includes moieties which are capable of interacting with the MarR family polypeptide such that the compound is capable of performing its intended function, e.g., modulate MarR. In certain embodiments, the hydrophobic moiety may be substituted with substituents capable of hydrogen bonding such as, but not limited to, hydroxy, thiol, carbonyl, amino, carboxylate, or thiol. Examples of hydrophobic moieties include, but are not limited to, substituted and unsubstituted alkyl, alkenyl, alkynyl, and aryl moieties.

In certain embodiments, the hydrophobic moiety is aryl. The aryl moiety may be cyclic, bicyclic or tricyclic. Preferably, the hydrophobic moiety is selected such that it is capable of interacting with MarR, such that its activity is modulated. In a further embodiment, the MarR family modulating compound is selected such that it is capable of interacting with hydrophobic or neutral amino acid residues, such as, but not limited to, Pro 57 or Met 74 or an amino acid residue corresponding to these amino acids of SEQ NO:1.

The term "polar moiety" includes moieties which are capable of interacting with MarR family polypeptide such that the activity of the MarR family polypeptide is modulated. In one embodiment, the polar moiety interacts with Arg 86 or Arg 77 or an amino acid residue corresponding to these amino acids of SEQ ID NO:1. In one embodiment, polar moiety is negatively charged. Examples of polar moieties include carboxylate and isoteres thereof. Other examples include, but are not limited to, phosphate, phosphite, sulfate, sulfite, nitrate, nitrite, nitro, hydroxy, oxalate, and perchlororate.

In one embodiment, the MarR family modulating compound is a MarR inhibitor. In another embodiment, the polar moiety and the interacting moiety are separated by a distance of about 1.5 Angstroms.

In a further embodiment, the MarR modulating compound is of the formula:

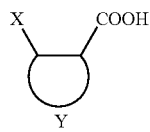

wherein Y is a substituted or unsubstituted cyclic or bicyclic moiety, and pharmaceutically acceptable salts and esters thereof. In a further embodiment, X is hydroxyl. In another further embodiment, Y is monocyclic or bicyclic, optionally substituted with a hydrophilic substituent. Examples of MarR modulating compounds include those listed below.

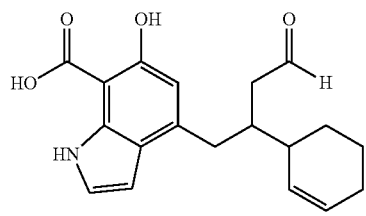

-continued

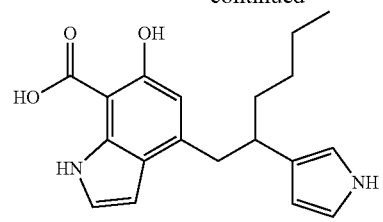

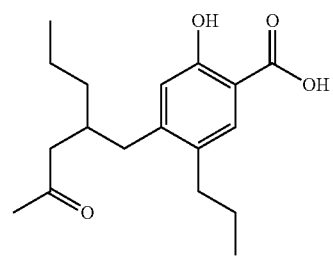

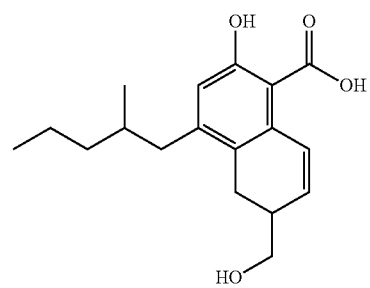

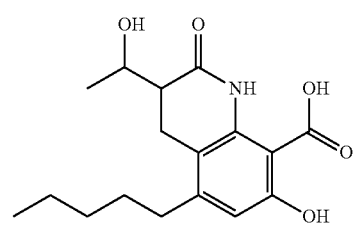

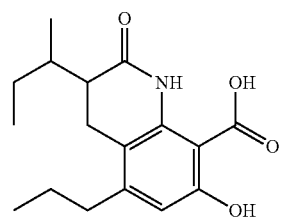

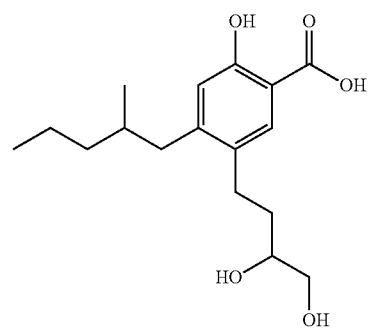

-continued

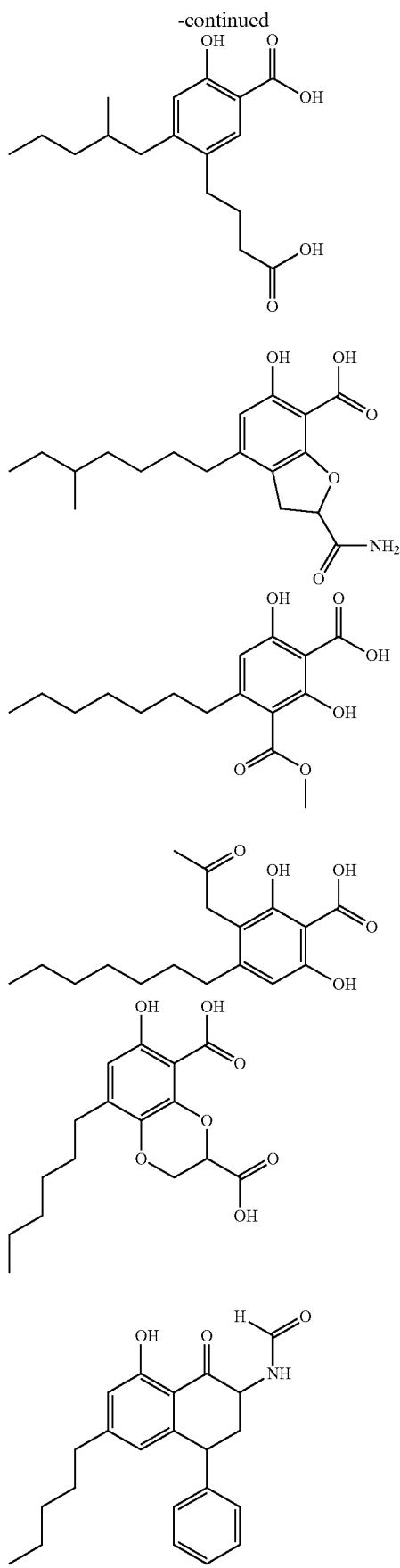

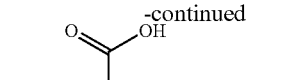

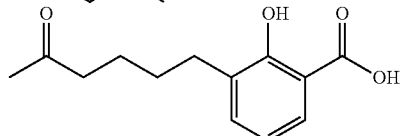

The compounds described herein can be synthesized by methods known in the art. An ordinarily skilled artisan will be able to consult the chemical literature and will be able to synthesize the compounds described herein.

The term "alkenyl" includes unsaturated aliphatic groups, including straight-chain alkenyl groups, branched-chain alkenyl groups, cycloalkenyl (alicyclic) groups, alkenyl substituted cycloalkyl or cycloalkenyl groups, and cycloalkenyl substituted alkyl or alkenyl groups. The term alkenyl further includes alkenyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkenyl group has 10 or fewer carbon atoms in its backbone (e.g., $C_1$-$C_{10}$ for straight chain, $C_3$-$C_{10}$ for branched chain), and more preferably 6 or fewer. Likewise, preferred cycloalkenyl groups have from 4-7 carbon atoms in their ring structure, and more preferably have 5 or 6 carbons in the ring structure, e.g., cyclopentene or cyclohexene.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer.

Likewise, preferred cycloalkyls have from 4-7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively. Examples of substituents of alkynyl groups include, for example alkyl, alkenyl (e.g., cycloalkenyl, e.g., cyclohenxenyl), and aryl groups.

Unless the number of carbons is otherwise specified, "lower alkyl" includes an alkyl group, as defined above, but having from one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "alkylsulfinyl" include groups which have one or more sulfinyl (SO) linkages, typically 1 to about 5 or 6 sulfinyl linkages. Advantageous alkylsulfinyl groups include groups having 1 to about 12 carbon atoms, preferably from 1 to about 6 carbon atoms.

The term "alkylsulfonyl" includes groups which have one or more sulfonyl ($SO_2$) linkages, typically 1 to about 5 or 6 sulfonyl linkages. Advantageous alkylsulfonyl groups include groups having 1 to about 12 carbon atoms, preferably from 1 to about 6 carbon atoms.

The term "alkanoyl" includes groups having 1 to about 4 or 5 carbonyl groups. The term "aroyl" includes aryl groups, such as phenyl and other carbocyclic aryls, which have carbonyl substituents. The term "alkaroyl" includes aryl groups with alkylcarbonyl substituents, e.g., phenylacetyl.

The invention also includes a method for inhibiting expression of MarA. The method includes contacting MarR with a MarR inhibiting compound. In an embodiment, the MarR inhibiting compound is of the formula (I):

$$X-Y-Z \quad (I)$$

wherein X is an interacting moiety, Y is a hydrophobic moiety; and Z is a polar moiety, and acceptable salts thereof. In an embodiment, the MarR inhibiting compound inhibits the binding of MarR to DNA (e.g., the marO operon).

Figure 10:
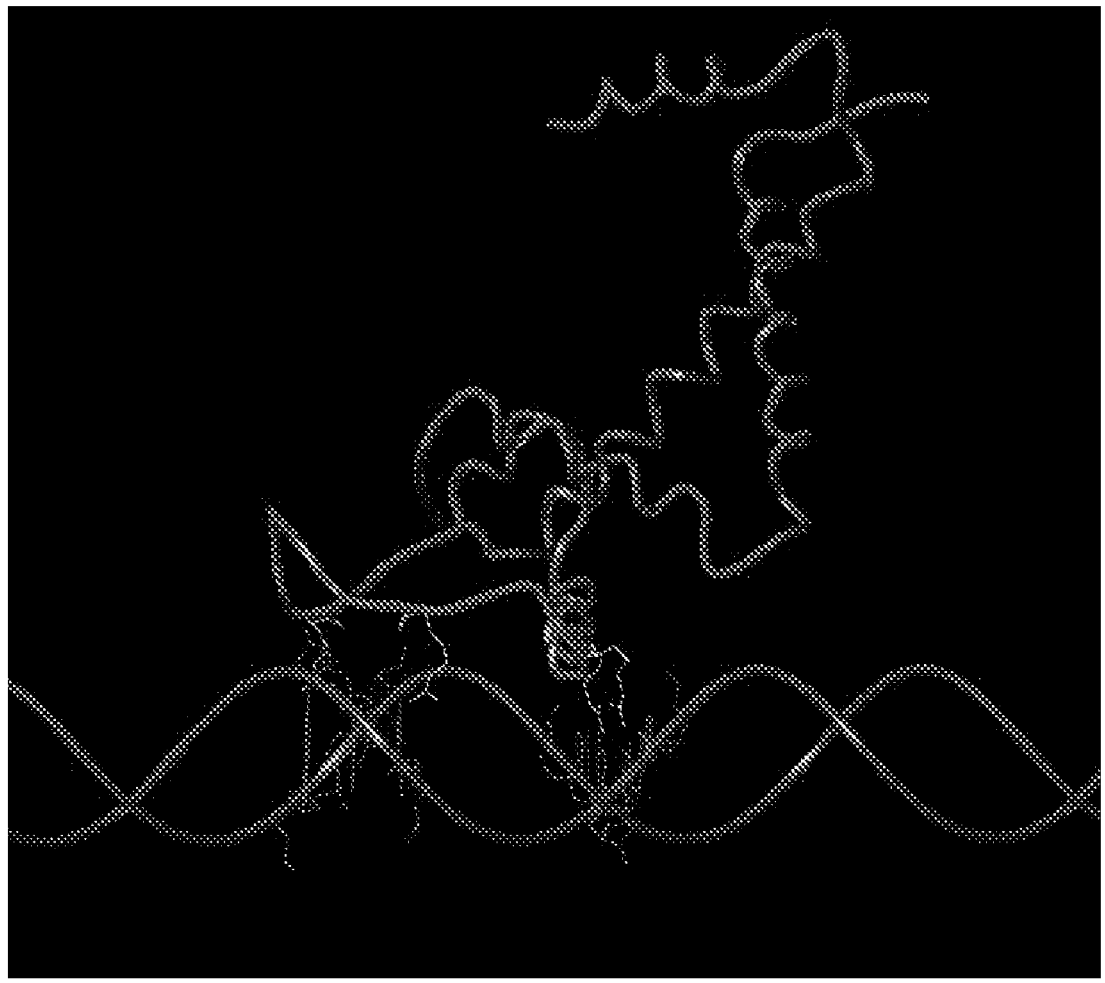
FIG. 10 is a computer model of MarR interacting with DNA.

Biological systems generally function through carefully choreographed interactions of their respective components. The operative mechanisms for many disease states implicate protein-protein interactions as key. For transcription factors, such as MarR, protein-DNA and protein-RNA interactions control the regulation events for the biological system. The drug design approaches discussed above are targeted in part to disrupt the interaction between MarR and the mar operon. Knowledge of the three dimensional structure of the MarR-marO complex can provide clues as to the key interactions (pharmacophore) made between them. A computer model of an interaction between MarR and DNA is shown in FIG. 10.

The invention also pertains to a method for decreasing multidrug resistance in a microbe, e.g., *E. coli*. The invention includes contacting *E. coli* with a MarR inhibiting compound, such that said multidrug resistance in *E. coli* is decreased. In an embodiment, the MarR inhibiting compound is of the formula (I):

$$X-Y-Z \quad (I)$$

wherein X is an interacting moiety; Y is a hydrophobic moiety; and Z is a polar moiety, and acceptable salts thereof.

The invention also pertains to methods for modulating activity of a MarR family polypeptide. The method includes contacting a MarR family polypeptide with a MarR family modulating compound identified by any method described herein (e.g., the computer modeling techniques, etc.). The invention also pertains to any compound discovered using techniques described herein.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

Example 1

Crystallization of MarR with Salicylate

Protein Production and Purification

Native and selenomethionine (Se-Met) containing MarR was prepared from *E. coli* BL21(DE3) (Novagen) bearing pMarR-WT, a wild type MarR expression vector that has been previously described (Alekshun, M. N. & Levy, S. B. *J. Bact.* 181, 4669-4672 (1999)). Native MarR was produced in whole cells according to previous methods (Alekshun, M. N. & Levy, S. B. *J. Bact.* 181, 4669-4672 (1999)). Se-Met MarR was produced by diluting an overnight culture of *E. coli* BL21(DE3)+pMarR-WT 1:1000 in M9 medium supplemented with 2 mM $MgSO_4$, 0.2% glucose, 0.1 mM $CaCl_2$, 0.00005% thiamine, 0.04 mg $ml^{-1}$ each of the following amino acids phenylalanine, leucine, isoleucine, valine, serine, threonine, tyrosine, histidine, lysine, aspartic acid, glutamic acid, tryptophan, and tryptophan, and kanamycin (Miller, J. H. In *Experiments in Molecular Genetics*. (Cold Spring Harbor Laboratories, Cold Spring Harbor, N.Y.; 1972). This culture was grown at 37° C. to an OD600≈0.6 and 100 mg each of amino acids threonine, lysine-hydrochloride, phenylalanine, 50 mg each of amino acids leucine, isoleucine, and valine (single letter abbreviations), and 60 mg L-(+)-selenomethionine (Sigma) were then added. The culture was grown for 15 min at 37° C.; IPTG was subsequently added to a final concentration of 1 mM and protein production was allowed to proceed for 14.5 hr at 37° C. Cell pellets were collected and processed as previously described (Alekshun, M. N. & Levy, S. B. *J. Bact.* 181, 4669-4672 (1999)).

Frozen cell pellets containing native or Se-Met MarR were resuspended in 100 mM sodium phosphate buffer (pH 7.4) containing a bacterial protease inhibitor cocktail (Sigma) and sonicated on ice. All buffers contained 2 mM DTT when Se-Met MarR was prepared. Insoluble matter was removed by centrifugation at 4° C. at 30,000×g for 40 min. The supernatant was passed over prepacked 5 ml SP-sepharose HiTrap columns (Amersham Pharmacia Biotech) previously equilibrated with 10 mM sodium phosphate buffer (pH 7.4). The column was washed with 50 ml of 10 mM sodium phosphate buffer (pH 7.4) and the pure proteins were eluted with a linear gradient (0-0.5 M) of NaCl in 10 mM sodium phosphate buffer (pH 7.4). Protein containing fractions were dialyzed vs. 10 mM HEPES (pH 7.4), 200 mM NaCl, and 1 mM DTT, or 2 mM DTT in the case of Se-Met MarR, and the protein in these samples was judged to be greater than 99% pure via SDS-PAGE and electrospray ionization mass spectrophotometry. The latter also demonstrated that more than 95% of the three methionine residues in Se-Met MarR were substituted with selenomethionine.

Crystallization:

MarR crystals were originally grown in 18% PEG MME 5000, 200 mM ammonium sulfate, 100 mM citrate buffer (pH 5.6) but showed anisotropic disorder in the diffraction data that made them unsuitable for structure determination. To stabilize the protein, the citrate was substituted by the known inhibitor salicylate. Crystals of the MarR-salicylate complex were grown at 17° C. by hanging droplet vapor diffusion. 6 μl of a 11.4 mg $ml^{-1}$ protein solution in 200 mM NaCl, 20 mM HEPES (pH 7.4), and 10 mM DTT were added to 2 μl of reservoir buffer (18% PEG MME 5000, 50 mM ammonium sulfate, 250 mM sodium salicylate, 10 mM DTT, and 15% glycerol, pH 5.5), and 0.8 μl 15% heptanetriol. The droplets were equilibrated with 1 ml of reservoir buffer. Crystals grew within 1 week reaching dimensions of approximately 0.3 mm per side.

X-Ray Data Collection, Structure Determination, and Refinement:

Diffraction data were collected at the Brookhaven National. Synchrotron Light Source, beamline X8C. Crystals were flash frozen in mother liquor at the beam line before data collection. All data were processed and reduced using DENZO and SCALEPACK (Otwinowski, Z. In *CCP4 Proceedings*. 56-62 (Daresbury Laboratory, Warrington, UK, 1993). The space group of the MarR-salicylate co-crystals was determined to be $I4_122$ with one molecule in the asymmetric unit and with unit cell dimensions of a=b=62.0 Å, c=132.9 Å, $\alpha=\beta=\gamma=90°$ for both the native and the selenoprotein. Data were collected on the selenoprotein crystals at three wavelengths to enable MAD phasing. Phases were determined from the MAD data using the program SOLVE (Terwilliger, T. C. & Berendzen, J. *Acta Crystallogr. D*. 55, 849-861 (1999)). This showed two selenium sites per asymmetric unit, with the third selenomethionine, at the N-terminus, apparently disordered. Maps were solvent-flattened using the program DM and the model was built into density using the program O (Collaborative Computational Project, Number 4. *Acta Crystallogr. D*. 50, 760-763 (1994); Jones, T. A. et al. *Acta Crystallogr. A* 47, 110-119 (1991)). Model and refinement parameters for salicylate were obtained from the Hetero Compound Information Center (Kleywegt, G. J. & Jones, T. A. *Acta Crystallogr. D*. 54, 1119-1131 (1998)). Model refinement was performed using CNS and cycles of rebuilding and refinement continued to give the final model (Brunger, A. T. et al. *Acta Crystallogr. D*. 54, 905-921 (1998)). Model quality was assessed by sa-omit, Fo-Fc, maps generated over the whole molecule omitting no more than 7% of the structure at a time. The model extends from residue 6 to the C-terminus at residue 144. In common with several other transcription factors (e.g. TetR, (1A6I), ArgR (1B4B) and TreR (1BYK)), MarR shows relatively high thermal mobility throughout the structure, as reflected by the B-factors. Certain regions appear to be particularly mobile, including the extended structure at the N-terminus, the tip of the "wing" (residues 91-94), parts of the α5 helix, especially around Gly 116 and the connecting loop (128-131) between the α5 and the C-terminal α6 helix. Consistent with the high B-factors, the molecule shows few well-ordered solvent molecules. PROCHECK reports overall g-factors of 0.25 (dihedrals) and 0.55 (main chain covalent forces) and shows that 91% of the residues fall within the most favored region of the Ramachandran plot, with only residue Ala 53 in a disallowed region. This residue is located at the start of the loop connecting the α2 and α3 helices.

The coordinates of the MarR-salicylate cocrystal are shown in FIG. 1. Data collection, phasing and refinement statistics for the MarR-sal cocrystal structure is shown in Table 1.

TABLE 1

| Data set | Native | Se-met edge | Se-met peak | Se-met remote |
| --- | --- | --- | --- | --- |
| Wavelength (Å) | 1.072 | 0.9795 | 0.9793 | 0.9500 |
| Resolution range (Å) | 50-2.3 | 50-2.3 | 50-2.3 | 50-2.3 |
| Measured reflections | 56,495 | 84,173 | 96,582 | 87,365 |
| Unique reflections | 6,069 | 5,534 | 5,564 | 5,472 |
| Completeness (%) overall (final shell) | 99.5 (100) | 91.3 (99.8) | 91.7 (99.8) | 90.4 (99.7) |
| <I/σI> (final shell) | 21.1 (12.0) | 12.2 (7.2) | 12.0 (7.0) | 12.9 (7.9) |
| $R_{merge}$(%) (final shell) | 6.0 (20.0) | 6.4 (29.7) | 5.7 (30.3) | 4.9 (25.5) |

TABLE 1-continued

| Data set | Native | Se-met edge | Se-met peak | Se-met remote |
|---|---|---|---|---|
| Rano(%) | | 4.9 | 5.0 | 3.5 |
| Overall FOM (centric/acentric) | 0.59/0.71 | | | |
| Resolution | 50-2.3 | | | |
| Rfree | 28.7% | | | |
| Rcryst | 24.7% | | | |
| Atoms/AU | | | | |
| Protein | 1078 | | | |
| Salicylate | 20 | | | |
| Water | 18 | | | |
| Average B (Å²) | | | | |
| main chain | 49.7 | | | |
| side chain | 59.2 | | | |
| salicylate | 42.7 | | | |
| water | 50.0 | | | |
| R.m.s. deviation | | | | |
| Bonds (Å) | 0.009 | | | |
| Angles (°) | 1.3 | | | |

Example 2

Crystallization of MarR

MarR was produced and purified as described in Example 1.

Crystallization:

Crystals of MarR were grown by hanging droplet vapor diffusion. 3 µl of a 10 mg ml⁻¹ 2:1 (mol:mol) DNA-protein solution in 200 mM NaCl, 20 mM HEPES, pH 7.4, mM TRIS-HCl, pH 8.0, and 2 mM MgCl₂ was added to 1 µl of reservoir buffer (23% PEG MME 5000, 100 mM sodium citrate, 200 mM ammonium sulfate, 10 mM DTT, 10% glycerol, 5% Isopropanol, pH 5.6), and 0.4 µl 15% heptanetriol. The droplets were equilibrated with 0.5 ml of reservoir buffer.

X-Ray Data Collection, Structure Determination, and Refinement:

Diffraction data were collected at the Brookhaven National Synchrotron Light Source, beamline X8C. Crystals were flash frozen in mother liquor at the beam line before data collection. All data were processed and reduced using DENZO and SCALEPACK (Otwinowski, Z. In *CCP4 Proceedings*. 56-62 (Daresbury Laboratory, Warrington, UK, 1993).

The coordinates of the MarR crystal without salicylate are shown in FIG. 2. Data collection, phasing, and refinement statistics for the MarR co-crystal structure is shown in Table 2.

TABLE 2

| Space group | C222 |
|---|---|
| Unit cell (Å) | a = 65.8, b = 137.7, c = 96.4 |
| Resolution | 50-2.7 |
| Rfree | 26.7% |
| Rcryst | 23.2% |
| Atoms/AU | |
| Protein | 2093 |
| Water | 14 |
| Average B (Å²) | |
| main chain | 40.0 |
| side chain | 48.0 |
| Water | 32.6 |

TABLE 2-continued

| R.m.s. deviation | |
|---|---|
| Bonds (Å) | 0.009 |
| Angles (°) | 1.3 |

Example 3

Use of the Crystal Structure of MarR to Model Other MarR Family Polypeptides

The amino acid sequences of MarR and SlyA are shown in FIG. 11. This alignment is generated automatically using the subroutines in COMPOSER, however it can be generated by a variety of other programs. FIG. 12 shows the results of the COMPOSER program in identifying the structurally conserved regions (SCRs).

The amino acids colored magenta are the regions of MarR and SlyA where the amino acid sequences are predicted to exhibit the same tertiary structure. These predictions are based on a knowledge base of information derived from the compilation of known crystal structures. Specifically, statistical correlations are made for protein tertiary structure with the respective amino acid sequences, and it was found that the correlations could be used in a predictive manner.

Figures 13A, 13B:
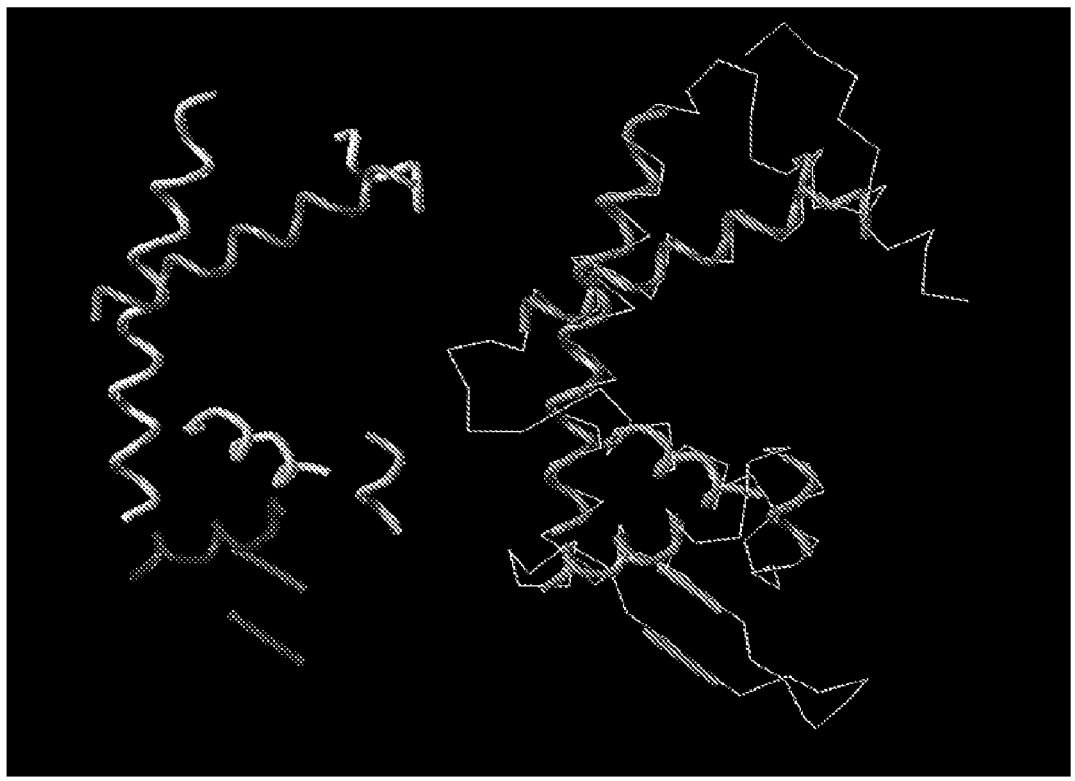
FIG. 13a represents the SCRs of MarR derived from the MarR crystal structure. The basic framework of SlyA is shown in FIG. 13b.

In the comparative molecular modeling process, the three-dimensional coordinates of the MarR backbone in the SCRs were directly transposed to create a general framework for SlyA as seen in FIGS. 13*a* and 13*b*. FIG. 13*a* is the $C_\alpha$-trace of MarR with the SCRs highlighted as orange tubes. The SCRs were "extracted" in their same mutual orientation to produce the basic framework of SlyA, which is shown in FIG. 13*b*. The process at this point generally includes only the backbone chain coordinates; the sidechains are added computationally to the SCR's on the left to create the SlyA protein. This model can, in all respects, be subjected to the identical regimen of computational protocols as the bona fide MarR crystal structure (Podlogar, B. L. et al. *J. Med. Chem.* 1997, 40, 3453-3455).

Figure 14:
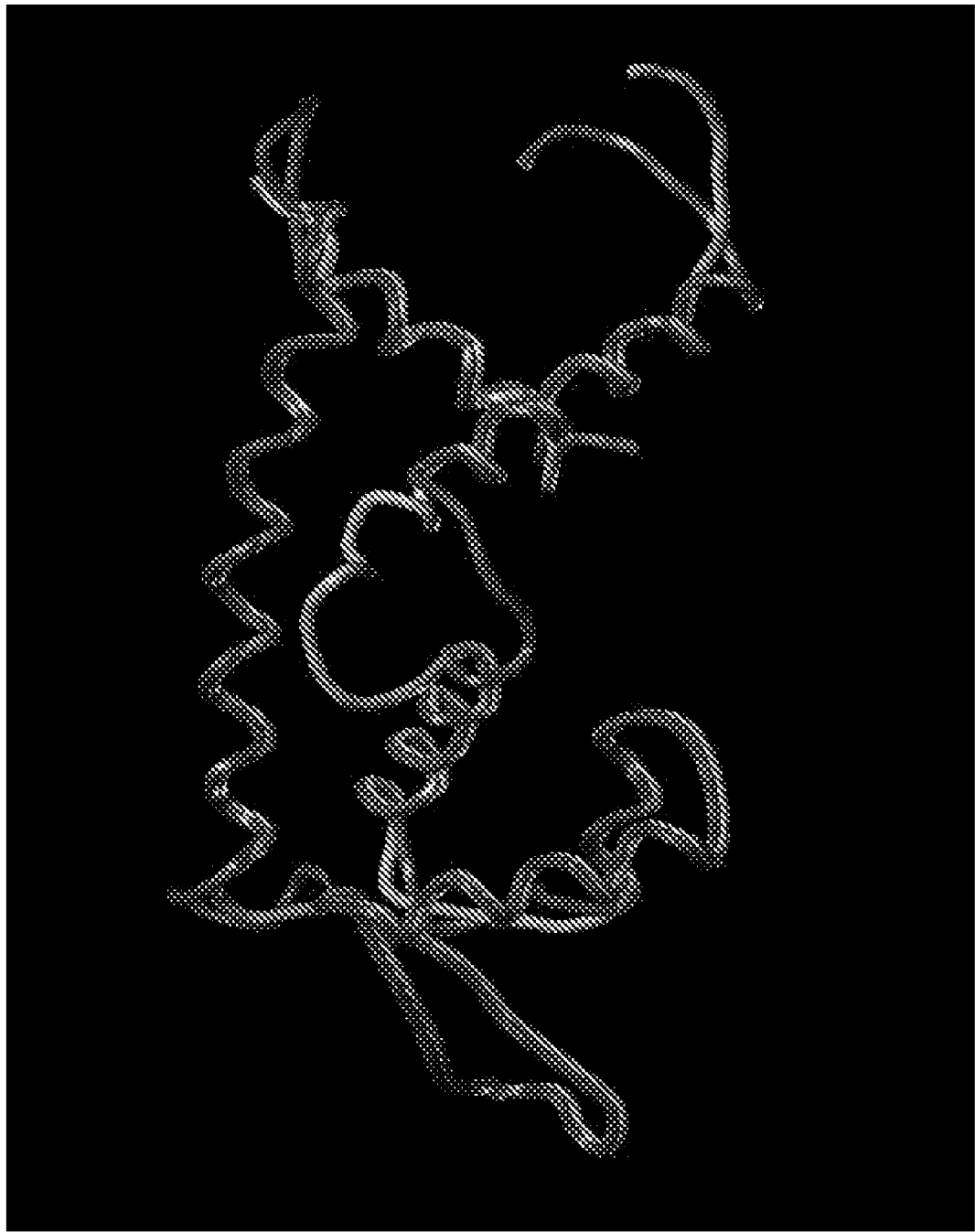
FIG. 14 shows a $C_\alpha$-tube representations of MarR from the crystal structure and its homology with a model of SlyA.

The regions in yellow (FIG. 12) are the "loops" that connect the SCRs. Loop regions, in general, exhibit the greatest variation among members in the same family. As such, no logical template for their construction is available. Again, use is made of the vast knowledge contained in the database of determined protein structures to construct the loop regions. FIG. 14 shows the fully constructed SlyA structure (purple) in comparison to the template protein, MarR.

Example 4

Use of the Computer Modeling to Characterize the MarR Active Site

For example, the program LigBuilder was used to characterize the MarR active site in terms of its spatial and electronic properties. The results represent a collection of colored crosses that depict an "inverse cast" of the MarR active site. Each cross represents a point where a mathematical determination was made. The shape of the inverse cast is dependent upon the van der Waals radii of the target's atoms constituting the active site as defined by the crystal structure of MarR. The colors indicate where the active site prefers positive or negative charge complemetarity. For example, arginine #86 of MarR is positively charged at physiologic pH. Consequently, atoms or atom fragments that are negatively charged would produce the optimal complimentarily about that point, which is correctly depicted by the LigBuilder program.

Once the active site has been graphically defined, the spatial and electronic representations of a MarR modulating compound candidate can be fit or docked within the target active site. Specific modifications of an initial candidate can be made electronically, and then tested to determine whether the complementarity between the active site and the modulating compound candidate has been increased. To demonstrate the use of the crystal structure for docking, the coordinates of the salicylate were artificially removed from the MarR active site. Using this newly created empty active site as input, the program FLEXX is able to predict the proper binding orientation of salicylate with MarR (FLEXX Module, in SYBYL. Tripos, Inc. 1699 Hanley Rd. St. Louis, Mo. 63144. Rarey, M. et al. *J. Mol. Bio.* 1996, 261, 470-489). The result of this docking experiment can be compared to the original salicylate orientation as determined crystallographically. The dominant molecular interactions between the salicylate and the active site residues may be predicted by the docking algorithm, e.g. the carboxylate and hydroxyl groups.

Example 5

Use of Rational Drug Design to Identify MarR Modulating Compounds

One method of rational drug design techniques includes de novo drug design which utilizes the structure of the protein to generate molecules to dock within the active site. In this approach, a "seed" atom, or seed-molecule with pre-defined attachment points is placed within the active site. Programs are available to systematically "grow" chemical modifications at the attachment points resulting in novel molecules. Through an iterative process of growing and assessing the complimentarily of the new structures, productive attachments can be saved, while unproductive attachments are discarded. Subsequent redefinition of the seed based on productive attachments can produce large number of drug candidates for the specified target. This is an unbiased approach since the result is not taken from a pre-existing virtual library, and is often used to generate compounds that would otherwise not be considered based on current proprietary knowledge or chemist's intuition.

This approach was applied to the MarR protein using the program LigBuilder to produce a list of novel potential drug candidates.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference. The entire contents of Alekshun et al. "The Crystal Structure of MarR a Regulator of Multiple Antibiotic Resistance at 2.3 Å resolution," *Nature Structural Biology* 8(8) is hereby incorporated herein by reference.

The invention claimed is:

1. A method for inhibiting expression of MarA, comprising contacting MarR with a MarR modulating compound, wherein said MarR modulating compound is of the formula:

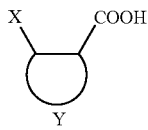

wherein, X is an interacting moiety selected from the group consisting of hydroxyl, thiol, sulfonyl, sulfonyl, amino, carbonyl, alkyl, and acyl moieties;

Y is a selected from the group consisting of substituted or unsubstituted cyclic or bicyclic moiety, optionally substituted with a hydrophilic substituent; and wherein X and the carboxylate group of said formula are separated by a distance of about 1.5 Angstroms.

2. The method of claim 1 wherein the MarR modulating compound is a MarR activator.

3. The method of claim 1 wherein said interacting moiety X interacts with the amino acid Asn corresponding to position 72 of SEQ ID NO:1.

4. The method of claim 1 wherein said interacting moiety X interacts with the amino acid Asn corresponding to position 70 of SEQ ID NO:1.

5. The method of claim 1, wherein X is a hydroxy, thiol or amino.

6. The method of claim 1, wherein Y is aryl.

7. The method of claim 1, wherein Y is capable of interacting hydrophobically with the corresponding amino acid positions Asp 57 or Lys 74 of SEQ ID NO:1.

8. The method of claim 1, wherein the MarR modulating compound is a MarR inhibitor.

9. The method of claim 1, wherein X is hydroxyl.

10. The method of claim 1, wherein Y is monocyclic.

11. The method of claim 1, wherein Y is bicyclic.

12. The method of 1 wherein the MarR modulating compound is selected from the group consisting of:

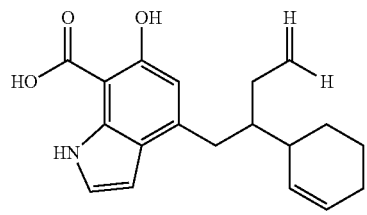

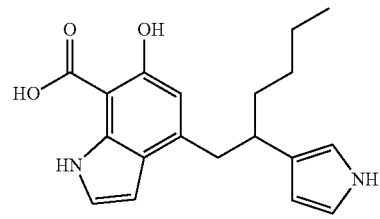

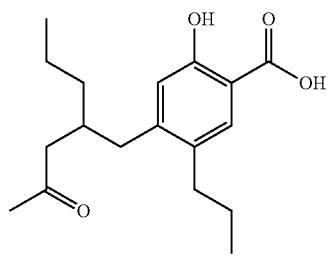

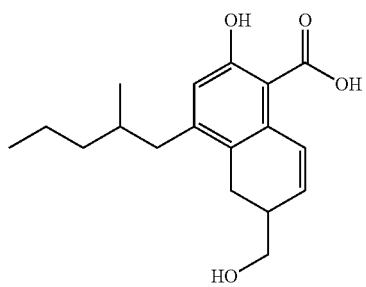

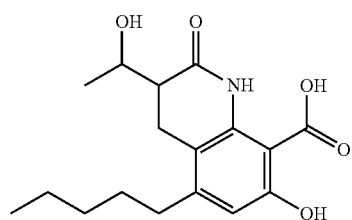

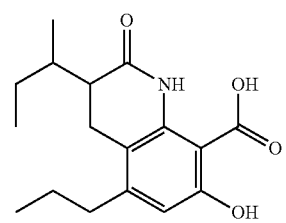

41
-continued
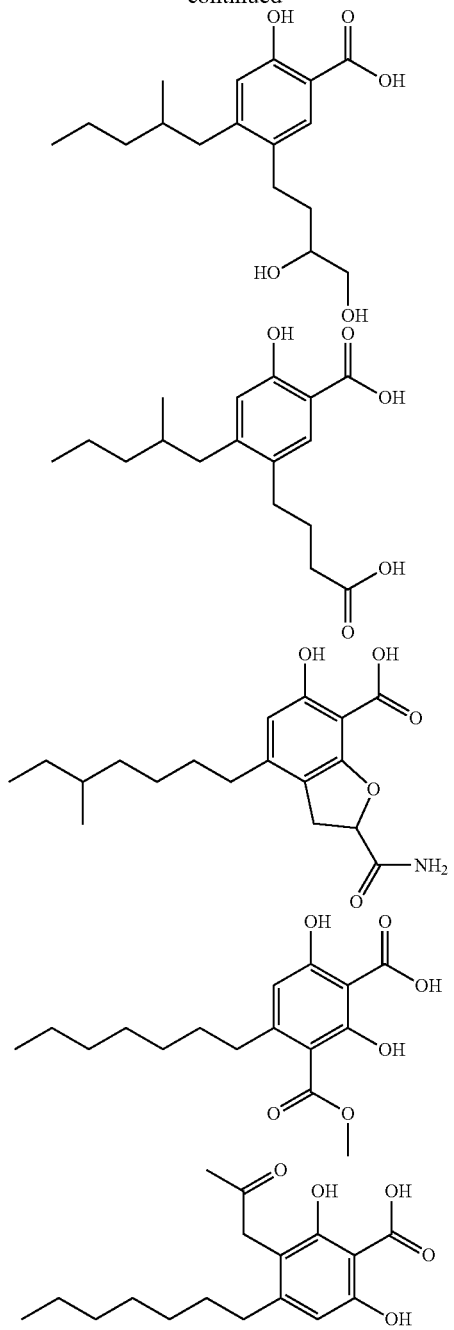
42
-continued
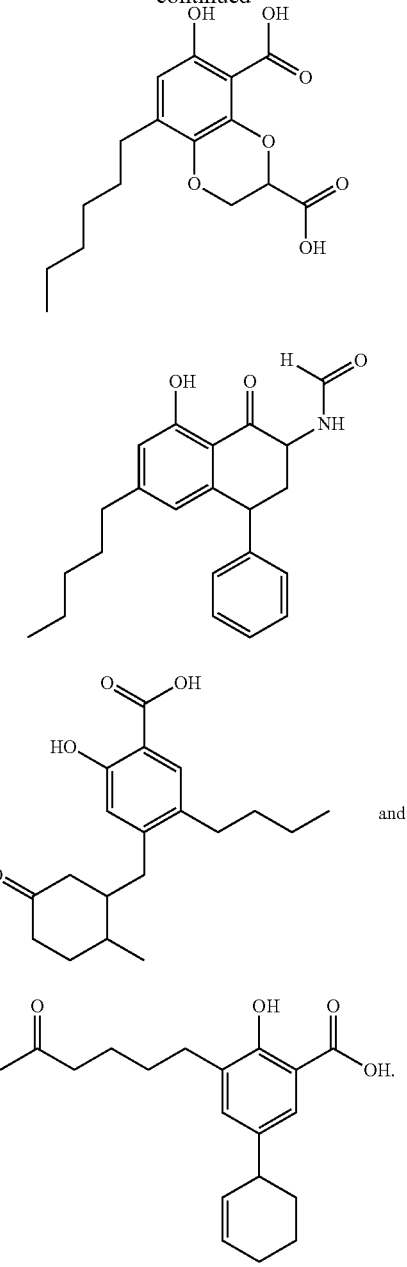
* * * * *